(12) United States Patent
Chung et al.

(10) Patent No.: US 12,296,020 B2
(45) Date of Patent: May 13, 2025

(54) COMPOUND COMPRISING FC-BINDING UNIT, AND CONJUGATE PREPARED USING SAME

(71) Applicants: ABTIS CO., LTD., Gyeonggi-do (KR); RESEARCH & BUSINESS FOUNDATION SUNGKYUNKWAN UNIVERSITY, Gyeonggi-do (KR)

(72) Inventors: Sang Jeon Chung, Gyeonggi-do (KR); Yeong Soo Oh, Gyeonggi-do (KR); Juhwan Kim, Gyeonggi-do (KR); Younggeun Lee, Gyeonggi-do (KR); Jinwoo Seo, Gyeonggi-do (KR); Geonmin Lee, Gyeonggi-do (KR); Gahyeon Kim, Gyeonggi-do (KR); Sejeong Kwon, Gyeonggi-do (KR); Sunhee Park, Gyeonggi-do (KR); Hojin Yeom, Incheon (KR); Hui Jo Oh, Gyeonggi-do (KR); Jinyoung Son, Gyeonggi-do (KR)

(73) Assignees: ABTIS CO., LTD., Gyeonggi-do (KR); RESEARCH & BUSINESS FOUNDATION SUNGKYUNKWAN UNIVERSITY, Gyeonggi-do (KR)

(*) Notice: Subject to any disclaimer, the term of this patent is extended or adjusted under 35 U.S.C. 154(b) by 0 days.

(21) Appl. No.: 18/802,353

(22) Filed: Aug. 13, 2024

(65) Prior Publication Data
US 2024/0415975 A1    Dec. 19, 2024

Related U.S. Application Data

(63) Continuation of application No. PCT/KR2023/017274, filed on Nov. 1, 2023.

(30) Foreign Application Priority Data

Nov. 1, 2022 (KR) .......................... 10-2022-0143600
Sep. 7, 2023 (KR) .......................... 10-2023-0119252

(51) Int. Cl.
*A61K 47/68* (2017.01)

(52) U.S. Cl.
CPC .... *A61K 47/68031* (2023.08); *A61K 47/6849* (2017.08); *A61K 47/6889* (2017.08)

(58) Field of Classification Search
None
See application file for complete search history.

(56) References Cited

U.S. PATENT DOCUMENTS

2016/0310612 A1  10/2016  Lyon et al.
2022/0073643 A1   3/2022  Yin et al.

FOREIGN PATENT DOCUMENTS

EP    3299383 A1    3/2018
EP    3915973 A1   12/2021
(Continued)

OTHER PUBLICATIONS

International Search Report from corresponding PCT Application No. PCT-KR2024-005273, dated Jul. 26, 2024.
(Continued)

*Primary Examiner* — Karl J Puttlitz
(74) *Attorney, Agent, or Firm* — Harness, Dickey & Pierce, P.L.C.

(57) ABSTRACT

Some embodiments of the present application provide a compound comprising Fc binding unit. The compound comprising Fc binding unit of the present application may be used to transfer a group of interest to an antibody in a position-specific manner. Furthermore, some embodiments of the present application provide a method for preparing an antibody conjugate comprising a group of interest (for example, a reactive group) using the compound comprising Fc binding unit.

8 Claims, 59 Drawing Sheets

Specification includes a Sequence Listing.

(56) References Cited

FOREIGN PATENT DOCUMENTS

| KR | 10-2018-0002734 A | 1/2018 |
| KR | 10-2020-0091826 A | 7/2020 |
| KR | 10-2021-0110339 A | 9/2021 |
| KR | 10-2022-0018616 A | 2/2022 |
| KR | 10-2022-0024297 A | 3/2022 |
| WO | WO-2020/184944 A1 | 9/2020 |
| WO | WO-2022079031 A1 * | 4/2022 ........... A61K 47/557 |

OTHER PUBLICATIONS

Written Opinion of the International Searching Authoirty from corresponding PCT Application No. PCT-KR2024-005273, dated Jul. 26, 2024.

Fujii, T., et al.; "AJICAP Second Generation Improved Chemical Site-Specific Conjugation Technology for Antibody Drug Conjugate Production", *Bioconjugate Chem.* 2023, 34, 728-738.

Haque, M., et al.; "Site-selective lysine conjugation methods and applications towards antibody-drug conjugates", *Chem. Commun.*, 2021, 57, 10689-10702.

International Seach Report from corresponding PCT Application No. PCT-KR2023-017242, dated Feb. 5, 2024.

Written Opinion of the International Searching Authority from corresponding PCT Application No. PCT-KR2023-017242, dated Feb. 5, 2024.

Matsuda, Y., et al.; "Chemical Site-Specifc Conjugation Platform to Improve the Pharmacokinetics and Therapeutic Index of Antibody DrugConjugates", Mol. Pharmaceutics, 2021, 18, 4058-4066.

Zeng, Y., et al.; "A Traceless Site-Specific Conjugation on Native Antibodies Enables Efficient One-Step Payload Assembly", Angew, Chem, Int, Ed., 2022, 61, pp. 1-10.

Yamazaki, C. M., et al.; "Antibody-drug conjugates with dual payloads for combating breast tumor heterogeneity and drug resistance", Nature Communications | (2021) 12:3528, pp. 1-13.

NCBI, Genbank: AEV4332.1, Fc lgG1 heavy chain constant region, partial [*Homo sapiens*], Jul. 25, 2016.

International Search Report from corresponding PCT Application No. PCT-KR2023-017274, dated Feb. 5, 2024.

Written Opinion of the International Searching Authority from corresponding PCT Application No. PCT-KR2023-017274, dated Feb. 5, 2024.

* cited by examiner

Reaction time of compound with antibody – 10min

| Type | Peak | % area |
|---|---|---|
| mAb | 6.930 | 73.92 |
| DAR1 | 11.323 | 23.99 |
| DAR2 | 15.364 | 2.09 |

Reaction time of compound with antibody – 30min

| Type | Peak | % area |
|---|---|---|
| mAb | 6.935 | 56.24 |
| DAR1 | 11.341 | 37.3 |
| DAR2 | 15.556 | 6.46 |

Reaction time of compound with antibody – 1h

| Type | Peak | % area |
|------|------|--------|
| mAb | 6.941 | 35.56 |
| DAR1 | 11.353 | 49.17 |
| DAR2 | 15.592 | 15.27 |

Reaction time of compound with antibody – 3h

| Type | Peak | % area |
|------|------|--------|
| mAb | 6.970 | 12.2 |
| DAR1 | 11.387 | 46.22 |
| DAR2 | 15.584 | 41.58 |

Reaction time of compound with antibody – 10 min

| Type | Peak | % area |
|------|------|--------|
| mAb  | 7.000 | 3.17 |
| DAR1 | 11.150 | 33.48 |
| DAR2 | 15.241 | 63.35 |

Reaction time of compound with antibody – 30 min

| Type | Peak | % area |
|------|------|--------|
| mAb  | 6.937 | 1.1 |
| DAR1 | 11.183 | 22.29 |
| DAR2 | 15.293 | 74.15 |

FIG. 28

| Reaction time (min) | DAR0 (%) | DAR1 (%) | DAR2 (%) |
|---|---|---|---|
| 10 | 3.89 | 33.94 | 62.17 |
| 30 | 1.66 | 24.01 | 74.33 |
| 60 | 0.74 | 17.59 | 77.31 |
| 180 | 0.34 | 13.77 | 84.97 |

Reaction time of compound with antibody – 30min

Reaction time of compound with antibody – 1h

Reaction time of compound with antibody – 3h

Reaction time of compound with antibody – 30min

Reaction time of compound with antibody – 1h

Reaction time of compound with antibody – 3h

COMPOUND COMPRISING FC-BINDING UNIT, AND CONJUGATE PREPARED USING SAME

CROSS-REFERENCE TO RELATED APPLICATIONS

This application is a continuation application of PCT Application No. PCT/KR2023/017274, filed on 1 Nov. 2023, which claims the benefit and priority to Korean Patent Application Nos. 10-2022-0143600, filed on 1 Nov. 2022 and 10-2023-0119252, filed on 7 Sep. 2023. The entire disclosures of the applications identified in this paragraph are incorporated herein by references.

SEQUENCE LISTING

This application contains references to amino acid sequences and/or nucleic acid sequences which have been submitted concurrently herewith as the sequence listing XML file entitled "000096uscoa_SequenceListing.XML", file size 48,226 bytes, created on 2 Aug. 2024. The aforementioned sequence listing is hereby incorporated by reference in its entirety pursuant to 37 C.F.R. § 1.52(e)(5).

FIELD

The present application relates to a compound comprising Fc binding unit, a conjugate prepared using the same, and a method for preparing a conjugate using a compound comprising Fc binding unit. A compound comprising Fc binding unit provided according to some embodiments of the present application enables a material of interest (for example, a reactive group) to be transferred to a desired site of an antibody. That is, a material of interest may be transferred to an antibody through a compound comprising Fc binding unit in a site-specific manner.

Furthermore, the present application provides an antibody-functional group conjugate (for example, an antibody-drug conjugate) characterized by having a branched linker.

BACKGROUND

Antibodies are biomolecules having a function of recognizing specific molecules, and are used in various industrial applications. As an example, a specific material may be detected or searched for (screened) using antibodies, a path through which a specific material moves within the body or within cells may be identified, and the antibody may be used for therapeutic use by inducing an immune response to a specific material.

Attempts have been made to improve such antibodies to expand their functionality. Typically, attempts have been made to label or conjugate various materials (for example, drugs or radioactive moieties, and the like) to complement or expand the functionality of antibodies. Typically, an antibody may be labeled with a fluorescent material and used in a fluorescence assay, or an antibody may be labeled with or conjugated to an agent for treating a specific disease to maximize the therapeutic efficacy of the antibody. These attempts and techniques may be referred to as antibody labeling or antibody-target moiety conjugation, and the present application relates to antibody labeling or antibody-target moiety conjugation.

In past studies, antibody-target moiety conjugates were prepared using highly reactive amino acid residues (for example, amine groups or thiol groups) among the amino acid residues that constitute antibodies. Specifically, after reactive groups capable of reacting with the residues were introduced into a target moiety, a target moiety capable of reacting with the reactive residues of the antibody (more specifically, a modified target moiety into which the reactive groups have been introduced) was prepared, and an antibody-target moiety conjugate was prepared by reacting the modified target moiety with an antibody.

Such past studies were conducted by randomly attaching a target moiety material to an antibody, and such past methods had many problems.

Essentially, the past methods were unable to accurately control the 'site where the target moiety was bound to the antibody, and furthermore, it was not possible to accurately control the 'number' of target moieties which were bound to the antibody. That is, an antibody-target moiety conjugate prepared by methods in the prior method has an inhomogeneity problem of drug structure.

Such a problem of drug structure inhomogeneity inevitably causes a problem of inhomogeneity in drug effects caused by 'differences' in drug structure. These problems have become a major obstacle to the development of antibody-drug conjugate (ADC) technology, which requires high safety and reproducibility.

Further, the problem of drug structure inhomogeneity causes a problem in that the function of the antibody is inhibited. The antibody comprises a Fab region comprising an antigen-binding domain which recognizes an antigen and an Fc region which is involved in the crystallization of the antibody. Non-site specific conjugation/labeling makes it impossible to precisely control the binding position of a target moiety to an antibody, making it impossible to prevent the target moiety from binding to the antigen-binding domain of the antibody or a position adjacent to the antigen-binding domain, thereby disturbing the recognition function of the antibody.

As a result, there is a need in the art for techniques for labeling an antibody in a site-specific manner in order to ensure the structural homogeneity of an antibody-target moiety conjugate. Although some techniques have been developed, most of them lack technical and economic effectiveness, such as genetic manipulation or modification of antibodies.

Under the circumstances described above, techniques for transferring a group of interest to an antibody in a position-specific manner have been actively developed.

In particular, the document [Korean Patent Application No. 10-2020-0091826 (Application No. 10-2020-0009162)] discloses a technique for transferring a click chemical functional group, which is a material of interest, to an antibody using a compound comprising Fc binding unit. Specifically, the document discloses a technique for transferring a material of interest to an antibody using a compound comprising Fc binding unit in a site-specific manner, with the release of the Fc binding unit or with the Fc binding unit. Meanwhile, in regard to a compound comprising Fc binding unit for transferring a material of interest to an antibody with the release of the Fc binding unit, according to the research results disclosed in the present application by the inventors of the present application, it is confirmed that the compound comprising Fc binding unit disclosed in Korean Patent Application No. 10-2020-0091826 has several problems and is not suitable for use. Accordingly, the inventors of the present application have developed a compound comprising Fc binding unit with novel and improved effects based on Patent Application No. 10-2020-0091826.

SUMMARY

Although a method for transferring a material of interest (for example, a reactive group or a functional group) to an antibody through a compound comprising Fc binding unit in a site-specific manner was developed, it is confirmed, through the present application, that when the compound disclosed in Korean Patent Application No. 10-2020-0091826 is used, there is a problem in that the yield rate of a conjugate, which is a product of interest, is low, the reaction time is too long, or the conjugate cannot be obtained. Thus, the present application provides a compound comprising Fc binding unit with improved or enhanced effects (for example, improved reaction efficiency).

The present application provides a compound comprising Fc binding unit. The compound comprising Fc binding unit of the present application may be used in the preparation of an antibody conjugate.

Further, the present application provides a method for preparing an antibody conjugate (for example, an antibody conjugate comprising a group of interest or an antibody conjugate comprising reactive group) using the compound comprising Fc binding unit of the present application.

Furthermore, the present application provides a method for preparing an antibody-payload conjugate using the compound comprising Fc binding unit of the present application, antibody, and payload; or an antibody conjugate comprising reactive group of the present application and payload.

Further, the present application provides an antibody-payload conjugate comprising a branched linker with improved or enhanced effects (for example, improved plasma stability) and a method for preparing the same.

The present application provides a compound comprising Fc binding unit having an improved or enhanced effects (e.g., improved reaction efficiency).

Furthermore, the present application discloses an antibody-payload conjugate comprising branched linker, having improved or enhanced effects (e.g., improved plasma stability).

BRIEF DESCRIPTION OF DRAWINGS

FIG. 28 shows the results of confirming the conjugation efficiency of Compound 9.

DETAILED DESCRIPTION

Figure 1:
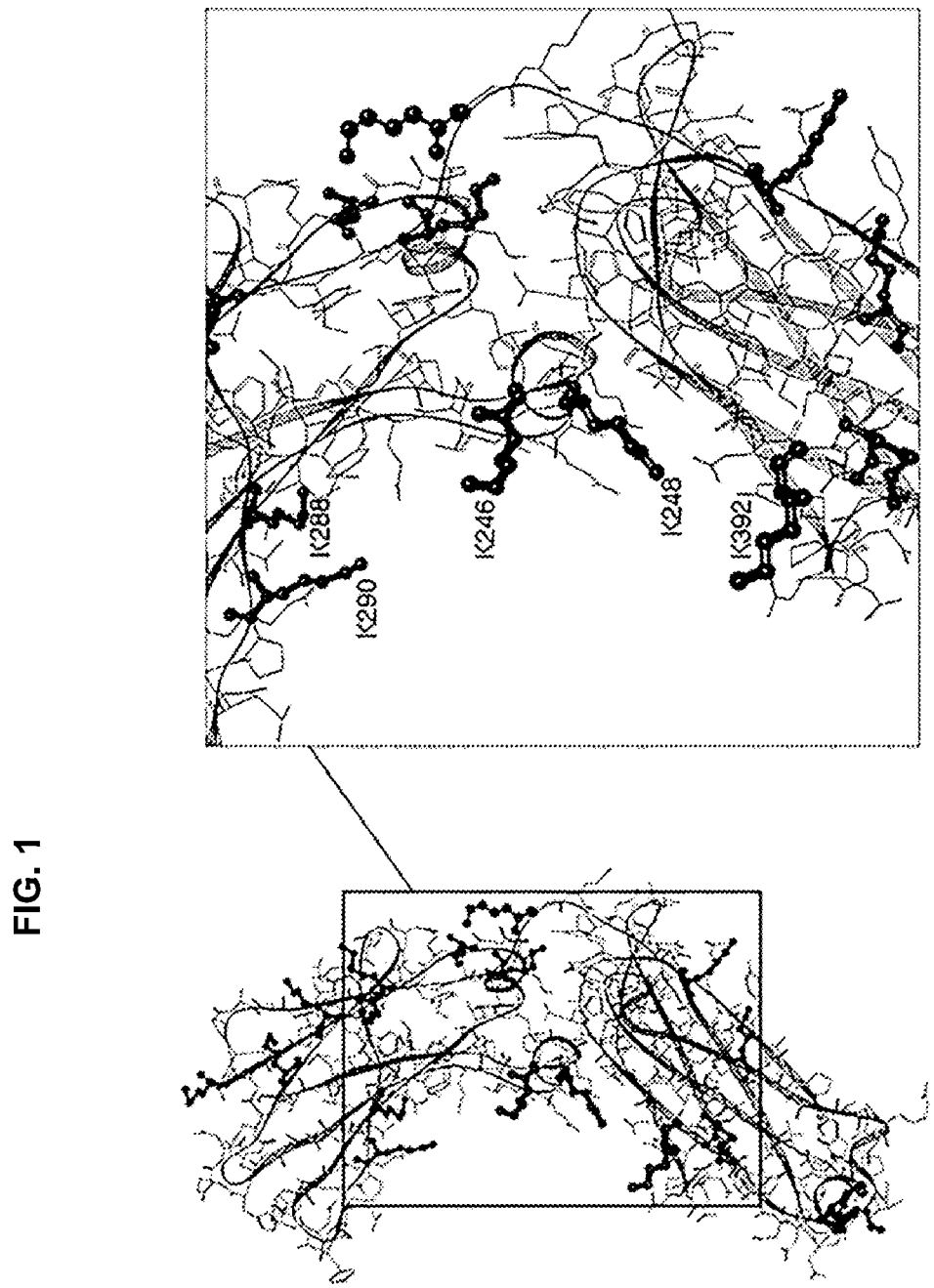
FIG. 1 illustrates the positions of lysine residues on an Fc region comprising lysine 246 and lysine 248.

Some embodiments of the present application provide a compound comprising Fc binding unit.

Some embodiments of the present application provide a compound comprising Fc binding unit having a structure of formula 2-2:

[formula 2-2]

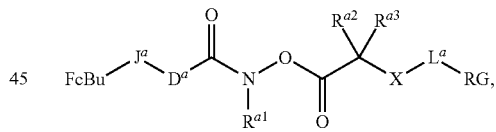

wherein $D^a$ is a spacer A, wherein the spacer A is a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H, herein the heteroalkylene, the heteroalkenylene, the heteroalkynylene, the heterocycloalkyl, or the heteroaryl comprises one or more heteroatoms, wherein each of the heteroatoms is independently selected from N, O, and S, $L^a$ is a linker A, wherein the linker A is a bond, substituted or unsubstituted $C_{1-100}$ alkylene, substituted or unsubstituted $C_{1-100}$ heteroalkylene, substituted or unsubstituted $C_{2-100}$ alkenylene, substituted or unsubstituted $C_{2-100}$ heteroalkenylene, substituted or unsubstituted $C_{2-100}$ alkynylene, or substituted or unsubstituted $C_{2-100}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H, herein heteroalkylene, heteroalkenylene, heteroalkynylene, heterocycloalkyl, or heteroaryl comprises one or more heteroatoms, wherein each of the heteroatoms is independently selected from N, O, and S, X is —CH$_2$—, —O—, or —NH—, $R^{a1}$ is H or $C_{1-6}$ alkyl, $R^{a2}$ is H or $C_{1-6}$ alkyl, $R^{a3}$ is H or $C_{1-6}$ alkyl, $J^a$ is —C(=O)—, —S—, —NH—, or —C(=NH)—, RG is a reactive group, wherein the reactive group comprises a reactive moiety, FcBU is a Fc binding unit, wherein the Fc binding unit has a structure of

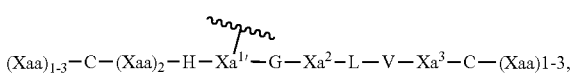

$(Xaa)_{1-3}$—C—$(Xaa)_2$—H—$Xa^{1'}$—G—$Xa^2$—L—V—$Xa^3$—C—$(Xaa)_{1-3}$, wherein each of Xaa is independently selected from any amino acid residue, $Xa^2$ is glutamic acid residue or asparagine residue, $Xa^3$ is tryptophan residue, naphthylalanine residue, or phenylalanine residue, a cysteine residue adjacent to the N terminus and a cysteine residue adjacent to the C terminus are, optionally, covalently linked,

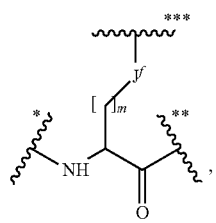

$Xa^{1'}$ is 0 herein, m is an integer of 1 to 5, $J^f$ is —NH—, —S—, or —C(=O)—, each of * and ** indicates an attachment point of $Xa^{1'}$ with the amino acid residue adjacent to $Xa^{1'}$, and

*** indicates an attachment point of $Xa^{1'}$ with a part, in the compound comprising Fc binding unit, that are not the Fc binding unit.

In specific embodiments, X may be —O— or —CH$_2$—.

In specific embodiments, X may be —O—.

In specific embodiments, $R^{a1}$ may be $C_{1-3}$ alkyl.

In specific embodiments, $R^{a1}$ may be methyl.

In specific embodiments, each of $R^{a2}$ and $R^{a3}$ may be independently any one selected from H and $C_{1-3}$ alkyl.

In specific embodiments, both $R^{a2}$ and $R^{a3}$ may be H.

In specific embodiments, $J^a$ may be —C(=O)—.

In specific embodiments, $D^a$ may be unsubstituted $C_{1-10}$ alkylene, unsubstituted $C_{1-10}$ heteroalkylene, unsubstituted $C_{2-10}$ alkenylene, or unsubstituted $C_{2-10}$ heteroalkenylene.

In specific embodiments, $D^a$ may be unsubstituted $C_{1-10}$ alkylene.

In specific embodiments, Fc binding unit may have the following structure:

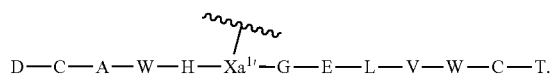

D—C—A—W—H—$Xa^{1'}$—G—E—L—V—W—C—T.

In specific embodiments, $J^f$ may be —NH—.

In specific embodiments, m may be an integer of 1 to 4.

In specific embodiments, m may be 3.

In specific embodiments, $L^a$ may be a bond, unsubstituted $C_{1-60}$ alkylene, unsubstituted $C_{1-60}$ heteroalkylene, unsubstituted $C_{2-60}$ alkenylene, or unsubstituted $C_{2-60}$ heteroalkenylene.

In specific embodiments, $L^a$ is a bond, unsubstituted $C_{1-60}$ alkylene, or unsubstituted $C_{1-60}$ heteroalkylene, wherein the unsubstituted heteroalkylene may comprise 0 to 20 of ethyleneglycol units.

In specific embodiments, $L^a$ is a bond, unsubstituted $C_{1-30}$ alkylene, or unsubstituted $C_{1-30}$ heteroalkylene, wherein the unsubstituted heteroalkylene may comprise 0 to 10 of ethyleneglycol units.

In specific embodiments, $L^a$ is a bond, unsubstituted $C_{1-24}$ alkylene, or unsubstituted $C_{1-24}$ heteroalkylene, wherein the unsubstituted heteroalkylene may comprise 0 to 8 of ethyleneglycol units.

In specific embodiments, $L^a$ is

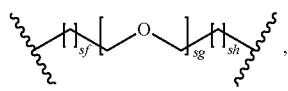

wherein sf is an integer of 0 to 8, sg is an integer of 0 to 15, and sh may be an integer of 0 to 8. In specific embodiments, sf is an integer of 0 to 3, sg is an integer of 0 to 10, and sh may be an integer of 0 to 3.

In specific embodiments, RG may be represented by the following structure:

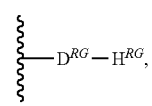

—$D^{RG}$—$H^{RG}$, wherein $D^{RG}$ is a spacer of the reactive group (spacer RG), wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(=O)H, —C(=O)NH$_2$, —NH$_2$, =NH, =O, =S, —OH, —NO$_2$ and —SH, herein heteroalkylene or heteroalkenylene comprises one or more heteroatoms, wherein each of the heteroatoms is independently selected from O, N, and S, $H^{RG}$ is the reactive moiety.

In specific embodiments, the reactive moiety may be a bio-orthogonal functional group.

In specific embodiments, the reactive moiety may have any one of the following structures:

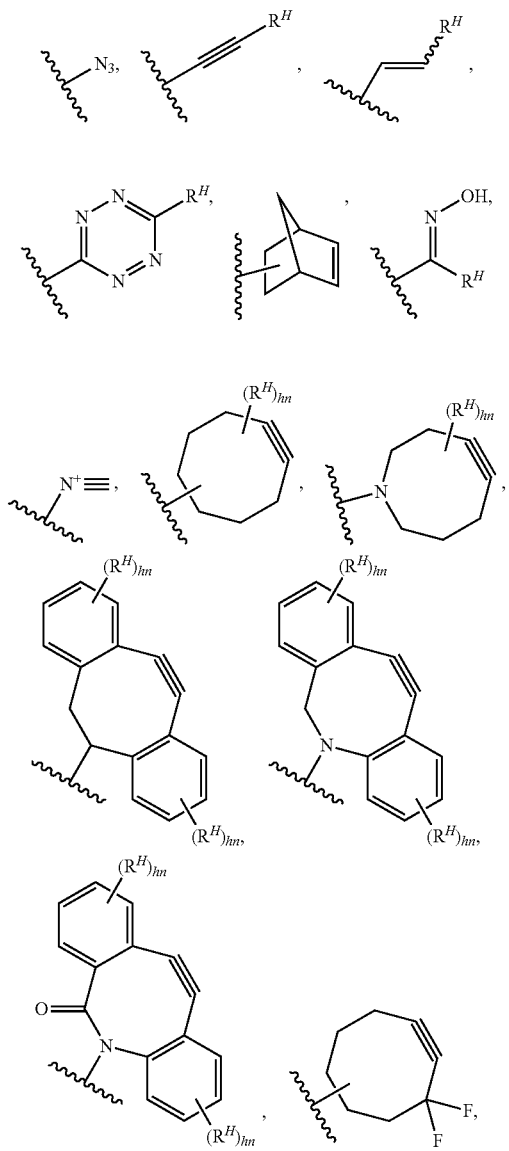

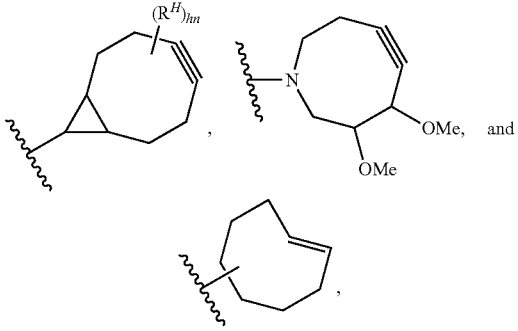

wherein
hn is an integer of 1 to 3,
$R^H$ is, each independently, H or selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein R is each independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH.

In specific embodiments, the reactive moiety may be selected from azide group, terminal alkyne group, terminal alkene group, cyclooctyne group, tetrazine group, norbornene group, cyclooctene group, oxime group, and isocyanide group, wherein the cyclooctyne group may be any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group may be any one selected from cis-cyclooctene group and trans-cyclooctene group.

Some embodiments of the present application provide a compound comprising Fc binding unit having a structure of the following formula 2-15:

[formula 2-15]

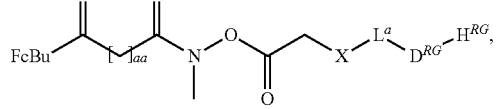

wherein
aa is an integer of 1 to 10,
X is —O— or —CH$_2$—,
$L^a$ is a linker A, wherein the linker A is a bond, unsubstituted $C_{1-30}$ alkylene, or unsubstituted $C_{1-30}$ heteroalkylene comprising 0 to 10 of ethyleneglycol units,

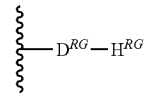

is a reactive group,
$D^{RG}$ is a spacer of the reactive group (spacer RG), wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(═O)H, —C(═O)CH$_3$, —C(═O)OH, —C(═O)NH$_2$, —NH$_2$, ═NH, ═O, ═S, —OH, —NO$_2$ and —SH, herein, heteroalkylene or heteroalkenylene comprises one or more heteroatoms, wherein each of the heteroatoms is independently selected from O, N, and S, $H^{RG}$ is the reactive moiety, FcBU is a Fc binding unit, wherein the Fc binding unit has a structure of

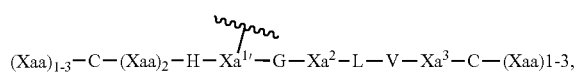

$(Xaa)_{1-3}$—C—$(Xaa)_2$—H—$Xa^{1'}$—G—$Xa^2$—L—V—$Xa^3$—C—$(Xaa)_{1-3}$, wherein each of Xaa is independently selected from any amino acid, $Xa^2$ is glutamic acid residue or asparagine residue, $Xa^3$ is tryptophan residue, naphthylalanine residue, or phenylalanine residue, a cysteine residue adjacent to the N terminus and a cysteine residue adjacent to the C terminus are, optionally, covalently linked, $Xa^{1'}$ is

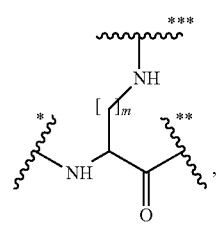

herein, m is an integer of 1 to 4, each of * and ** indicates an attachment point of $Xa^{1'}$ with the amino acid residue adjacent to $Xa^{1'}$,

*** indicates an attachment point of $Xa^{1'}$ with a part, in the compound comprising Fc binding unit, that are not the Fc binding unit.

In specific embodiments, aa may be an integer of 1 to 6.

In specific embodiments, aa may be 3.

In specific embodiments, Fc binding unit may have the following structure:

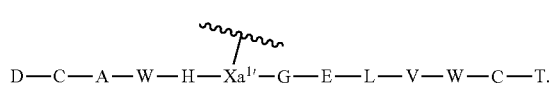

D—C—A—W—H—$Xa^{1'}$—G—E—L—V—W—C—T.

In specific embodiments, m may be 3.

In specific embodiments, the reactive moiety may be a bio-orthogonal functional group.

In specific embodiments, the reactive moiety may have any one of the following structures:

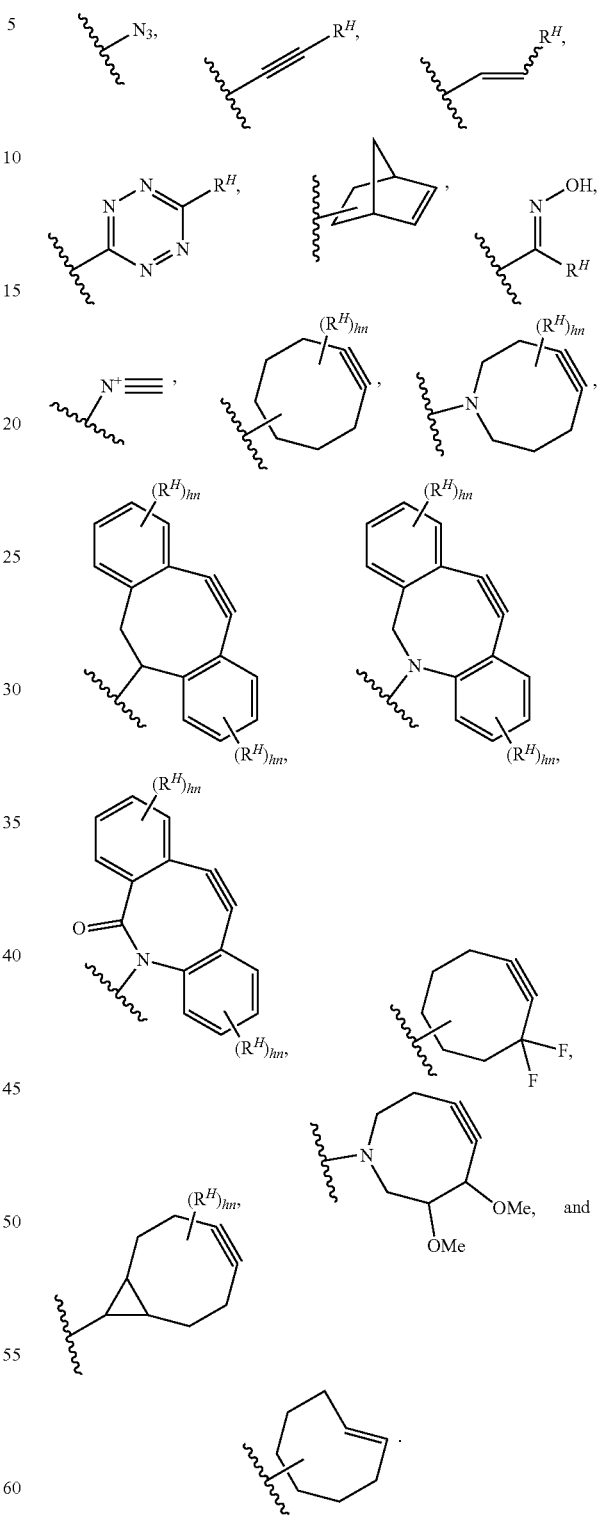

wherein hn is an integer of 1 to 3, $R^H$ is, each independently, H or selected from —R, ═O, ═S, —NO$_2$, —CR$_3$, —NR$_2$, ═NR, —OR, —SR, —C(═O)R, —C(═O)CR$_3$, —C(═O)OR, and —C(=O)NR$_2$, wherein R is each independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH.

In specific embodiments, wherein the reactive moiety may be selected from azide group, terminal alkyne group, terminal alkene group, cyclooctyne group, tetrazine group, norbornene group, cyclooctene group, oxime group, and isocyanide group, wherein the cyclooctyne group may be any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group may be any one selected from cis-cyclooctene group and trans-cyclooctene group.

Some embodiments of the present application provide a method for preparing an antibody conjugate comprising reactive group.

Some embodiments of the present application provide a method for preparing an antibody conjugate comprising reactive group, wherein the method comprises:
contacting a compound comprising Fc binding unit of the present application with an antibody, wherein the compound comprising Fc binding unit comprises reactive group.

In specific embodiments, the antibody may be an IgG antibody.

In specific embodiments, the antibody is an IgG antibody, and the IgG antibody may be a human IgG antibody, a humanized IgG antibody, or a chimeric IgG antibody.

In specific embodiments, a Fc region of the antibody comprises an amino acid sequence of SEQ ID NO: 14 or an amino acid sequence having 80% or more identity thereof, which may comprise an amino acid sequence of KPKDTLM (SEQ ID NO: 10) and an amino acid sequence of MHEALHNHY (SEQ ID NO: 12).

In specific embodiments, according to contacting the compound comprising Fc binding unit with the antibody, a reactive group is transferred to a target region of the antibody, wherein the target region consists of five consecutive amino acid residues and may comprise K246 and K248 of the Fc region of the antibody.

In specific embodiments, according to contacting the compound comprising Fc binding unit with the antibody, a reactive group may be transferred to one or more of K246 and K248 of the Fc region of the antibody.

In specific embodiments, the method for preparing an antibody conjugate comprising reactive group may further comprise obtaining the antibody conjugate comprising reactive group.

In specific embodiments, according to contacting the compound comprising Fc binding unit with the antibody, the antibody conjugate comprising reactive group is prepared, wherein the antibody conjugate comprising reactive group may comprise 1 to 4 reactive groups.

In specific embodiments, according to contacting the compound comprising Fc binding unit with the antibody, the antibody conjugate comprising reactive group is prepared,
wherein the antibody conjugate comprising reactive group comprises two reactive groups,
wherein, in the antibody conjugate comprising reactive group, one (a first reactive group) of the two reactive groups is linked to one of K246 and K248 of one (a first heavy chain) of two heavy chains of the antibody,
wherein, in the antibody conjugate comprising reactive group, the other reactive group (a second reactive group) of the two reactive groups may be linked to one of K246 and K248 of the other heavy chain (a second heavy chain) of the two heavy chains of the antibody.

In specific embodiments, according to contacting the compound comprising Fc binding unit with the antibody, the antibody conjugate comprising reactive group is prepared,
wherein the antibody conjugate comprising reactive group comprises two reactive groups,
wherein each of the two reactive groups may be linked to K246 of one heavy chain of the antibody and to K246 of the other heavy chain of the antibody respectively, or may be linked to K248 of one heavy chain of the antibody and to K248 of the other heavy chain of the antibody respectively.

In specific embodiments, contacting the compound comprising Fc binding unit with the antibody may be achieved by a method comprising: mixing a composition comprising the compound comprising Fc binding unit with a composition comprising the antibody. In specific embodiments, wherein, the mixing the composition comprising the compound comprising Fc binding unit with the composition comprising the antibody may be performed under conditions of pH 6 to pH 8.5.

MODE OF THE INVENTIONS

Hereinafter, the content of the invention will be described in more detail through embodiments and examples. The invention disclosed by the present application can be implemented in various forms, and is not limited to specific embodiments described herein.

A person with ordinary skill in the art to which the invention disclosed in the present application pertains will be able to conceive of various modifications and other aspects of the content of the invention disclosed in the present application. Therefore, it should be understood that the content of the invention disclosed in the present specification is not limited to the specific embodiments or examples described herein, and modifications thereof and other embodiments are also included within the invention disclosed in the present application.

Explanation of Terms

Unless otherwise described, all technical and scientific terms used in the present application have the same meaning as commonly understood by those skilled in the art to which the present application pertains. All publications, patents, and other references mentioned herein are incorporated by reference in their entireties.

"Halogen" or "halo" refers to a group including fluorine, chlorine, bromine, and iodine, which are included in the halogen group of elements in the periodic table.

As used herein, the term "hetero" refers to a compound or group including one or more heteroatoms. That is, the term hetero can be used with a term used to refer to a molecule itself or a term used to refer to a portion of a molecule. For example, heteroalkylene refers to an alkylene group including one or more heteroatoms in the main chain. As another example, heteroaryl refers to an aryl group including one or more heteroatoms on a ring (for example, a C$_6$ aryl group in which one or more carbons on a ring are each substituted with an independently selected heteroatom). The term "heteroatom" refers to an atom other than carbon or hydrogen, and includes for example, B, Si, N, P, O, S, F, Cl, Br, I and Se, and the like. Preferably, the term includes a polyvalent element such as N, O, and S. For example, when a structure includes one or more heteroatoms, each heteroatom may be independently selected from N, O, and S.

The term "alkyl" or "alkane" used to refer to a molecule by itself or to refer to a part of a molecule is used to mean a fully saturated straight-chained or branched hydrocarbon group. The straight chain and branched alkyl groups are, for example, methyl, ethyl, n-propyl, iso-propyl, n-butyl, sec-butyl, tert-butyl, iso-butyl, pentyl, hexyl, heptyl, octyl, nonyl, decyl, and the like. The alkyl group may include a cyclic structure. The term "$C_{x-y}$" is intended to include residues including x to y carbon atoms in the chain or ring, for example, when used with the term alkyl. For example, the term "$C_{x-y}$ alkyl" may mean including x to y carbon atoms as a substituted or unsubstituted, chained alkyl group, branched alkyl group, or alkyl group including a cyclic structure. $C_0$ alkyl means hydrogen. Examples of the $C_{1-4}$ alkyl include methyl, ethyl, n-propyl, iso-propyl, n-butyl, sec-butyl, tert-butyl, and iso-butyl, but are not limited thereto. For example, a straight-chained or branched alkyl group may have 1 to about 60, 1 to 20, or 1 to 10 carbon atoms.

As used herein, the term "heteroalkyl" refers to an alkyl including one or more heteroatoms. In this case, the heteroatom is each independently selected.

The term "alkylene" used to refer to a molecule by itself or to refer to a part of a molecule means a divalent radical derived from alkyl. The term "alkylene" may be used with the term "substituted" or "unsubstituted", as needed. When the term "alkylene" is not used with the term "substituted" or "unsubstituted," the term "alkylene" is intended to encompass the aspects of substituted and unsubstituted alkylene. For example, alkylene may refer to a group having 1 to 100 carbon atoms in the main chain. Examples of the alkylene may include —$CH_2$—, —$CH_2CH_2$—, —$CH_2CH_2CH_2$—, and —$CH_2CH_2CH_2CH_2$—, but are not limited thereto. For example, alkylene may be used as $C_2$ alkylene, which refers to an alkylene group having two carbon atoms in the main chain. Illustratively, "$C_{x-y}$ alkylene" is used herein to mean substituted or unsubstituted alkylene having X to Y carbon atoms in the main chain.

The term "heteroalkylene" used to refer to a molecule by itself or to refer to a part of a molecule means a divalent radical derived from heteroalkyl. The term "heteroalkylene" may be used with the term "substituted" or "unsubstituted", if necessary. When the term "heteroalkylene" is not used with the term "substituted" or "unsubstituted," the term "heteroalkylene" is intended to encompass the aspects of substituted and unsubstituted heteroalkylene. For example, heteroalkylene may refer to a group having 1 to 100 carbon atoms and heteroatoms in the main chain (for example, the sum of the number of carbon atoms and the number of heteroatoms in the main chain is 1 to 100). Examples of the heteroalkylene group include —$CH_2$—$CH_2$—O—$CH_2$—$CH_2$—, and —$CH_2$—O—$CH_2$—$CH_2$—NH—$CH_2$—, but are not limited thereto. The heteroalkylene group may comprise one or more heteroatoms, and each heteroatom may be the same or different. For example, the heteroalkylene group may comprise one or more heteroatoms at a position that is not the end of a chain or branch, and each heteroatom may be the same or different. For example, the heteroalkylene group may comprise one or more heteroatoms at each end of a chain or branch or all the ends of the chain or branch, and each heteroatom may be the same or different. Illustratively, "$C_{x-y}$ heteroalkylene" in the present specification is used to refer to substituted or unsubstituted heteroalkylene having a total of x to y atoms in the main chain (for example, the sum of the number of carbon atoms and the number of heteroatoms located in the main chain is x to y). For example, $C_3$ heteroalkylene may be used to mean a heteroalkylene having two carbon atoms and one heteroatom in the main chain. As another example, $C_5$ heteroalkylene may be used to mean a heteroalkylene having 3 carbon atoms and 2 heteroatoms in the main chain. $C_5$ heteroalkylene encompasses a structure such as, for example, —$CH_2$—$CH_2$—O—$CH_2$—$CH_2$— and —$CH_2$—O—$CH_2$—NH—$CH_2$— and the like.

The term "cycloalkyl" is used to refer to a fully saturated cyclic hydrocarbon group. The "cycloalkyl" comprises monocyclic and polycyclic groups. Unless otherwise defined, a monocyclic cycloalkyl group generally has 3 to about 20, preferably 3 to 10 carbon atoms on the ring. A ring other than the first ring of the polycyclic cycloalkyl may be selected from saturated, unsaturated and aromatic rings. The cycloalkyl comprises bicyclic molecules in which one, two or three or more atoms are shared between two rings. The term "fused cycloalkyl" refers to a polycyclic cycloalkyl group in which each ring shares two adjacent atoms with other rings. A ring other than the first ring of the fused polycyclic cycloalkyl may be selected from saturated, unsaturated and aromatic rings. The cycloalkyl may be used with the term substituted or unsubstituted, and the substituted cycloalkyl refers to a group provided when one or more hydrogen atoms linked to carbon atom on the ring are substituted with one or more independent substituents. Furthermore, the cycloalkyl may be used with the term hetero, wherein heterocycloalkyl refers to a cycloalkyl group comprising one or more heteroatoms on the ring.

The term "cycloalkylene" is used to mean a divalent radical derived from cycloalkyl. For example, the term cycloalkylene may be used with the term substituted or unsubstituted. For example, the term cycloalkylene may be used with the term hetero.

The term "alkene" or "alkenyl" used to refer to a molecule by itself or to refer to a part of a molecule comprises one or more double bonds as a straight-chained or branched non-aromatic hydrocarbon. For example, a straight-chained or branched alkenyl group may have 2 to about 60, 2 to 20, or 2 to 10 carbon atoms.

The term "heteroalkene" or "heteroalkenyl" means an alkenyl comprising one or more heteroatoms. In this case, the heteroatom is each independently selected.

The term "alkenylene" used to refer to a molecule by itself or to refer to a part of a molecule means a divalent radical derived from alkenyl. The term "alkenylene" may be used with the term "substituted" or "unsubstituted", as needed. When the term alkenylene is not used with the term substituted or unsubstituted, the term alkenylene is intended to encompass the aspects of substituted and unsubstituted alkenylene. For example, alkenylene may refer to a group having 2 to 100 carbon atoms in the main chain. Examples of the alkenylene may include —C=C—, —C—C—C=C—C=C—, or —C—C—C—C=C—, and the like, but are not limited thereto. In the present specification, when used with "$C_{x-y}$ alkenylene," $C_{x-y}$ alkenylene is used to mean a substituted or unsubstituted alkenylene having x to y carbon atoms in the main chain.

The term "heteroalkenylene" used to refer to a molecule by itself or to refer to a part of a molecule means a divalent radical derived from heteroalkenyl. For example, the term "heteroalkenylene" may be used to refer to an alkenylene group comprising one or more heteroatoms in the main chain. For example, heteroalkenylene may refer to a group having 2 to 100 carbon atoms and heteroatoms in the main chain (for example, the sum of the number of carbon atoms and the number of heteroatoms is 2 to 100). The term "heteroalkenylene" may be used with the term "substituted"

or "unsubstituted", as needed. In the present specification, when used with "$C_{x-y}$ heteroalkenylene," $C_{x-y}$ heteroalkenylene is used to mean a substituted or unsubstituted heteroalkenylene having the number of x to y carbon atoms and heteroatoms (for example, the sum of the number of carbon atoms and the number of heteroatoms is x to y) in the main chain.

The term "cycloalkene" or "cycloalkenyl" is a cyclic hydrocarbon comprising one or more double bonds on the ring. The "cycloalkenyl" comprises monocyclic and polycyclic groups. Unless otherwise defined, monocyclic cycloalkenyl generally has 3 to about 20, preferably 3 to 10 carbon atoms on the ring. A ring other than the first ring of the polycyclic cycloalkenyl may be selected from saturated, unsaturated and aromatic rings. The cycloalkenyl comprises bicyclic molecules in which one, two or three or more atoms are shared between two rings. The term "fused cycloalkenyl" means a polycyclic cycloalkenyl in which each ring shares two adjacent atoms with other rings. A ring other than the first ring of the fused polycyclic cycloalkenyl may be selected from saturated, unsaturated and aromatic rings. The term "cycloalkenyl" may be used with the term "substituted" or "unsubstituted," and the substituted cycloalkenyl refers to a group provided when one or more hydrogen atoms linked to carbon atom on the ring are substituted with one or more independent substituents. Furthermore, the term "cycloalkenyl" may be used with the term "hetero", wherein heterocycloalkenyl refers to a cycloalkenyl group comprising one or more heteroatoms on the ring.

The term "cycloalkenylene" is used to mean a divalent radical derived from cycloalkenyl. For example, the term cycloalkenylene may be used with the term substituted or unsubstituted. For example, the term cycloalkenylene may be used with the term hetero.

The term "alkyne" or "alkynyl" used to refer to a molecule by itself or to refer to a part of a molecule comprises one or more triple bonds as a straight-chained or branched non-aromatic hydrocarbon. For example, a straight-chained or branched alkynyl group may have 2 to about 60, 2 to 20, or 2 to 10 carbon atoms.

The term "heteroalkynyl" or "heteroalkyne" means an alkynyl comprising one or more heteroatoms. In this case, the heteroatom is each independently selected.

The term "alkynylene" used to refer to a molecule by itself or to refer to a part of a molecule means a divalent radical derived from alkynyl. The term "alkynylene" may be used with the term "substituted" or "unsubstituted," as needed. When the term alkynylene is not used with the term of substituted or unsubstituted, the term alkynylene is intended to encompass the aspects of substituted and unsubstituted alkynylene. For example, alkynylene may refer to a group having 2 to 100 carbon atoms in the main chain. In the present specification, when used with "$C_{x-y}$ alkynylene," $C_{x-y}$ alkynylene is used to mean a substituted or unsubstituted alkynylene having x to y carbon atoms in the main chain.

The term "heteroalkynylene" used to refer to a molecule by itself or to refer to a portion of a molecule means a divalent radical derived from heteroalkynyl. For example, the term "heteroalkynylene" may be used to refer to an alkynylene group comprising one or more heteroatoms in the main chain. For example, heteroalkynylene may refer to a group having 2 to 100 carbon atoms and heteroatoms in the main chain (for example, the sum of the number of carbon atoms and the number of heteroatoms in the main chain is 2 to 100). The term "heteroalkynylene" may be used with the term "substituted" or "unsubstituted," as needed. In the present specification, when used with "$C_{x-y}$ heteroalkynylene," $C_{x-y}$ heteroalkynylene is used to mean a substituted or unsubstituted heteroalkynylene having x to y carbon atoms and heteroatoms (for example, the sum of the number of carbon atoms and the number of heteroatoms is x to y) in the main chain.

The term "cycloalkyne" or "cycloalkynyl" refers to a cyclic hydrocarbon comprising one or more triple bonds on the ring, and is also referred to as a "strained alkyne." The "cycloalkynyl" comprises monocyclic and polycyclic groups. Unless otherwise defined, monocyclic cycloalkynyl generally has 3 to about 10 carbon atoms on the ring. A ring other than the first ring of the polycyclic cycloalkynyl may be selected from saturated, unsaturated and aromatic rings. The cycloalkynyl comprises bicyclic molecules in which one, two or three or more atoms are shared between two rings. The term "fused cycloalkynyl" means a polycyclic cycloalkynyl in which each ring shares two adjacent atoms with other rings. A ring other than the first ring of the fused polycyclic cycloalkynyl may be selected from saturated, unsaturated and aromatic rings. The term "cycloalkynyl" may be used with the term "substituted" or "unsubstituted," and the substituted cycloalkynyl refers to a group provided when one or more hydrogen atoms linked to carbon atom on the ring are substituted with one or more independent substituents. Furthermore, the term "cycloalkynyl" may be used with the term "hetero," wherein heterocycloalkynyl refers to a cycloalkynyl group comprising one or more heteroatoms on the ring.

The term "cycloalkynylene" is used to mean a divalent radical derived from cycloalkynyl. For example, the term cycloalkynylene may be used with the term substituted or unsubstituted. For example, the term cycloalkynylene may be used with the term hetero.

The term "aryl" is used to refer to a group comprising an aromatic ring, and refers to a group derived from arene which is an aromatic compound. The term aryl comprises monocyclic and polycyclic groups. The term "aryl" may be used with the term "hetero," and the heteroaryl is used to refer to an aryl group having one or more heteroatoms on the ring. The term "aryl" may be used with the term "substituted" or "unsubstituted," and the substituted aryl refers to an aryl group in which one or more hydrogen atoms linked to carbon atom on the ring are substituted with one or more substituents. The term "aryl" may be used to encompass both substituted or unsubstituted aryl and substituted or unsubstituted heteroaryl. Examples of aryl include phenyl, pyridyl, naphthyl, biphenyl, and the like, but are not limited thereto.

The term "arylene" is used to mean a divalent radical derived from aryl. For example, the term arylene may be used with the term substituted or unsubstituted. For example, the term arylene may be used with the term hetero. The term arylene may be used to encompass all of the substituted or unsubstituted arylene and the substituted or unsubstituted heteroarylene.

As used herein, the term "substituted" means that, in which the valence of the atom is normal and a substituted compound is stable, one or more hydrogen atoms on an atom are substituted with a substituent including deuterium and hydrogen variants. When the substituent is oxygen (that is, =O), this means that two hydrogen atoms are substituted. When one substituent is a halogen (for example, Cl, F, Br, and I, and the like), this means that one hydrogen atom is substituted with a halogen. When two or more substituents are present in one group, the substituents present in the group may be the same or different. Unless otherwise specified, the type and number of substituents may be arbitrary as long as chemically achievable. Illustratively, the substituent may be selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein R may be each independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH, but are not limited thereto (provided that the substituent is not —H). Representative examples of the substituent include —C$_{1-4}$ alkyl, —C(=O)H, —C(=O)CH$_3$, —C(=O)OH, —C(=O)NH$_2$, —NH$_2$, =NH, =O, =S, —OH, —NO$_2$ and —SH, but are not limited thereto. The term substituted or unsubstituted may be used with a term used to refer to a molecule itself or a term used to refer to a part of a molecule. For example, substituted C$_{10-20}$ alkylene may mean that one or more hydrogen atoms linked to the main chain are substituted with substituents, wherein each substituent may be independently selected.

In the present specification, when expressing the structure (partial structure) of a compound, when indicating a portion where another group and the group of the partial structure are linked, a wavy line drawn in a direction roughly perpendicular to the bond (for example,

)

is used. For example, when expressed as a structure

it indicates that group X in a material, molecule, or compound is linked to another part through a bond. For example, when expressed as a structure

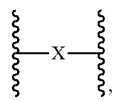

it indicates that group X in a material, molecule, or compound is linked to other parts through the bond. For example, in a compound having the structure of "A-X," when only the structure of the X group is illustrated, it may be expressed as a structure

For example, in a compound having the structure "A-X—B", when only the X structure is illustrated, it may be expressed as a structure

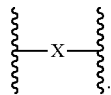

If necessary, a wavy line drawn nearly perpendicular to the bond may be represented through an additional notation. For example, in a compound having the structure of A-X—B, when only the structure of the X group is illustrated, the structure of the X group may be illustrated, as in

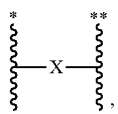

if needed, wherein by mentioning things like "* is the portion linked to A and ** is the portion linked to B," it is possible to provide information about what part each wavy line indicates linkage to.

Furthermore, a wavy line drawn in a direction roughly perpendicular to the bond expresses that "a structure illustrated with the wavy line" is covalently and directly linked to "a group other than the structure illustrated with the wavy line." The wavy line should not be construed to mean that other additional elements may be included between "a structure illustrate with the wavy line" and "a group other than the structure illustrated with the wavy line." When additional elements may be included, they will be described through separate related descriptions. The following structure is described as an example.

Example A

[example formula A]

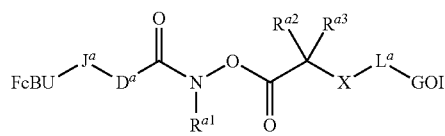

wherein FcBU is a Fc binding unit, and the Fc binding unit has the following structure:

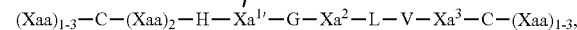

Herein, Xa$^{1'}$ will be interpreted as being directly linked to J$^a$ (that is, Xa$^{1'}$ and J$^a$ are linked without any additional elements between J$^a$ and Xa$^{1'}$).

Based on the above description, the structure of example formula A is illustrated as follows:

[example formula A-1]

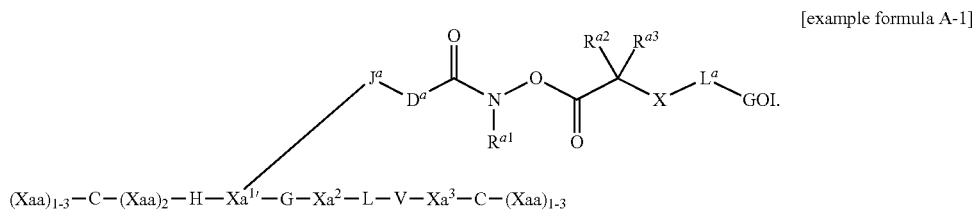

$(Xaa)_{1-3}-C-(Xaa)_2-H-Xa^{1'}-G-Xa^2-L-V-Xa^3-C-(Xaa)_{1-3}$

Example B

[example formula B]

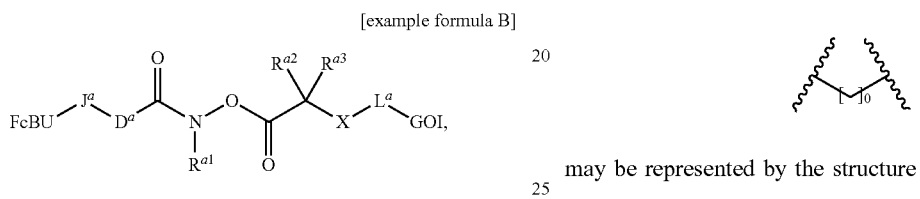

wherein GOI is a desired group, wherein the desired group is a reactive group, and the reactive group has the following structure:

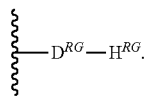

Herein, $D^{RG}$ will be interpreted as being directly linked to $L^a$ (that is, $D^{RG}$ and $L^a$ are linked without any additional elements between $D^{RG}$ and $L^a$).

Based on the above description, the structure of example formula B is illustrated as follows:

[example formula B-1]

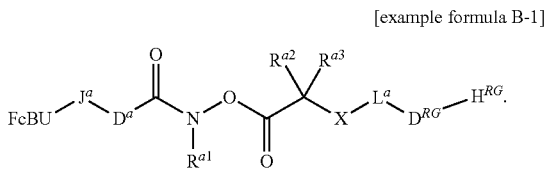

The structure

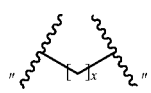

as used in the structures or formulas disclosed herein is used to mean $C_x$ alkylene. For example, the structure

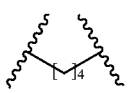

may be used to represent a $C_4$ alkylene such as $-CH_2-CH_2-CH_2-CH_2-$. Herein, the case where x is 0 means a bond. That is, the structure

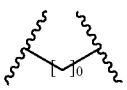

may be represented by the structure

The compound of the present specification may have a specific geometric or stereoisomeric form. When compounds are disclosed in the present application without being specified, isomers such as cis and trans isomers, (−)- and (+)-enantiomers, (R)- and (S)-enantiomers, diastereoisomers, (D)-isomers, (L)-isomers, and racemates of the compounds are included in the scope of the present application. That is, when a formula or structure disclosed in the present specification does not have a notation associated with isomers (for example, ⌇⌇⌇, ▰▰▰, ▱▱▱, and the like), it means that the disclosed formula or structure includes all possible isomers.

As used herein, the term "amino acid" may be used to refer to both amino acids that are not bonded to other amino acids and amino acid residues that are bonded to other amino acids included in proteins or peptides, and may be interpreted appropriately according to the content or context of the paragraph in which the term amino acid is used. As used herein, the term "amino acid" may be used to include both natural and unnatural amino acids. As used herein, natural amino acids refer to 20 types of amino acids that are synthesized in the human body through gene transcription and translation processes. Specifically, the natural amino acids include alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys K), methionine (Met, M), phenylalanine (Phe, F), proline (Pro, P), serine (Ser, S), threonine (Thr, T), tryptophan (Trp, W), tyrosine (Tyr, Y), and valine (Val, V). As used herein, unnatural amino acids mean amino acids that are not synthesized in the human body through gene transcription and translation processes, are synthesized through other processes that are not transcription and translation processes, or are artificially synthesized, or can be synthesized by other organisms that are not human. The unnatural amino acids may include, for example, ornithine (Orn), diaminopropionic acid (Dap), diaminobutyric acid (Dab), naphthylalanine, and the like. As described above, the term "amino acid" as used herein may be used to refer to both amino acids that are not bonded to other amino acids and amino acid residues that are bonded to other amino acids included in proteins or peptides. For example, alanine may be used to refer to alanine and/or alanine residue. For example, arginine may be used to refer to arginine and/or arginine residue. As used herein, the term "amino acid" may be used to include both L-type and D-type amino acids. In some embodiments, when there is no mention to L-type or D-type, an amino acid may be interpreted as an L-type amino acid.

As used herein, the term "amino acid residue" refers to a structure derived from amino acids included in compounds, peptides, and/or proteins (for example, antibodies, and the like), which are covalently linked to other parts of the compounds, peptides, and/or proteins. For example, when alanine, arginine, and glutamic acid are linked through an amide bond to form a peptide having an ARE sequence, the peptide comprises three amino acid residues, wherein A, R, and E may be referred as an alanine residue, an arginine residue, and a glutamic acid residue, respectively. Furthermore, as described above, in the peptide having an ARE sequence, the peptide may comprise three amino acids, and A, R, and E may also be referred to as alanine, arginine, and glutamic acid, respectively. As another example, when aspartic acid, phenylalanine, and lysine are linked through an amide bond to form a peptide having a DFK sequence, the peptide comprises three amino acid residues, wherein D, F, and K may be referred to as an aspartic acid residue, a phenylalanine residue, and a lysine residue, respectively. Furthermore, as described above, in the peptide having a DFK sequence, the peptide may comprise three amino acids, and D, F, and K may also be referred to as aspartic acid, phenylalanine, and lysine, respectively.

Unless otherwise stated, when describing the sequence of an amino acid sequence in the present specification, one-letter notation or three-letter notation of an amino acid is used, and it is described in the direction from the N-terminus to the C-terminus. For example, when expressed as RNVP, it refers to a peptide in which arginine, asparagine, valine, and proline are sequentially linked in the direction from the N-terminus to the C-terminus. As another example, when expressed as Thr-Leu-Lys, it refers to a peptide in which threonine, leucine, and lysine are sequentially linked in the direction from the N-terminus to the C-terminus. In the case of amino acids that cannot be represented by the one-letter notation, other letters are used to describe these amino acids, and will be described via additional description.

As used herein, the term "click-chemistry" refers to a chemical concept introduced by K. Barry Sharpless of the Scripps Research Institute to describe complementary chemical functional groups and chemical reactions designed such that two molecules can rapidly and stably form a covalent bond. The click chemistry of the present specification does not mean a specific reaction but means a concept for a fast and stable reaction. In one embodiment, several conditions should be satisfied in order to form bonds between molecules by click-chemistry. The above conditions include high yield rate, excellent selectivity to reactive sites, operation in a modular manner to combine molecules organically, and proceeding in a thermodynamically stabilized direction to create a product fast and accurately. The click-chemistry of the present specification includes the reaction of mutually reactive pairs in click-chemistry functional groups (for example, including terminal alkyne, azide, strained alkyne, diene (for example, Diels-Alder diene), dienophile (for example, Diels-Alder dienophile), trans-cyclooctene, alkene, thiol, tetrazine, triazine, dibenzocyclooctyne (DBCO) and bicyclononyne (including bicyclo[6.1.0]non-4-yne)). Examples of click chemical reactions include Huisgen 1,3-dipolar cycloaddition (see Tornoe et al. Journal of Organic Chemistry (2002) 67: 3075-3064, and the like); Diels-Alder reaction; inverse electron demand Diels-Alder reaction; nucleophilic addition to small strained rings like epoxide and aziridine; nucleophilic addition to an activated carbonyl group; Staudinger ligation; and an addition reaction to a carbon-carbon double bond or triple bond.

The term "bio-orthogonal functional group" is used to refer to a chemically reactive group that is biologically inert. That is, the term "bio-orthogonal functional group" is used to refer to a chemical functional group that participates in bio-orthogonal chemistry or bio-orthogonal reactions to perform bio-orthogonal reactions. The term "bio-orthogonal functional group" may also be referred to as a bio-orthogonal chemical functional group or a bio-orthogonal chemical group. The bio-orthogonal functional group refers to a group that does not react with endogenous molecules or functional groups in living cells or organisms. These bio-orthogonal functional groups are designed to react with specific groups in complex biological systems without interfering with normal cellular processes. The term "bio-orthogonal chemistry" was first proposed by Carolyn R. Bertozzi in 2003, and the bio-orthogonal chemistry is still widely used in the fields of organic chemistry and conjugation. The term "bio-orthogonal" refers that chemical reactions carried out through bio-orthogonal functional groups can be carried out without interfering with natural biological processes. One of the main characteristics of the bio-orthogonal functional group is that the bio-orthogonal function group reacts specifically and efficiently with the corresponding reactive group in a biological environment. Bio-orthogonal functional groups, bio-orthogonal chemistry, or bio-orthogonal reactions are described in detail in the literatures [Sletten, Ellen M., and Carolyn R. Bertozzi. "Bioorthogonal chemistry: fishing for selectivity in a sea of functionality." Angewandte Chemie International Edition 48.38 (2009): 6974-6998; Mbua, Ngalle Eric, et al. "Strain-promoted alkyne-azide cycloadditions (SPAAC) reveal new features of glycoconjugate biosynthesis." ChemBioChem 12.12 (2011): 1912-1921; Bird, Robert E., et al. "Bioorthogonal chemistry and its applications." Bioconjugate Chemistry 32.12 (2021): 2457-2479; Devaraj, Neal K. "The future of bioorthogonal chemistry." ACS central science 4.8 (2018): 952-959; and Scinto, Samuel L., et al. "Bioorthogonal chemistry." Nature Reviews Methods Primers 1.1 (2021): 30.], the whole contents of which are incorporated by reference in the present specification. Bio-orthogonal chemistry may overlap considerably with the broader field of click-chemistry. In specific embodiments, the bio-orthogonal functional group may be used to refer to a chemical group that is not reactive with an antibody, but is capable of bio-orthogonal reactions. Representative types of the bio-orthogonal reaction (or bio-orthogonal chemistry) include Staudinger ligation, copper-catalyzed azide-alkyne cycloaddition (CuAAC), copper-free azide alkyne cycloaddition including strain-promoted azide-alkyne cycloaddition (SPAAC), tetrazine ligation, tetrazole ligation, oxime ligation, isocyanide click reaction, and the like, but are not particularly limited thereto. The bio-orthogonal functional group includes, for example, azide, terminal alkyne, cyclic alkyne (for example, cyclooctyne), tetrazine, norbornene, cycloalkene (for example, cyclooctene), tetrazole, oxime, or isocyanide groups, but is not particularly limited thereto. For example, in copper-free azide alkyne cycloaddition (strain-promoted azide-alkyne cycloaddition; SPAAC), an azide group and a cyclooctyne group undergo a bio-orthogonal reaction. The cyclooctyne group participating in SPAAC may be a monocyclic cyclooctyne or a polycyclic cyclooctyne comprising a fused polycyclic. Specific examples of the cyclooctyne group participating in SPAAC include bicyclononyne (BCN), dibenzocyclooctyne (DBCO), aza-dibenzocyclooctynes (DIBAC), dibenzocyclooctynol (DIBO), difluorinated cyclooctynes (DIFO), biarylazacyclooctynone (BARAC), dimethoxyazacyclooctyne (DIMAC), difluorobenzocyclooctyne (DIFBO), and the like, but are not particularly limited thereto.

As used herein, the term antibody is used to refer to an immunoglobulin molecule or a fragment thereof. Immunoglobulins are typically well known and have the ability to specifically bind to one or more antigens. As used herein, the term antibody is also used to encompass a fragment thereof, so it does not matter if it does not have the ability to bind to a specific antigen, as in the case of an Fc fragments. Unless used with specific limitations in regard to antibodies, the term antibody may be interpreted without particular limitation as including all of monospecific antibodies, bispecific antibodies, trispecific antibodies, monoclonal antibodies, human antibodies, humanized antibodies, recombinant antibodies, chimeric antibodies, and the like. For example, an antibody may comprise two heavy chains and two light chains. For example, in this case, it is known that the antibody may have a structure in which two heavy chains are linked through one or more bridges (for example, a disulfide bond), one heavy chain and one light chain are linked through one or more bridges, and another heavy chain and another light chain are linked through one or more bridges. Antibodies may be divided into a Fc region (or Fc domain) and a Fab region, with the Fab region comprising a site capable of binding to an antigen, and the Fc region comprising part of a constant region of a heavy chain. As used herein, the term "antibody" may be used to comprise both conjugated antibody and unconjugated antibody (for example, free antibody).

In the present specification, an active moiety is used to refer to a moiety having one or more functions or activities. The active moiety may include, for example, a drug (for example, toxin), an imaging moiety (for example, a fluorescent moiety, a luminescent moiety comprising a luminescent material such as luciferin, and the like), a radioactive moiety, a protein having a specific function, an affinity substance (for example, biotin, streptavidin, an aptamer, and the like), a stabilizing material, a vitamin, a nucleic acid (DNA or RNA), or a polyethylene glycol (PEG) moiety, but is not limited thereto. In this case, one or more active moieties may be each independently selected. In some embodiments of the present application, the active moiety may be included in functional groups. Furthermore, in some embodiments of the present application, the active moiety may be included in the payload.

As used herein, the term "radioactive moiety" refers to a moiety comprising a ligand for radioisotope designed to bind to a radioisotope and/or a moiety comprising a radioisotope (for example, a radiometal nuclide). A ligand for radioisotope may be referred to as, for example, a chelator. The chelator may be selected from among, for example, tetraxetan (DOTA), 2,2',2''-(1,4,7-triazacyclononane-1,4,7-triyl)triacetic acid (NOTA), diethylenetriaminepentaacetic acid (DTPA), and ethylenediaminetetraacetic acid (EDTA), but is not limited thereto. Radiolabeling is useful in diagnostic imaging, radioimmunotherapy (RIT), radiotherapy, and the like. The radioactive moiety may include, for example, $^{18}F$, $^{11}C$, $^{76}Cu$, $^{90}Y$, $^{125}I$, $^{123}I$, $^{124}I$, $^{131}I$, $^{177}Lu$, $^{186}Re$, $^{188}Re$, $^{211}At$, $^{213}Bi$, $^{225}Ac$ or $^{99m}Tc$, but is not limited thereto.

As used herein, the term "fluorescent moiety" refers to a moiety including a dye, a protein, or a dye reagent for use in fluorescent applications. A molecule which can be used as a dye and a dye reagent is widely known in the art. The fluorescent moiety may include, for example, green fluorescent protein (GFP), Cy3, Cy5, Texas Red, FITC, Rhodamine, or DAPI, but is not limited thereto.

As used herein, the term "drug" or "drug moiety" is used to mean a molecule or a portion of a molecule, which has therapeutic efficacy against any disease. Drugs according to the present application include those known to those of ordinary skill in the art to be effective against any disease. Furthermore, as used herein, the term "drug" may be used to comprise both conjugated drug and unconjugated drug (for example, free drug). The drug may be any one selected from, for example, auristatin, eribulin, tubulysin, geldanamycin (Kerr et al., 1997, Bioconjugate Chem. 8(6):781-784), maytansinoid (EP 1391213, ACR 2008, 41, 98-107), calicheamicin (U.S. Patent Publication No. 2009/0105461, Cancer Res. 1993, 53, 3336-3342), Mertansine, daunomycin, doxorubicin, methotrexate, vindesine, SG2285 (Cancer Res. 2010, 70(17), 6849-6858), dolastatin, dolastatin analogs auristatin (U.S. Pat. No. 5,635,483), cryptophycin, camptothecin, camptothecin analogs (for example, SN38, FL118, or exatecan), rhizoxin derivatives, CC 1065 analogs or derivatives, duocarmycin, enediyne antibiotics, esperamicin, epothilone, pyrrolobenzodiazepine (PBD) derivatives, α-amanitin, toxoid, toll-like receptor 5 (TLR5) agonist toll-like receptor 7 (TLR7) agonist, toll-like receptor 8 (TLR8) agonist, 1,4,7-triazacyclononane-1,4,7-triacetic acid (NOTA), and 1,4,7, 10-tetraazacyclododecane-1,4,7,10-tetraacetic acid (DOTA), or an analog thereof, but is not particularly limited thereto.

In the present application, when reference is made to the numbering of amino acid residues in the Fc domain (or Fc region) of an antibody, the numbering of amino acid residues follows the EU numbering system unless otherwise stated. The EU numbering system has been widely used as a sequencing system for the Fc region since the sequence of IgG was studied, as described in Edelman G M, et al., The covalent structure of an entire gammaG immunoglobulin molecule, Proc Natl Acad Sci USA., 1969 May; 63(1):78-85. For example, in lysine 246 in the Fc region, number 246 is the number assigned according to the EU numbering system. As another example, in lysine 248 in the Fc region, number 248 is the number assigned according to the EU numbering system.

As used herein, the term "linked" or "link" means that two or more elements that are present within a conceptualizable structure are linked directly or indirectly (for example, by other elements such as a linker), and is not intended to mean that other additional elements cannot be present between the two or more elements. For example, a description such as "element B linked to element A" is intended to include both a case where one or more other elements are included between element A and element B (that is, when element A is linked to element B through one or more other elements) and a case where one or more other elements are not present between element A and element B (that is, when element A and element B are directly linked), and is not interpreted in a limited manner.

As used herein, the term "sequence identity" is a term used in connection with the degree of similarity between two or more sequences. For example, the term "sequence identity" is used with a term that refers to a reference sequence and a term that represent a proportion (for example, a percentage). For example, the term "sequence identity" may be used to describe a sequence that is similar or substantially identical to a reference amino acid sequence. When a description such as "a sequence that has 90% or more sequence identity with sequence A" is used, herein, the reference sequence is sequence A. For example, the percentage of sequence identity may be calculated by aligning a reference sequence and a sequence to be measured for the percentage of sequence identity. The method of calculating and/or determining the percentage of sequence identity is not particularly limited, and may be calculated and/or determined through any reasonable method or algorithm which can be used by a person with ordinary skill in the art.

As used herein, "unit" is used in some embodiments to separate conjugated substances from free substances. The term "unit" used in some embodiments will be described by exemplifying an antibody unit and a free antibody. The free antibody refers to an antibody molecule that is not covalently bound to other molecules or groups. The antibody unit refers to a group derived from a free antibody that is covalently linked to other molecules or groups. For example, when a free antibody and a functional substance are combined through the reaction of the reactive group of the functional group with the primary amine group of the lysine residue of the free antibody, an antibody-functional group conjugate may be prepared. At this time, a portion derived from the free antibody may be referred to as an antibody unit. In an antibody-functional group conjugate, the antibody unit may be understood to be structurally the same as the free antibody from which the antibody unit originates, except for the portion which is conjugated with a non-antibody portion of the antibody-functional group conjugate. For example, when the primary amine group of the lysine residue that participates in the reaction in a free antibody is separately illustrated, the structure of the free antibody may be expressed as "Ab-NH$_2$". In an antibody unit, when a junction between the antibody unit and a part other than the antibody unit is separately illustrated, the structure of the antibody unit may be expressed as

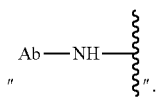

Thus, it can be understood that the antibody unit and the free antibody are structurally identical, except for the primary amine group of the lysine residue used in the reaction. Thus, in some embodiments, the antibody unit and the free antibody may not be separately distinguished and may be referred to as "antibody," and these terms may be interpreted appropriately according to the context. In some embodiments, when a description such as "the antibody unit is derived from an antibody" is used, it can be understood that the antibody unit and the antibody have the relationship as described above. In some embodiments, when a description such as "the Fc binding unit is derived from a Fc binding substance" is used, it can be understood that the "Fc binding unit and the Fc binding substance" have a similar relationship as described above. That is, it can be understood that the Fc binding unit has the same structure as the Fc binding substance from which it originates, except for a junction where the Fc binding unit is joined to a portion other than the Fc binding unit. As with the antibody unit, in some embodiments, a Fc binding unit may be referred to as a Fc binding substance from which it originates, and these terms may be interpreted appropriately according to the context.

In the present specification, when a description such as "A comprises B" is used, the description of "A comprises B" should be construed as not excluding that A further comprises additional components other than B. That is, "A comprises B" is intended to encompass cases such as the case where additional elements besides B are present in A (for example, the case where B and C are present in A), the case where A is B, and the case where A consists of B. Meanwhile, since "A comprises B" encompasses all of the above cases, it may be used again while being modified into "A is B," "A consists of B," or "A is represented by B." The fact that the description "A comprises B" may be used again while being modified into "A is B" means that the description "A is B" may be newly produced from the description "A comprises B" already present in the specification, and does not mean that the description "A comprises B" should be limitedly interpreted as "A is B." When a description such as "A comprises B" is used, it will be interpreted that additional elements may be further present in A in addition to B. That is, in the present specification, when a description such as "A comprises B" is used, it should be construed as encompassing both the case where A is B and the case where additional elements are further present in A in addition to B.

In the present specification, when a description such as "A has B" is used, the description of "A has B" should be construed as not excluding that A further has additional components other than B. That is, "A has B" is intended to encompass cases such as the case where additional elements besides B are present in A (for example, the case where B and C are present in A), the case where A is B, and the case where A consists of B. Meanwhile, since "A has B" encompasses all of the above cases, it may be used again while being modified into "A is B," "A consists of B," or "A is represented by B." The fact that the description "A has B" may be used again while being modified into "A is B" means that description "A is B" may be newly produced from the description "A has B" already present in the specification, and does not mean that the description "A has B" should be limitedly interpreted "A is B." When a description such as "A has B" is used, it will be interpreted that additional elements may be further present in A in addition to B. That is, in the present specification, when a description such as "A has B" is used, it should be construed as encompassing both the case where A is B and the case where additional elements are further present in A in addition to B.

When compounds (for example, small compounds, peptides, antibodies, conjugates, and the like) are disclosed in the present specification, it should be understood that their salt forms are also disclosed. Examples of ions that form salts of compounds include ammonium, calcium, sodium, potassium, acetate ($CH_3COO^-$), carbonate ($CO_3^{2-}$), chloride ($Cl^-$), citrate, cyanide, fluoride ($F^-$), nitrate ($NO_3^-$), nitrite ($NO_2^-$), phosphate ($PO_3^-$), sulfate ($SO_4^{2-}$), and the like, but are not particularly limited thereto. Salt-forming ions typically used in the art may be used for the formation of salts of the compounds if needed. The salt may be, for example, a pharmaceutically acceptable salt, wherein the pharmaceutically acceptable salt refers to a salt that has the efficacy of a parent agent and is not biologically undesirable (for example, less toxic or toxic-free). Suitable salts include, for example, salts which may be formed by mixing a solution of a parent agent with a solution of a pharmaceutically acceptable acid such as hydrochloric acid, phosphoric acid, sulfuric acid, or acetic acid. For example, when a compound involves acidic residues, pharmaceutically acceptable salts may comprise salts formed with suitable organic ligands such as alkali metal ions (sodium or potassium), alkaline earth metal ions (calcium or magnesium), and ammonium ions.

Hereinafter, the structure of an antibody will be specifically explained based on contents generally known in the art for better understanding, and the scope of the present application is not limited by the following description.

The structure of an antibody is divided into a heavy chain region and a light chain region, depending on the type of chain. The structure of an antibody is divided into a fragment antigen-binding region (Fab region) and a fragment crystallizable region (Fc region) according to its antigen-binding function. The structure of an antibody is divided into a variable region and a constant region according to the variability of the amino acid sequence. Other structures of an antibody include a hinge portion and a tail portion. The heavy chain region and the light chain region may be explained as functionally being broadly divided into a fragment antigen-binding region (Fab region) and a fragment crystallizable region (Fc region). The Fab region is a portion that comprises a portion which binds to an antigen (antigen-binding portion). The Fc region is a portion capable of binding to a fc receptor. The heavy chain region may be explained as having both a Fab region and a Fc region, and the light chain region may be explained as having a Fab region.

The Fab region of the heavy chain region comprises a heavy chain variable region (VH) and a heavy chain constant region 1 (CH1). For example, in IgG1, the Fc region is known to comprise a heavy chain constant region 2 ($CH_2$) and a heavy chain constant region 3 (CH3). In this case, the entire heavy chain constant region of the antibody may be referred to as CH. For example, the entire region combining CH1, CH2, and CH3 of IgG1 may be expressed as CH.

The Fab region of the light chain region comprises a light chain variable region (VL) and a light chain constant region (CL). The light chain region may be explained as having no Fc region.

The above-described VH, CH1, CH2, CH3, VL, CL, and the like may each be referred to as an immunoglobulin domain.

The immunoglobulin domains included in the heavy chain region are known to be located in the order of VH, CH1, CH2, and CH3 or in the order of VH, CH1, CH2, CH3, and CH4 in the direction from the N-terminus to the C-terminus. The immunoglobulin domain included in the light chain region is known to be located in the order of VL and CL in the direction from the N-terminus to the C-terminus. In general, it is known that the heavy chain region and the light chain region are linked by a disulfide bond, and the Fab region and Fc region are linked by a hinge portion. Specifically, the C-terminal portion of CH1 and the N-terminal portion of CH2 in the heavy chain region are known to be linked by a hinge portion.

The variable regions (VH and VL) are regions that comprise an antigen-binding portion, and even among the variable regions, there is a portion with the greatest variability (hypervariable region), and the corresponding part is called a complementarity-determining region (CDR). The VH comprises three CDRs, and the three CDRs included in the VH are generally referred to as CDRH1, CDRH2, or CDRH3, respectively. The CDRs in the VH may be understood to be located in the order of CDRH1, CDRH2, and CDRH3 in the direction from the N-terminus to the C-terminus. The VL comprises three CDRs, and the three CDRs included in the VL are generally referred to as CDRL1, CDRL2, or CDRL3, respectively. The CDRs in the VH may be understood to be located in the order of CDRL1, CDRL2, and CDRL3 in the direction from the N-terminus to the C-terminus.

The constant region of an antibody is a region separate from the antigen-binding portion, and it is known that the constant region may interact with cells or molecules of the immune system. For example, the constant region may interact with (may bind to or may be linked to) the cell membrane of immune cells (for example, lymphocytes, neutrophils, dendritic cells, and/or macrophages, and the like). Specifically, the hinge region and/or CH2 portion of the constant region may bind to receptors (FcεRIII, and the like) on the cell membrane of the immune cells. As another embodiment, the constant region may bind to FcRn.

The constant region of the heavy chain region mentioned above (hereinafter referred to as "heavy chain constant region") is roughly divided into five types (classes or isotypes): alpha (α), gamma (γ), delta (δ), epsilon (ε) and mu (μ). In this case, the types of heavy chain constant regions mentioned above are not determined individually for CH1, $CH_2$, $CH_3$, and CH4, but are determined in consideration of all heavy chain constant regions (CH1, CH2, and CH3; or CH1, CH2, CH3, and CH4) included in the antibody.

There are two types of constant regions of the light chain region (hereinafter referred to as "light chain constant regions"), and the two types are lambda (λ) and kappa (κ).

It is known that antibody types may be roughly divided into five types (classes or isotypes). The five types are determined by the type of heavy chain constant region.

The five types of antibodies described above are immunoglobulin M (IgM), immunoglobulin D (IgD), immunoglobulin G (IgG), immunoglobulin A (IgA), immunoglobulin A (IgA), and immunoglobulin E (IgE). When the type of heavy chain constant region of an antibody is classified as alpha, the type of antibody may be recognized as IgA. When the type of heavy chain constant region of an antibody is classified as gamma, the type of antibody may be recognized as IgG. When the type of heavy chain constant region of an antibody is classified as delta, the type of antibody may be recognized as IgD. When the type of heavy chain constant region of an antibody is classified as epsilon, the type of antibody may be recognized as IgE. When the type of heavy chain constant region of an antibody is classified as mu, the type of antibody may be recognized as IgM. For example, each heavy chain of IgG is known to comprise four immunoglobulin domains (VH, CH1, CH2, and CH3).

It is known that among the five antibody types, IgG and IgA may be classified into more detailed subclasses. For example, when the case where the antibody is a human antibody is described, when the type of heavy chain constant region of the antibody is gamma 1 (γ1), the type of antibody is IgG1; when the type of heavy chain constant region of the antibody is gamma 2 (γ2), the type of antibody is IgG2; when the type of heavy chain constant region of the antibody is gamma 3 (γ3), the type of antibody is IgG3; and when the type of heavy chain constant region of the antibody is gamma 4 (γ4), the type of antibody is IgG4. When the heavy chain constant region of the human antibody is alpha 1 (α1), the type of antibody is IgA1; and when the heavy chain constant region of the human antibody is alpha 2 (α2), the type of antibody is IgA2.

Hereinafter, a compound comprising Fc binding unit, which is provided in some embodiments of the present application, will be described in detail.

Compound Comprising Fc Binding Unit

Related Art and Problems with Related Art

As described above, research has been conducted on a compound comprising Fc binding unit for transferring a substance of interest (for example, a bio-orthogonal functional group) to an antibody in a site-specific manner. The document [Korean Patent Application No. 10-2020-0091826 (Application No. 10-2020-0009162)] discloses a compound having a structure of the following formula 1-1 as a compound comprising Fc binding unit.

[formula 1-1]

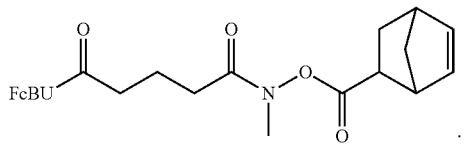

In the compound of formula 1-1, the Fc binding unit (FcBU) induces a compound comprising Fc binding unit near lysine residues 246 and 248 located in the Fc region of an antibody, and a carbonyl group directly linked to a norbornene group which is a bio-orthogonal functional group, reacts with the amino group of the lysine residue 246 (K246) or lysine residue 248 (K248) of the antibody. Through the reaction, the Fc binding unit is released and the norbornene group is transferred to lysine 246 or lysine 248 of the Fc region of the antibody. In the compound of formula 1-1, the

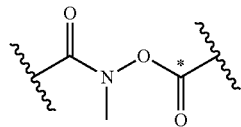 [SMILES: *C(=O)ON(C)C(*)=O]

structure (in this case, in the structure, * indicates a carbonyl group that reacts with the amino group of the lysine residue of the antibody) enables the compound comprising Fc binding unit to react with the antibody under physiological conditions (for example, conditions with pH 7.4), and enables the norbornene group to be transferred to a desired position (for example, K246 or K248). Meanwhile, although NHS ester is used as a group that reacts with an antibody in some cases, when a N-hydroxysuccinimide ester (NHS ester) group is used, the reaction conditions need to be adjusted to acidic conditions. When acidic conditions are used as the reaction conditions, additional substances or additional processes are required to adjust the pH, and furthermore, acidic conditions may affect the structure of the antibody, so that the reaction under acidic conditions has disadvantages.

Meanwhile, the inventors of the present application confirmed that there is a problem with the reaction efficiency of the compound of formula 1-1 (that is, the reaction efficiency with an antibody) disclosed in the conventional document [Korean Patent Application No. 10-2020-0091826 (Application No. 10-2020-0009162)].

Development of Compound Comprising Novel Fc Binding Unit

As described above, the inventors of the present application confirmed that there is a problem with the reaction efficiency of the compound of formula 1-1 disclosed in the conventional document. The results of the study on the reaction between the compound of formula 1-1 and the antibody are disclosed in Example 02. As disclosed in Example 02, the compound of formula 1-1 showed low reaction efficiency in the reaction with the antibody.

In order to improve the low reaction efficiency of the compound of formula 1-1, first, the inventors of the present application intended to develop a compound of formula 1-2, which is a compound in which a norbornene group is changed to an azide group from chemical formula 1-1. However, it was confirmed that the compound of formula 1-2 is extremely unstable. Accordingly, the inventors of the present application determined that the compound of formula 1-2 cannot be used to transfer a substance of interest to an antibody.

[formula 1-2]

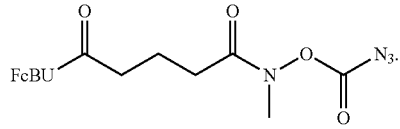

In order to improve the low reaction efficiency of the compound of formula 1-1, second, the inventors of the present application designed a novel compound comprising Fc binding unit, in which a peptide linker (Val-Gly or Ala-Gly) is added between the azide group and the carbonyl group. The newly designed compounds with the addition of the peptide linker have the structures of formulae 1-3 and 1-4. The inventors of the present application prepared compounds having the structures of formulae 1-3 and 1-4, and conducted conjugation experiments on these compounds and antibodies. However, as described in Examples 03 and 04, compounds comprising a peptide linker between the azide group and the carbonyl group react irregularly with antibodies. Therefore, the inventors of the present application determined that it is also difficult for the compounds of formulae 1-3 and 1-4 to be used for transferring a substance of interest to antibodies. The following formula 1-3 is a compound into which a Val-Gly peptide linker is introduced. The following formula 1-4 is a compound into which an Ala-Gly peptide linker is introduced.

[formula 1-3]

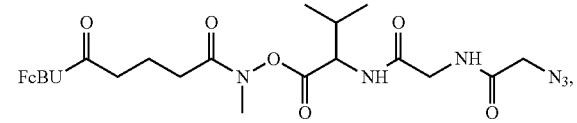

[formula 1-4]

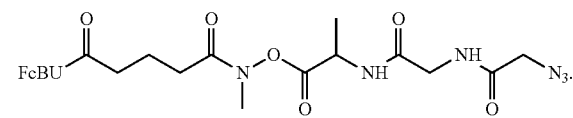

As described above, the inventors of the present application have attempted to make various structural changes in order to improve the low reaction efficiency of the compound comprising Fc binding unit in the related art, but could not easily find a compound containing Fc binding unit suitable for the reaction. Furthermore, since the positions at which structural changes can occur are diverse and the structures resulting from structural changes are also diverse, it was difficult to develop a new compound comprising Fc binding unit with improved reaction efficiency. However, after a lot of effort, the inventors of the present application finally succeeded in developing a new compound comprising Fc binding unit with improved reaction efficiency.

Hereinafter, a compound comprising Fc binding unit, which is provided by the present application, will be described in detail.

Overview of Compound Comprising Fc Binding Unit of Present Application

Some embodiments of the present application provide a compound comprising Fc binding unit. The compound comprising Fc binding unit may be referred to as a compound for transferring a group of interest to an antibody. The compound comprising Fc binding unit may be referred to as a compound for transferring a group of interest to an antibody in a site-specific manner.

The compound comprising Fc binding unit may be used to transfer a group of interest (for example, a bio-orthogonal functional group) to an antibody.

The compound comprising Fc binding unit may be used to transfer a group of interest (for example, a bio-orthogonal functional group) to the target region of an antibody.

The compound comprising Fc binding unit may be used to transfer a group of interest (for example, a bio-orthogonal functional group) to a site of interest of an antibody (for example, K246 or K248 of the Fc region of an antibody).

Hereinafter, the structure of a compound comprising Fc binding unit, which is provided according to some embodiments of the present application, will be described.

The compound comprising Fc binding unit according to some embodiments of the present application may have the structure of formula 2.

Some embodiments of the present application provide a compound having the structure of formula 2:

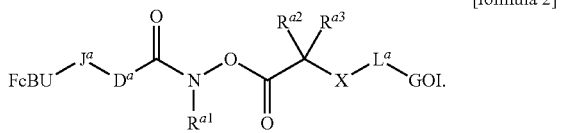

[formula 2]

In formula 2, $D^a$ is a spacer A.
In formula 2, $L^a$ is a linker A.
In formula 2, X is C, O, or N (that is, —X— is —CH$_2$—, —O—, or —NH—).
In formula 2, GOI is a group of interest.
In formula 2, FcBU is a Fc binding unit.
In formula 2, $R^{a1}$ is H or $C_{1-6}$ alkyl.
In formula 2, $R^{a2}$ is H or $C_{1-6}$ alkyl.
In formula 2, $R^{a3}$ is H or $C_{1-6}$ alkyl.
In formula 2, $J^a$ is —C(=O)—, —S—, —NH—, or —C(=NH)—.

Hereinafter, each element of the compound of formula 2 will be described in detail.

Spacer A ($D''a$)

In formula 2, $D^a$ is a spacer A. In the table of contents "Spacer A ($D''a$)", the "a of $D''a$" indicates the superscript a. That is, $D''a$ will be understood as $D^a$.

In some embodiments, the spacer A may be a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In specific embodiments, the spacer A may be unsubstituted $C_{1-20}$ alkylene, unsubstituted $C_{1-20}$ heteroalkylene, unsubstituted $C_{2-20}$ alkenylene, unsubstituted $C_{2-20}$ heteroalkenylene, unsubstituted $C_{2-20}$ alkynylene, or unsubstituted $C_{2-20}$ heteroalkynylene. Herein, each of heteroalkylene, heteroalkenylene, and heteroalkynylene independently comprises one or more heteroatoms, wherein each of heteroatoms may be independently selected from N, O, and S.

In specific embodiments, the spacer A may be unsubstituted $C_{1-10}$ alkylene, unsubstituted $C_{1-10}$ heteroalkylene, unsubstituted $C_{2-10}$ alkenylene, unsubstituted $C_{2-10}$ heteroalkenylene, unsubstituted $C_{2-10}$ alkynylene, or unsubstituted $C_{2-10}$ heteroalkynylene. Herein, each of the heteroalkylene, heteroalkenylene, and heteroalkynylene independently comprises one or more heteroatoms, wherein each of heteroatoms may be independently selected from N, O, and S.

In specific embodiments, the spacer A may be unsubstituted $C_{1-6}$ alkylene, or unsubstituted $C_{1-6}$ heteroalkylene. Herein, heteroalkylene comprises one or more heteroatoms, wherein each of heteroatoms may be independently selected from N, O, or S. In specific embodiments, each of the heteroatoms may be O.

In specific embodiments, the spacer A may be unsubstituted $C_3$ alkylene, or unsubstituted $C_3$ heteroalkylene. Herein, heteroalkylene comprises one or more heteroatoms, wherein each of heteroatoms may be independently selected from N, O, or S. In specific embodiments, each of heteroatoms may be O.

In specific embodiments, the spacer A may be unsubstituted $C_{1-6}$ alkylene.

In specific embodiments, the spacer A may be unsubstituted $C_3$ alkylene.

In some embodiments, the spacer may be designed to adjust the distance between groups in a molecule. For example, the spacer A may be designed to adjust the distance between two adjacent carbonyl groups. For example, the length of the spacer A may be 0 to 20 based on the number of atoms in the main chain (that is, the number of atoms located in the main chain) (when the number of atoms in the main chain is 0, the spacer A is bond). For example, the spacer A may comprise a ring group in the main chain, and in this case, the number of atoms in the main chain may be counted based on the two atoms which form a bond with other non-ring parts on the ring for convenience, and at this time, the number may be counted in a direction that achieves the lowest number. For example, when the ring of

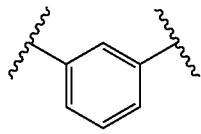 [SMILES: *c1cccc(*)c1]

is present in the main chain of the spacer A, the number of atoms in the main chain counted by the ring is 3. For example, when the ring of

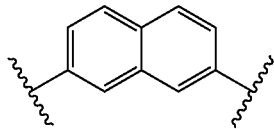 [SMILES: *c1ccc2ccc(*)cc2c1]

is present in the main chain of the spacer A, the number of atoms in the main chain counted by the ring is 5.

Linker A (L"a)

In formula 2, $L^a$ is a linker A.

In some embodiments, the length of the linker A may be 0 to 100 based on the number of atoms in the main chain. For example, the linker A may comprise a ring group in the main chain.

In some embodiments, the linker A may be a bond, substituted or unsubstituted $C_{1-100}$ alkylene, substituted or unsubstituted $C_{1-100}$ heteroalkylene, substituted or unsubstituted $C_{2-100}$ alkenylene, substituted or unsubstituted $C_{2-100}$ heteroalkenylene, substituted or unsubstituted $C_{2-100}$ alkynylene, or substituted or unsubstituted $C_{2-100}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In specific embodiments, the linker A may be a bond, unsubstituted $C_{1-60}$ alkylene, unsubstituted $C_{1-60}$ heteroalkylene, unsubstituted $C_{2-60}$ alkenylene, unsubstituted $C_{2-60}$ heteroalkenylene, unsubstituted $C_{2-60}$ alkynylene, or unsubstituted $C_{2-60}$ heteroalkynylene. Herein, each of the heteroalkylene, the heteroalkenylene, and the heteroalkynylene independently comprises one or more heteroatoms, wherein each of the heteroatoms may be independently selected from N, O, and S.

In specific embodiments, the linker A may be a bond, unsubstituted $C_{1-30}$ alkylene, unsubstituted $C_{1-30}$ heteroalkylene, unsubstituted $C_{2-30}$ alkenylene, unsubstituted $C_{2-30}$ heteroalkenylene, unsubstituted $C_{2-30}$ alkynylene, or unsubstituted $C_{2-30}$ heteroalkynylene. Herein, each of the heteroalkylene, the heteroalkenylene, and the heteroalkynylene independently comprises one or more heteroatoms, wherein each of the heteroatoms may be independently selected from N, O, and S. In specific embodiments, each of the heteroatoms may be O.

In specific embodiments, the linker A may be a bond, unsubstituted $C_{1-30}$ alkylene, or unsubstituted $C_{1-30}$ heteroalkylene. At this time, the heteroalkylene comprises one or more heteroatoms, wherein each of the heteroatoms may be independently selected from N, O, or S. In specific embodiments, each of the heteroatoms may be O.

In specific embodiments, the linker A may be a bond, unsubstituted $C_{1-30}$ alkylene, or unsubstituted $C_{1-30}$ heteroalkylene. Herein, the heteroalkylene may comprise one or more heteroatoms, wherein each of the heteroatoms may be independently selected from N, O, and S. In specific embodiments, each of the heteroatoms may be O. At this time, when the linker A is unsubstituted $C_{1-30}$ heteroalkylene, the linker A may be unsubstituted $C_{1-30}$ heteroalkylene comprising 0 to 10 of ethyleneglycol units.

The ethyleneglycol unit may be represented by -[EG]-, wherein -[EG]- is —[CH$_2$OCH$_2$]—, —[OCH$_2$CH$_2$]— or —[CH$_2$CH$_2$O]—.

In specific embodiments, the linker A may be a bond, unsubstituted $C_{1-25}$ alkylene, or unsubstituted $C_{1-25}$ heteroalkylene. Herein, the heteroalkylene may comprise one or more heteroatoms, wherein each of the heteroatoms may be independently selected from N, O, and S. In specific embodiments, each of the heteroatoms may be O. At this time, when the linker A is unsubstituted $C_{1-25}$ heteroalkylene, the linker A may be unsubstituted $C_{1-25}$ heteroalkylene comprising 0 to 8 of ethyleneglycol units.

In specific embodiments, the linker A may be a bond, unsubstituted $C_{1-20}$ alkylene, or unsubstituted $C_{1-20}$ heteroalkylene. Herein, the heteroalkylene may comprise one or more heteroatoms, wherein each of the heteroatoms may be independently selected from N, O, and S. In specific embodiments, each of the heteroatoms may be O. At this time, when the linker A is unsubstituted $C_{1-20}$ heteroalkylene, the linker A may be unsubstituted $C_{1-20}$ heteroalkylene comprising 0 to 6 of ethyleneglycol units.

In specific embodiments, the linker A may be a bond, unsubstituted $C_{1-10}$ alkylene, or unsubstituted $C_{1-10}$ heteroalkylene. Herein, the heteroalkylene may comprise one or more heteroatoms, wherein each of the heteroatoms may be independently selected from N, O, and S. In specific embodiments, each of the heteroatoms may be O. At this time, when the linker A is unsubstituted $C_{1-10}$ heteroalkylene, the linker A may be unsubstituted $C_{1-10}$ heteroalkylene comprising 0 to 3 of ethyleneglycol units.

In specific embodiments, the linker A may be a bond, unsubstituted $C_{1-5}$ alkylene, or unsubstituted $C_{1-5}$ heteroalkylene. Herein, the heteroalkylene may comprise one or more heteroatoms, wherein each of the heteroatoms may be independently selected from N, O, and S. In specific embodiments, each of the heteroatoms may be O. At this time, when the linker A is unsubstituted $C_{1-5}$ heteroalkylene, the linker A may be unsubstituted $C_{1-5}$ heteroalkylene comprising 0 to 1 of ethyleneglycol units.

In some embodiments, the linker A may have the following structure:

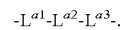

At this time, $L^{a1}$ may be linked to X of formula 2. At this time, $L^{a3}$ may be linked to the group of interest (GOI) of formula 2.

In some embodiments, $L^{a1}$ may be a bond, or substituted or unsubstituted $C_{1-10}$ alkylene, substituted or unsubstituted $C_{1-10}$ heteroalkylene, substituted or unsubstituted $C_{2-10}$ alkenylene, substituted or unsubstituted C$_{2-10}$ heteroalkenylene, substituted or unsubstituted C$_{2-10}$ alkynylene, or substituted or unsubstituted C$_{2-10}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In some embodiments, L$^{a2}$ may be a bond, or -[EG]$_x$-. Herein, x may be an integer of 1 to 20. Herein, -[EG]- is an ethyleneglycol unit, and is —[CH$_2$OCH$_2$]—, —[OCH$_2$CH$_2$]— or —[CH$_2$CH$_2$O]—. -[EG]$_x$- may be expressed as —[CH$_2$OCH$_2$]$_{1-20}$—, —[OCH$_2$CH$_2$]$_{1-20}$— or —[CH$_2$CH$_2$O]$_{1-20}$—. That is, L$^{a2}$ may be a bond or may consist of 1 to 20 of ethyleneglycol units.

In some embodiments, L$^{a3}$ may be a bond, or substituted or unsubstituted C$_{1-10}$ alkylene, substituted or unsubstituted C$_{1-10}$ heteroalkylene, substituted or unsubstituted C$_{2-10}$ alkenylene, substituted or unsubstituted C$_{2-10}$ heteroalkenylene, substituted or unsubstituted C$_{2-10}$ alkynylene, or substituted or unsubstituted C$_{2-10}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In specific embodiments, L$^{a1}$ may be a bond, or unsubstituted C$_{1-3}$ alkylene, or unsubstituted C$_{1-3}$ heteroalkylene. At this time, the heteroalkylene comprises one or more heteroatoms, wherein each of the heteroatoms may be independently selected from N, O, and S. In specific embodiments, the heteroalkylene comprises one or more heteroatoms, wherein each of the heteroatoms may be O.

In specific embodiments, L$^{a2}$ may be a bond or -[EG]$_x$-. At this time, x may be an integer of 1 to 10. In specific embodiments, x may be an integer of 1 to 7. In specific embodiments, x may be an integer of 1 to 5. In specific embodiments, x may be an integer of 1 to 3.

In specific embodiments, L$^{a3}$ may be a bond, or unsubstituted C$_{1-3}$ alkylene, or unsubstituted C$_{1-3}$ heteroalkylene. At this time, the heteroalkylene comprises one or more heteroatoms, wherein each of the heteroatoms may be independently selected from N, O, and S. In specific embodiments, the heteroalkylene comprises one or more heteroatoms, wherein each of the heteroatoms may be O.

In some embodiments, the linker A may have any one of the following structures:

wherein
se is an integer of 0 to 15,
sb is an integer of 0 to 3,
sc is an integer of 1 to 15, and
sd is an integer of 0 to 3.

In some embodiments, the linker A may have the following structure:

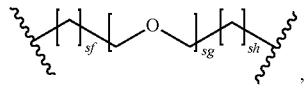

wherein
sf is an integer of 0 to 8,
sg is an integer of 0 to 15, and
sh is an integer of 0 to 8.

In specific embodiments, sf may be an integer of 0 to 6. In specific embodiments, sf may be an integer of 0 to 3. In specific embodiments, sg may be an integer of 0 to 10. In specific embodiments, sg may be an integer of 0 to 7. In specific embodiments, sh may be an integer of 0 to 6. In specific embodiments, sh may be an integer of 0 to 3.

In some embodiments, when X (X linked to L$^a$) of formula 2 is O, the sum of sf, sg, and sh may not be 0 (that is, at least any one of sf, sg, and sh is an integer of 1 or more).

In some embodiments, the linker A may have any one selected from the following structures:

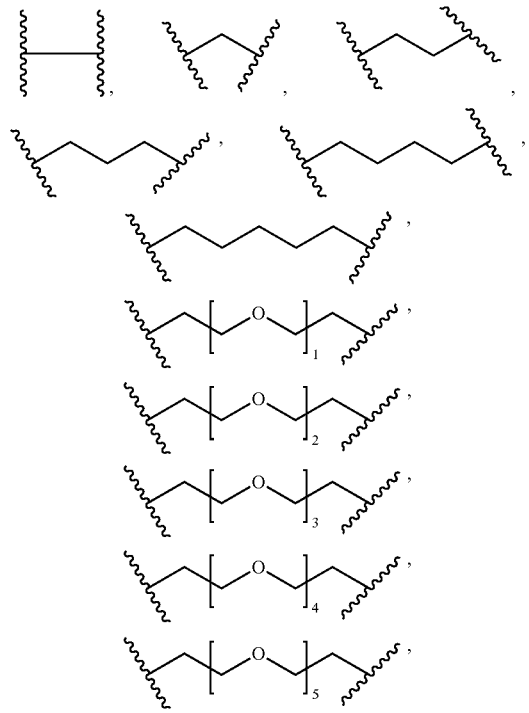

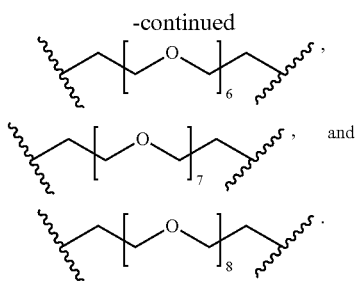

In some embodiments, it may be preferred that the linker A is designed to have little or no reactivity. That is, it may be preferred that the linker A is designed in an unsubstituted form, or comprises substituent with little or no reactivity even though the linker A comprises substituent.

As will be described below, the reaction of an antibody with a compound comprising Fc binding unit may be specifically explained as the reaction between a carbonyl group of the compound comprising Fc binding unit (a carbonyl group marked as * in the structure

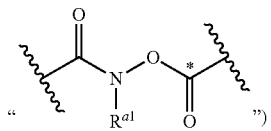

")

and an amino group of lysine residue 246 or lysine residue 248 of an antibody (that is, a primary amine group of a lysine side chain). Meanwhile, the Fc binding unit comprised in the compound comprising Fc binding unit induces the compound to the Fc region of the antibody to make the carbonyl group marked as * and the amino group of lysine residue 246 or lysine residue 248 of the antibody close to each other. That is, the guide of the Fc binding unit enables the carbonyl group marked as * to react with the amino group of lysine residue 246 or lysine residue 248 of the antibody. Therefore, rather than the structure between the Fc binding unit and the carbonyl group marked as *, the length of the linker A may be designed more freely than the other structures of the compound comprising Fc binding unit. Furthermore, the inventors of the present application conducted experiments on various lengths of linker A, and confirmed that even when the length of linker A is changed, the compound comprising Fc binding unit has excellent reaction efficiency in a reaction with the antibody (see Examples 07 and 08).

R"a1

As described above, in formula 2, $R^{a1}$ may be H or $C_{1-6}$ alkyl. In some embodiments, $R^{a1}$ may be H or $C_{1-4}$ alkyl. At this time, the $C_{1-4}$ alkyl encompasses methyl, ethyl, n-propyl, iso-propyl, n-butyl, sec-butyl, iso-butyl, and tert-butyl. In specific embodiments, $R^{a1}$ may be H or $C_{1-3}$ alkyl. In specific embodiments, $R^{a1}$ may be H or $C_{1-2}$ alkyl. In specific embodiments, $R^{a1}$ may be methyl.

R"a2 and R"a3

As described above, in formula 2, $R^{a2}$ may be H or $C_{1-6}$ alkyl. In some embodiments, $R^{a2}$ may be H or $C_{1-4}$ alkyl. At this time, the $C_{1-4}$ alkyl encompasses methyl, ethyl, n-propyl, iso-propyl, n-butyl, sec-butyl, iso-butyl, and tert-butyl. In specific embodiments, $R^{a2}$ may be H or $C_{1-3}$ alkyl. In specific embodiments, $R^{a2}$ may be H or $C_{1-2}$ alkyl. In specific embodiments, $R^{a2}$ may be H or methyl. In specific embodiments, $R^{a2}$ may be H.

As described above, in formula 2, $R^{a3}$ may be H or $C_{1-6}$ alkyl. In some embodiments, $R^{a3}$ may be H or $C_{1-4}$ alkyl. At this time, the $C_{1-4}$ alkyl encompasses methyl, ethyl, n-propyl, iso-propyl, n-butyl, sec-butyl, iso-butyl, and tert-butyl. In specific embodiments, $R^{a3}$ may be H or $C_{1-3}$ alkyl. In specific embodiments, $R^{a3}$ may be H or $C_{1-2}$ alkyl. In specific embodiments, $R^{a3}$ may be H or methyl. In specific embodiments, $R^{a3}$ may be H.

In specific embodiments, when $R^{a2}$ is not H, $R^{a3}$ may be H. In specific embodiments, when $R^{a3}$ is not H, $R^{a2}$ may be H. In specific embodiments, both $R^{a2}$ and $R^{a3}$ may be H.

X

As described above, X may be C, O, or N (that is, X is —$CH_2$—, —O—, or —NH—). In some embodiments, X may be C or O. In specific embodiments, X may be C. In specific embodiments, X may be O.

J"a

As described above, in formula 2, $J^a$ is —C(=O)—, —S—, —NH—, or —C(=NH)—. In formula 2, $J^a$ represents a junction moiety of FcBU and other portions that are not FcBU. $J^a$ may be, for example, referred to as conjugation moiety A or junction moiety A. In specific embodiments, $J^a$ may be —C(=O)—.

Group of Interest (GOI)

Overview of Group of Interest

In formula 2, GOI is a group of interest. In some embodiments, the group of interest may comprise a reactive group. The group of interest may comprise one or more reactive groups. In some embodiments, the group of interest may comprise a functional group. The group of interest may comprise one or more functional groups. The group of interest may comprise one or more reactive groups and one or more functional groups. For example, the group of interest may comprise one or two or more reactive groups. For example, the group of interest may comprise one or two or more functional groups. For example, the group of interest may comprise one reactive group and one functional group. For example, the group of interest may comprise one reactive group and two or more functional groups. For example, the group of interest may comprise two or more reactive groups and one functional group. For example, the group of interest may comprise two or more reactive groups and two or more functional groups. When the group of interest comprises a plurality of reactive groups, each of the reactive groups is independently selected. When the group of interest comprises a plurality of functional groups, each of the functional groups is independently selected. In some embodiments, the group of interest may be a reactive group or a functional group. In specific embodiments, the group of interest may be a reactive group. For example, the group of interest may be a group intended to transfer to an antibody.

In some embodiments, the sum of the atomic masses of all atoms constituting the group of interest may be 5000 dalton or less, 4000 dalton or less, 3000 dalton or less, 2000 dalton or less, 1500 dalton or less, 1000 dalton or less, 900 dalton or less, 800 dalton or less, 700 dalton or less, 600 dalton or less, 500 dalton or less, 400 dalton or less, 300 dalton or less, or 100 dalton or less.

Hereinafter, the reactive group and the functional group will be described in detail.

Reactive Group (RG)

The group of interest may comprise a reactive group.

In some embodiments, the group of interest may be a reactive group.

The reactive group may comprise a reactive moiety. The reactive moiety may refer to a moiety that is reactive with other molecules or groups in other molecules.

In some embodiments, the reactive moiety may be a click chemistry functional group or a bio-orthogonal functional group, but is not limited thereto, and may be selected from groups having reactivity.

In some embodiments, the sum of the atomic masses of all atoms constituting the reactive group may be 3000 dalton or less, 2500 dalton or less, 2000 dalton or less, 1500 dalton or less, 1000 dalton or less, 900 dalton or less, 800 dalton or less, 700 dalton or less, 600 dalton or less, 500 dalton or less, 400 dalton or less, 300 dalton or less, 200 dalton or less, or 100 dalton or less.

In some embodiments, the reactive group may have the following structure:

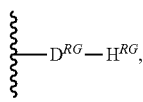

wherein $D^{RG}$ is a spacer of the reactive group (spacer RG), and $H^{RG}$ is the reactive moiety. In some embodiments, the reactive moiety may be a click chemistry functional group. In some embodiments, the reactive moiety may be a bio-orthogonal functional group.

In some embodiments, the length of the spacer of the reactive group ($D^{RG}$) may be 0 to 6 based on the number of atoms in the main chain. In some embodiments, $D^{RG}$ may be a bond, or substituted or unsubstituted 01-6 alkylene, substituted or unsubstituted $C_{1-6}$ heteroalkylene, substituted or unsubstituted $C_{2-6}$ alkenylene, substituted or unsubstituted $C_{2-6}$ heteroalkenylene, substituted or unsubstituted $C_{2-6}$ alkynylene, substituted or unsubstituted $C_{2-6}$ heteroalkynylene, substituted or unsubstituted $C_{3-8}$ cycloalkylene, substituted or unsubstituted $C_{3-8}$ heterocycloalkylene, substituted or unsubstituted $C_{3-8}$ cycloalkenylene (for example, aryl), or substituted or unsubstituted $C_{3-8}$ heterocycloalkenylene (for example, heteroaryl). Herein, the substituted indicates that one or more hydrogen atoms in a group modified by the term of substituted are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O) OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. In specific embodiments, each of the substituent may be independently selected from —$C_{1-4}$ alkyl, —C(=O)H, —C(=O)CH$_3$, —C(=O)OH, —C(=O)NH$_2$, —NH$_2$, =NH, =O, =S, —OH, —NO$_2$ and —SH. Herein, each of the heteroalkylene, the heteroalkenylene, and the heteroalkynylene independently comprises one or more heteroatoms, wherein each of the heteroatoms may be independently selected from N, O, and S.

In specific embodiments, $D^{RG}$ may be a bond, or substituted or unsubstituted $C_{1-6}$ alkylene, substituted or unsubstituted $C_{1-6}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be independently selected from O, N, and S.

In specific embodiments, $D^{RG}$ may be a bond, or substituted or unsubstituted $C_{1-3}$ alkylene, substituted or unsubstituted $C_{1-3}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be independently selected from O, N, and S.

In specific embodiments, $D^{RG}$ may be a bond.

In specific embodiments, the reactive group may have the following structure:

Reactive Moiety

The reactive moiety may refer to a moiety having reactivity with other groups. According to a reaction between the reactive moiety and a moiety that can react with the reactive moiety (wherein, the reactive moiety can be referred to as a first reactive moiety, and the moiety that can react with the first reactive moiety can be referred to as a second reactive moiety), a substance, molecule, or compound having the first reactive moiety (for example, a compound comprising Fc binding unit) may be bound with a substance, molecule, or compound having the second reactive moiety. At this time, the substance, molecule, or compound having the first reactive moiety and the substance, molecule, or compound having the second reactive moiety may be covalently conjugated.

In some embodiments, the reactive moiety may be a bio-orthogonal functional group. The bio-orthogonal functional group refers to a chemical functional group which participates in bio-orthogonal chemistry or bio-orthogonal reactions to perform bio-orthogonal reactions. The bio-orthogonal reaction may be, for example, Staudinger ligation, copper-catalyzed azide-alkyne cycloaddition (CuAAC), copper-free azide alkyne cycloaddition including strain-promoted azide-alkyne cycloaddition (SPAAC), tetrazine ligation, tetrazole ligation, oxime ligation, isocyanide click reaction, or the like, but is not limited thereto.

The bio-orthogonal functional group may be selected from, for example, an azaide group, a terminal alkyne group, a terminal alkene group, a cyclic alkyne (for example, a cyclooctyne) group, a tetrazine group, a norbornene group, a cycloalkene (for example, a cyclooctene) group, an oxime group, and an isocyanide group, and is not particularly limited thereto. The cyclooctyne may be any one selected from cyclooctyne (OCT), bicyclononyne (BCN), dibenzocyclooctyne (DBCO), aza-dibenzocyclooctynes (DIBAC), dibenzocyclooctynol (DIBO), difluorinated cyclooctynes (DIFO), biarylazacyclooctynone (BARAC), dimethoxyazacyclooctyne (DIMAC), and difluorobenzocyclooctyne (DIFBO), and is not particularly limited thereto. The cyclooctene may be any one selected from, for example, a cis-cyclooctene group and a trans-cyclooctene group. In some embodiments, the group exemplified as a bio-orthogonal functional group may have one or more substituents. Each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, =O, =S, and —SH.

In some embodiments, the bio-orthogonal functional group may have the structure of any one of the following structures:

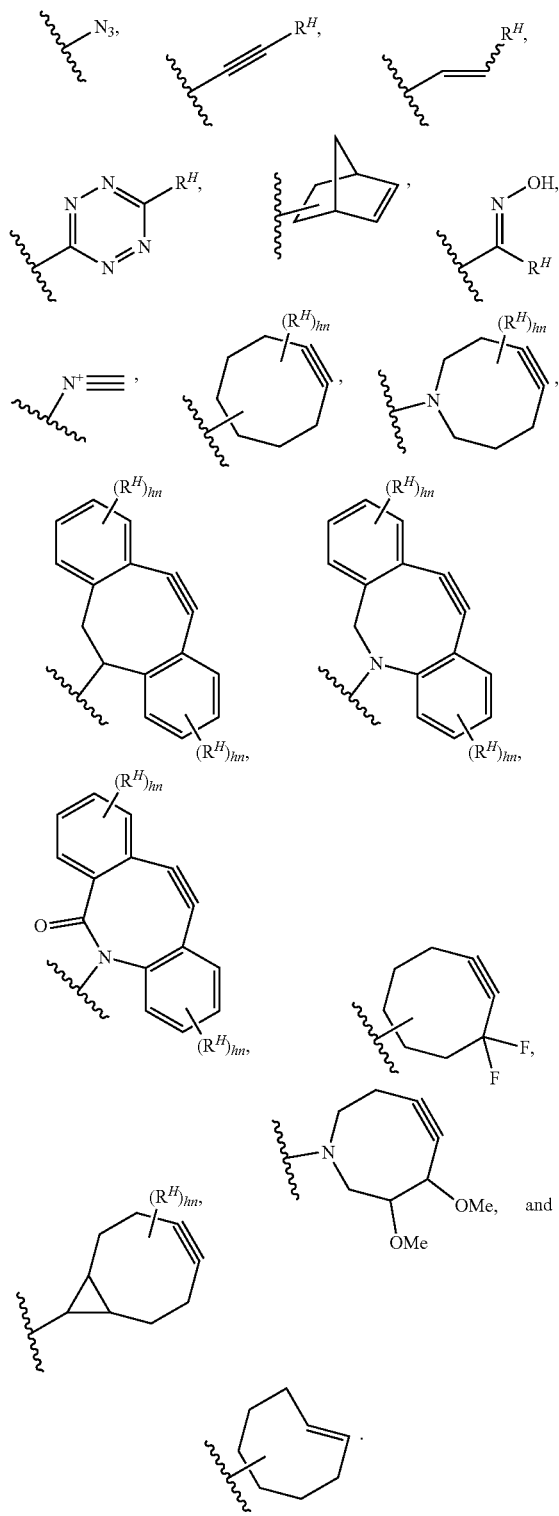

In some embodiments, hn may be an integer of 1 to 3, and each $R^H$ may be independently H, or selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein each R may be independently selected from H, halogen, C$_{1-6}$ alkyl, C$_{3-10}$ cycloalkyl, C$_{3-10}$ heterocycloalkyl, aryl, heteroaryl, —OH, —NH$_2$, =O, =S, and —SH. When $R^H$ is =O or =S, it should be understood that two $R^H$ form one =O or =S.

In some embodiments, the reactive moiety may be a click chemistry functional group. The click chemistry functional group refers to a group which participates in a click chemical reaction. The click chemical reaction may be any one selected from Huisgen 1,3-dipolar cycloaddition; the Diels-Alder reaction; an inverse-electron-demand Diels-Alder (IEDDA) reaction; nucleophilic addition to small strained rings such as epoxide and aziridine; nucleophilic addition to an activated carbonyl group; and Staudinger ligation and an addition reaction to a carbon-carbon double bond or triple bond. In some embodiments, the click chemistry functional group may be selected from a Diels-Alder diene, a Diels-Alder dienophile, an IEDDA diene, and an IEDDA dienophile.

In some embodiments, the reactive moiety may be selected from an azide group, a terminal alkyne group, a cyclic alkyne (for example, cyclooctyne) group, a tetrazine group, a norbornene group, a cycloalkene (for example, cyclooctene) group, a tetrazole group, a triazine group, an oxime group, and an isocyanide group, a halogen group, an aldehyde group, a nitrone group, a hydroxyamine group, a nitrile group, a hydrazine group, a ketone group, a bronic acid group, a cyanobenzothiazole group, an allyl group, a phosphine group, a maleimide group, a disulfide group, a thioester group, a halocarbonyl group, an isonitrile group, a sydnone group, a selene group, a thiol group, and a protected thiol group.

Functional Group (FG)

The group of interest may comprise a functional group.

In some embodiments, the group of interest may be a functional group.

The functional group may comprise an active moiety. The active moiety may be, for example, a drug, an imaging moiety, a radioactive moiety, a protein with a specific function, a peptide with a specific function, an affinity substance (for example, biotin, streptavidin, an aptamer, and the like), a stabilizing substance, a vitamin, a nucleic acid (for example, DNA or RNA) or a PEG moiety, but is not limited thereto. In some embodiments, the active moiety may be a drug moiety, an imaging moiety, a radioactive moiety, or an affinity substance.

In some embodiments, the functional group may have a molecular weight (that is, the sum of the atomic masses of all atoms constituting the functional group) of 5000 dalton or less, 4000 dalton or less, 3000 dalton or less, 2500 dalton or less, 2000 dalton or less, 1500 dalton or less, or 1000 dalton or less.

In some embodiments, the functional group may have the following structure:

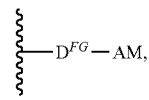

wherein $D^{FG}$ is a spacer of the functional group (spacer FG), and AM is an active moiety. In some embodiments, the active moiety may be a drug (for example, toxin). In some embodiments, the active moiety may be a radioactive moiety. In some embodiments, the active moiety may be an imaging moiety.

In some embodiments, the length of the spacer of the functional group ($D^{FG}$) may be 0 to 6 based on the number of atoms in the main chain. In some embodiments, $D^{FG}$ may be a bond, or substituted or unsubstituted $C_{1-6}$ alkylene, substituted or unsubstituted $C_{1-6}$ heteroalkylene, substituted or unsubstituted $C_{2-6}$ alkenylene, substituted or unsubstituted $C_{2-6}$ heteroalkenylene, substituted or unsubstituted $C_{2-6}$ alkynylene, substituted or unsubstituted $C_{2-6}$ heteroalkynylene, substituted or unsubstituted $C_{3-8}$ cycloalkylene, substituted or unsubstituted $C_{3-8}$ heterocycloalkylene, substituted or unsubstituted $C_{3-8}$ cycloalkenylene (for example, aryl), or substituted or unsubstituted $C_{3-8}$ heterocycloalkenylene (for example, heteroaryl). Herein, the substituted indicates that one or more hydrogen atoms in a group modified by the term of substituted are substituted with one or more substituents. That is, the substituted alkylene, and the like may comprise one or more substituents. For example, each of the substituents may be independently selected from —R, =O, =S, —NO₂, —CR₃, —NR₂, =NR, —OR, —SR, —C(=O)R, —C(=O)CR₃, —C(=O)OR, and —C(=O)NR₂, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH₂, =O, =S, and —SH. In specific embodiments, each of the substituents may be independently selected from —$C_{1-4}$ alkyl, —C(=O)H, —C(=O)CH₃, —C(=O)OH, —C(=O)NH₂, —NH₂, =O, =S, —OH, —NO₂ and —SH. Herein, each of the heteroalkylene, the heteroalkenylene, and the heteroalkynylene independently comprises one or more heteroatoms, wherein each of the heteroatoms may be independently selected from N, O, and S.

In specific embodiments, $D^{FG}$ may be a bond, or substituted or unsubstituted $C_{1-3}$ alkylene, substituted or unsubstituted $C_{1-3}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be independently selected from O, N, and S.

In specific embodiments, $D^{FG}$ may be a bond.

In specific embodiments, the functional group may have the following structure:

In some embodiments, the active moiety may be a drug (for example, a drug unit or a conjugated drug). The drug may be any one selected from, for example, auristatin (for example, monomethyl auristatin E), eribulin, tubulysin, geldanamycin (Kerr et al., 1997, Bioconjugate Chem. 8(6): 781-784), maytansinoid (EP 1391213, ACR 2008, 41, 98-107), calicheamicin (U.S. Patent Publication No. 2009/0105461, Cancer Res. 1993, 53, 3336-3342), Mertansine, daunomycin, doxorubicin, methotrexate, vindesine, SG2285 (Cancer Res. 2010, 70(17), 6849-6858), dolastatin, dolastatin analogs auristatin (U.S. Pat. No. 5,635,483), cryptophycin, camptothecin, camptothecin analogs (for example, SN38, FL118, or exatecan), rhizoxin derivatives, CC 1065 analogs or derivatives, duocarmycin, enediyne antibiotics, esperamicin, epothilone, pyrrolobenzodiazepine (PBD) derivatives, α-amanitin, toxoid, toll-like receptor 5 (TLR5) agonist toll-like receptor 7 (TLR7) agonist, toll-like receptor 8 (TLR8) agonist, 1,4,7-triazacyclononane-1,4,7-triacetic acid (NOTA), and 1,4,7,10-Tetraazacyclododecane-1,4,7,10-tetraacetic acid (DOTA), and an analog thereof, but is not particularly limited thereto.

In some embodiments, the active moiety may comprise a radioactive moiety. The radioactive moiety may be a ligand (for example, a chelator) designed to bind to a radioisotope. In some embodiments, the radioactive moiety may comprise a complex of a chelator and a radioisotope (for example, chelate).

Fc Binding Unit (FcBU)

Overview of Fc Binding Unit

As described above, in formula 2, FcBU is a Fc binding unit. The Fc binding unit may be derived from a Fc binding substance. Hereinafter, the Fc binding substance will be described in detail.

Fc Binding Substance

Overview of Fc Binding Substance

The Fc binding substance is a substance having binding properties to the Fc region of an antibody, and was used as an element of a compound for transferring a group of interest (for example, a compound comprising Fc binding unit) in order to transfer the group of interest to a target site of the antibody. A technique for introducing a substance of interest (for example, a bio-orthogonal functional group, a drug, and the like) into a specific position of an antibody using a Fc binding substance and a compound comprising the same is described in detail in the documents [EP 19818561.3, Publication No. EP 3811978; PCT Patent Application No. PCT/KR2020/003282, Publication No. WO2020/184944; and Korean Patent Application No. 10-2020-0009162, Publication No. 10-2020-0091826], all of which are hereby incorporated by reference in their entireties. If necessary, the Fc binding substance may be referred to as an affinity substance to an antibody, an IgG binding substance, a site-specific antibody interactome, a site-specific Fc interactome, and the like, but is not limited thereto.

Fc Binding Substance of Present Application

Some embodiments of the present application provide a Fc binding substance comprising a Fc binding peptide having an amino acid sequence of SEQ ID NO: 01. Some embodiments of the present application provide a Fc binding substance comprising an amino acid sequence of SEQ ID NO: 01.

The amino acid sequence of SEQ ID NO: 01 is as follows:

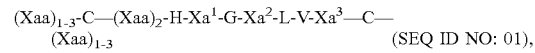

wherein each of Xaa is independently selected from any amino acid,

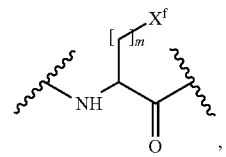

$Xa^1$ is O, wherein m is an integer of 1 to 10, and $X^f$ is —NH₂, —SH, or —C(=O)OH, $Xa^2$ is glutamic acid residue or asparagine residue, and $Xa^3$ is tryptophan residue, naphthylalanine residue, or phenylalanine residue.

In some embodiments, in the amino acid sequence of SEQ ID NO: 01, a cysteine residue adjacent to the N-terminus (that is, a cysteine residue located 2 to 4 amino acids from the N-terminus) and a cysteine residue adjacent to the C-terminus (that is, a cysteine residue located 2 to 4 amino acids from the C-terminus) may optionally be covalently linked. For example, a cysteine residue adjacent to the N-terminus and a cysteine residue adjacent to the C-terminus may optionally be covalently linked through a disulfide bond. For example, a cysteine residue adjacent to the N-terminus and a cysteine residue adjacent to the C-terminus may optionally be covalently linked through a structure

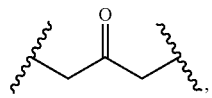 [SMILES: *CC(=O)C*]

comprising a carbonyl group.

In some embodiments, each Xaa may be independently any amino acid other than cysteine.

In some embodiments, $Xa^1$ may be diaminopropionic acid (Dap) residue, diaminobutyric acid (Dab) residue, ornithine (Orn) residue, lysine (Lys) residue, 2,7-diaminoheptanoic acid residue, 2,8-diaminooctanoic acid residue, 2,9-diaminononanoic acid residue, cysteine residue, or 2-aminosuberic acid residue.

For example, in the structure

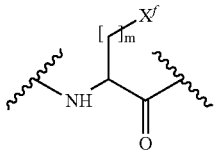

of $Xa^1$, when m is 1 and $X^f$ is —$NH_2$, $Xa^1$ is Dap residue. When m is 2 and $X^f$ is —$NH_2$, $Xa^1$ is Dab residue. When m is 3 and $X^f$ is —$NH_2$, $Xa^1$ is Orn residue. When m is 4 and $X^f$ is —$NH_2$, $Xa^1$ is Lys residue. When m is 5 and $X^f$ is —$NH_2$, $Xa^1$ is 2,7-diaminoheptanoic acid residue. When m is 1 and $X^f$ is —SH, $Xa^1$ is Cys residue. When m is 5 and $X^f$ is —COOH, $Xa^1$ is 2-aminosuberic acid residue.

In some embodiments, in the structure

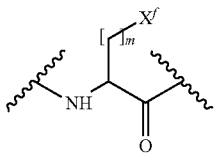

of $Xa^1$, m may be an integer of 1 to 5. In some embodiments, m may be an integer of 1 to 4.

The structure

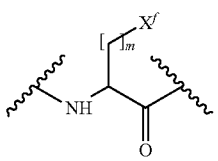

of $Xa^1$ may be referred to as a structure $Xa^1$, and is not particularly limited thereto. For example, $Xa^1$ may be referred to as an amino acid residue having the structure Xa1, and is not particularly limited thereto.

In specific embodiments, $Xa^1$ may be represented by the following structure:

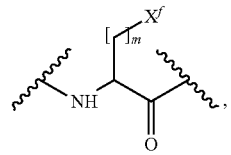

At this time, m may be an integer of 1 to 4.

In the structure, when m is 1, $Xa^1$ is Dap residue. When m is 2, $Xa^1$ is Dab residue. When m is 3, $Xa^1$ is Orn residue. When m is 4, $Xa^1$ is Lys residue.

Modifications typically used in the art may be added to a Fc binding peptide (for example, the amino acid sequence of SEQ ID NO: 01). In some embodiments, the Fc binding peptide may have modification, wherein the modification may be at a level that does not impair the inherent function of the Fc binding peptide. For example, the Fc binding peptide or Fc binding substance has binding affinity to the Fc region of an antibody, and may have modification that does not impair this function. For example, the modification may be a modification for adjusting the stability or hydrophilicity of the Fc binding peptide. For example, the modification may be the addition of a hydrophilic moiety, the addition of a hydrophobic moiety, the addition of a PEG moiety (for example, PEGylation), the addition of an amide group (for example, the amidation of the C-terminus), the addition of a carbohydrate group, the addition of a hydroxyl group, the addition of a phosphate group, the addition of a prenyl group (for example, prenylation), and/or the addition of a farnesyl group (for example, farnesylation), and the like.

For example, the Fc binding substance may further comprise one or more PEG moieties in addition to a Fc binding peptide having an amino acid sequence of SEQ ID NO: 01. At this time, the PEG moiety may be covalently linked to the N-terminus and/or C-terminus of the Fc binding peptide. For example, the Fc binding substance comprises a Fc binding peptide and a PEG moiety, wherein the PEG moiety may be covalently linked to the C-terminus of the Fc binding peptide. As another example, the Fc binding substance comprises a Fc binding peptide and a PEG moiety, wherein the PEG moiety may be covalently linked to the N-terminus of the Fc binding peptide. The PEG moiety may comprise, for example, 1 to 30, 1 to 20, or 1 to 10 of ethyleneglycol units.

Hereinafter, as an example, the structure of a Fc binding peptide with or without modifications added to the N-terminus and/or C-terminus of the amino acid sequence of SEQ ID NO: 01 will be illustrated through a formula.

For example, the Fc binding substance may have a structure of the following formula 3:

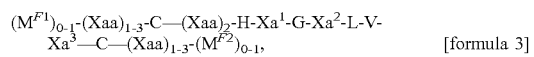    [formula 3]

wherein each of $M^{F1}$ and $M^{F2}$ is independently a modification, each of Xaa is independently any amino acid rather than cysteine, Xa¹ is wherein m is an integer of 1 to 10, and $X^f$ is —NH$_2$, —SH, or —C(=O)OH, Xa² is glutamic acid residue or asparagine residue, and Xa³ is tryptophan residue, naphthylalanine residue, or phenylalanine residue.

In formula 3, a cysteine residue adjacent to the N-terminus (that is, a cysteine residue located 2nd to 4th from the N-terminus) and a cysteine residue adjacent to the C-terminus (that is, a cysteine residue located 2nd to 4th from the C-terminus) may optionally be covalently linked. For example, a cysteine residue adjacent to the N-terminus and a cysteine residue adjacent to the C-terminus may optionally be linked through a disulfide bond.

In some embodiments, Xa¹ may be diaminopropionic acid residue, diaminobutyric acid residue, ornithine residue, lysine residue, 2,7-diaminoheptanoic acid residue, 2,8-diaminooctanoic acid residue, 2,9-diaminononanoic acid residue, cysteine residue, or 2-aminosuberic acid residue.

As illustrated in formula 3, $M^{F1}$ may or may not be present.

As illustrated in formula 3, $M^{F2}$ may or may not be present.

As described above, the modification may be selected from, for example, the addition of a hydrophilic moiety, the addition of a hydrophobic moiety, the addition of a PEG moiety (for example, PEGylation), the addition of an amide group (for example, the amidation of the C-terminus), the addition of a carbohydrate group, the addition of a hydroxyl group, the addition of a phosphate group, the addition of a prenyl group (for example, prenylation), and the addition of a farnesyl group (for example, farnesylation).

In some embodiments, $M^{F1}$ may be selected from a PEG moiety, an amide group, a carbohydrate group, a hydroxyl group, a phosphate group, a prenyl group, and a farnesyl group. In specific embodiments, $M^{F1}$ may be a PEG moiety.

In some embodiments, $M^{F2}$ may be selected from a PEG moiety, an amide group, a carbohydrate group, a hydroxyl group, a phosphate group, a prenyl group, and a farnesyl group. In specific embodiments, $M^{F2}$ may be an amide group.

At this time, the PEG moiety may comprise 1 to 30, 1 to 20, or 1 to 10 of ethyleneglycol units (for example, —CH$_2$OCH$_2$—, —OCH$_2$CH$_2$— or —CH$_2$CH$_2$O—).

For example, the PEG moiety may have the following structure:

$$R^{PEG}-[EG]_p-D^{PEG}-$$

At this time, $D^{PEG}$ is a spacer of the PEG moiety.

For example, $D^{PEG}$ may be a group having a main chain length of 0 to 6 (that is, a group in which the sum of the number of atoms located in the main chain is 0 to 6).

For example, $D^{PEG}$ is a bond, or substituted or unsubstituted C$_{1-6}$ alkylene, substituted or unsubstituted C$_{1-6}$ heteroalkylene, substituted or unsubstituted C$_{1-6}$ alkenylene, substituted or unsubstituted C$_{1-6}$ heteroalkenylene, substituted or unsubstituted alkynylene, or substituted or unsubstituted heteroalkynylene, wherein the substituted alkylene, substituted heteroalkylene, substituted alkenylene, or substituted heteroalkynylene may comprise one or more substituents, and may be selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, C$_{1-6}$ alkyl, C$_{3-10}$ cycloalkyl, C$_{3-10}$ heterocycloalkyl, aryl, heteroaryl, —OH, —NH$_2$, =O, =S, and —SH. In specific embodiments, the substituent may be selected from —C$_{1-4}$ alkyl, —C(=O)H, —C(=O)CH$_3$, —C(=O)OH, —C(=O)NH$_2$, —NH$_2$, =O, =S, —OH, —NO$_2$ and —SH. Herein, each of the heteroalkylene, the heteroalkenylene, and the heteroalkynylene independently comprises one or more heteroatoms, wherein each of the heteroatoms may be independently selected from N, O, and S.

In specific embodiments, $D^{PEG}$ may be a bond, or substituted or unsubstituted C$_{1-3}$ alkylene, or substituted or unsubstituted C$_{1-3}$ heteroalkylene, wherein the substituted alkylene or the substituted heteroalkylene comprises one or more substituents, wherein the substituent is =O, wherein the heteroalkylene comprises one or more heteroatoms, wherein each of the heteroatoms may be independently selected from N, O, and S.

In the structure of the PEG moiety, $R^{PEG}$ is a PEG capping group. At this time, the PEG capping group may not be present, or may be —CH$_3$, C$_2$ alkyl, C$_3$ alkyl, —NH$_2$, —CH$_2$NH$_2$, —SC(=O)CH$_3$, —SC(=O)CH$_2$CH$_3$, —CH$_2$SC(=O)CH$_3$, —CH$_2$SC(=O)CH$_2$CH$_3$, —OH, —CH$_2$OH, —SH, —CH$_2$SH, —OCH$_3$, —CH$_2$OCH$_3$, —CH$_2$OCH$_2$CH$_3$, —C(=O)CH$_3$, —C(=O)CH$_2$CH$_3$, —CH$_2$C(=O)CH$_3$, —CH$_2$C(=O)CH$_2$CH$_3$, —NHC(=O)CH$_3$, —NHC(=O)CH$_2$CH$_3$, —CH$_2$NHC(=O)CH$_3$, —CH$_2$CH$_2$NHC(=O)CH$_3$, —CH$_2$CH$_2$NHC(=O)CH$_2$CH$_3$, —CH$_2$NHC(=O)CH$_2$CH$_3$, —CH$_2$CH$_2$COOH, glucose or —O-glucose, but is not limited thereto. In specific embodiments, the PEG capping group may not be present, or may be —CH$_3$, —OCHs, —CH$_2$OCH$_3$, —C(=O)CH$_3$, —CH$_2$C(=O)CH$_3$, —NHC(=O)CH$_3$, —CH$_2$NHC(=O)CH$_3$ or —CH$_2$CH$_2$COOH. In some embodiments, the sum of the atomic masses of the atoms belonging to the PEG capping group may be 300 dalton or less, 200 dalton or less, 150 dalton or less, 100 dalton or less, or 50 dalton or less, but is not limited thereto.

In the structure of the PEG moiety, p may be an integer of 1 to 30, preferably 1 to 10.

In the structure of the PEG moiety, [EG] refers to an ethyleneglycol unit, and the ethyleneglycol unit is as described above in the relevant paragraph.

The structure of formula 3 described above is an example of a case where the Fc binding substance or Fc binding peptide comprises modification, and hereinafter, it should be understood that even when the modifications illustrated in the structure of formula 3 (for example, $M^{F1}$ and/or $M^{F2}$) are not indicated, the Fc binding substance or Fc binding peptide can further comprise modification.

In some embodiments, the Fc binding substance may comprise an amino acid sequence of SEQ ID NO: 02.

(SEQ ID NO: 02)
$^L$P-D-C-(Xaa)$_2$-H-Xa$^1$-G-Xa$^2$-L-V-Xa$^3$-C-T-$^D$P,

At this time, each of Xaa, Xa¹, Xa², and Xa³ is the same as those described above.

At this time, the $^L$P (L-proline residue) and the $^D$P (D-proline residue) of the N-terminus may optionally form a D-proline-L-proline template.

In some embodiments, the Fc binding substance may comprise an amino acid sequence of SEQ ID NO: 03.

```
                                          (SEQ ID NO: 03)
C-D-C-(Xaa)₂-H-Xa¹-G-Xa²-L-V-Xa³-C-T-C,
```

At this time, each of Xaa, Xa¹, Xa², and Xa³ is the same as those described above.

At this time, the cysteine of the N-terminus and the cysteine of the C-terminus may be optionally covalently linked.

In specific embodiments, the Fc binding substance may comprise an amino acid sequence of SEQ ID NO: 04:

```
                                        (SEQ ID NO: 04)
D-C-(Xaa)₂-H-Xa¹-G-Xa²-L-V-Xa³-C-T,
```

At this time, each of Xaa, Xa¹, Xa², and Xa³ is the same as those described above.

At this time, a cysteine residue adjacent to the N-terminus (in SEQ ID NO: 04, cysteine linked to D) and a cysteine residue adjacent to the C-terminus (in SEQ ID NO: 04, cysteine linked to T) may optionally be linked covalently (for example, through a disulfide bond).

In specific embodiments, Xa¹ may be diaminopropionic acid (Dap) residue, diaminobutyric acid (Dab) residue, ornithine (Orn) residue, or lysine (Lys) residue.

In specific embodiments, the Fc binding substance may comprise an amino acid sequence of SEQ ID NO: 05:

D-C-A-W—H-Xa¹-G-E-L-V—W—C-T    (SEQ ID NO: 05), wherein
Xa¹ is wherein m is an integer of 1 to 10, and $X^f$ is —NH₂, —SH, or —C(=O)OH. In some embodiments, m may be an integer of 1 to 4.

In some embodiments, Xa¹ may be diaminopropionic acid (Dap) residue, diaminobutyric acid (Dab) residue, ornithine (Orn) residue, lysine (Lys) residue, 2,7-diaminoheptanoic acid residue, 2,8-diaminooctanoic acid residue, 2,9-diaminononanoic acid residue, cysteine residue, or 2-aminosuberic acid residue. In specific embodiments, Xa¹ may be diaminopropionic acid (Dap) residue, diaminobutyric acid (Dab) residue, ornithine (Orn) residue, or lysine (Lys) residue.

At this time, a cysteine residue adjacent to the N-terminus (in SEQ ID NO: 05, cysteine linked to D) and a cysteine residue adjacent to the C-terminus (in SEQ ID NO: 05, cysteine linked to T) may optionally be linked covalently (for example, through a disulfide bond).

In specific embodiments, the Fc binding substance may comprise any one selected from the amino acid sequences of SEQ ID NO: 06 to SEQ ID NO: 09:

```
                                     (SEQ ID NO: 06)
D-C-A-W-H-Dap-G-E-L-V-W-C-T;

(SEQ ID NO: 07)
D-C-A-W-H-Dab-G-E-L-V-W-C-T;

(SEQ ID NO: 08)
D-C-A-W-H-Orn-G-E-L-V-W-C-T;
and
                                     (SEQ ID NO: 09)
D-C-A-W-H-Lys-G-E-L-V-W-C-T.
```

At this time, a cysteine residue adjacent to the N-terminus (for example, cysteine linked to D) and a cysteine residue adjacent to the C-terminus (for example, cysteine linked to T) may optionally be linked covalently (for example, through a disulfide bond).

Design of Fc Binding Substance

As previously described, the Fc binding substance of the present application has binding activity to the Fc region of an antibody. At this time, the Fc binding substance and the Fc region may be arranged in a specific positional relationship through interactions between amino acid residues. Representative interactions between the Fc binding peptide of a Fc binding substance and the Fc region of an antibody include (1) salt linkage between the Fc binding substance and histidine 433 in the Fc region, (2) hydrogen bond between the Fc binding substance and asparagine 434 in the Fc region, (3) salt linkage between the Fc binding substance and glutamic acid 380 in the Fc region, and (4) salt linkage between the Fc binding substance and arginine 255, and the like. Through already known research results, such interactions and the specific positional relationships resulting therefrom may be identified. (see the document [DeLano, W. L., Ultsch, M. H., de, A. M., Vos, N., & Wells, J. A. Baumannii (2000). Convergent solutions to binding at a protein-protein interface. Science, 287(5456), 1279-1283.])

In designing the Fc binding substance of the present application, it is important to ensure that the Fc binding substance forms a stable positional relationship with the Fc region of an antibody. This is because the compound comprising Fc binding unit of the present application and the labeling process for antibodies using the same (that is, a process of transferring a group of interest) are designed based on the positional relationship between the Fc binding unit and the Fc region, which has been revealed through research.

An example of the design principles of Fc binding substances will be described through a Fc binding peptide having an amino acid sequence of SEQ ID NO: 05 (DCAWHXa¹GELVWCT).

Figure 2:
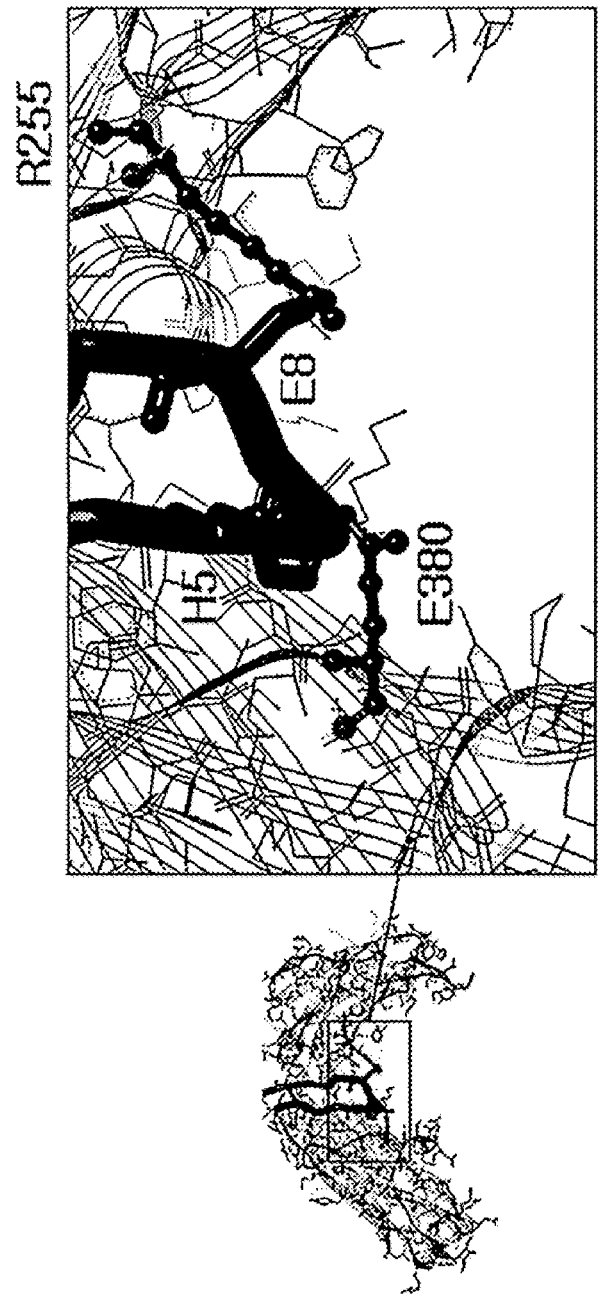
FIGS. 2 and 3 show the positional relationship between the Fc binding peptide and the Fc region.
Figure 3:
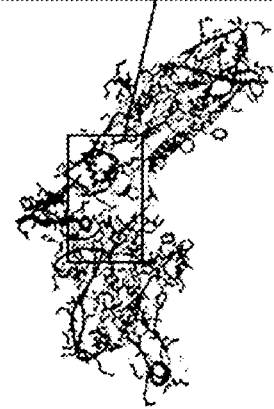
Figure 3:
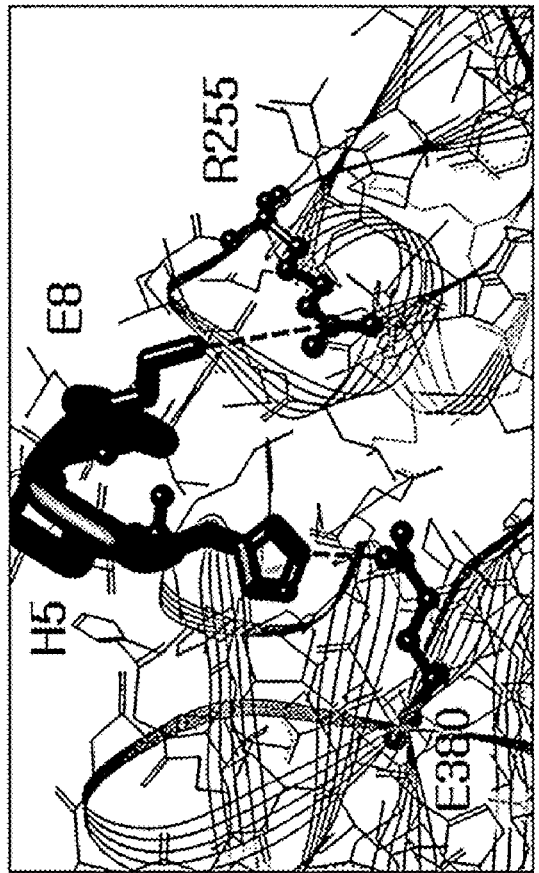
Figure 4:
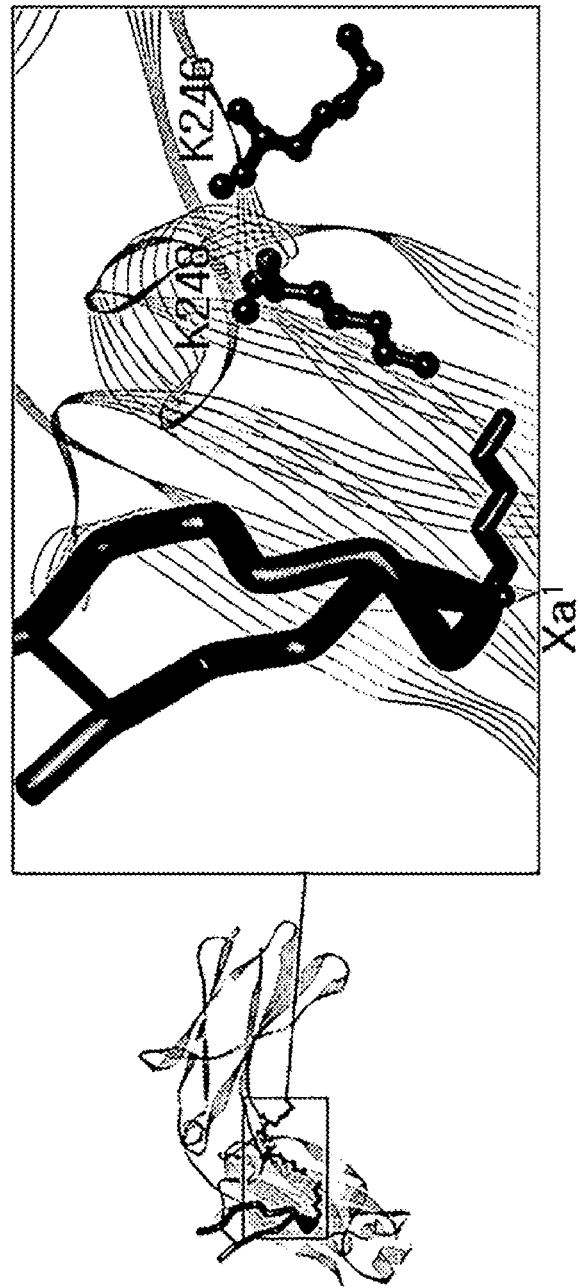
FIG. 4 illustrates $Xa^1$ of the Fc binding peptide and lysine 246 and lysine 248 of the Fc region.

The results of simulating the positional relationship between the Fc binding peptide having the amino acid sequence of SEQ ID NO: 05 and the Fc region based on thesis data and the like are shown in FIGS. 01 to 03. At this time, it was confirmed that the histidine residue 5 of the Fc binding peptide forms a salt linkage with glutamic acid 380 of the Fc region, and the salt linkage has an important effect on the positional relationship between the Fc binding peptide and the Fc region (see dotted line in FIG. 03). For this reason, it is desirable not to change the histidine residue and its position in designing a Fc binding peptide. Furthermore, it was confirmed that glutamic acid residue 8 is an electronegative residue that forms a salt linkage with arginine 255 of the Fc region, which is electropositive, and thus is importantly affected to the positional relationship between the Fc binding peptide and the Fc region (see the dotted line in FIG. 03). Therefore, this residue is preferably an acidic amino acid that can be corresponded to glutamic acid, and may be replaced with asparagine. When these amino acid residues are changed to other amino acid residues or replaced with other functional groups, this may affect the positional relationship between the Fc binding peptide and the Fc region by affecting the interactions between molecules. In addition, glycine 7 in SEQ ID NO: 05 is an amino acid with a small volume and is required to form the folded structure of the Fc binding peptide. Therefore, it is desirable not to change glycine and its position in designing a Fc binding peptide. FIG. 04 illustrates the positional relationship between lysine residues in the Fc domain and Fc binding peptides. In the positional relationship, it could be confirmed that the lysines in the Fc region located most adjacent to $Xa^1$ were lysine 246 and lysine 248 (FIG. 04).

Antibodies with Affinity to Fc Binding Substance

As described above, the Fc binding substance has binding affinity to the Fc region of an antibody.

In the present specification, the term antibody is used to encompass all antibodies or fragments thereof that have affinity to the Fc binding substance, and even when there is no binding ability for a specific antigen, such as in the case of a Fc fragment, it may be recognized as an antibody. Furthermore, the term antibody may be interpreted to encompass monospecific antibodies, bispecific antibodies, trispecific antibodies, monoclonal antibodies, human antibodies, humanized antibodies, recombinant antibodies, chimeric antibodies, antibody variants, and the like.

Furthermore, an antibody comprises a Fc region, and thus may be referred to as a Fc protein.

In some embodiments, the antibody may comprise the Fc region of IgG. In some embodiments, the Fc region of the antibody may be the Fc region of IgG.

In some embodiments, the antibody may be an IgG antibody. The IgG antibody encompasses a human IgG antibody, a humanized IgG antibody, and a chimeric IgG antibody.

It is known that IgG is classified into IgG1, IgG2, IgG3, and IgG4.

In some embodiments, the antibody may be an IgG1 antibody. The IgG1 antibody encompasses a human IgG1 antibody, a humanized IgG1 antibody, and a chimeric IgG1 antibody.

In some embodiments, the antibody may comprise the Fc region of IgG1. The Fc region of the antibody may be the Fc region of IgG1.

In some embodiments, the antibody may be an IgG2 antibody. The IgG2 antibody encompasses a human IgG2 antibody, a humanized IgG2 antibody, and a chimeric IgG2 antibody.

In some embodiments, the antibody may comprise the Fc region of IgG2. The Fc region of the antibody may be the Fc region of IgG2.

In some embodiments, the antibody may be an IgG3 antibody. The IgG3 antibody encompasses a human IgG3 antibody, a humanized IgG3 antibody, and a chimeric IgG3 antibody.

In some embodiments, the antibody may comprise the Fc region of IgG3. The Fc region of the antibody may be the Fc region of IgG3.

In some embodiments, the antibody may be an IgG4 antibody. The IgG4 antibody encompasses a human IgG4 antibody, a humanized IgG4 antibody, and a chimeric IgG4 antibody.

In some embodiments, the antibody may comprise the Fc region of IgG4. The Fc region of the antibody may be the Fc region of IgG4.

In some embodiments, the antibody may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody may have an amino acid sequence of SEQ ID NO: 14 or an amino acid sequence having 90%, 95%, 96%, 97%, 98%, or 99% or more sequence identity thereof.

In some embodiments, the antibody comprises an IgG Fc region (for example, the Fc region of the antibody is the Fc region of IgG), wherein the IgG Fc region may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody comprises the Fc region of IgG, wherein the IgG Fc region may have an amino acid sequence of SEQ ID NO: 14 or an amino acid sequence having 90%, 95%, 96%, 97%, 98%, or 99% or more identity thereof.

In some embodiments, the antibody or the Fc region of the antibody may comprise an amino acid sequence of KPKDTLM (SEQ ID NO: 10) and MHEALHNH (SEQ ID NO: 11).

In some embodiments, the antibody or the Fc region of the antibody may comprise an amino acid sequence of KPKDTLM (SEQ ID NO: 10) and MHEALHNHY (SEQ ID NO: 12).

In some embodiments, the antibody or the Fc region of the antibody may comprise an amino acid sequence of GPSVFLFPPKPKDTLM (SEQ ID NO: 13).

In some embodiments, the antibody has any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, and may essentially comprise an amino acid sequence of KPKDTLM (SEQ ID NO: 10) and MHEALHNH (SEQ ID NO: 11). In some embodiments, the antibody comprises an IgG Fc region, wherein the IgG Fc region has any one amino acid sequence selected from SEQ ID NO: 14 to SEQ ID NO: 18 or an amino acid sequence having 80%, 85%, 90%, 95%, 96%, 97%, 98%, or 99% or more identity thereof, and may essentially comprise an amino acid sequence of KPKDTLM (SEQ ID NO: 10) and MHEALHNH (SEQ ID NO: 11).

In some embodiments, the antibody has any one amino acid sequence selected from SEQ ID: 14 to SEQ ID 15 and SEQ ID NO: 17 to SEQ ID NO: 18, or an amino acid sequence having 80%, 85%, 90%, 95%, 96%, 97%, 98%, or 99% or more sequence identity thereof, and may essentially comprise an amino acid sequence of KPKDTLM (SEQ ID NO: 10) and MHEALHNHY (SEQ ID NO: 12). In some embodiments, the antibody comprises an IgG Fc region, wherein the IgG Fc region has any one amino acid sequence selected from SEQ ID NO: 14 to SEQ ID NO: 15 and SEQ ID NO: 17 to SEQ ID NO: 18 or an amino acid sequence having 80%, 85%, 90%, 95%, 96%, 97%, 98%, or 99% or more sequence identity thereof, and may essentially comprise an amino acid sequence of KPKDTLM (SEQ ID NO: 10) and MHEALHNHY (SEQ ID NO: 12).

In some embodiments, the antibody has any one amino acid sequence selected from SEQ ID NO: 14 to SEQ ID NO: 18 or an amino acid sequence having 80%, 85%, 90%, 95%, 96%, 97%, 98%, or 99% or more sequence identity thereof, and may essentially comprise GPSVFLFPPKPKDTLM (SEQ ID NO: 13). In some embodiments, the antibody comprises an IgG Fc region, wherein the IgG Fc region has any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, and may essentially comprise GPSVFLFPPKPKDTLM (SEQ ID NO: 13).

In some embodiments, the antibody with binding affinity to the Fc binding peptide of the present application may be an antibody of the IgG isotype. In some embodiments, the antibody with binding affinity to the Fc binding peptide of the present application may be an antibody of IgG1 isotype, an antibody of IgG2 isotype, an antibody of IgG3 isotype, or an antibody of IgG4 isotype. In some embodiments, the antibody with binding affinity to the Fc binding peptide of the present application may be an antibody of IgG1 isotype, an antibody of IgG2 isotype, or IgG4 isotype.

As described above, herein, the antibody may be an antibody having binding affinity to the Fc binding substance. For example, an antibody having binding affinity to a Fc binding substance (for example, an antibody comprising an IgG1 Fc region) even when one or more of the Fab, antigen binding region, and light chain and heavy chain variable regions are changed may have binding affinity to the Fc binding substance because it still comprises a Fc region to which the Fc binding substance can bind. Furthermore, even a protein having only a Fc region to which a Fc binding substance can bind may be recognized as an antibody in the present application because it has binding affinity to the Fc binding substance. In the present application, the protein that essentially comprises a Fc region is referred to as a Fc protein, and in some embodiments, for convenience, the antibody may be recognized as encompassing the aspect of the Fc protein.

Furthermore, the present application provides an amino acid sequence of 237 to 444 of the Fc region of human IgG1 (SEQ ID NO: 14) and amino acid sequence of a human IgG2 Fc region corresponding to the same (SEQ ID NO: 15), an amino acid sequence of an IgG3 Fc region (SEQ ID NO: 16), an amino acid sequence of an IgG4 Fc region (SEQ ID NO: 17), and an amino acid sequence of the Fc region of trastuzumab (SEQ ID NO: 18) which is an antibody well known in the art.

The Fc binding substance (for example, a Fc binding substance comprising any one amino acid sequence of SEQ ID NO: 06 to SEQ ID NO: 09) is known to interact with the amino acid sequence KPKDTLM (SEQ ID NO: 10)(a sequence of amino acid residues 246 to 252 based on the sequence of the Fc region of trastuzumab) of the Fc region, and the amino acid sequence MHEALHNHY (SEQ ID NO: 12)(a sequence of amino acid residues 428 to 436 based on the sequence of the Fc region of trastuzumab) of the Fc region.

Structure of Fc Binding Unit

The compound comprising Fc binding unit comprises Fc binding unit. The Fc binding unit of the compound is derived from the Fc binding substance. Specifically, the Fc binding substance or Fc binding unit is linked to other parts of the compound comprising Fc binding unit through an amino acid residue represented by $Xa^1$ (for example, through the amine group of an amino acid residue represented by $Xa^1$).

The Fc binding substance from which the Fc binding unit originates was described in detail in the previous paragraph. Hereinafter, the structure of the Fc binding unit will be described in detail.

In some embodiments, the Fc binding unit may have the following structure:

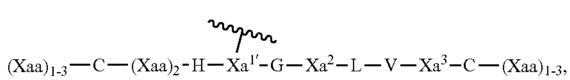

, wherein each of Xaa is independently selected from any amino acid residue, $Xa^{1'}$ is

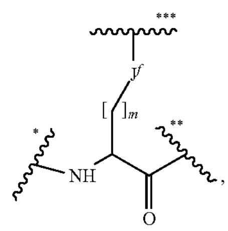

, wherein m is an integer of 1 to 10, $Y^f$ is —NH—, —S—, —O—, or —C(═O)—, *** indicates an attachment point (or a linking point) of $Xa^{1'}$ with a portion, in the compound comprising Fc binding unit, that are not the Fc binding unit, * indicates an attachment point of $Xa^{1'}$ with the amino acid residue adjacent to $Xa^{1'}$ (for example, histidine residue), and ** indicates an attachment point of $Xa^{1'}$ with the amino acid residue adjacent to $Xa^{1'}$ (for example, glycine residue), $Xa^2$ is glutamic acid residue or asparagine residue, and $Xa^3$ is tryptophan residue, naphthylalanine residue, or phenylalanine residue.

In the structure, a cysteine residue adjacent to the N-terminus (that is, a cysteine residue located 2 to 4 amino acids from the N-terminus) and a cysteine residue adjacent to the C-terminus (that is, a cysteine residue located 2 to 4 amino acids from the C-terminus) may optionally be covalently linked. For example, a cysteine residue adjacent to the N-terminus and a cysteine residue adjacent to the C-terminus may optionally be linked through a disulfide bond. For example, a cysteine residue adjacent to the N-terminus and a cysteine residue adjacent to the C-terminus may optionally be covalently linked through a structure 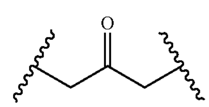 [SMILES: *CC(=O)C*] which comprises a carbonyl group.

In some embodiments, each Xaa may be independently any amino acid other than cysteine.

In some embodiments, $Xa^{1'}$ may be a conjugated diaminopropionic acid (Dap) residue, a conjugated diaminobutyric acid (Dab) residue, a conjugated ornithine (Orn) residue, a conjugated lysine (Lys) residue, a conjugated 2,7-diaminoheptanoic acid residue, a conjugated 2,8-diaminooctanoic acid residue, a conjugated 2,9-diaminononanoic acid residue, a conjugated cysteine residue, or a conjugated 2-aminosuberic acid residue. In specific embodiments, $Xa^{1'}$ may be a conjugated diaminopropionic acid (Dap) residue, a conjugated diaminobutyric acid (Dab) residue, a conjugated ornithine (Orn) residue, or a conjugated lysine (Lys) residue.

In the structure of the Fc binding unit, for convenience, the term conjugated may be omitted and described in regard with $Xa^{1'}$, which refers to an amino acid residue conjugated to another part of the compound comprising Fc binding unit. For example, the conjugated diaminopropionic acid residue may be referred to as diaminopropionic acid residue or diaminopropionic acid. For example, the conjugated diaminobutyric acid residue may be referred to as diaminobutyric acid residue or diaminobutyric acid. For example, the conjugated ornithine residue may be referred to as ornithine residue or ornithine. For example, the conjugated lysine residue may be referred to as lysine residue or lysine.

When formula 2 is illustrated together with the structure of the Fc binding unit above, formula 2 may be represented by the following formula 4:

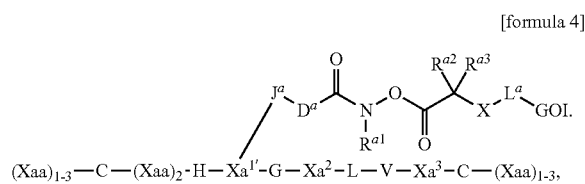

[formula 4]

In some embodiments, $Xa^{1\prime}$ may have the following structure:

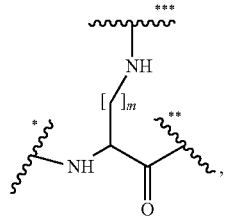

At this time, m is an integer of 1 to 4,

*** indicates an attachment point of $Xa^{1\prime}$ with a portion, in the compound comprising Fc binding unit, that are not the Fc binding unit,

* indicates an attachment point of $Xa^{1\prime}$ with the amino acid residue adjacent to $Xa^{1\prime}$ (for example, histidine residue), and

** indicates an attachment point of $Xa^{1\prime}$ with the amino acid residue adjacent to $Xa^{1\prime}$ (for example, glycine residue).

As described above, the Fc binding substance which is the origin of the Fc binding unit may include a modification. For example, the Fc binding substance comprises a Fc binding peptide, wherein one or more modifications may be added to the Fc binding peptide. As described above, the modification may be at a level that does not impair the inherent function of the Fc binding peptide. The Fc binding unit may be derived from the Fc binding substance. For example, the Fc binding unit may further comprise a PEG moiety, wherein the PEG moiety may be linked to the N-terminus and/or the C-terminus of the Fc binding unit.

Hereinafter, by way of example, the structure of a Fc binding unit derived from a Fc binding substance with or without modifications (for example, a Fc binding peptide with or without modifications added to the N-terminus and/or C-terminus of the amino acid sequence) will be illustrated.

For example, the Fc binding unit may have the following structure:

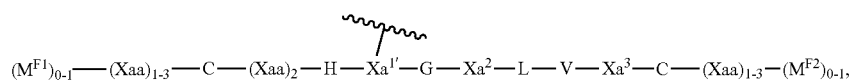

At this time, each of Xaa, $Xa^{1'}$, $Xa^2$, and $Xa^3$ is the same as those described above, and each of $M^{F1}$ and $M^{F2}$ is as described in the paragraphs describing the modifications added to the Fc binding peptide.

The illustrated structure exemplifies the structure of a Fc binding unit derived from a Fc binding substance comprising a modification or a Fc binding peptide to which a modification is added, and hereinafter, it will be understood that the Fc binding unit may further comprise a modification, even though the modification illustrated in the structure (for example, $M^{F1}$ and/or $M^{F2}$) is not indicated in the structure of the Fc binding unit.

In some embodiments, the Fc binding unit may have the following structure:

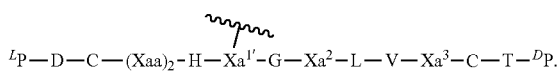

$^L P-D-C-(Xaa)_2-H-Xa^{1'}-G-Xa^2-L-V-Xa^3-C-T-^D P.$

At this time, each of Xaa, $Xa^{1'}$, $Xa^2$, and $Xa^3$ is the same as those described above.

At this time, the $^L P$ (L-proline residue) of the N-terminus and the $^D P$ (D-proline residue) may optionally form a D-proline-L-proline template.

In some embodiments, the Fc binding unit may have the following structure:

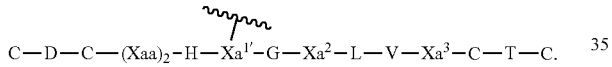

$C-D-C-(Xaa)_2-H-Xa^{1'}-G-Xa^2-L-V-Xa^3-C-T-C.$

At this time, each of Xaa, $Xa^{1'}$, $Xa^2$, and $Xa^3$ is the same as those described above.

At this time, the cysteine of the N-terminus and the cysteine of the C-terminus may be optionally linked covalently (for example, through a disulfide bond).

In specific embodiments, the Fc binding unit may have the following structure:

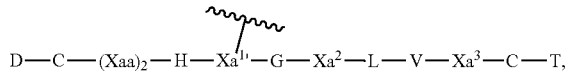

$D-C-(Xaa)_2-H-Xa^{1'}-G-Xa^2-L-V-Xa^3-C-T,$

At this time, each of Xaa, $Xa^{1'}$, $Xa^2$, and $Xa^3$ is the same as those described above.

At this time, a cysteine residue adjacent to the N-terminus and a cysteine residue adjacent to the C-terminus may optionally be linked covalently (for example, through a disulfide bond).

In specific embodiments, Fc binding unit may have the following structure:

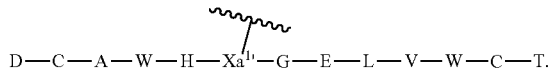

$D-C-A-W-H-Xa^{1'}-G-E-L-V-W-C-T.$ wherein $Xa^{1'}$ is

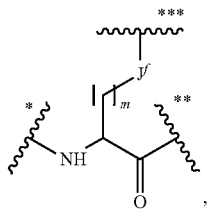

wherein m is an integer of 1 to 10, $J'$ is —NH—, —S—, —O—, or —C(=O)—, *** indicates an attachment point (or a linking point) of $Xa^{1'}$ with a portion that are not the Fc binding unit in the compound comprising Fc binding unit, * indicates an attachment point of $Xa^{1'}$ with the amino acid residue adjacent to $Xa^{1'}$ (for example, histidine residue), and ** indicates an attachment point of $Xa^{1'}$ with the amino acid residue adjacent to $Xa^{1'}$ (for example, glycine residue).

At this time, a cysteine residue adjacent to the N-terminus and a cysteine residue adjacent to the C-terminus may optionally be linked covalently (for example, through a disulfide bond).

In specific embodiments, $Xa^{1'}$ may be a conjugated diaminopropionic acid (Dap) residue, a conjugated diaminobutyric acid (Dab) residue, a conjugated ornithine (Orn) residue, a conjugated lysine (Lys) residue, a conjugated 2,7-diaminoheptanoic acid residue, a conjugated 2,8-diaminooctanoic acid residue, a conjugated 2,9-diaminononanoic acid residue, a conjugated cysteine residue, or a conjugated 2-aminosuberic acid residue.

In specific embodiments, $Xa^{1'}$ is

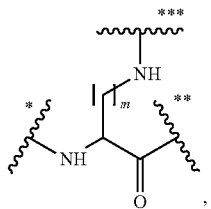

wherein m may be an integer of 1 to 4.

In specific embodiments, $Xa^{1'}$ may be a conjugated diaminopropionic acid (Dap) residue, a conjugated diaminobutyric acid (Dab) residue, a conjugated ornithine (Orn) residue, or a conjugated lysine (Lys) residue.

For example, in a compound comprising Fc binding unit, the Fc binding unit (FcBU) may be described through the Fc binding substance from which it is derived, and examples of such descriptions are as follows, but are not limited thereto:

The Fc binding unit is derived from the Fc binding substance,
wherein the Fc binding substance comprises an amino acid sequence of SEQ ID NO: 01, and
wherein the Fc binding unit and portions other than the Fc binding unit are linked or conjugated through $Xa^1$ of the Fc binding substance (specifically, through the side chain of $Xa^1$).

As another example, in a compound comprising Fc binding unit, the Fc binding unit (FcBU) may be described as follows:

The Fc binding unit comprises an amino acid sequence of SEQ ID NO: 01, wherein the Fc binding unit and portion other than the Fc binding unit are linked or conjugated through $Xa^1$ of the amino acid sequence of SEQ ID NO: 01 (specifically, through the side chain of $Xa^1$).

The elements of the compound comprising Fc binding unit have been described in detail in previous paragraphs. Hereinafter, the reaction of an antibody with a compound comprising Fc binding unit will be described in detail.

Reaction Between Compound Comprising Fc Binding Unit and Antibody

Position to which Group of Interest is Transferred

As described above, a compound comprising Fc binding unit may be used to transfer a substance of interest to an antibody in a site-specific manner.

For example, a compound comprising Fc binding unit may be used to transfer a bio-orthogonal functional group, a drug, or the like to a target region of an antibody. A region in the antibody to which the group of interest is transferred (for example, the target region) may be located in the Fc region of an antibody. That is, when the compound comprising Fc binding unit of the present application is used, a group of interest may be transferred to the Fc region of an antibody.

In some embodiments, when the compound comprising Fc binding unit of the present application is used, a group of interest may be transferred to any one or more selected from lysine 246 (K246) and lysine 248 (K248) of the Fc region of the antibody.

In some embodiments, when the compound comprising Fc binding unit of the present application is used, a group of interest may be transferred to any one or more selected from K246 and K248 of the Fc region of the antibody in a site-specific manner.

For example, the case where the group of interest is transferred to the target region of the antibody by contact or reaction of the antibody with the compound containing Fc binding unit of the present application may be 50% or more, 60% or more, 70% or more, 80% or more, 90% or more, 95% or more, 96% or more, 97% or more, 98% or more, 99% or more, 99.5% or more, or 100% of the total cases (that is, a case that encompasses both the case where the group of interest is transferred to the target region and the case where the group of interest is transferred to a region other than the target region). For example, when using 100 compounds comprising Fc binding unit (wherein one compound comprising Fc binding unit has one group of interest), when 100 groups of interest are transferred to the target region, the case where the group of interest is transferred to the target region may be described as 100%. For example, when 100 compounds comprising Fc binding unit are used, when 80 groups of interest are transferred to the target region and 20 compounds comprising Fc binding unit does not react with the antibodies (that is, when 20 groups of interest are not transferred to the antibodies), the case where the group of interest is transferred to the target region may be described as 100%. For example, when a 100 compounds comprising Fc binding unit are used, when 80 groups of interest are transferred to the target region and 20 groups of interest are transferred to the antibodies but are transferred to positions other than the target region of the antibody, the case where the group of interest is transferred to the target region may be described as 80%. At this time, for example, when the group of interest is transferred to the target region of the antibody, it may be determined based on the reaction time (for example, 3 hours) of the antibody with a compound comprising Fc binding unit. At this time, the target region may be a region consisting of 20, 10, 5, or 3 amino acid residues comprising lysine residue 246 (K246) of the Fc region and lysine residue 248 (K248) of the Fc region. For example, when the target region is a region consisting of 5 amino acid residues, comprising lysine residue 246 (K246) of the Fc region and lysine residue 248 (K248) of the Fc region, the target region may be $PK^{246}PK^{248}D$ (SEQ ID NO: 27). For example, when the target region is a region consisting of 3 amino acid residues, comprising lysine residue 246 (K246) of the Fc region and lysine residue 248 (K248) of the Fc region, the target region may be $K^{246}PK^{248}$ (SEQ ID NO: 28).

In some embodiments, among the cases in which the group of interest is transferred to the target region, the case where the group of interest is transferred to lysine residue 246 (K246) of the Fc region may be 10%, 20%, 30%, 40%, 50%, 60%, 70%, 80%, 90%, 99%, 99% or 99.5% or more, or 100%. In some embodiments, among the cases in which the group of interest is transferred to the target region, the case where the group of interest is transferred to lysine residue 248 (K248) of the Fc region may be 10%, 20%, 30%, 40%, 50%, 60%, 70%, 80%, 90%, 99%, 99% or 99.5% or more, or 100%.

For example, the case where the group of interest is transferred to at least any one of K246 and K248 of the Fc region of the antibody by contact or reaction of the antibody with the compound comprising Fc binding unit of the present application may be 50% or more, 60% or more, 70% or more, 80% or more, 90% or more, 95% or more, 96% or more, 97% or more, 98% or more, 99% or more, 99.5% or more, or 100% of the total cases (that is, the cases that encompass both the case where the group of interest is transferred to at least any one K246 and K248 of the Fc region of the antibody and the case where the group of interest is transferred to a position other than K246 and K248).

For example, the case where the group of interest is transferred to K246 of the Fc region of the antibody by contact or reaction of the antibody with the compound comprising Fc binding unit of the present application may be 50% or more, 60% or more, 70% or more, 80% or more, 90% or more, 95% or more, 96% or more, 97% or more, 98% or more, 99% or more, 99.5% or more, or 100% of the total cases (that is, the cases that encompass both the case where the group of interest is transferred to K246 of the Fc region of the antibody and the case where the group of interest is transferred to a position other than K246).

For example, the case where the group of interest is transferred to K248 of the Fc region of the antibody by contact or reaction of the antibody with the compound comprising Fc binding unit of the present application may be 50% or more, 60% or more, 70% or more, 80% or more, 90% or more, 95% or more, 96% or more, 97% or more, 98% or more, 99% or more, 99.5% or more, or 100% of the total cases (that is, the cases that encompass both the case where the group of interest is transferred to K248 of the Fc region of the antibody and the case where the group of interest is transferred to a position other than K248).

In some embodiments, when the compound comprising Fc binding unit of the present application is used, it is possible to transfer a group of interest to any one or more selected from K246 and K248 of the Fc region of the antibody, while not transferring the group of interest to a position other than any one or more selected from K246 and K248. In some embodiments, when using the compound comprising Fc binding unit of the present application, transfer of the group of interest to a position other than one or more selected from K246 and K248 may be suppressed.

The compound comprising Fc binding unit was designed to react with the free amino group of the lysine residue of an antibody. That is, in some embodiments, when the compound comprising Fc binding unit of the present application is used, a group of interest may be transferred to lysine of the Fc region of an antibody.

Furthermore, as described in the design of the Fc binding substance, when the antibody and the Fc binding substance interact (for example, bind), it was described that the lysine of the Fc region located adjacent to $Xa^1$ are lysine 246 and lysine 248 (the lysine numbers are set by the Eu numbering system).

As an example, through the amino acid sequence included in trastuzumab, lysines 246 and 248 are expressed as follows: GPSVFLFPPK$^{246}$PK$^{248}$DTLM (SEQ ID NO: 13).

In some documents or antibodies, there is also the case where lysine residues corresponding to positions 246 and 248 may be indicated by numbers other than 246 and 248, and when the residues indicated in some documents are amino acid residues corresponding to lysine 246 and 248, these positions will be understood as the positions of lysine 246 and lysine 248. For example, some documents refer to the amino acid residues corresponding to K246 and K248 of denosumab as K247 and K249, respectively. As another example, some documents refer to the amino acid residues corresponding to K246 and K248 of dupilumab as K251 and K253, respectively (see the documents [EP 19818561.3, Publication No. EP 3811978; and EP 18791007.0, Publication No. EP 3617235]). As described above, lysine 246 and lysine 248 may be understood to refer to lysine residues corresponding to lysine 246 and lysine 248, respectively, in addition to lysine 246 and lysine 248, respectively.

In some embodiments, when the compound comprising Fc binding unit of the present application is used, a group of interest may be transferred to any one or more selected from lysine 246 (Lys246; K246) and/or lysine 248 (Lys248; K248) of the Fc region of the antibody. In specific embodiments, when the compound comprising Fc binding unit of the present application is used, a group of interest may be transferred to lysine 246 (Lys246; K246) of the Fc region of the antibody. In specific embodiments, when the compound comprising Fc binding unit of the present application is used, a group of interest may be transferred to lysine 248 (Lys248; K248) of the Fc region of the antibody. The site to which the substance of interest is transferred by reaction of the antibody with the compound comprising Fc binding unit may be lysine 246 (Lys246; K246) and/or lysine 248 (Lys248; K248).

Hereinafter, the reaction of the antibody with the compound comprising Fc binding unit of the present application will be described in detail.

Description of Reaction of Antibody with Compound Comprising Fc Binding Unit

A compound comprising Fc binding unit is induced to the Fc region of an antibody by the Fc binding unit. At this time, the effect induced by the Fc binding unit to a specific region of the antibody may be referred to as a proximity effect. When described based on a Fc binding substance, the $Xa^1$ amino acid residue of the Fc binding substance is adjacent to lysine 246 or lysine 248 of the Fc region of an antibody. The reaction of a compound comprising Fc binding unit of the present application with a lysine residue (for example, lysine 246 or lysine 248) of an antibody may be exemplarily described through the following reaction scheme. In the following, see that the lysine residue of the antibody that participates in the reaction is shown separately for illustrative purposes.

[Reaction Scheme 1]

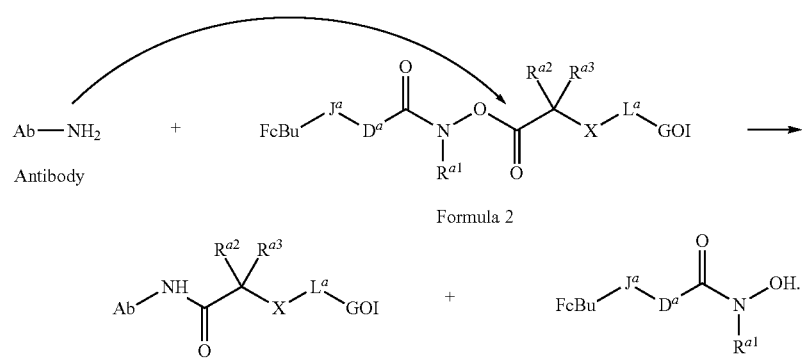

As illustrated in Reaction Scheme 1 above, the reaction of an antibody with a compound comprising Fc binding unit (illustrated as a compound of Formula 2 in the Reaction Scheme above) specifically may be a reaction of a primary amine group (for example, an amino group, —NH$_2$) of the antibody with a carbonyl group of the compound comprising Fc binding unit. For example, the reaction of an antibody with a compound comprising Fc binding unit may be a reaction of the primary amine group of the Fc region of the antibody with the carbonyl group of the compound comprising Fc binding unit. For example, the reaction of an antibody with a compound comprising Fc binding unit may be a reaction of the primary amine group of the lysine residue 246 of the Fc region of the antibody with the carbonyl group of the compound comprising Fc binding unit. For example, the reaction of an antibody with a compound comprising Fc binding unit may be a reaction of the primary amine group of the lysine 248 residue of the Fc region of the antibody with the carbonyl group of the compound comprising Fc binding unit. As shown in Reaction Scheme 1, a group of interest (for example, a bioorthogonal functional group, and the like) is transferred to the antibody through the reaction of the antibody with the compound comprising Fc binding unit.

For example, the reaction of the antibody with the compound comprising Fc binding unit may be referred to as a nucleophilic substitution reaction. At this time, the primary amine group of the antibody may be understood to act as a nucleophile in a nucleophilic substitution reaction. For example, the reaction of the antibody with the compound comprising Fc binding unit may be referred to as an $S_N^2$ reaction. For example, the reaction of the antibody with the compound comprising Fc binding unit may be referred to as an acyl transfer reaction. As such, the terminology used to refer to the reaction is not particularly limited, and the reaction of the antibody with the Fc binding unit may be described through terms that are understandable to those of ordinary skill in the art.

The carbonyl group of the compound comprising Fc binding unit, shown to react with the primary amine group of the antibody in Reaction Scheme 1, is marked separately in formula 2 as follows:

[Chemical Formula 2]

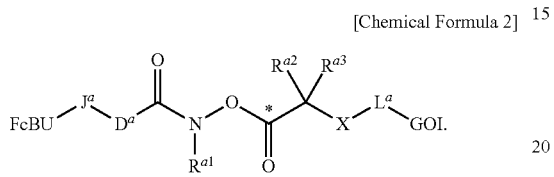

In formula 2, the carbonyl group (—C(=O)—) marked as * indicates the reaction site with the primary amine group of the antibody. In some embodiments, the carbonyl group marked as * may be referred to as the "reactive group with the antibody" or "reaction site with the antibody" or "reactive carbonyl" of the compound comprising Fc binding unit, but is not limited thereto.

Meanwhile, as shown in Reaction Scheme 1, a group comprising Fc binding unit is leaved from a product by the reaction of the antibody with the compound comprising Fc binding unit. As described above, a conjugation using a reaction mechanism in which the Fc binding unit is leaved through a reaction is referred to as traceless cross-linking, traceless reaction, traceless conjugation, or the like. The advantages of the traceless conjugation and the conjugate (for example, antibody conjugate) prepared by such traceless conjugation have been described in detail in previous studies (see the documents [EP 19818561.3, Publication No. EP 3811978; PCT Patent Application No. PCT/KR2020/003282, Publication No. WO2020/184944; and Korean Patent Application No. 10-2020-0009162, Publication No. 10-2020-0091826]). Furthermore, in the document [PCT Patent Application No. PCT/KR2020/003282, Publication No. WO2020/184944], the contents of which are hereby incorporated by reference in their entity, it was confirmed that when the compound comprising Fc binding unit disclosed in the corresponding document was used, norbornene, one of the examples of the group of interest, was transferred to K248 of the Fc region of the antibody.

As shown in Reaction Scheme 1, a group that is leaved from the compound comprising Fc binding unit by the reaction of the antibody with the compound comprising Fc binding unit may be illustratively shown as follows:

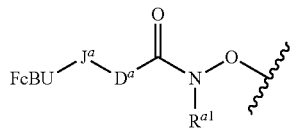

In some embodiments, in the illustrated group which is leaved, —N($R^{a}1$)—O— may be referred to a leaving group, but is not limited thereto.

As shown in Reaction Scheme 1, a group transferred from the compound comprising Fc binding unit to the antibody by the reaction of the antibody with the compound comprising Fc binding unit may be illustratively shown as follows:

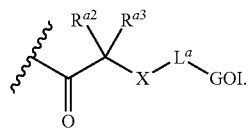

Furthermore, to help understanding, the present application provides a schematic view of the reaction of an antibody with a compound comprising Fc binding unit, using the compound of formula 2-1 as an example of the compound comprising Fc binding unit.

[Reaction Scheme 2]

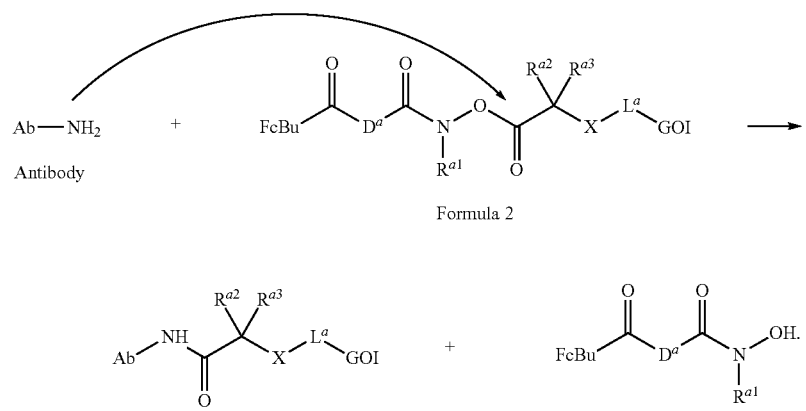

Hereinafter, specific embodiments of the compound comprising Fc binding unit of the present application are disclosed. Meanwhile, the specific embodiments of the compound comprising Fc binding unit of the present application are not limited to the disclosed formulae or structures below, and specific embodiments can be drawn or newly created based on the content of the above-described compound comprising Fc binding unit.

Specific Embodiments of Compound Comprising Fc Binding Unit

As described above, the compound comprising Fc binding unit of the present application may have the structure of formula 2:

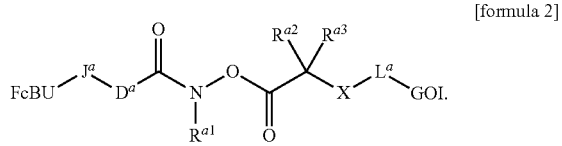

[formula 2]

Hereinafter, specific examples of the compound comprising Fc binding unit of the present application will be described in detail.

Some embodiments of the present application provide a compound of formula 2-1.

In some embodiments, formula 2 may be represented by the following formula 2-1. In formula 2, when $J^a$ is —C(=O)—, formula 2 is represented by the following formula 2-1.

In some embodiments, the compound comprising Fc binding unit of the present application may have the structure of the following formula 2-1:

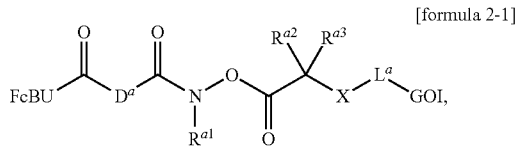

[formula 2-1]

wherein
FcBU is a Fc binding unit,
GOI is a group of interest,
$L^a$ is a linker A,
$D^a$ is a spacer A,
X is C, O, or N (that is, —X— is —CH$_2$—, —O—, or —NH—),
$R^{a1}$ is H or $C_{1-6}$ alkyl,
$R^{a2}$ is H or $C_{1-6}$ alkyl, and
$R^{a3}$ is H or $C_{1-6}$ alkyl.

In formula 2-1, FcBU is a Fc binding unit. The Fc binding unit (FcBU) has been described in detail in previous paragraphs, and is as described in previous paragraphs. For example, the Fc binding unit (FcBU) is as described in the subsections "Overview of compound comprising Fc binding unit of present application" and "Fc binding unit (FcBU)" of the section "Compound comprising Fc binding unit."

In formula 2-1, GOI is a group of interest. The group of interest (GOI) has been described in detail in previous paragraphs, and is as described in previous paragraphs. For example, the group of interest (GOI) is as described in the subsections "Overview of compound comprising Fc binding unit of present application" and "Group of interest (GOI)" of the section "Compound comprising Fc binding unit."

In formula 2-1, $L^a$ is a linker A. The linker A ($L^a$) has been described in detail in previous paragraphs, and is as described in previous paragraphs. For example, the linker ($L^a$) is as described in the subsections "Overview of compound comprising Fc binding unit of present application" and "Linker A (L"a)" of the section "Compound comprising Fc binding unit."

In formula 2-1, $D^a$ is a spacer A. The spacer A ($D^a$) has been described in detail in previous paragraphs, and is as described in previous paragraphs. For example, the spacer A ($D^a$) is as described in the subsections "Overview of compound comprising Fc binding unit of present application" and "Spacer A (D"a)" of the section "Compound comprising Fc binding unit."

Some embodiments of the present application provide a compound of formula 2-2.

In some embodiments, formula 2 may be represented by the following formula 2-2. In formula 2, when the group of interest (GOI) is a reactive group (RG), formula 2 is represented by the following formula 2-2.

In some embodiments, the compound comprising Fc binding unit of the present application may have the structure of the following formula 2-2:

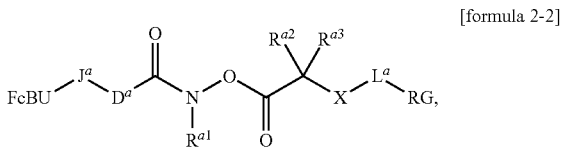

[formula 2-2]

wherein
FcBU is a Fc binding unit,
RG is a reactive group,
$L^a$ is a linker A,
$D^a$ is a spacer A,
X is C, O, or N (that is, —X— is —CH$_2$—, —O—, or —NH—),
$J^a$ is —C(=O)—, —S—, —NH—, or —C(=NH)—,
$R^{a1}$ is H or $C_{1-6}$ alkyl,
$R^{a2}$ is H or $C_{1-6}$ alkyl, and
$R^{a3}$ is H or $C_{1-6}$ alkyl.

In formula 2-2, FcBU is a Fc binding unit. The Fc binding unit (FcBU) has been described in detail in the previous paragraphs, and is as described in previous paragraphs. For example, the Fc binding unit (FcBU) is as described in the subsections "Overview of compound comprising Fc binding unit of present application" and "Fc binding unit (FcBU)" of the section "Compound comprising Fc binding unit."

In formula 2-2, RG is a reactive group. The reactive group (RG) has been described in detail in the previous paragraphs, and is as described in previous paragraphs. For example, the reactive group (RG) is as described in the subsections "Overview of compound comprising Fc binding unit of present application" and "Group of interest (GOI)" of the section "Compound comprising Fc binding unit."

In formula 2-2, $L^a$ is a linker A. The linker A ($L^a$) has been described in detail in previous paragraphs, and is as described in previous paragraphs. For example, the linker ($L^a$) is as described in the subsections "Overview of compound comprising Fc binding unit of present application" and "Linker A (L"a)" of the section "Compound comprising Fc binding unit."

In formula 2-2, $D^a$ is a spacer A. The spacer A ($D^a$) has been described in detail in previous paragraphs, and is as described in previous paragraphs. For example, the spacer A ($D^a$) is as described in the subsections "Overview of compound comprising Fc binding unit of present application" and "Spacer A (D"a)" of the section "Compound comprising Fc binding unit."

Some embodiments of the present application provide a compound of formula 2-3.

In some embodiments, formula 2 may be represented by the following formula 2-3. In formula 2, when the group of interest (GOI) is a reactive group (RG), and at this time, when the reactive group is

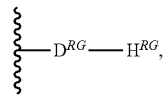

formula 2 is represented by the following formula 2-3.

In some embodiments, the compound comprising Fc binding unit of the present application may have the structure of the following formula 2-3:

[formula 2-3]

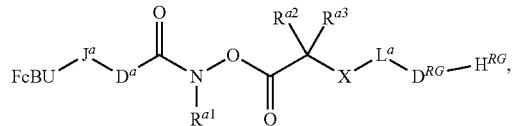

wherein
FcBU is a Fc binding unit,
$H^{RG}$ is a reactive moiety,
$D^{RG}$ is a spacer of the reactive group (spacer RG),
$L^a$ is a linker A,
$D^a$ is a spacer A,
X is C, O, or N (that is, —X— is —CH$_2$—, —O—, or —NH—),
$J^a$ is —C(=O)—, —S—, —NH—, or —C(=NH)—,
$R^{a1}$ is H or $C_{1-6}$ alkyl,
$R^{a2}$ is H or $C_{1-6}$ alkyl, and
$R^{a3}$ is H or $C_{1-6}$ alkyl.

In formula 2-3, FcBU is a Fc binding unit. The Fc binding unit (FcBU) has been described in detail in the previous paragraphs, and is as described in the previous paragraphs. For example, the Fc binding unit (FcBU) is as described in the subsections "Overview of compound comprising Fc binding unit of present application" and "Fc binding unit (FcBU)" of the section "Compound comprising Fc binding unit."

In formula 2-3, $H^{RG}$ is the reactive moiety. The reactive moiety ($H^{RG}$) has been described in detail in the previous paragraphs, and is as described in the previous paragraphs. For example, the reactive moiety is as described in the subsections "Overview of compound comprising Fc binding unit of present application" and "Group of interest (GOI)" of the section "Compound comprising Fc binding unit."

In formula 2-3, $D^{RG}$ is a spacer of the reactive group. The spacer of the reactive group ($D^{RG}$) has been described in detail in previous paragraphs, and is as described in previous paragraphs. For example, the spacer of the reactive group is as described in the subsections "Overview of compound comprising Fc binding unit of present application" and "Group of interest (GOI)" of the section "Compound comprising Fc binding unit."

In formula 2-3, $L^a$ is a linker A. The linker A ($L^a$) has been described in detail in previous paragraphs, and is as described in previous paragraphs. For example, the linker ($L^a$) is as described in detail in the subsections "Overview of compound comprising Fc binding unit of present application" and "Linker A (L"a)" of the section "Compound comprising Fc binding unit."

In formula 2-3, $D^a$ is a spacer A. The spacer A ($D^a$) has been described in detail in previous paragraphs, and is as described in previous paragraphs. For example, the spacer A ($D^a$) is as described in the subsections "Overview of compound comprising Fc binding unit of present application" and "Spacer A (D"a)" of the section "Compound comprising Fc binding unit."

Some embodiments of the present application provide a compound of formula 2-4.

In some embodiments, formula 2 may be represented by the following formula 2-4. In formula 2, when $J^a$ is —C(=O)—, the spacer A ($D^a$) is unsubstituted $C_{1-10}$ alkylene, and $R^{a3}$ is H, formula 2 is represented by the following formula 2-4.

In some embodiments, the compound comprising Fc binding unit of the present application may have the structure of the following formula 2-4:

[formula 2-4]

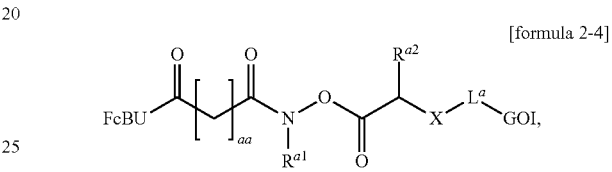

wherein
aa is an integer of 1 to 10,
FcBU is a Fc binding unit,
GOI is a group of interest,
$L^a$ is a linker A,
X is C or O (that is, —X— is —CH$_2$— or —O—),
$R^{a1}$ is H or $C_{1-6}$ alkyl, and
$R^{a2}$ is H or $C_{1-6}$ alkyl.

In formula 2-4, FcBU is a Fc binding unit. The Fc binding unit (FcBU) has been described in detail in the previous paragraphs, and is as described in previous paragraphs. For example, the Fc binding unit (FcBU) is as described in the subsections "Overview of compound comprising Fc binding unit of present application" and "Fc binding unit (FcBU)" of the section "Compound comprising Fc binding unit."

In formula 2-4, GOI is a group of interest. The group of interest (GOI) has been described in detail in the previous paragraphs, and is as described in previous paragraphs. For example, the group of interest (GOI) is as described in the subsections "Overview of compound comprising Fc binding unit of present application" and "Group of interest (GOI)" of the section "Compound comprising Fc binding unit."

In formula 2-4, $L^a$ is a linker A. The linker A ($L^a$) has been described in detail in the previous paragraphs, and is as described in previous paragraphs. For example, the linker ($L^a$) is as described in the subsections "Overview of compound comprising Fc binding unit of present application" and "Linker A (L"a)" of the section "Compound comprising Fc binding unit."

Some embodiments of the present application provide a compound of formula 2-5.

In some embodiments, formula 2 may be represented by the following formula 2-5.

In some embodiments, the compound comprising Fc binding unit of the present application may have the structure of the following formula 2-5:

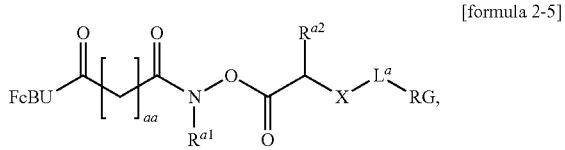

[formula 2-5]

wherein aa is an integer of 1 to 10,

FcBU is a Fc binding unit,

RG is a reactive group, $L^a$ is a linker A,

X is C or O (that is, —X— is —$CH_2$— or —O—), $R^{a1}$ is H or $C_{1-6}$ alkyl, and $R^{a2}$ is H or $C_{1-6}$ alkyl.

In formula 2-5, FcBU is a Fc binding unit. FcBU is as described in previous paragraphs. For example, the FcBU is as described in the subsections "Overview of compound comprising Fc binding unit of present application" and "Fc binding unit (FcBU)" of the section "Compound comprising Fc binding unit."

In specific embodiments, the FcBU may have the following structure:

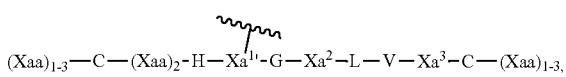

wherein each of Xaa is independently any amino acid residue other than a cysteine residue, $Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue, $Xa^2$ is glutamic acid residue or asparagine residue, and $Xa^3$ is tryptophan residue, naphthylalanine residue, or phenylalanine residue, in the structure, a cysteine residue adjacent to the N-terminus (that is, a cysteine residue located 2 to 4 amino acids from the N-terminus) and a cysteine residue adjacent to the C-terminus (that is, a cysteine residue located 2 to 4 amino acids from the C-terminus) may optionally be covalently linked.

For example, a cysteine residue adjacent to the N-terminus and a cysteine residue adjacent to the C-terminus may optionally be linked through a disulfide bond.

In specific embodiments, Fc binding unit may have the following structure:

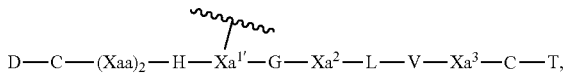

wherein each of Xaa is independently any amino acid other than cysteine, $Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue, $Xa^2$ is glutamic acid residue or asparagine residue, $Xa^3$ is tryptophan residue, naphthylalanine residue, or phenylalanine residue, and wherein, the cysteine residue adjacent to the N-terminus and the cysteine residue adjacent to the C-terminus are optionally be linked covalently (for example, through a disulfide bond).

In specific embodiments, Fc binding unit may have the following structure:

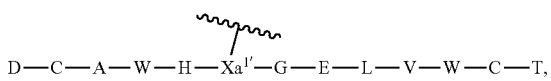

wherein $Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue.

In formula 2-5, RG is a reactive group. RG is as described in previous paragraphs. For example, RG is as described in the subsections "Overview of compound comprising Fc binding unit of present application" and "Group of interest (GOI)" of the section "Compound comprising Fc binding unit."

In specific embodiments, RG may comprise a reactive moiety.

In specific embodiments, RG may comprise a reactive moiety, and the sum of the atomic masses of all atoms constituting the RG may be 3000 dalton or less, 2500 dalton or less, 2000 dalton or less, 1500 dalton or less, 1000 dalton or less, 900 dalton or less, 800 dalton or less, 700 dalton or less, 600 dalton or less, 500 dalton or less, 400 dalton or less, 300 dalton or less, 200 dalton or less, or 100 dalton or less.

In specific embodiments, the RG may have the following structure:

wherein $D^{RG}$ is a spacer of the reactive group (spacer R), and $H^{RG}$ is the reactive moiety.

In specific embodiments, $D^{RG}$ may be a bond, or substituted or unsubstituted $C_{1-6}$ alkylene, substituted or unsubstituted $C_{1-6}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be selected from O, N, and S. In specific embodiments, $D^{RG}$ may be a bond, or substituted or unsubstituted $C_{1-3}$ alkylene, substituted or unsubstituted $C_{1-3}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be independently selected from O, N, and S.

In formula 2-5, $L^a$ is a linker A. The linker A is as described in the previous paragraphs. For example, the $L^a$ is as described in the subsections "Overview of compound comprising Fc binding unit of present application" and "Linker A (L"a)" of the section "Compound comprising Fc binding unit."

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be selected from O, N, and S.

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be O.

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be O, and the heteroalkylene may comprise 0 to 20 of ethyleneglycol units.

In specific embodiments, the linker A may be a bond, unsubstituted $C_{1-50}$ alkylene, or unsubstituted $C_{1-50}$ heteroalkylene, wherein the heteroalkylene comprises one or more heteroatoms, wherein each of the heteroatoms may be O, and the heteroalkylene may comprise 0 to 16 of ethyleneglycol units.

In specific embodiments, the linker A may be a bond, unsubstituted $C_{1-30}$ alkylene, or unsubstituted $C_{1-30}$ heteroalkylene, wherein the heteroalkylene comprises one or more heteroatoms, wherein each of the heteroatoms may be O, and the heteroalkylene may comprise 0 to 10 of ethyleneglycol units.

In specific embodiments, the linker A may be a bond, unsubstituted $C_{1-25}$ alkylene, or unsubstituted $C_{1-25}$ heteroalkylene, wherein the heteroalkylene comprises one or more heteroatoms, wherein each of the heteroatoms may be O, and the heteroalkylene may comprise 0 to 8 of ethyleneglycol units.

In specific embodiments, the linker A may be a bond, unsubstituted $C_{1-15}$ alkylene, or unsubstituted $C_{1-15}$ heteroalkylene, wherein the heteroalkylene comprises one or more heteroatoms, wherein each of the heteroatoms may be O, and the heteroalkylene may comprise 0 to 5 of ethyleneglycol units.

In specific embodiments, the linker A may be a bond, or unsubstituted $C_{1-6}$ alkylene.

In specific embodiments, the linker A may be a bond or unsubstituted $C_{1-3}$ alkylene.

Some embodiments of the present application provide a compound of formula 2-6.

In some embodiments, formula 2 may be represented by the following formula 2-6.

In some embodiments, the compound comprising Fc binding unit of the present application may have the structure of the following formula 2-6:

[formula 2-6]

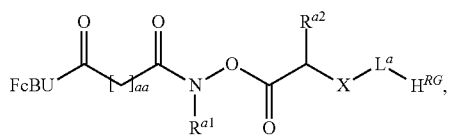

wherein
aa is an integer of 1 to 10,
FcBU is a Fc binding unit,
$H^{RG}$ is the reactive moiety,
$L^a$ is a linker A,
X is C or O (that is, —X— is —CH$_2$— or —O—),
$R^{a1}$ is H or $C_{1-6}$ alkyl, and
$R^{a2}$ is H or $C_{1-6}$ alkyl.

In formula 2-6, FcBU is a Fc binding unit. The Fc binding unit is as described in the previous paragraphs. For example, the FcBU is as described in the subsections "Overview of compound comprising Fc binding unit of present application" and "Fc binding unit (FcBU)" of the section "Compound comprising Fc binding unit."

In specific embodiments, the FcBU may have the following structure:

$(Xaa)_{1-3}$—C—$(Xaa)_2$—H—$Xa^{1'}$—G—$Xa^2$—L—V—$Xa^3$—C—$(Xaa)_{1-3}$, wherein
each of Xaa is independently any amino acid residue rather than a cysteine residue,
$Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue,
$Xa^2$ is glutamic acid residue or asparagine residue,
$Xa^3$ is tryptophan residue, naphthylalanine residue, or phenylalanine residue,
in the structure, a cysteine residue adjacent to the N-terminus (that is, a cysteine residue located 2 to 4 amino acids from the N-terminus) and a cysteine residue adjacent to the C-terminus (that is, a cysteine residue located 2 to 4 amino acids from the C-terminus) may optionally be covalently linked.

For example, a cysteine residue adjacent to the N-terminus and a cysteine residue adjacent to the C-terminus may optionally be linked through a disulfide bond.

In specific embodiments, Fc binding unit may have the following structure:

D—C—$(Xaa)_2$—H—$Xa^{1'}$—G—$Xa^2$—L—V—$Xa^3$—C—T, wherein
each of Xaa is independently any amino acid other than cysteine,
$Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue,
$Xa^2$ is glutamic acid residue or asparagine residue, and
$Xa^3$ is tryptophan residue, naphthylalanine residue, or phenylalanine residue.

At this time, a cysteine residue adjacent to the N-terminus and a cysteine residue adjacent to the C-terminus may optionally be covalently linked (for example, through a disulfide bond).

In specific embodiments, Fc binding unit may have the following structure:

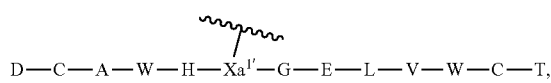

D—C—A—W—H—Xa¹'—G—E—L—V—W—C—T, wherein

Xa¹' is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue.

In formula 2-6, $H^{RG}$ is the reactive moiety. The reactive moiety is as described in previous paragraphs. For example, $H^{RG}$ is as described in the subsections "Overview of compound comprising Fc binding unit of present application" and "Group of interest (GOI)" of the section "Compound comprising Fc binding unit."

In specific embodiments,

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be independently selected from O, N, and S.

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be O.

In specific embodiments, the linker A may be a bond, unsubstituted $C_{1-60}$ alkylene, or unsubstituted $C_{1-60}$ heteroalkylene, wherein the heteroalkylene comprises one or more heteroatoms, wherein each of the heteroatoms may be O, and the heteroalkylene may comprise 0 to 20 of ethyleneglycol units.

In specific embodiments, the linker A may be a bond, unsubstituted $C_{1-50}$ alkylene, or unsubstituted $C_{1-50}$ heteroalkylene, wherein the heteroalkylene comprises one or more heteroatoms, wherein each of the heteroatoms may be O, and the heteroalkylene may comprise 0 to 16 of ethyleneglycol units.

In specific embodiments, the linker A may be a bond, unsubstituted $C_{1-30}$ alkylene, or unsubstituted $C_{1-30}$ heteroalkylene, wherein the heteroalkylene comprises one or more heteroatoms, wherein each of the heteroatoms may be O, and the heteroalkylene may comprise 0 to 10 of ethyleneglycol units.

In specific embodiments, the linker A may be a bond, unsubstituted $C_{1-25}$ alkylene, or unsubstituted $C_{1-25}$ heteroalkylene, wherein the heteroalkylene comprises one or more heteroatoms, wherein each of the heteroatoms may be O, and the heteroalkylene may comprise 0 to 8 of ethyleneglycol units.

In specific embodiments, the linker A may be a bond, unsubstituted $C_{1-15}$ alkylene, or unsubstituted $C_{1-15}$ heteroalkylene, wherein the heteroalkylene comprises one or more heteroatoms, wherein each of the heteroatoms may be O, and the heteroalkylene may comprise 0 to 5 of ethyleneglycol units.

In specific embodiments, the linker A may be a bond, or unsubstituted $C_{1-6}$ alkylene.

In specific embodiments, the linker A may be a bond or unsubstituted $C_{1-3}$ alkylene.

In specific embodiments, $R^{a1}$ may be $C_{1-3}$ alkyl. In specific embodiments, $R^{a2}$ may be H or $C_{1-3}$ alkyl.

Some embodiments of the present application provide a compound of formula 2-7.

In some embodiments, formula 2 may be represented by the following formula 2-7.

In some embodiments, the compound comprising Fc binding unit of the present application may have the structure of the following formula 2-7:

[formula 2-7]

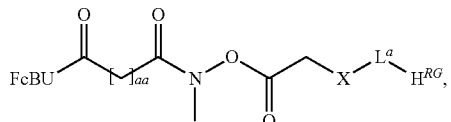

wherein
aa is an integer of 1 to 10,
FcBU is a Fc binding unit,
$H^{RG}$ is a reactive moiety,
$L^a$ is a linker A, and
X is C or O.

In formula 2-7, FcBU is a Fc binding unit. The Fc binding unit is as described in the previous paragraphs. For example, the FcBU is as described in the subsections "Overview of compound comprising Fc binding unit of present application" and "Fc binding unit (FcBU)" of the section "Compound comprising Fc binding unit."

In specific embodiments, the FcBU may have the following structure:

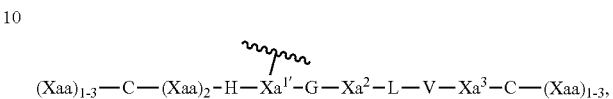

wherein
each of Xaa is independently any amino acid residue rather than a cysteine residue,
$Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue,
$Xa^2$ is glutamic acid residue or asparagine residue, and
$Xa^3$ is tryptophan residue, naphthylalanine residue, or phenylalanine residue,
in the structure, a cysteine residue adjacent to the N-terminus (that is, a cysteine residue located 2nd to 4th from the N-terminus) and a cysteine residue adjacent to the C-terminus (that is, a cysteine residue located 2nd to 4th from the C-terminus) may optionally be covalently linked.

For example, a cysteine residue adjacent to the N-terminus and a cysteine residue adjacent to the C-terminus may optionally be linked through a disulfide bond.

In specific embodiments, Fc binding unit may have the following structure:

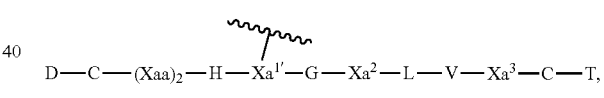

wherein
each of Xaa is independently any amino acid other than cysteine,
$Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue,
$Xa^2$ is glutamic acid residue or asparagine residue, and
$Xa^3$ is tryptophan residue, naphthylalanine residue, or phenylalanine residue, and
wherein, a cysteine residue adjacent to the N-terminus and a cysteine residue adjacent to the C-terminus are optionally be linked covalently (for example, through a disulfide bond).

In specific embodiments, Fc binding unit may have the following structure:

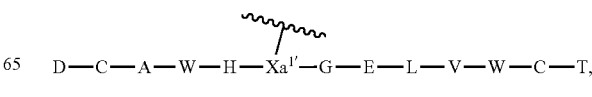

wherein

Xa$^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue.

In formula 2-7, H$^{RG}$ is the reactive moiety. The reactive moiety is as described in previous paragraphs. For example, H$^{RG}$ is as described in the subsections "Overview of compound comprising Fc binding unit of present application" and "Group of interest (GOI)" of the section "Compound comprising Fc binding unit."

In specific embodiments, H$^{RG}$ may be a bio-orthogonal functional group.

In specific embodiments, H$^{RG}$ may have any one of the following structures:

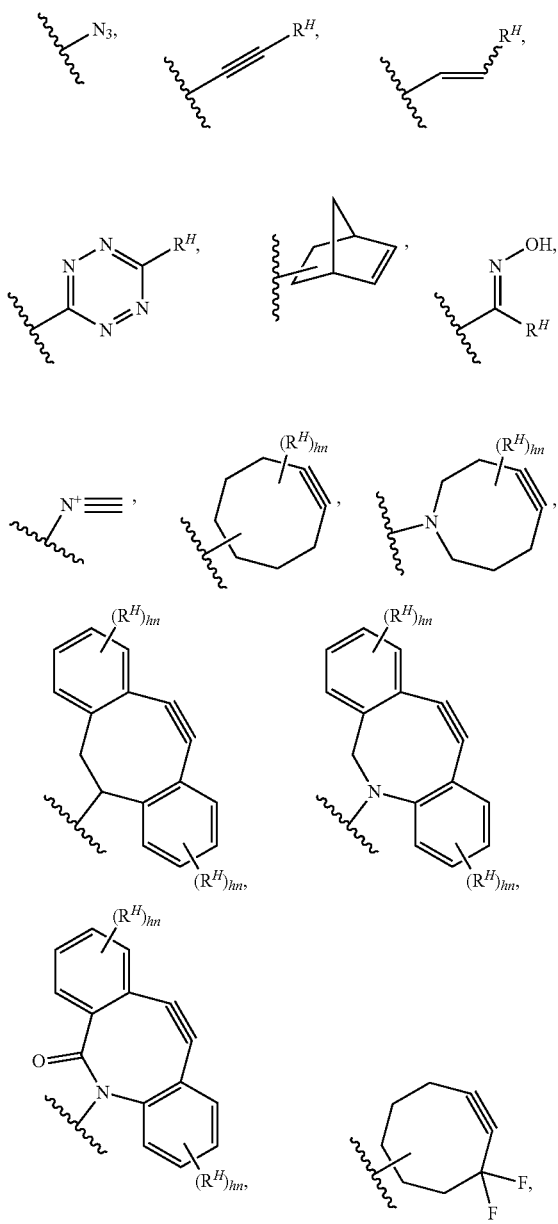

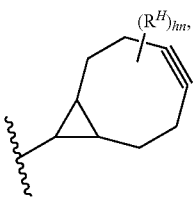

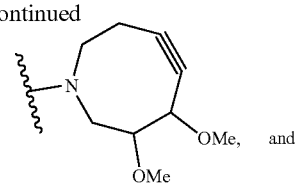

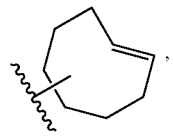

wherein hn is an integer of 1 to 3, and

R$^H$ may be each independently H or selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein R is each independently selected from H, halogen, C$_{1-6}$alkyl, C$_{3-10}$ cycloalkyl, C$_{3-10}$ heterocycloalkyl, aryl, heteroaryl, —OH, —NH$_2$, =O, =S, and —SH.

In specific embodiments, H$^{RG}$ may be selected from azide group, terminal alkyne group, terminal alkene group, cyclic alkyne (for example, cyclooctyne) group, tetrazine group, norbornene group, cycloalkene (for example, cyclooctene) group, oxime group, and isocyanide group. Here, cyclooctyne may be any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), but not limited thereto. Here, the cyclooctene, for example, may be selected from cis-cyclooctene group and trans-cyclooctene group.

In specific embodiments, H$^{RG}$ may be an azide group or a norbornene group.

In specific embodiments, H$^{RG}$ may be a click chemistry functional group.

In specific embodiments, H$^{RG}$ may be selected from a Diels-Alder diene, a Diels-Alder dienophile, an IEDDA diene, and an IEDDA dienophile.

In formula 2-7, L$^a$ is a linker A. The linker A is as described in the previous paragraphs. For example, the L$^a$ is as described in the subsections "Overview of compound comprising Fc binding unit of present application" and "Linker A (L"a)" of the section "Compound comprising Fc binding unit."

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be independently selected from O, N, and S.

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be O.

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be O, and the heteroalkylene may comprise 0 to 20 of ethyleneglycol units.

In specific embodiments, the linker A may be a bond, unsubstituted $C_{1-50}$ alkylene, or unsubstituted $C_{1-50}$ heteroalkylene, wherein the heteroalkylene comprises one or more heteroatoms, wherein each of the heteroatoms may be O, and the heteroalkylene may comprise 0 to 16 of ethyleneglycol units.

In specific embodiments, the linker A may be a bond, unsubstituted $C_{1-30}$ alkylene, or unsubstituted $C_{1-30}$ heteroalkylene, wherein the heteroalkylene comprises one or more heteroatoms, wherein each of the heteroatoms may be O, and the heteroalkylene may comprise 0 to 10 of ethyleneglycol units.

In specific embodiments, the linker A may be a bond, unsubstituted $C_{1-25}$ alkylene, or unsubstituted $C_{1-25}$ heteroalkylene, wherein the heteroalkylene comprises one or more heteroatoms, wherein each of the heteroatoms may be O, and the heteroalkylene may comprise 0 to 8 of ethyleneglycol units.

In specific embodiments, the linker A may be a bond, unsubstituted $C_{1-15}$ alkylene, or unsubstituted $C_{1-15}$ heteroalkylene, wherein the heteroalkylene comprises one or more heteroatoms, wherein each of the heteroatoms may be O, and the heteroalkylene may comprise 0 to 5 of ethyleneglycol units.

In specific embodiments, the linker A may be a bond, or unsubstituted $C_{1-6}$ alkylene.

In specific embodiments, the linker A may be a bond or unsubstituted $C_{1-3}$ alkylene.

Hereinafter, specific examples of the compound comprising Fc binding unit of the present application will be additionally illustrated. The description for each element of the Fc binding unit is described in detail in previous paragraphs, and the description for each element is as described above.

Some embodiments of the present application provide a compound of formula 2-8.

In some embodiments, formula 2 may be represented by the following formula 2-8.

In some embodiments, the compound comprising Fc binding unit of the present application may have the structure of the following formula 2-8:

[formula 2-8]

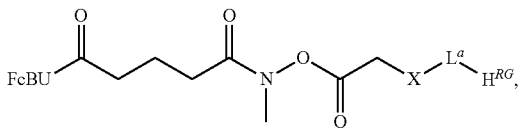

wherein
FcBU is a Fc binding unit,
$H^{RG}$ is a reactive moiety,
$L^{a}$ is a linker A, and
X is C or O.

In specific embodiments, the FcBU may have the following structure:

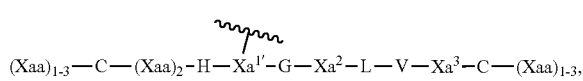

wherein
each of Xaa is independently any amino acid residue other than a cysteine residue, $Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue, $Xa^{2}$ is glutamic acid residue or asparagine residue, and $Xa^{3}$ is tryptophan residue, naphthylalanine residue, or phenylalanine residue, in the structure, a cysteine residue adjacent to the N-terminus (that is, a cysteine residue located 2 to 4 amino acids from the N-terminus) and a cysteine residue adjacent to the C-terminus (that is, a cysteine residue located 2 to 4 amino acids from the C-terminus) may optionally be covalently linked.

For example, a cysteine residue adjacent to the N-terminus and a cysteine residue adjacent to the C-terminus may optionally be linked through a disulfide bond.

In specific embodiments, Fc binding unit may have the following structure:

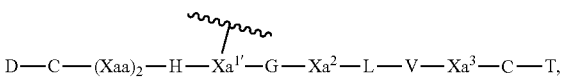

wherein
each of Xaa is independently any amino acid other than cysteine, $Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue, $Xa^{2}$ is glutamic acid residue or asparagine residue, and $Xa^{3}$ is tryptophan residue, naphthylalanine residue, or phenylalanine residue, and at this time, a cysteine residue adjacent to the N-terminus and a cysteine residue adjacent to the C-terminus are optionally be linked covalently (for example, through a disulfide bond).

In specific embodiments, Fc binding unit may have the following structure:

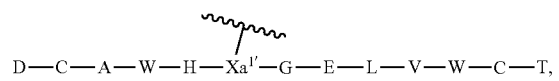

wherein
$Xa^{1'}$ is conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, or conjugated 2-aminosuberic acid residue.

In specific embodiments, $H^{RG}$ may be a bio-orthogonal functional group.

In specific embodiments, $H^{RG}$ may have the structure of any one of the following structures:

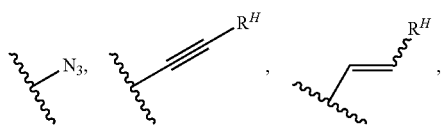

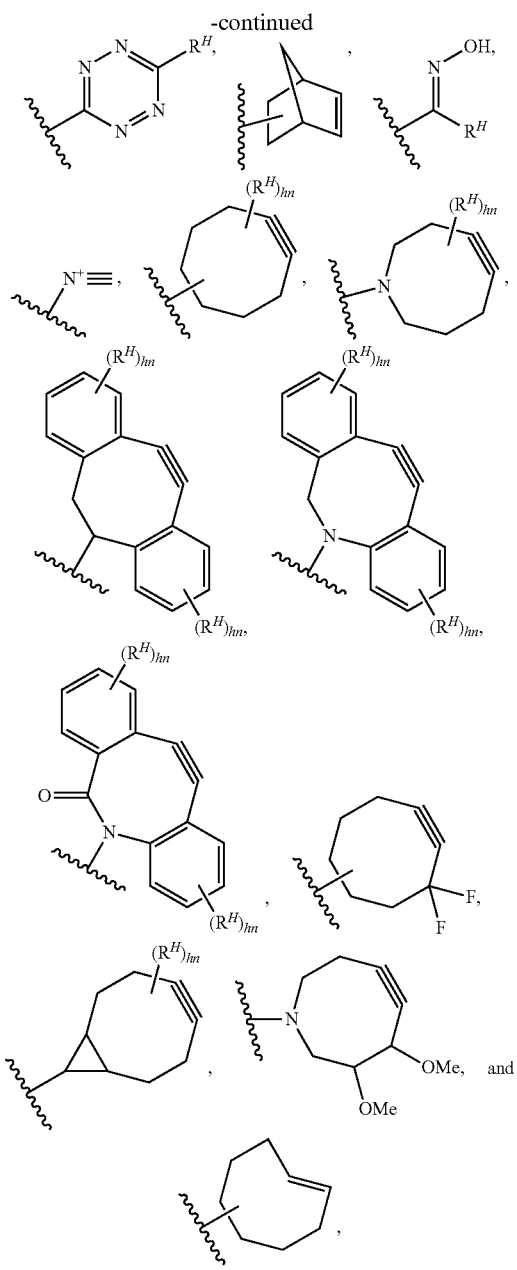

wherein hn is an integer of 1 to 3, and $R^H$ may be each independently, H or selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein R is each independently selected from H, halogen, C$_{1-6}$alkyl, C$_{3-10}$ cycloalkyl, C$_{3-10}$ heterocycloalkyl, aryl, heteroaryl, —OH, —NH$_2$, =O, =S, and —SH.

In specific embodiments, $H^{RG}$ may be selected from azide group, terminal alkyne group, terminal alkene group, cyclic alkyne (for example, cyclooctyne) group, tetrazine group, norbornene group, cycloalkene (for example, cyclooctene) group, oxime group, and isocyanide group. Here, cyclooctyne may be any one selected from OCT cyclooctyne, Bicyclononyne (BCN), Dibenzocyclooctyne (DBCO), aza-dibenzocyclooctynes (DIBAC), dibenzocyclooctynol (DIBO), difluorinated cyclooctynes (DIFO), biarylazacy-clooctynone (BARAC), dim ethoxyazacyclooctyne (DI-MAC) and difluorobenzocyclooctyne (DIFBO), but not limited thereto. Here, the cyclooctene, for example, may be selected from cis-cyclooctene group and trans-cyclooctene group.

In specific embodiments, $H^{RG}$ may be an azide group or a norbornene group.

In specific embodiments, $H^{RG}$ may be a click chemistry functional group.

In specific embodiments, $H^{RG}$ may be selected from a Diels-Alder diene, a Diels-Alder dienophile, an IEDDA diene, and an IEDDA dienophile.

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be selected from O, N, and S.

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be O.

In specific embodiments, the linker A may be a bond, unsubstituted C$_{1-60}$ alkylene, or unsubstituted C$_{1-60}$ heteroalkylene, wherein the heteroalkylene comprises one or more heteroatoms, wherein each of the heteroatoms may be O, and the heteroalkylene may comprise 0 to 20 of ethyleneglycol units.

In specific embodiments, the linker A may be a bond, unsubstituted C$_{1-50}$ alkylene, or unsubstituted C$_{1-50}$ heteroalkylene, wherein the heteroalkylene comprises one or more heteroatoms, wherein each of the heteroatoms may be O, and the heteroalkylene may comprise 0 to 16 of ethyleneglycol units.

In specific embodiments, the linker A may be a bond, unsubstituted C$_{1-30}$ alkylene, or unsubstituted C$_{1-30}$ heteroalkylene, wherein the heteroalkylene comprises one or more heteroatoms, wherein each of the heteroatoms may be O, and the heteroalkylene may comprise 0 to 10 of ethyleneglycol units.

In specific embodiments, the linker A may be a bond, unsubstituted C$_{1-25}$ alkylene, or unsubstituted C$_{1-25}$ heteroalkylene, wherein the heteroalkylene comprises one or more heteroatoms, wherein each of the heteroatoms may be O, and the heteroalkylene may comprise 0 to 8 of ethyleneglycol units.

In specific embodiments, the linker A may be a bond, unsubstituted C$_{1-15}$ alkylene, or unsubstituted C$_{1-15}$ heteroalkylene, wherein the heteroalkylene comprises one or more heteroatoms, wherein each of the heteroatoms may be O, and the heteroalkylene may comprise 0 to 5 of ethyleneglycol units.

In specific embodiments, the linker A may be a bond, or unsubstituted C$_{1-6}$ alkylene.

In specific embodiments, the linker A may be a bond or unsubstituted C$_{1-3}$ alkylene.

Hereinafter, specific examples of the compound comprising Fc binding unit of the present application will be additionally shown, and specific examples of the compound comprising Fc binding unit are not limited to the structures provided below. The description for each element of the Fc binding unit is described in detail in previous paragraphs, and the description for each element is as described above.

Some embodiments of the present application provide a compound of formula 2-9.

In some embodiments, formula 2 may be represented by the following formula 2-9.

In some embodiments, the compound comprising Fc binding unit of the present application may have the structure of the following formula 2-9:

[formula 2-9]

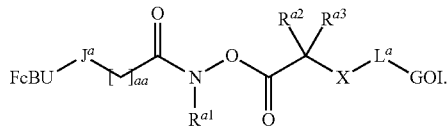

Some embodiments of the present application provide a compound of formula 2-10.

In some embodiments, formula 2 may be represented by the following formula 2-10.

In some embodiments, the compound comprising Fc binding unit of the present application may have the structure of the following formula 2-10:

[formula 2-10]

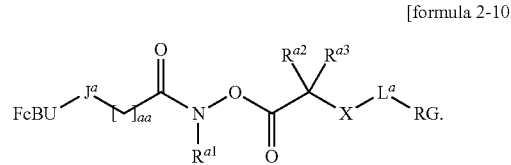

Some embodiments of the present application provide a compound of formula 2-11.

In some embodiments, formula 2 may be represented by the following formula 2-11.

In some embodiments, the compound comprising Fc binding unit of the present application may have the structure of the following formula 2-11:

[formula 2-11]

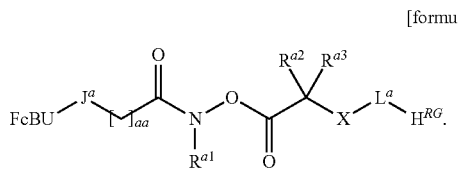

Some embodiments of the present application provide a compound of formula 2-12.

In some embodiments, formula 2 may be represented by the following formula 2-12.

In some embodiments, the compound comprising Fc binding unit of the present application may have the structure of the following formula 2-12:

[formula 2-12]

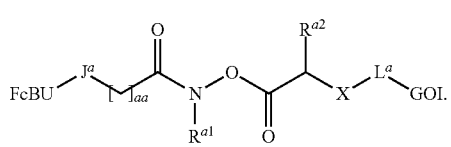

Some embodiments of the present application provide a compound of formula 2-13.

In some embodiments, formula 2 may be represented by the following formula 2-13.

In some embodiments, the compound comprising Fc binding unit of the present application may have the structure of the following formula 2-13:

[formula 2-13]

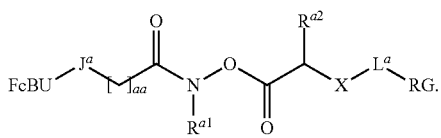

Some embodiments of the present application provide a compound of formula 2-14.

In some embodiments, formula 2 may be represented by the following formula 2-14.

In some embodiments, the compound comprising Fc binding unit of the present application may have the structure of the following formula 2-14:

[formula 2-14]

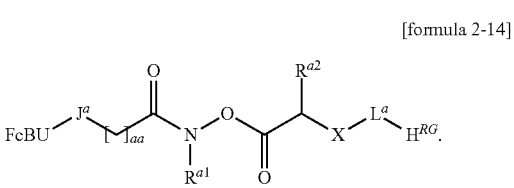

Some embodiments of the present application provide a compound of formula 2-15.

In some embodiments, formula 2 may be represented by the following formula 2-15.

In some embodiments, the compound comprising Fc binding unit of the present application may have the structure of the following formula 2-15:

[formula 2-15]

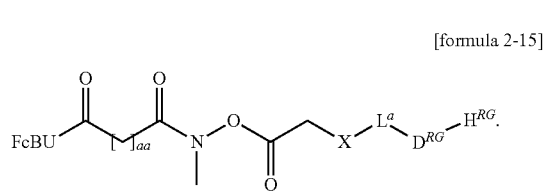

Some embodiments of the present application provide a compound of formula 2-16.

In some embodiments, formula 2 may be represented by the following formula 2-16.

In some embodiments, the compound comprising Fc binding unit of the present application may have the structure of the following formula 2-16:

[formula 2-16]

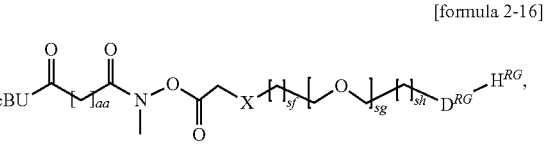

wherein sf is an integer of 0 to 8, sg is an integer of 0 to 15, and sh is an integer of 0 to 8.

Some embodiments of the present application provide a compound of formula 2-17.

In some embodiments, formula 2 may be represented by the following formula 2-17.

In some embodiments, the compound comprising Fc binding unit of the present application may have the structure of the following formula 2-17:

[formula 2-17]

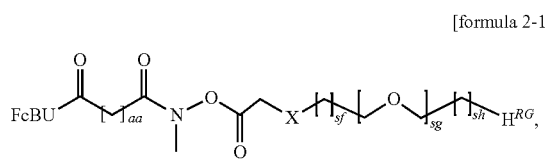

wherein
sf is an integer of 0 to 8,
sg is an integer of 0 to 15, and
sh is an integer of 0 to 8.

Some embodiments of the present application provide a compound of formula 2-18.

In some embodiments, formula 2 may be represented by the following formula 2-18.

In some embodiments, the compound comprising Fc binding unit of the present application may have the structure of the following formula 2-18:

[formula 2-18]

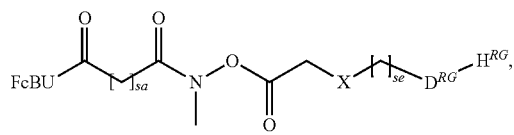

wherein
sa is an integer of 1 to 6, and
se is an integer of 0 to 15.

Some embodiments of the present application provide a compound of formula 2-19.

In some embodiments, formula 2 may be represented by the following formula 2-19.

In some embodiments, the compound comprising Fc binding unit of the present application may have the structure of the following formula 2-19:

[formula 2-19]

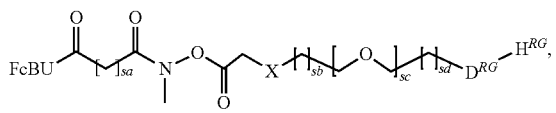

wherein
sa is an integer of 1 to 6,
sb is an integer of 0 to 3,
sc is an integer of 1 to 15, and
sd is an integer of 0 to 3.

Hereinafter, specific structures that a compound comprising Fc binding unit can have will be shown. The following formulae will be understood as specific examples that the compound comprising Fc binding unit of the present application can take, and the scope of the compound comprising Fc binding unit provided by the present application is not to be construed as limited to the following examples.

In some embodiments, the compound comprising Fc binding unit may have any one structure of the structures of the following formulae:

[formula 2-20]

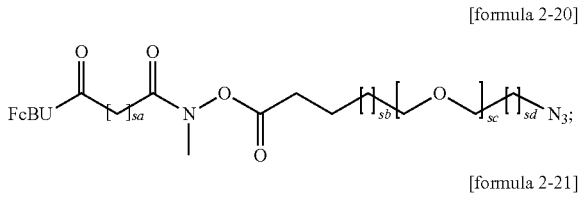

[formula 2-21]

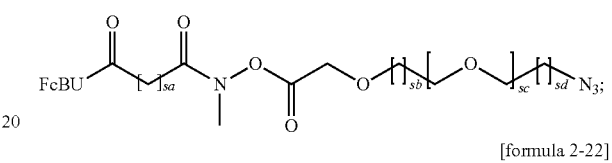

[formula 2-22]

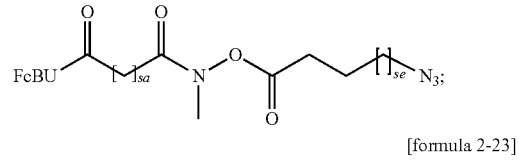

[formula 2-23]

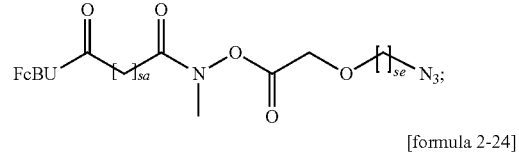

[formula 2-24]

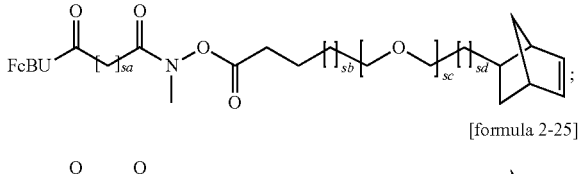

[formula 2-25]

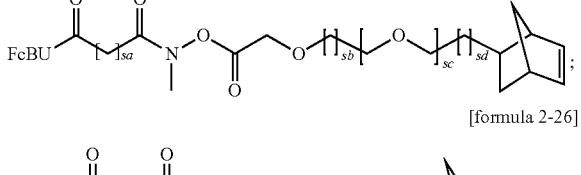

[formula 2-26]

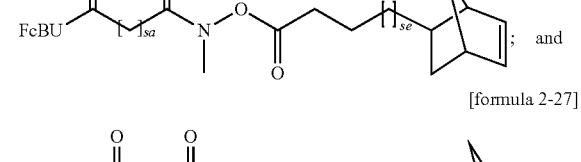

; and

[formula 2-27]

wherein
sa is an integer of 1 to 6,
sb is an integer of 0 to 3,
sc is an integer of 1 to 15,
sd is an integer of 0 to 3,
se is an integer of 0 to 15, FcBU has a structure

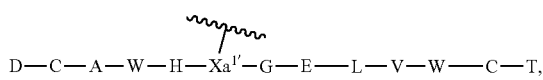

and wherein $Xa^{1\prime}$ is conjugated diaminopropionic acid (Dap) residue, conjugated diaminobutyric acid (Dab) residue, conjugated ornithine (Orn) residue, or conjugated lysine (Lys) residue.

Preparation of Compound Comprising Fc Binding Unit

The above-described compound comprising Fc binding unit may be prepared by a reaction of a Fc binding substance with a compound for preparing a compound comprising Fc binding unit (for example, may be referred to as a precursor compound for the compound comprising Fc binding unit).

The Fc binding substance has been described in detail in previous paragraphs.

Hereinafter, the compound for preparing compound comprising Fc binding unit is described in detail.

A compound for preparing compound comprising Fc binding unit may be referred to as a precursor compound for the compound comprising Fc binding unit.

Hereinafter, a precursor compound for the compound comprising Fc binding unit is described using a compound that can be used to prepare the compound of formula 2-1 as an example.

A precursor compound for compound comprising Fc binding unit may have, for example, the structure of formula 5:

[formula 5]

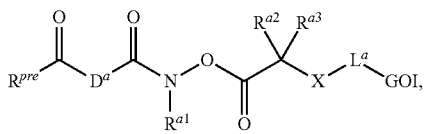

wherein $R^{pre}$ is —OH, an N-hydroxysuccinimide (NHS) group, or a pentafluorophenol group.

For example, $R^{pre}$ may have any one of the following structures:

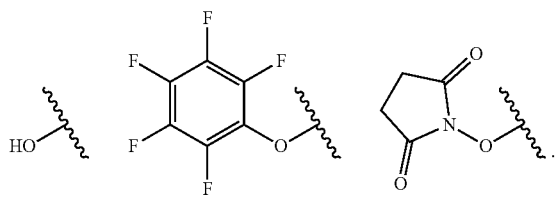

For example, through a reaction of the $Xa^1$ amino acid residue of the amino acid sequence included in the Fc binding substance with the carbonyl group adjacent to $R^{pre}$ of the compound of formula 5, a compound comprising Fc binding unit (for example, a compound of formula 2-1) may be prepared, but is not limited thereto.

Furthermore, some embodiments of the present application provide a method for preparing a compound comprising Fc binding unit.

In some embodiments, the method for preparing a compound comprising Fc binding unit may comprise the following:

Contacting or reacting a Fc binding substance with a precursor compound (for example, a compound of formula 5) for compound comprising Fc binding unit.

Herein, contacting the precursor for compound comprising Fc binding unit with the Fc binding substance may be conducted by various methods. For example, contacting may be achieved by mixing a composition comprising the precursor for compound comprising Fc binding unit with a composition comprising the Fc binding substance. For another example, contacting may be achieved by adding the precursor for compound comprising Fc binding unit and the Fc binding substance to a pre-prepared solution, and is not particularly limited.

Furthermore, the method for preparing a compound comprising Fc binding unit may further comprise a process of obtaining a compound comprising Fc binding unit. Furthermore, the method for preparing a compound comprising Fc binding unit may further comprise a process of incubating a composition or solution comprising a precursor for compound comprising Fc binding unit and a Fc binding substance.

In some embodiments, contacting or reacting a precursor for compound comprising Fc binding unit with a Fc binding substance may be conducted under appropriate conditions. For example, the contacting or reacting may be carried out at pH 4 to pH 12. For example, the contacting or reacting may be carried out at 10° C. to 50° C. For example, the contacting or reacting may be carried out for 10 minutes to 3 days.

In addition to the precursor compound of formula 5 described above, various compounds may be used to prepare a compound comprising Fc binding unit, and the aspects of the precursor compound for the compound comprising Fc binding unit and the aspects of the method for preparing a compound comprising Fc binding unit are not limited to the above-described examples.

Composition or Kit Comprising Compound Comprising Fc Binding Unit

Some embodiments of the present application provide a composition comprising a compound comprising Fc binding unit.

In some embodiments, the composition comprising the compound comprising Fc binding unit may be used to prepare an antibody conjugate comprising a group of interest described below.

In some embodiments, the composition comprising the compound comprising Fc binding unit may be used for the use of transferring a group of interest to an antibody.

The compound comprising Fc binding unit is as described above. In some embodiments, the compound comprising Fc binding unit may have the structure of any one of the structures of formula 2 and formulae 2-1 to 2-27.

In some embodiments, the composition comprising the compound comprising Fc binding unit may further comprise an additional element in addition to the compound comprising Fc binding unit. For example, the additional element included in the composition may be a pharmaceutically acceptable salt, an excipient, a diluent, a stabilizer, a pH modifier, and the like, but is not limited thereto.

Some embodiments of the present application provide a kit comprising a compound comprising Fc binding unit.

In some embodiments, the kit comprising the compound comprising Fc binding unit may be used to prepare an antibody comprising a group of interest described below.

In some embodiments, the kit comprising the compound comprising Fc binding unit may be used for the use of transferring a group of interest to an antibody.

The compound comprising Fc binding unit is as described above. In some embodiments, the compound comprising Fc binding unit may have the structure of any one of the structures of formula 2 and formulae 2-1 to 2-27.

In some embodiments, the kit comprising the compound comprising Fc binding unit may further comprise an additional element in addition to the compound comprising Fc binding unit. For example, the additional element included in the kit may be, for example, a pharmaceutically acceptable salt, an excipient, a diluent, a stabilizer, a pH modifier, and the like, but is not limited thereto.

The above-described compound comprising Fc binding unit of the present application may have high reaction efficiency in a reaction with an antibody. For example, the compound comprising Fc binding unit may exhibit enhanced efficiency of transfer of the group of interest in a reaction with an antibody.

Hereinafter, a method for preparing an antibody conjugate using a compound comprising Fc binding unit will be described in detail. A product produced by the reaction of an antibody with a compound comprising Fc binding unit may be referred to as an antibody comprising a group of interest, a conjugate comprising a group of interest (for example, an antibody conjugate), or a modified antibody, and the like, but is not limited thereto.

Length Design of Partial Structure of Compound Comprising Fc Binding Unit

The compound comprising Fc binding unit of the present application may be used to transfer a group of interest to an antibody in a site-specific manner. For example, the Fc binding unit of the present application can be used to transfer a group of interest to K246 and/or K248 of an antibody.

The following content is only provided for the purpose of describing the length design of the partial structure of the compound comprising Fc binding unit of the present application, and the scope of the present application should not be limited by the following content.

As described above, the reaction of an antibody with a compound comprising Fc binding unit is induced by the proximity effect of the Fc binding unit derived from the Fc binding substance, and the interaction between the Fc binding substance and the antibody may be partially identified through simulation. For example, the Fc binding substance and the Fc region of an antibody may be arranged in a specific positional relationship, and such positional relationship may be confirmed through simulation.

Meanwhile, a person of ordinary skill in the art may understand that when the reaction site with an antibody (reactive carbonyl marked as *) of a compound comprising Fc binding unit is adjacent to the primary amine group of the target lysines (K246 and/or K248) of the antibody, the reaction of the primary amine group with the reactive carbonyl marked as * of the compound comprising Fc binding unit may occur more successfully.

Hereinafter, the positional relationship with an antibody will be described using an example of an Fc binding substance having an amino acid sequence of SEQ ID NO: 05 (DCAWHXa$^1$GELVWCT).

Figure 5:
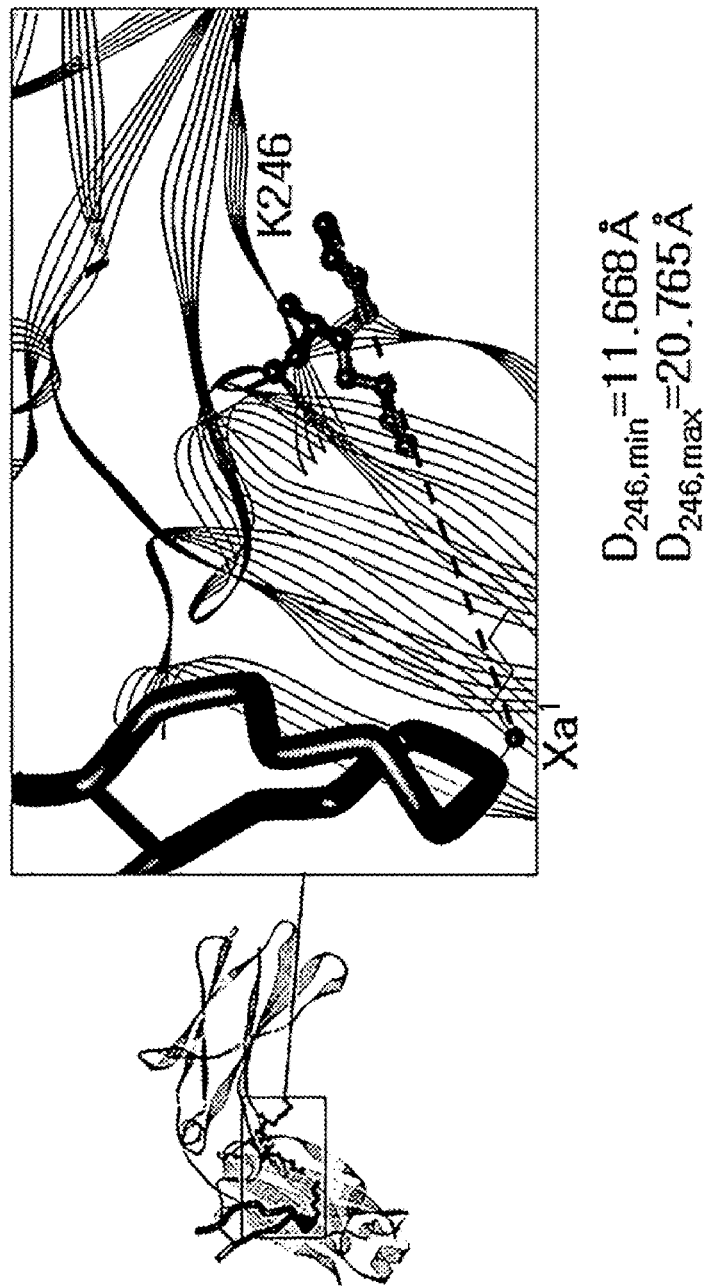
FIG. 5 relates to the distance between the amine group of lysine 246 of the Fc region and the beta carbon of $Xa^1$ of the Fc binding peptide.
Figure 6:
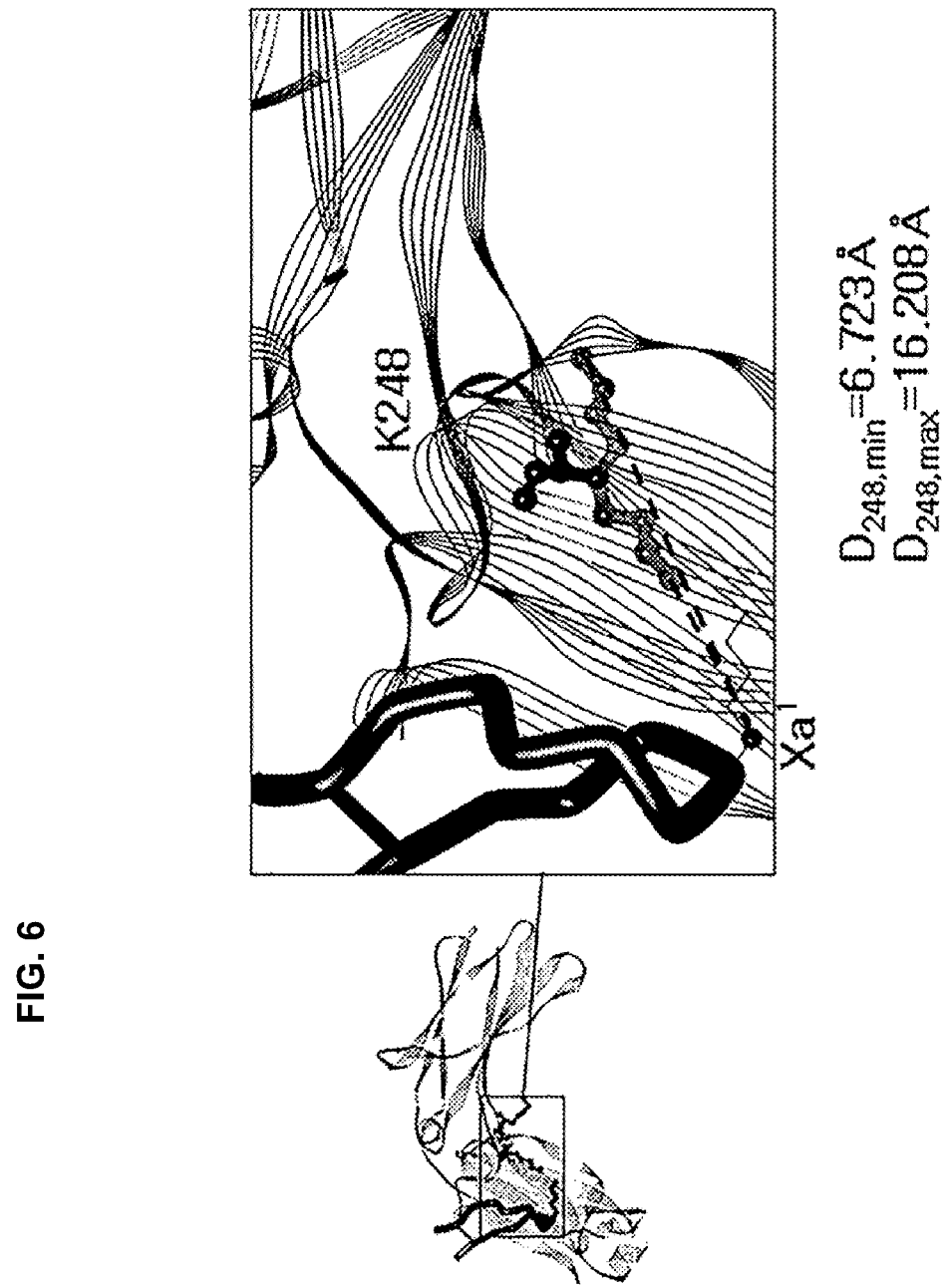
FIG. 6 relates to the distance between the amine group of lysine 248 of the Fc region and the beta carbon of $Xa^1$ of the Fc binding peptide.

FIGS. 05 and 06 illustrate the positional relationship between the primary amine group of lysine 246 and lysine 248 of the Fc region of the antibody and the Fc binding substance when the antibody and the Fc binding substance interact with each other. Specifically, in FIGS. 05 and 06, the minimum and maximum distances from the beta carbon of Xa$^1$ of the Fc binding substance to K246 and K248 are illustrated. Through FIGS. 05 and 06, it can be expected that when (1) the distance between the beta carbon of Xa$^{1'}$ of the Fc binding unit of the compound comprising Fc binding unit and the reactive carbonyl carbon marked as * (hereinafter, commonly referred to as distance A) belongs within the range of the distances illustrated in FIGS. 05 and 06 or is similar to the illustrated distances, a substance of interest can be more successfully transferred to K246 and/or K248.

For illustrative purposes, the structure from the beta carbon of Xa$^{1'}$ to the carbon of the reactive carbonyl is illustrated as follows in the structure of formula 2:

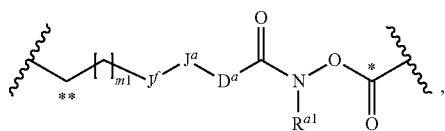

wherein ** represents the beta carbon of Xa$^{1'}$, * represents the carbon of reactive carbonyl, and m1 is an integer of 0 to 9.

In the above structure, it is expected that when the sum of the number of atoms located in the main chain (hereinafter referred to as the length of the main chain) in relation to the distance A is between 8 and 20, a group of interest may be more successfully transferred to K246 and/or K248 because the length formed by the structure falls within the range of the distances illustrated in FIGS. 05 and 06 or is similar to the illustrated distances.

For example, when m1 is 0 and $D^a$ is $C_1$ alkylene, the number of atoms located in the main chain in the above structure is 8. That is, in this case, the length of the main chain is 8. According to that described above, one atom each of $J^f$ and $J^a$ are located in the main chain, and accordingly, when the length of the main chain is counted, $J^f$ is counted as 1 and $J^a$ is counted as 1. For example, when m1 is 2 and $D^a$ is $C_3$ alkylene, the length of the main chain of the structure is 12. For example, when m1 is 2 and $D^a$ is $C_3$ heteroalkenylene, the length of the main chain of the above structure is 12.

For convenience, the number of atoms located in the main chain of $D^a$ is called k. In some embodiments, the sum of m1 and k may be 1 to 13. For example, m1 may be 0, and k may be an integer of 1 to 13. Illustratively, m1 may be 2, and k may be an integer of 1 to 11. Illustratively, m1 may be 3, and k may be an integer of 1 to 10. Illustratively, m1 may be 4, and k may be an integer of 1 to 9. Illustratively, m1 may be 4, and k may be an integer of 1 to 8. In specific embodiments, the sum of m1 and k may be 1 to 12. In specific embodiments, the sum of m1 and k may be 1 to 11. In specific embodiments, the sum of m1 and k may be 1 to 10.

Preparation of Antibody Conjugate Using Compound Comprising Fc Binding Unit

Reaction Between Compound Comprising Fc Binding Unit and Antibody and Antibody Conjugate Prepared Thereby A compound comprising Fc binding unit can transfer a group of interest to an antibody through contacting or reacting with the antibody. Specifically, a compound comprising Fc binding unit can transfer site-specifically a group of interest to an antibody by contacting or reacting with the antibody. Herein, the site to which the group of interest is transferred (for example, a target site or labeling site) may be K246 and/or K248 of the Fc region of the antibody. That is, by contacting, mixing, or reacting an antibody with a compound comprising Fc binding unit, an antibody conjugate comprising a group of interest (for example, comprising in a site-specifically) may be prepared. At this time, in the prepared antibody conjugate, the group of interest may be linked to any one or more of K246 and K248. Specifically, since the antibody have two heavy chains, and each of the two heavy chains may comprise lysine 246 and lysine 248 (for example, in the case of trastuzumab, it has a total of four labeling sites), an antibody conjugate comprising one to four groups of interest may be prepared by reacting, contacting, or mixing an antibody with a compound comprising Fc binding unit.

For example, an antibody conjugate comprising one group of interest may be prepared, and at this time, the antibody conjugate comprising one group of interest may be referred to as a group of interest-to-antibody ratio (GAR) 1 antibody conjugate.

For example, an antibody conjugate comprising two groups of interest may be prepared, and at this time, the antibody conjugate comprising two groups of interest may be referred to as a GAR2 antibody conjugate.

For example, an antibody conjugate comprising three groups of interest may be prepared, and at this time, the antibody conjugate comprising three groups of interest may be referred to as a GAR3 antibody conjugate.

For example, an antibody conjugate comprising four groups of interest may be prepared, and at this time, the antibody conjugate comprising four groups of interest may be referred to as a GAR4 antibody conjugate.

The antibody conjugate comprising a group of interest is used as a term which encompasses all embodiments of the antibody conjugate comprising one to four groups of interest as described above. Preferably, the antibody conjugate comprising a group of interest may be an antibody conjugate comprising two groups of interest.

Figure 7:
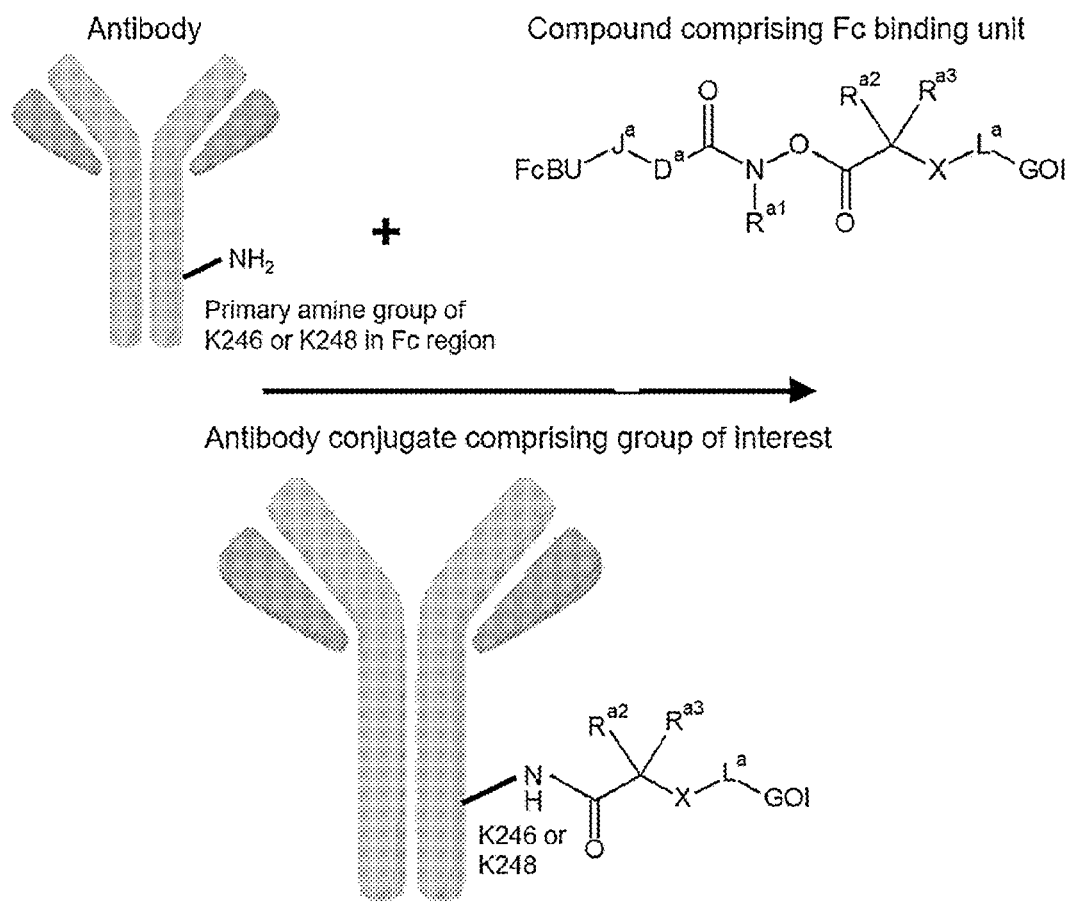
FIG. 7 exemplifies the reaction of an antibody with a compound comprising Fc binding unit of the present application, and an antibody conjugate comprising a group of interest prepared by the reaction.

FIG. 07 illustrates a reaction of an antibody with a compound comprising Fc binding unit of the present application, and an antibody conjugate comprising a group of interest prepared by the reaction. As illustrated in FIG. 07, a group of interest may be transferred to a target site in the antibody (for example, any one of K246 and K248 of the Fc region of the antibody) by the reaction of the antibody with the compound comprising Fc binding unit.

Hereinafter, the antibody conjugate comprising one to four groups of interest will be described in more detail.

Before describing an antibody conjugate comprising one to four groups of interest, a target site that may be present in the antibody will be named. An antibody is generally known to have two heavy chains and two light chains. One heavy chain of the two heavy chains may be referred to as a first heavy chain, and the other heavy chain may be referred to as a second heavy chain. K246 and K248 present in one heavy chain (first heavy chain) of the two heavy chains may be referred to as the first K246 and the first K248, respectively. K246 and K248 present in the other heavy chain (second heavy chain) of the two heavy chains may be referred to as the second K246 and the second K248, respectively.

In some embodiments, the antibody conjugate comprising a group of interest may comprise one group of interest. In some embodiments, the one group of interest may be linked to any one of the first K246, the first K248, the second K246, and the second K248. In specific embodiments, the one group of interest may be linked to any one of the first K246 and the second K246. In specific embodiments, the one group of interest may be linked to any one of the first K248 and the second K248.

Figure 8:
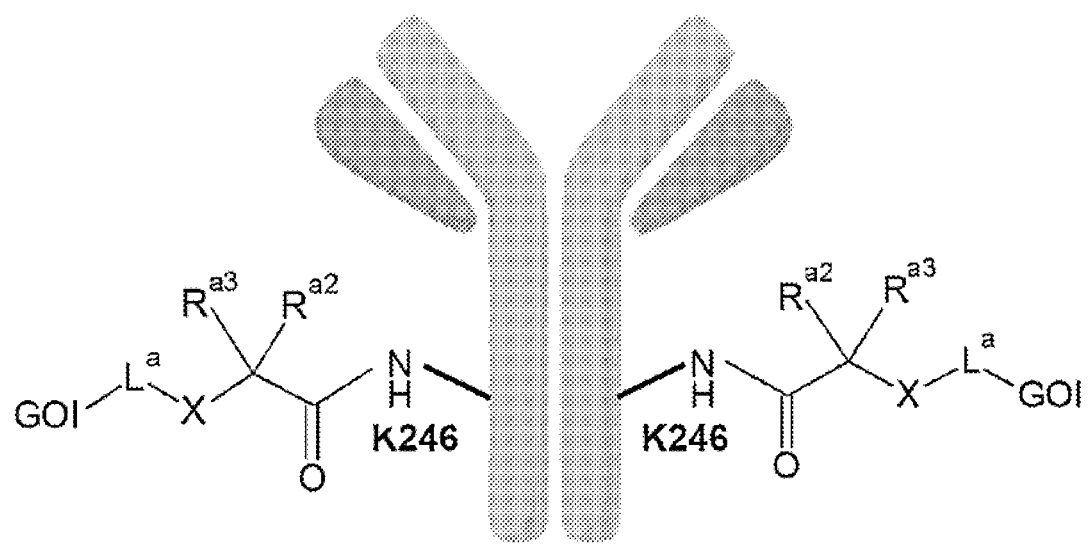
FIG. 8 exemplifies an antibody conjugate comprising group of interest, where two groups of interest are linked to K246 of the Fc region of the antibody.
Figure 9:
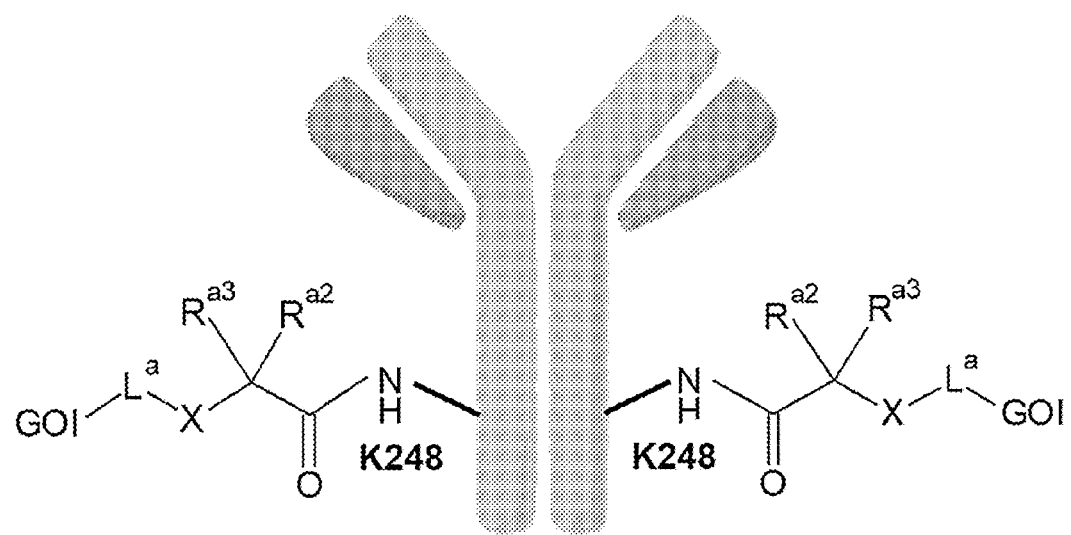
FIG. 9 exemplifies an antibody conjugate comprising group of interest, where the two groups of interest are linked to K248 of the Fc region of the antibody.
Figure 10:
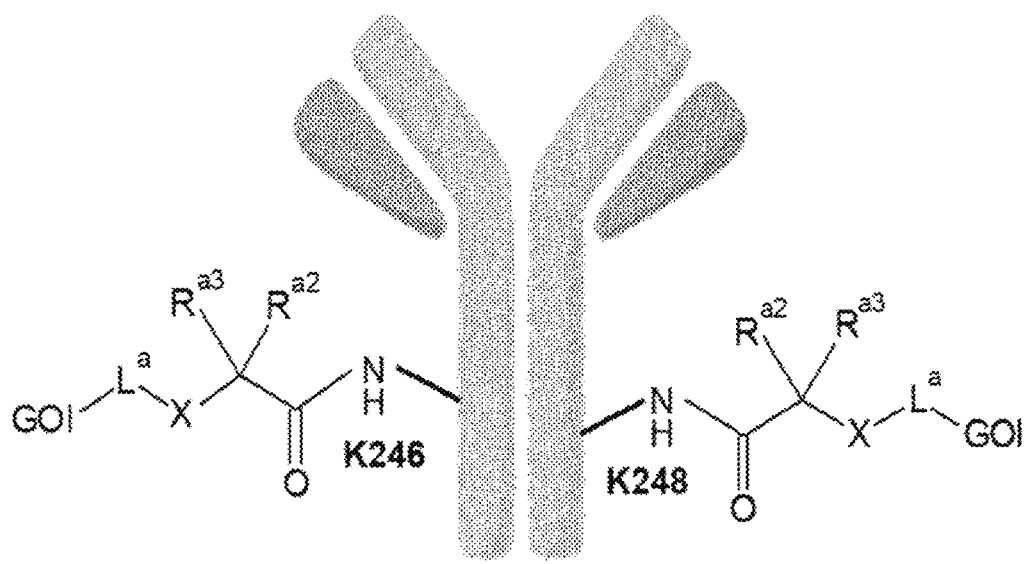
FIG. 10 exemplifies an antibody conjugate comprising group of interest, where one of the two groups of interest is linked to K246 and the other group of interest is linked to K248.

In some embodiments, the antibody conjugate comprising a group of interest may comprise two groups of interest (for example, a first group of interest and a second group of interest). In this case, the two groups of interest may be linked through two lysines selected from K246 of the first heavy chain (first K246), K248 of the first heavy chain (first K248), K246 of the second heavy chain (second K246), and K248 of the second heavy chain (second K248). In some embodiments, among the two groups of interest, the first group of interest may be linked to one heavy chain (first heavy chain) of an antibody, and the second group of interest may be linked to the other heavy chain (second heavy chain) of an antibody. In some embodiments, the first group of interest may be linked to any one of K246 and K248 of the first heavy chain, and the second group of interest may be linked to any one of K246 and K248 of the second heavy chain. In specific embodiments, both groups of interest may be linked to K246. In this case, any one of the two groups of interest may be linked to K246 of the first heavy chain, and the other may be linked to K246 of the second heavy chain. In specific embodiments, both the groups of interest may be linked to K248. In this case, any one of the two groups of interest may be linked to K248 of the first heavy chain, and the other may be linked to K248 of the second heavy chain. In specific embodiments, the two groups of interest may be linked to K246 and K248, respectively. In this case, any one of the two groups of interest (for example, the first group of interest) may be linked to K246 of the first heavy chain, and the other (for example, the second group of interest) may be linked to K248 of the second heavy chain. Illustratively, through FIGS. 08 to 10, an antibody comprising a group of interest wherein two groups of interest are linked to K246 (FIG. 08); an antibody conjugate comprising a group of interest wherein two groups of interest are linked to K248 (FIG. 09); and an antibody conjugate comprising two groups of interest, wherein one group of interest (first group of interest) of the two groups of interest is linked to K246, and the other group of interest (second group of interest) is linked to K248 (FIG. 10) are shown.

In some embodiments, the antibody conjugate comprising a group of interest may comprise three groups of interest. In this case, the three groups of interest may be linked through three lysines selected from the first K246, the first K248, the second K246, and the second K248, respectively.

In some embodiments, the antibody conjugate comprising a group of interest may comprise four groups of interest. In this case, the four groups of interest may be linked to the first K246, the first K248, the second K246, and the second K248, respectively.

As described above, the following two elements are essentially used for the preparation of a conjugate (for example, an antibody conjugate comprising a group of interest) using a compound comprising Fc binding unit:
 a compound comprising Fc binding unit; and
 an antibody.

Hereinafter, the elements used for the preparation of a conjugate using a compound comprising Fc binding unit will be described in detail.

Element 1 Used for Preparation of Conjugate—Compound Comprising Fc Binding Unit

As described above, a compound comprising Fc binding unit of the present application is used for the preparation of a conjugate (for example, an antibody conjugate comprising a group of interest). The compound comprising Fc binding unit of the present application have been described in detail in the section "Compound comprising Fc binding unit" of the present application, and the compound comprising Fc binding unit used for the preparation of a conjugate is as described in the section above.

Element 2 Used for Preparation of Conjugate—Antibody

As described above, an antibody is used for the preparation of a conjugate (for example, an antibody conjugate comprising a group of interest). The Fc binding substance or Fc binding unit has binding affinity to the Fc region of the antibody.

In some embodiments, the antibody may comprise the Fc region of IgG. In some embodiments, the Fc region of the antibody may be the Fc region of IgG.

In some embodiments, the antibody may be an IgG antibody. The IgG antibody encompasses a human IgG antibody, a humanized IgG antibody, and a chimeric IgG antibody.

It is known that IgG is classified into IgG1, IgG2, IgG3, and IgG4.

In some embodiments, the antibody may be an IgG1 antibody. The IgG1 antibody encompasses a human IgG1 antibody, a humanized IgG1 antibody, and a chimeric IgG1 antibody.

In some embodiments, the antibody may comprise the Fc region of IgG1. The Fc region of the antibody may be the Fc region of IgG1.

In some embodiments, the antibody may be an IgG2 antibody. The IgG2 antibody encompasses a human IgG2 antibody, a humanized IgG2 antibody, and a chimeric IgG2 antibody.

In some embodiments, the antibody may comprise the Fc region of IgG2. The Fc region of the antibody may be the Fc region of IgG2.

In some embodiments, the antibody may be an IgG3 antibody. The IgG3 antibody encompasses a human IgG3 antibody, a humanized IgG3 antibody, and a chimeric IgG3 antibody.

In some embodiments, the antibody may comprise the Fc region of IgG3. The Fc region of the antibody may be the Fc region of IgG3.

In some embodiments, the antibody may be an IgG4 antibody. The IgG4 antibody encompasses a human IgG4 antibody, a humanized IgG4 antibody, and a chimeric IgG4 antibody.

In some embodiments, the antibody may comprise the Fc region of IgG4. The Fc region of the antibody may be the Fc region of IgG4.

In some embodiments, the antibody may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody may have an amino acid sequence of SEQ ID NO: 14 or an amino acid sequence having 90%, 95%, 96%, 97%, 98%, or 99% or more sequence identity thereof.

In some embodiments, the antibody comprises an IgG Fc region (for example, the Fc region of the antibody is the Fc region of IgG), wherein the IgG Fc region may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody comprises the Fc region of IgG, wherein the IgG Fc region may have an amino acid sequence of SEQ ID NO: 14 or an amino acid sequence having 90%, 95%, 96%, 97%, 98%, or 99% or more identity thereof.

In some embodiments, the antibody or the Fc region of the antibody may comprise an amino acid sequence of KPKDTLM (SEQ ID NO: 10) and MHEALHNH (SEQ ID NO: 11).

In some embodiments, the antibody or the Fc region of the antibody may comprise an amino acid sequence of KPKDTLM (SEQ ID NO: 10) and MHEALHNHY (SEQ ID NO: 12).

In some embodiments, the antibody or the Fc region of the antibody may comprise an amino acid sequence of GPSVFLFPPKPKDTLM (SEQ ID NO: 13).

In some embodiments, the antibody has any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, which may essentially comprise an amino acid sequence of KPKDTLM (SEQ ID NO: 10) and MHEALHNH (SEQ ID NO: 11). In some embodiments, the antibody comprises an IgG Fc region, wherein the IgG Fc region has any one amino acid sequence selected from SEQ ID NO: 14 to SEQ ID NO: 18 or an amino acid sequence having 80%, 85%, 90%, 95%, 96%, 97%, 98%, or 99% or more identity thereof, which may essentially comprise an amino acid sequence of KPKDTLM (SEQ ID NO: 10) and MHEALHNH (SEQ ID NO: 11).

In some embodiments, the antibody has any one amino acid sequence selected from SEQ ID: 14 to SEQ ID 15 and SEQ ID NO: 17 to SEQ ID NO: 18, or an amino acid sequence having 80%, 85%, 90%, 95%, 96%, 97%, 98%, or 99% or more sequence identity thereof, and may essentially comprise an amino acid sequence of KPKDTLM (SEQ ID NO: 10) and MHEALHNHY (SEQ ID NO: 12). In some embodiments, the antibody comprises an IgG Fc region, wherein the IgG Fc region has any one amino acid sequence selected from SEQ ID NO: 14 to SEQ ID NO: 15 and SEQ ID NO: 17 to SEQ ID NO: 18 or an amino acid sequence having 80%, 85%, 90%, 95%, 96%, 97%, 98%, or 99% or more sequence identity thereof, which may essentially comprise an amino acid sequence of KPKDTLM (SEQ ID NO: 10) and MHEALHNHY (SEQ ID NO: 12).

In some embodiments, the antibody has any one amino acid sequence selected from SEQ ID NO: 14 to SEQ ID NO: 18 or an amino acid sequence having 80%, 85%, 90%, 95%, 96%, 97%, 98%, or 99% or more sequence identity thereof, which may essentially comprise GPSVFLFPPKPKDTLM (SEQ ID NO: 13). In some embodiments, the antibody comprises an IgG Fc region, wherein the IgG Fc region has any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, which may essentially comprise GPSVFLFPPKPKDTLM (SEQ ID NO: 13).

In some embodiments, the antibody having binding affinity to the Fc binding substance or peptide of the present application may be an antibody of the IgG isotype. In some embodiments, the antibody with binding affinity to the Fc binding substance or peptide of the present application may be an antibody of the IgG1 isotype, an antibody of the IgG2 isotype, an antibody of the IgG3 isotype, or an antibody of the IgG4 isotype. In some embodiments, the antibody with binding affinity to the Fc binding substance or peptide of the present application may be an antibody of the IgG1 isotype, an antibody of the IgG2 isotype, or an antibody of the IgG4 isotype.

The inventors of the present application have confirmed that, for various types of antibodies, a group of interest (for example, a bio-orthogonal functional group) is transferred to an antibody by a reaction of the antibody with the compound comprising Fc binding unit of the present application. More specifically, the inventors of the present application have confirmed that when the compound comprising Fc binding unit of the present application (Compound 9 of the Example) is used, a group of interest (for example, an azide group) is transferred to each of trastuzumab (IgG1 type antibody), an IgG1 type anti-CLDN18.2 antibody, an IgG1 type anti-CD154 antibody, denosumab (IgG2 type antibody), and dupilumab.

In some embodiments, the antibody may be any one selected from adalimumab (Humira), rituximab (Rituxan), trastuzumab (Herceptin), bevacizumab (Avastin), infliximab (Remicade), pembrolizumab (Keytruda), nivolumab (Opdivo), eculizumab (Soliris), alemtuzumab (Lemtrada, Campath), daratumumab (Darzalex), ipilimumab (Yervoy), golimumab) (Simponi), tocilizumab (Actemra), ranibizumab (Lucentis), secukinumab (Cosentyx), ixekizumab (Taltz), dupilumab (Dupixent), denosumab, ustekinumab (Stelara), palivizumab (Synagis), durvalumab (Imfinzi), atezolizumab (Tecentriq), omalizumab (Xolair), vedolizumab (Entyvio), abciximab (ReoPro), basiliximab (Simulect), alefacept (Amevive), daclizumab (Zinbryta), and elotuzumab (Empliciti).

In some embodiments, the antibody may be an antibody having binding properties to any one of EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptors, EphB receptors, EGFR, EGFRvIII, HER2, HER3, mesothelin, cripto, alphavbeta3, alphavbeta5, Nectin-4, TROP2, PD1, PD-L1, BCMA, B3H7, FOLR-a, tissue factors, claudine 1 (CLDN 1), claudin 3 (CLDN 3), claudin 4 (CLDN 4), claudin 6 (CLDN 6), claudin 18.2 (CLDN 18.2) and alpha v beta 6 integrin.

In some embodiments, the antibody may be an anti-CLDN18.2 antibody (see the document [Korean Patent Application No. 10-2021-7023724]).

In some embodiments, the heavy chain of the anti-CLDN18.2 antibody may comprise CDRH1 having an amino acid sequence having SEQ ID NO: 19 (TYGVH) or 90% or more sequence identity thereof, CDRH2 having an amino acid sequence having SEQ ID NO: 20 (VIWAGGSTNYNSALMS) or 90% or more sequence identity thereof, and CDRH3 having an amino acid sequence having SEQ ID NO: 21 (AAYYGNGLDY) or 90% or more identity thereof. In specific embodiments, the anti-CLDN18.2 antibody may have two heavy chains, and each heavy chain may comprise CDRH1 having an amino acid sequence of SEQ ID NO: 19, CDRH2 having an amino acid sequence of SEQ ID NO: 20, and CDRH3 having an amino acid sequence of SEQ ID NO: 21.

In some embodiments, the light chain of the anti-CLDN18.2 antibody may comprise CDRL1 having an amino acid sequence having SEQ ID NO: 22 (KSSQTLLNSGNQKNYLT) or 90% or more sequence identity thereof, CDRL2 having an amino acid sequence having SEQ ID NO: 23 (WASTGES) or 90% or more sequence identity thereof, and CDRL3 having an amino acid sequence having SEQ ID NO: 24 (QNAYFYPFT) or 90% or more sequence identity thereof. In specific embodiments, the anti-CLDN18.2 antibody may have two light chains, and each light chain may comprise CDRL1 having an amino acid sequence of SEQ ID NO: 22, CDRL2 having an amino acid sequence of SEQ ID NO: 23, and CDRL3 having an amino acid sequence of SEQ ID NO: 24.

In some embodiments, the heavy chain of the anti-CLDN18.2 antibody may comprise CDRH1 having an amino acid sequence having SEQ ID NO: 19 or 90% or more sequence identity thereof, CDRH2 having an amino acid sequence having SEQ ID NO: 20 or 90% or more sequence identity thereof, and CDRH3 having an amino acid sequence having SEQ ID NO: 21 or 90% or more sequence identity thereof, and the light chain of the anti-CLDN18.2 antibody may comprise CDRL1 having an amino acid sequence having SEQ ID NO: 22 or 90% or more sequence identity thereof, CDRL2 having an amino acid sequence having SEQ ID NO: 23 or 90% or more sequence identity thereof, and CDRL3 having an amino acid sequence having SEQ ID NO: 24 or 90% or more sequence identity thereof. In specific embodiments, the anti-CLDN18.2 antibody may have two heavy chains comprising CDRH1 having an amino acid sequence of SEQ ID NO: 19, CDRH2 having an amino acid sequence of SEQ ID NO: 20, and CDRH3 having an amino acid sequence of SEQ ID NO: 21 and two light chains comprising CDRL1 having an amino acid sequence of SEQ ID NO: 22, CDRL2 having an amino acid sequence of SEQ ID NO: 23, and CDRL3 having an amino acid sequence of SEQ ID NO: 24.

In some embodiments, the anti-CLDN18.2 antibody may be an antibody comprising a heavy chain having an amino acid sequence having SEQ ID NO: 25 or 90% or more sequence identity thereof, and a light chain having an amino acid sequence having SEQ ID NO: 26 or 90% or more sequence identity thereof. In specific embodiments, the anti-CLDN18.2 antibody may be an antibody comprising a heavy chain having an amino acid sequence of SEQ ID NO; 25, and a light chain having an amino acid sequence of SEQ ID NO: 26. Specifically, the anti-CLDN18.2 antibody may have two heavy chains having an amino acid sequence of SEQ ID NO: 25 and two light chains having an amino acid sequence of SEQ ID NO: 26.

The binding affinity with a Fc binding substance and an antibody or the Fc region of an antibody may be expressed as a dissociation constant (Kd). In some embodiments, the dissociation constant (Kd) of an Fc binding substance for an antibody may be 10 µM, 1 µM ($1 \times 10^{-6}$ M), 900 nM, 800 nM, 700 nM, 600 nM, 500 nM, 450 nM, 400 nM, 350 nM, 300 nM, 250 nM, 200 nM, 180 nM, 160 nM, 140 nM, 120 nM, 100 nM, 90 nM, 80 nM, 70 nM, 60 nM, 50 nM, 40 nM, 30 nM, 20 nM, 10 nM, 5 nM, 2 nM, 1 nM ($1 \times 10^{-9}$ M), 0.5 nM, 0.1 nM, 0.05 nM, or 0.01 nM or less, or may be within a range set by any two values selected from the above-described values, but is not limited thereto. In some embodiments, the dissociation constant (Kd) of an Fc binding substance for the Fc domain of an antibody may be 10 µM, 1 µM ($1 \times 10^{-6}$ M), 900 nM, 800 nM, 700 nM, 600 nM, 500 nM, 450 nM, 400 nM, 350 nM, 300 nM, 250 nM, 200 nM, 180 nM, 160 nM, 140 nM, 120 nM, 100 nM, 90 nM, 80 nM, 70 nM, 60 nM, 50 nM, 40 nM, 30 nM, 20 nM, 10 nM, 5 nM, 2 nM, 1 nM ($1 \times 10^{-9}$ M), 0.5 nM, 0.1 nM, 0.05 nM, or 0.01 nM or less, or may be within a range set by any two values selected from the above-described values, but is not limited thereto.

Method for Preparing Antibody Conjugate Using Compound Comprising Fc Binding Unit Some embodiments of the present application provide a method for preparing an antibody conjugate comprising a group of interest. The method for preparing an antibody conjugate comprising a group of interest may be referred to as a method for preparing an antibody conjugate comprising a group of interest in a site-specific manner, a method for transferring a group of interest to an antibody, a method for transferring a group of interest to an antibody in a site-specific manner, a method for transferring a reactive group (for example, a bio-orthogonal functional group) to an antibody in a site-specific manner, and the like. As described above, the method may be freely referred to as appropriate to a purpose sought to be achieved by a reaction of an antibody with a compound comprising Fc binding unit.

Some embodiments of the present application provide a method for preparing an antibody conjugate comprising a group of interest, wherein the method comprises:

contacting an antibody with a compound comprising Fc binding unit.

Herein, the term "contacting" may be replaced by terms such as the term "reacting" or "mixing."

Herein, a compound comprising Fc binding unit is a compound comprising Fc binding unit provided by the present application. For example, the compound comprising Fc binding unit may be a compound of formula 2. For example, the compound comprising Fc binding unit may be any one compound of the compounds of formula 2 and formula 2-1 to formula 2-27 (that is, the compound comprising Fc binding unit may be a compound having the structure of any one formula of formula 2 and formula 2-1 to formula 2-27). The compound comprising Fc binding unit of the present application and elements included therein are described in detail in the section "Compounds comprising Fc binding unit", and the compound comprising Fc binding unit and the elements included therein are as described in the previous paragraphs.

Herein, contacting the compound comprising Fc binding unit and the antibody may be conducted by various methods. For example, contacting may be achieved by mixing a composition comprising a compound comprising Fc binding unit with a composition comprising an antibody. For another example, contacting may be achieved by adding a compound comprising Fc binding unit and an antibody to a prepared solution, and is not particularly limited.

In some embodiments, an antibody conjugate comprising a group of interest may be prepared by contacting an antibody with a compound comprising Fc binding unit. In some embodiments, in the antibody conjugate comprising a group of interest, the group of interest may be linked to any one or more selected from K246 and K248 of the Fc region of an antibody. In some embodiments, in the antibody conjugate comprising a group of interest, the group of interest may be linked to K246 of the Fc region of the antibody. In some embodiments, in the antibody conjugate comprising a group of interest, the group of interest may be linked to K248 of the Fc region of the antibody. In some embodiments, the antibody conjugate comprising a group of interest may comprise one to four groups of interest. In some embodiments, the antibody conjugate comprising a group of interest may comprise one group of interest. In specific embodiments, the antibody conjugate comprising a group of interest may comprise two groups of interest.

In some embodiments, a group of interest may be transferred to an antibody in a site-specific manner (for example, to a target region of the antibody) through contact of the antibody with a compound containing Fc binding unit. For example, the target region may consist of 1 to 20, 1 to 10, 1 to 5, or 1 to 3 contiguous amino acid residues comprising K246 and K248 of the Fc region. In some embodiments, a group of interest may be transferred to one or more lysine residues selected from K246 and K248 of the Fc region of the antibody through contact of the antibody with the compound containing Fc binding unit. In some embodiments, a group of interest may be transferred to K246 of the Fc region of the antibody through contact of the antibody with the compound comprising Fc binding unit. In some embodiments, a group of interest may be transferred to K248 of the Fc region of the antibody through contact of the antibody with the compound comprising Fc binding unit.

In some embodiments, the contact or reaction of an antibody with a compound comprising Fc binding unit may be performed in a solution or composition.

In some embodiments, the contact or reaction of an antibody with a compound comprising Fc binding unit may be carried out at any one pH selected from pH 4, 4.5, 5, 5.5, 6.5, 7, 7.5, 8, 8.5, 9, 9.5, 10, 10.5, 11, 11.5, and 12, or at a pH within a range set by two values selected from the above-described values. In some embodiments, the contact or reaction of an antibody with a compound comprising Fc binding unit may be performed under pH conditions of 5 to 10, 6 to 10, 7 to 10, 5 to 9, 5 to 8, 6 to 9, 6 to 8, 7 to 9, or 7 to 8. In specific embodiments, the reaction of the antibody with the compound comprising Fc binding unit may be performed under pH conditions of 6.5 to 8.5 or 7 to 8. In specific embodiments, the reaction of the antibody with the compound comprising Fc binding unit may be carried out at about pH 7.4.

In some embodiments, the contact or reaction of the antibody with the compound comprising Fc binding unit may be carried out at 10° C. to 50° C., 10° C. to 45° C., 15° C. to 45° C., 15° C. to 40° C., 20° C. to 45° C., 20° C. to 40° C., 20° C. to 35° C., 20° C. to 30° C., 25° C. to 45° C., 25° C. to 40° C., 25° C. to 35° C., or 20° C. to 30° C. In some embodiments, the reaction of the antibody with the compound comprising Fc binding unit may be carried out at room temperature.

In some embodiments, the method for preparing an antibody conjugate comprising a group of interest may further comprise incubating a solution (or a composition) comprising a compound comprising Fc binding unit and an antibody conjugate. At this time, a process such as stirring or vortexing may be optionally performed during the incubation, but is not limited thereto. The incubation may be carried out for a period of time of about 10 minutes, 20 minutes, 30 minutes, 40 minutes, 50 minutes, 1 hour, 1.5 hours, 2 hours, 2.5 hours, 3 hours, 4 hours, 5 hours, 6 hours, 7 hours, 8 hours, 9 hours, 10 hours, 14 hours, 16 hours, 18 hours, 20 hours, 22 hours, 24 hours, 30 hours, 36 hours, 42 hours, 48 hours, 60 hours, or 72 hours, or more, and the period of time is not particularly limited.

In some embodiments, the method for preparing an antibody conjugate comprising a group of interest may further comprise a process of obtaining an antibody conjugate comprising a group of interest. At this time, obtaining the antibody conjugate comprising a group of interest may comprise a process of purifying the antibody conjugate comprising the group of interest, and the like, but is not limited thereto.

Figure 11:
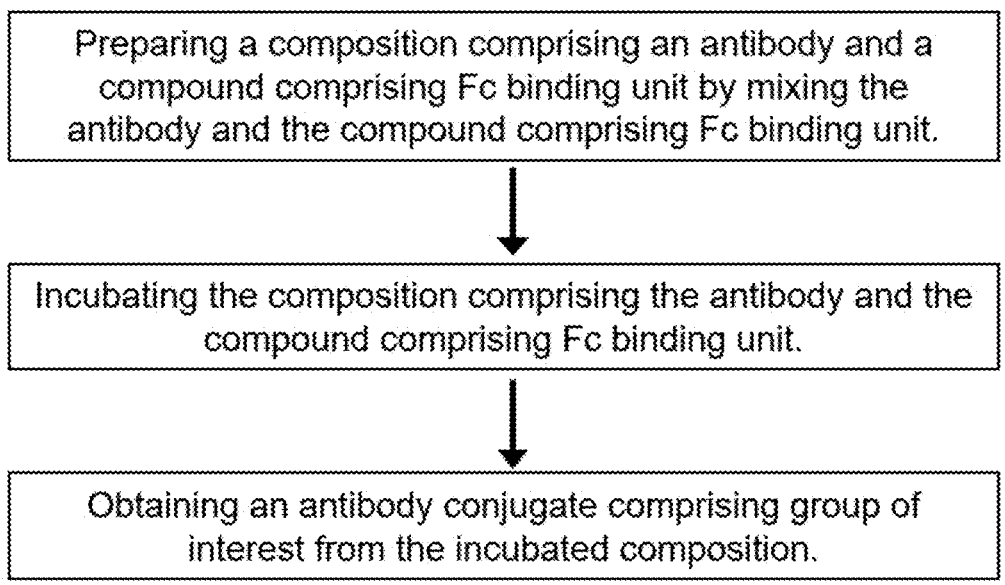
FIG. 11 relates to one embodiment of a method for preparing an antibody conjugate comprising group of interest.

Illustratively, a method for preparing an antibody conjugate comprising a group of interest may comprise (see FIG. 11):

preparing a composition comprising a compound comprising Fc binding unit and an antibody by mixing the compound comprising Fc binding unit and the antibody;

incubating the composition comprising the compound comprising Fc binding unit and the antibody; and obtaining an antibody conjugate comprising a group of interest from the incubated composition.

Advantages of Using Compound Comprising Fc Binding Unit of Present Application

As described above, the compound comprising Fc binding unit of the present application may exhibit enhanced reaction efficiency in a reaction with an antibody. For example, the reaction of an antibody with a compound comprising Fc binding unit of the present application may have an enhanced reaction rate. Accordingly, the preparation yield of a conjugate prepared by the reaction of the antibody with the compound comprising Fc binding unit may be increased, or the time required to prepare the conjugate may be decreased. Hereinafter, the advantages of using the compound comprising Fc binding unit of the present application, that is, the advantages of the method for preparing an antibody conjugate comprising a group of interest provided by the present application will be described.

As described above, when a compound comprising Fc binding unit in the related art (a compound of formula 1-1) is used, there has been a problem in that an antibody conjugate comprising a group of interest is not prepared or it takes a lot of time to prepare the antibody conjugate comprising a group of interest because the reaction efficiency of the compound of formula 1-1 with an antibody is not good. According to experiments conducted by the inventors of the present application, it was confirmed that only 5% of an antibody conjugate was obtained despite reacting the antibody with the compound of formula 1-1 for 3 hours, and even the obtained antibody conjugate was a GAR1 antibody conjugate (see Example 02).

In contrast, it is confirmed that when the compound comprising Fc binding unit of the present application is used, the preparation yield of the antibody conjugate is improved.

In some embodiments, reaction efficiency may be calculated based on the amount of antibody conjugate comprising the group of interest prepared through the reaction for a predetermined time. The reaction efficiency may be calculated, for example, from the yield rate of an antibody conjugate prepared through reaction for a predetermined time. For example, when 60 of antibody conjugates comprising group of interest are prepared from initially added 100 antibodies through 1-hour reaction, the yield rate of antibody conjugate comprising the group of interest is 60%. For example, when 80 of antibody conjugates comprising group of interest is prepared from initially added 100 antibodies through a 3-hour reaction, the yield rate of antibody conjugate comprising the group of interest is 80%. At this time, the antibody conjugate comprising the group of interest may comprise all of GAR1, GAR2, GAR3, and GAR4 antibody conjugates. At this time, the antibody conjugate comprising the group of interest may refer to a GAR2 antibody conjugate. For example, when 60 GAR1 antibody conjugates and 20 GAR2 antibody conjugates are prepared from 100 antibodies initially added through a 3-hour reaction, the yield rate of the GAR2 antibody conjugate is 20%. In some embodiments, reaction efficiency may be calculated based on the amount of antibody-payload conjugate described below. At this time, the antibody-payload conjugate may comprise all of a payload to antibody ratio (PAR) 1 antibody conjugate in which one payload (i.e., one cargo moiety) is linked to an antibody unit, a PAR2 antibody conjugate in which two payloads are linked to an antibody unit, a PAR3 antibody conjugate in which three payloads are linked to an antibody unit, and a PAR4 antibody conjugate in which four payloads are linked to an antibody unit. For example, when 60 PAR2 antibody conjugates are prepared from initially added 100 antibodies through a reaction for 3 hours, the yield rate thereof is 60%. An antibody conjugate which is basis of yield rate may be appropriately selected. For example, an antibody conjugate on which the yield rate is based may be GAR1 and GAR2 antibody conjugates. For example, an antibody conjugate on which the yield rate is based may be PAR1 and PAR2 antibody conjugates. For example, an antibody conjugate on which the yield rate is based may be a GAR2 antibody conjugate. For example, an antibody conjugate on which the yield rate is based may be a PAR2 antibody conjugate.

In some embodiments, the yield of antibody conjugate comprising the group of interest obtained through a reaction for a predetermined time may be 10%, 20%, 30%, 40%, 50%, 60%, 70%, 80%, 90%, or 95% or more. Here, the predetermined time may be, for example, 10 minutes, 20 minutes, 30 minutes, 40 minutes, 50 minutes, 1 hour, 1.5 hours, 2.5 hours, 2.5 hours, 3 hours, 4 hours, 5 hours, 6 hours, 7 hours, 8 hours, 9 hours, 10 hours, 14 hours, 16 hours, 18 hours, 20 hours, 22 hours, 24 hours, 30 hours, 36 hours, 42 hours, 48 hours, 60 hours, or 72 hours or more.

Composition or Kit for Preparing Antibody Conjugate Comprising Group of Interest Some embodiments of the present application provide a composition or kit for preparing an antibody conjugate comprising a group of interest. The composition or kit for preparing an antibody conjugate comprising a group of interest may be used to prepare an antibody conjugate comprising a group of interest. The composition or kit for preparing an antibody conjugate comprising a group of interest comprises a compound comprising Fc binding unit, and an antibody. Each of the compound comprising Fc binding unit and the antibody is as described above.

Some embodiments of the present application provide a composition for preparing an antibody conjugate comprising a group of interest.

In some embodiments, the composition for preparing an antibody conjugate comprising a group of interest may further comprise an additional element in addition to the compound comprising Fc binding unit and the antibody. For example, the additional element included in the composition may be a carrier, an excipient, a diluent, a stabilizer, a pH modifier, and the like, but is not limited thereto.

Some embodiments of the present application provide a kit for preparing an antibody conjugate comprising a group of interest.

In some embodiments, the kit for preparing an antibody conjugate comprising a group of interest may further comprise an additional element in addition to the compound comprising Fc binding unit and the antibody. For example, the additional element included in the kit may be a carrier, an excipient, a diluent, a stabilizer, a pH modifier, and the like, but is not limited thereto.

Hereinafter, an antibody conjugate comprising a group of interest prepared by a reaction or contact of an antibody with a compound comprising Fc binding unit will be described in detail.

Antibody Conjugate Comprising Group of Interest

Overview of Antibody Conjugate Comprising Group of Interest

As described above, an antibody conjugate comprising a group of interest may be prepared by reacting an antibody with a compound comprising Fc binding unit.

A compound of the following formula 6 may be referred to as an antibody conjugate comprising a group of interest.

Some embodiments of the present application provide a compound having the structure of the following formula 6:

[formula 6]

In formula 6, Ab is an antibody unit.
In formula 6, $L^b$ is a linker B.

In formula 6, GOI is a group of interest. The group of interest has been described in detail in previous paragraphs, and is as described in previous paragraphs.

In formula 6, n is an integer of 1 to 4.

At this time, in formula 6, the group of interest may be linked to one or more of lysine residue 246 (K246) and lysine residue 248 (K248) of the Fc region of the antibody unit.

Hereinafter, each element of the compound of formula 6 will be described in detail.

Antibody Unit

Figure 12:
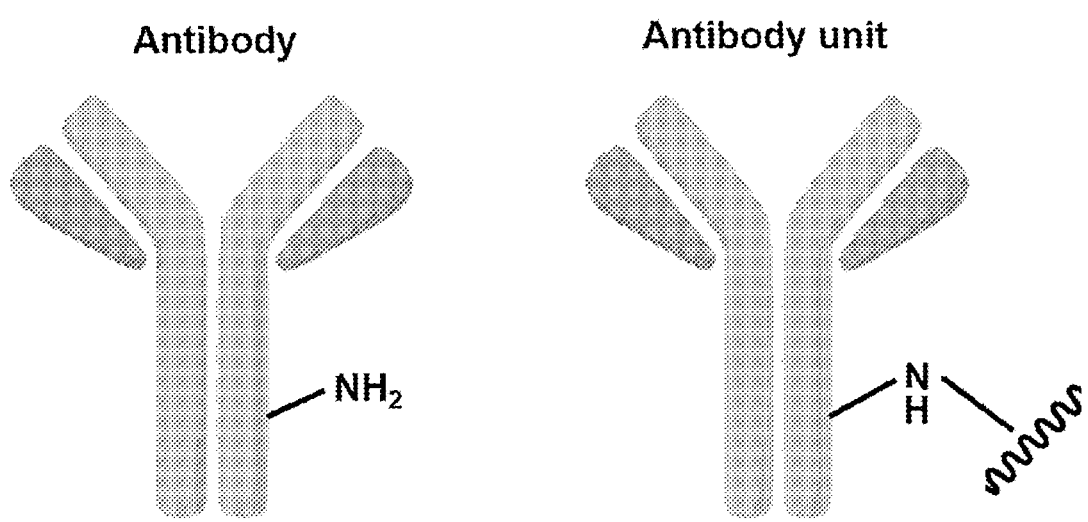
FIG. 12 illustrates an antibody and an antibody unit.

An antibody unit is derived from antibodies and may be referred to as a conjugated antibody. Furthermore, since the structure of the antibody unit is the same as the antibody which is the origin of the antibody unit excepting the conjugated part, the antibody unit may be referred to as an antibody, and the description described in the paragraphs for describing antibodies may be applied as it is. FIG. 12 compares the structures of the antibody and the antibody unit by specifying the conjugated part. As illustrated in FIG. 12, the antibody unit derived from the antibody and the antibody from which the antibody unit is derived are almost identical in structure.

In some embodiments, the antibody (or antibody unit) may comprise the Fc region of IgG. In some embodiments, the Fc region of the antibody may be the Fc region of IgG.

In some embodiments, the antibody may be an IgG antibody. The IgG antibody encompasses a human IgG antibody, a humanized IgG antibody, and a chimeric IgG antibody.

It is known that IgG is classified into IgG1, IgG2, IgG3, and IgG4.

In some embodiments, the antibody may be an IgG1 antibody. The IgG1 antibody encompasses a human IgG1 antibody, a humanized IgG1 antibody, and a chimeric IgG1 antibody.

In some embodiments, the antibody may comprise the Fc region of IgG1. The Fc region of the antibody may be the Fc region of IgG1.

In some embodiments, the antibody may be an IgG2 antibody. The IgG2 antibody encompasses a human IgG2 antibody, a humanized IgG2 antibody, and a chimeric IgG2 antibody.

In some embodiments, the antibody may comprise the Fc region of IgG2. The Fc region of the antibody may be the Fc region of IgG2.

In some embodiments, the antibody may be an IgG3 antibody. The IgG3 antibody encompasses a human IgG3 antibody, a humanized IgG3 antibody, and a chimeric IgG3 antibody.

In some embodiments, the antibody may comprise the Fc region of IgG3. The Fc region of the antibody may be the Fc region of IgG3.

In some embodiments, the antibody may be an IgG4 antibody. The IgG4 antibody encompasses a human IgG4 antibody, a humanized IgG4 antibody, and a chimeric IgG4 antibody.

In some embodiments, the antibody may comprise the Fc region of IgG4. The Fc region of the antibody may be the Fc region of IgG4.

In some embodiments, the antibody may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody may have an amino acid sequence of SEQ ID NO: 14 or an amino acid sequence having 90%, 95%, 96%, 97%, 98%, or 99% or more sequence identity thereof.

In some embodiments, the antibody may comprise an IgG Fc region (for example, the Fc region of the antibody may be the Fc region of IgG), wherein the IgG Fc region may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof. In specific embodiments, the antibody may comprise the Fc region of IgG, wherein the IgG Fc region may have an amino acid sequence of SEQ ID NO: 14 or an amino acid sequence having 90%, 95%, 96%, 97%, 98%, or 99% or more identity thereof.

In some embodiments, the antibody or the Fc region of the antibody may comprise an amino acid sequence of KPKDTLM (SEQ ID NO: 10) and MHEALHNH (SEQ ID NO: 11).

In some embodiments, the antibody or the Fc region of the antibody may comprise an amino acid sequence of KPKDTLM (SEQ ID NO: 10) and MHEALHNHY (SEQ ID NO: 12).

In some embodiments, the antibody or the Fc region of the antibody may comprise an amino acid sequence of GPSVFLFPPKPKDTLM (SEQ ID NO: 13).

In some embodiments, the antibody may have any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, and may essentially comprise an amino acid sequence of KPKDTLM (SEQ ID NO: 10) and MHEALHNH (SEQ ID NO: 11). In some embodiments, the antibody comprises an IgG Fc region, wherein the IgG Fc region may have any one amino acid sequence selected from SEQ ID NO: 14 to SEQ ID NO: 18 or an amino acid sequence having 80%, 85%, 90%, 95%, 96%, 97%, 98%, or 99% or more identity thereof, and may essentially comprise an amino acid sequence of KPKDTLM (SEQ ID NO: 10) and MHEALHNH (SEQ ID NO: 11).

In some embodiments, the antibody may have any one amino acid sequence selected from SEQ ID NOs: 14 to 15 and SEQ ID NOs: 17 to 18, or an amino acid sequence having 80%, 85%, 90%, 95%, 96%, 97%, 98%, or 99% or more sequence identity thereof, and may comprise an amino acid sequence of KPKDTLM (SEQ ID NO: 10) and MHEALHNHY (SEQ ID NO: 12). In some embodiments, the antibody comprises an IgG Fc region (for example, the Fc region of the antibody is the Fc region of IgG), wherein the IgG Fc region may have any one amino acid sequence selected from SEQ ID NOs: 14 to 15 and SEQ ID NOs: 17 to 18 or an amino acid sequence having 80%, 85%, 90%, 95%, 96%, 97%, 98%, or 99% or more sequence identity thereof, and may comprise an amino acid sequence of KPKDTLM (SEQ ID NO: 10) and MHEALHNHY (SEQ ID NO: 12).

In some embodiments, the antibody may have any one amino acid sequence selected from SEQ ID NO: 14 to SEQ ID NO: 18, or an amino acid sequence having 80%, 85%, 90%, 95%, 96%, 97%, 98%, or 99% or more sequence identity thereof, and may essentially comprise GPSVFLFPPKPKDTLM (SEQ ID NO: 13). In some embodiments, the antibody comprises an IgG Fc region, wherein the IgG Fc region may have any one amino acid sequence selected from SEQ ID NO: 14 to SEQ ID NO: 18 or an amino acid sequence having 80%, 85%, 90%, 95%, 96%, 97%, 98%, or 99% or more sequence identity thereof, and may essentially comprise an amino acid sequence of GPSVFLFPPKPKDTLM (SEQ ID NO: 13).

In some embodiments, the antibody having binding affinity to the Fc binding substance or peptide of the present application may be an antibody of the IgG isotype. In some embodiments, the antibody with binding affinity to the Fc binding substance or peptide of the present application may be an antibody of the IgG1 isotype, an antibody of the IgG2 isotype, an antibody of the IgG3 isotype, or an antibody of the IgG4 isotype. In some embodiments, the antibody with binding affinity to the Fc binding substance or peptide of the present application may be an antibody of the IgG1 isotype, an antibody of the IgG2 isotype, or an antibody of the IgG4 isotype.

In some embodiments, the antibody may be any one selected from adalimumab (Humira), rituximab (Rituxan), trastuzumab (Herceptin), bevacizumab (Avastin), infliximab (Remicade), pembrolizumab (Keytruda), nivolumab (Opdivo), eculizumab (Soliris), alemtuzumab (Lemtrada, Campath), daratumumab (Darzalex), ipilimumab (Yervoy), golimumab (Simponi), tocilizumab (Actemra), ranibizumab (Lucentis), secukinumab (Cosentyx), ixekizumab (Taltz), dupilumab (Dupixent), denosumab, ustekinumab (Stelara), palivizumab (Synagis), durvalumab (Imfinzi), atezolizumab (Tecentriq), omalizumab (Xolair), vedolizumab (Entyvio), abciximab (ReoPro), basiliximab (Simulect), alefacept (Amevive), daclizumab (Zinbryta), and elotuzumab (Empliciti).

In some embodiments, the antibody may be an antibody having binding properties to any one of EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptors, EphB receptors, EGFR, EGFRvIII, HER2, HER3, mesothelin, cripto, alphavbeta3, alphavbeta5, Nectin-4, TROP2, PD1, PD-L1, BCMA, B3H7, FOLR-a, tissue factor, claudin 1 (CLDN 1), claudin 3 (CLDN 3), claudin 4 (CLDN 4), claudin 6 (CLDN 6), claudin 18.2 (CLDN 18.2) and alpha v beta 6 integrin.

In some embodiments, the antibody may be an anti-CLDN18.2 antibody (see the document [Korean Patent Application No. 10-2021-7023724]).

In some embodiments, the heavy chain of the anti-CLDN18.2 antibody may comprise CDRH1 having an amino acid sequence having SEQ ID NO: 19 (TYGVH) or 90% or more sequence identity thereof, CDRH2 having an amino acid sequence having SEQ ID NO: 20 (VIWAGGSTNYNSALMS) or 90% or more sequence identity thereof, and CDRH3 having an amino acid sequence having SEQ ID NO: 21 (AAYYGNGLDY) or 90% or more identity thereof. In specific embodiments, the anti-CLDN18.2 antibody may have two heavy chains, and each heavy chain may comprise CDRH1 having an amino acid sequence of SEQ ID NO: 19, CDRH2 having an amino acid sequence of SEQ ID NO: 20, and CDRH3 having an amino acid sequence of SEQ ID NO: 21.

In some embodiments, the light chain of the anti-CLDN18.2 antibody may comprise CDRL1 having an amino acid sequence having SEQ ID NO: 22 (KSSQTLLNSGNQKNYLT) or 90% or more sequence identity thereof, CDRL2 having an amino acid sequence having SEQ ID NO: 23 (WASTGES) or 90% or more sequence identity thereof, and CDRL3 having an amino acid sequence having SEQ ID NO: 24 (QNAYFYPFT) or 90% or more sequence identity thereof. In specific embodiments, the anti-CLDN18.2 antibody may have two light chains, and each light chain may comprise CDRL1 having an amino acid sequence of SEQ ID NO: 22, CDRL2 having an amino acid sequence of SEQ ID NO: 23, and CDRL3 having an amino acid sequence of SEQ ID NO: 24.

In some embodiments, the heavy chain of the anti-CLDN18.2 antibody may comprise CDRH1 having an amino acid sequence having SEQ ID NO: 19 or 90% or more sequence identity thereof, CDRH2 having an amino acid sequence having SEQ ID NO: 20 or 90% or more sequence identity thereof, and CDRH3 having an amino acid sequence having SEQ ID NO: 21 or 90% or more sequence identity thereof, and the light chain of the anti-CLDN18.2 antibody may comprise CDRL1 having an amino acid sequence having SEQ ID NO: 22 or 90% or more sequence identity thereof, CDRL2 having an amino acid sequence having SEQ ID NO: 23 or 90% or more sequence identity thereof, and CDRL3 having an amino acid sequence having SEQ ID NO: 24 or 90% or more sequence identity thereof. In specific embodiments, the anti-CLDN18.2 antibody may have two of heavy chains comprising CDRH1 having an amino acid sequence of SEQ ID NO: 19, CDRH2 having an amino acid sequence of SEQ ID NO: 20, and CDRH3 having an amino acid sequence of SEQ ID NO: 21 and two of light chains comprising CDRL1 having an amino acid sequence of SEQ ID NO: 22, CDRL2 having an amino acid sequence of SEQ ID NO: 23, and CDRL3 having an amino acid sequence of SEQ ID NO: 24.

In some embodiments, the anti-CLDN18.2 antibody may be an antibody comprising a heavy chain having an amino acid sequence having SEQ ID NO: 25 or 90% or more sequence identity thereof, and a light chain having an amino acid sequence having SEQ ID NO: 26 or 90% or more sequence identity thereof. In specific embodiments, the anti-CLDN18.2 antibody may be an antibody comprising a heavy chain having an amino acid sequence of SEQ ID NO; 25, and a light chain having an amino acid sequence of SEQ ID NO: 26. Specifically, the anti-CLDN18.2 antibody may have two heavy chains having an amino acid sequence of SEQ ID NO: 25 and two light chains having an amino acid sequence of SEQ ID NO: 26.

Linker (L'b) of Antibody Conjugate Comprising Group of Interest

It has been described in detail in previous paragraphs that a portion comprising a group of interest is transferred to an antibody in a site-specific manner by a reaction of the antibody with the compound comprising Fc binding unit. The linker (Linker B; $L^b$) of the antibody conjugate comprising the group of interest has the same structure as a partial structure of the compound comprising Fc binding unit.

The linker B may have the following structure:

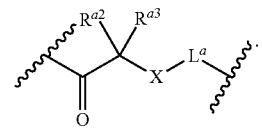

In the structure, each of $R^{a2}$, $R^{a3}$, X, and $L^a$ has been described in detail in previous paragraphs, and each of them is as described in previous paragraphs.

In specific embodiments, the linker B may be represented by the following structure:

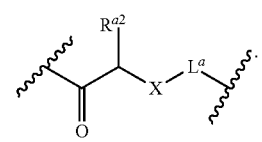

In the structure, each of $R^{a2}$, X, and $L^a$ has been described in detail in previous paragraphs, and each of them is as described in previous paragraphs.

In specific embodiments, the linker B may be represented by the following structure:

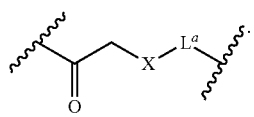

In the structure, each of X and $L^a$ has been described in detail in previous paragraphs, and each of them is as described in previous paragraphs.

Site to which Group of Interest is Linked

In formula 6, n is an integer of 1 to 4. In some embodiments, n may be an integer of 1 to 2. In specific embodiments, n may be 2.

The group of interest may be linked to one or more of lysine residue 246 (K246) and lysine residue 248 (K248) of the Fc region of the antibody unit (through the linker B). More specifically, the antibody unit may comprise two heavy chains (a first heavy chain and a second heavy chain), wherein "-$L^b$-GOI" may be linked to any one or more of K246 of the first heavy chain, K248 of the first heavy chain, K246 of the second heavy chain, and K248 of the second heavy chain.

For example, when one group of interest is linked (through the linker B) to K246 of the first heavy chain of the antibody unit, n is 1. For example, when one group of interest is linked to K248 of the first heavy chain of the antibody unit, n is 1.

For example, when two groups of interest are linked to K246 of the first heavy chain and K246 of the second heavy chain of the antibody unit, respectively, n is 2. For example, when two groups of interest are linked to K248 of the first heavy chain and K248 of the second heavy chain of the antibody unit, respectively, n is 2. For example, when two groups of interest are linked to K246 of the first heavy chain and K248 of the second heavy chain of the antibody unit, respectively, n is 2.

For example, when three groups of interest are linked to K246 of the first heavy chain, K248 of the first heavy chain, and K248 of the second heavy chain of the antibody unit, respectively, n is 3. For example, when three groups of interest are linked to K246 of the first heavy chain, K246 of the second heavy chain, and K248 of the second heavy chain of the antibody unit, respectively, n is 3.

For example, when four groups of interest are linked to K246 of the first heavy chain, K248 of the first heavy chain, K246 of the second heavy chain, and K248 of the second heavy chain of the antibody unit, respectively, n is 4.

Specific Embodiments of Antibody Conjugate Comprising Group of Interest—Antibody Conjugate Comprising Reactive Group The group of interest may comprise a reactive group or functional group. For example, when the group of interest comprises a reactive group, an antibody conjugate comprising the group of interest may be referred to as an antibody conjugate comprising reactive group.

For example, the compound of formula 6 may be a compound of formula 6-1.

Some embodiments of the present application provide an antibody conjugate comprising a group of interest (that is, herein an antibody conjugate comprising reactive group) having the structure of the following formula 6-1:

[formula 6-1]

At this time, $L^b$ is the linker B, and the linker B is as described above.

At this time, RG is a reactive group, and the reactive group is as described above.

Use of Antibody Conjugate Comprising Reactive Group
Overview of Use of Antibody Conjugate Comprising Reactive Group An antibody-payload conjugate (for example, an antibody-drug conjugate) may be prepared using an antibody conjugate comprising reactive group. The antibody-payload conjugate may be prepared by contacting, reacting, or mixing a payload with an antibody comprising reactive group.

The antibody conjugate comprising reactive group refers to a group that is capable of reacting with other groups. For example, the reactive group may be a reactive moiety or may comprise a reactive moiety, wherein the reactive moiety is a moiety that is reactive with other groups. For example, the reactive moiety may be a bio-orthogonal functional group (for example, azide or norbornene).

The payload may comprise a reactive group capable of reacting with a reactive group of the antibody conjugate.

The reactive group of the antibody conjugate comprising reactive group may be referred to as a first reactive group, and the reactive group of the payload can be referred to as a second reactive group.

When an antibody conjugate comprising reactive group and a payload are contacted, reacted, or mixed, an antibody-payload conjugate may be prepared by a reaction of the first reactive group with the second reactive group.

Hereinafter, the payload will be described in detail.

Payload
Overview of Payload

The payload may comprise a second reactive group and an active moiety. The payload may comprise one or more active moieties, wherein each of the one or more active moieties is independently selected. The active moiety has been described in detail in previous paragraphs, and is as described in previous paragraphs. For example, the active moiety may be a drug, an imaging moiety, a radioactive moiety, a protein with a specific function, a peptide with a specific function, an affinity substance (for example, biotin, streptavidin, an aptamer, and the like), a stabilizing substance, a vitamin, a nucleic acid (for example, DNA or RNA) or a PEG moiety, but is not limited thereto. In some embodiments, the active moiety may be a drug moiety, an imaging moiety, a radioactive moiety, or an affinity substance.

The second reactive group may be a group capable of reacting with the first reactive group. For example, when the first reactive group is azide or comprises azide, the second reactive group may be DBCO or comprise DBCO capable of reacting with the azide. As another example, when the first reactive group is norbornene or comprises norbornene, the second reactive group may be tetrazine or comprise tetrazine.

In some embodiments, the sum of the atomic masses of all atoms constituting the payload may be 10000 dalton, 9000 dalton, 8000 dalton, 7000 dalton, 6000 dalton, 5000 dalton, 4500 dalton, 4000 dalton, 3500 dalton, 3000 dalton, 2500 dalton, 2000 dalton, 1500 dalton, 1000 dalton, or 500 dalton or less. It is obvious to those skilled in the art that the sum of the atomic masses of all atoms belonging to the payload is 20 dalton or more.

For example, the payload may have a structure of the following formula 7:

$$CM\text{-}RG^2, \qquad [\text{formula 7}]$$

wherein CM is a cargo moiety (CM), and
$RG^2$ is a second reactive group.

The cargo moiety is characterized by comprising one or more active moieties.

Hereinafter, embodiments of the second reactive group will be described.

Second Reactive Group

For the description of the second reactive group, the description related to the reactive group described in the section "Compound comprising Fc binding unit" may be referenced.

The second reactive group comprises reactive moiety. Herein, the reactive moiety of the second reactive group is referred to as a second reactive moiety.

In some embodiments, the second reactive group may further comprise a spacer of the reactive group (for example, a spacer of the second reactive moiety) in addition to the reactive moiety (for example, a second reactive moiety), as described in the paragraph describing the reactive group. At this time, the reactive moiety is linked to a part other than the reactive group through the spacer of the reactive group. For example, the second reactive group may have the following structure:

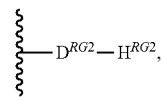

wherein $D^{RG2}$ is a spacer of the second reactive group, and $H^{RG2}$ is the second reactive moiety.

In some embodiments, the second reactive moiety may be a bio-orthogonal functional group (for example, a second bio-orthogonal functional group). At this time, the description of the bio-orthogonal functional group is as described in the description of the bio-orthogonal functional group in the section "Compound comprising Fc binding unit" of the present application.

In some embodiments, the reactive moiety may be a click chemistry functional group (for example, a second click chemistry functional group). At this time, the description of the click chemistry functional group is as described in the description of the click chemistry functional group in the section "Compound comprising Fc binding unit" of the present application.

In some embodiments, the reactive moiety may be selected from an azide group, a terminal alkyne group, a cyclic alkyne (for example, cyclooctyne) group, a tetrazine group, a norbornene group, a cycloalkene (for example, cyclooctene) group, a tetrazole group, an oxime group, and an isocyanide group, a halogen group, an aldehyde group, a nitrone group, a hydroxyamine group, a nitrile group, a hydrazine group, a ketone group, a bronic acid group, a cyanobenzothiazole group, an allyl group, a phosphine group, a maleimide group, a disulfide group, a thioester group, a halocarbonyl group, an isonitrile group, a sydnone group, a selene group, a thiol group, and a protected thiol group.

Embodiments of Payload

Some embodiments of the present application provide a payload having the structure of the following formula 7-1. Some embodiments of the present application provide a compound having the structure of the following formula 7-1:

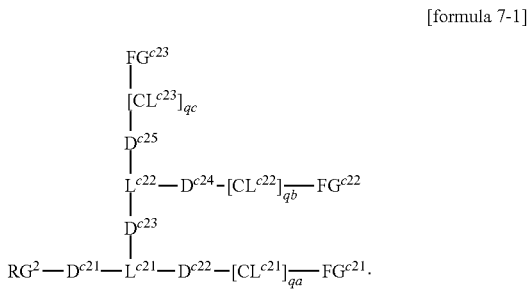

[formula 7-1]

wherein
$RG^2$ is a second reactive group,
$FG^{c21}$, $FG^{c22}$, and $FG^{c23}$ are a functional group C21, a functional group C22, and a functional group C23, respectively,
$CL^{c21}$, $CL^{c22}$, and $CL^{c23}$ are a cleavable linker C21, a cleavable linker C22, and a cleavable linker C23, respectively,
qa is an integer of 0 to 1, qb is an integer of 0 to 1, and qc is an integer of 0 to 1,
$D^{c21}$, $D^{c22}$, $D^{c23}$, $D^{c24}$, and $D^{c25}$ are a spacer C21, a spacer C22, a spacer C23, a spacer C24, and a spacer C25, respectively, and
$L^{c21}$ and $L^{c22}$ are a linker C21 and a linker C22, respectively.

The second reactive group has been described in detail in previous paragraphs, and is as described in previous paragraphs.

That is, the cargo moiety (CM) may have the following structure:

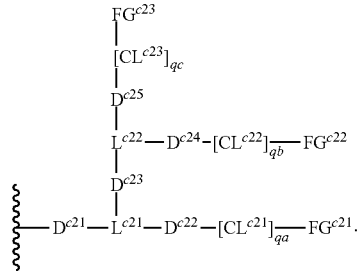

Hereinafter, each element of the payload of formula 7-1 will be described in detail.

Spacer C21 (D"c21), Spacer C22 (D"c22), Spacer C23 (D"c23), Spacer C24 (D"c24), and Spacer C25 (D"c25)

Each of Spacer C21 ($D^{c21}$), Spacer C22 ($D^{c22}$), Spacer C23 ($D^{c23}$), Spacer C24 ($D^{c24}$), and Spacer C25 ($D^{c25}$) may be referred to as Spacer C20. Furthermore, it should be understood that each of Spacer C21 ($D^c21$), Spacer C22 ($D^{c22}$), Spacer C23 ($D^{c23}$), Spacer C24 ($D^{c24}$), and Spacer C25 ($D^{c25}$) may be independently selected. For example, Spacer C21 ($D^{c21}$) and Spacer C22 ($D^{c22}$) may have different structures. For another example, Spacer C21 ($D^{c21}$) and Spacer C22 ($D^{c22}$) may have the same structure.

In some embodiments, the length of the main chain of Spacer C20 (that is, the number of atoms located in the main chain) may be 0 to 20. For example, Spacer C20 may be substituted or unsubstituted alkylene, substituted or unsubstituted heteroalkylene, substituted or unsubstituted alkenylene, substituted or unsubstituted heteroalkenylene, substituted or unsubstituted alkynylene, or substituted or unsubstituted heteroalkynylene, with the main chain having a length of 0 to 20.

In some embodiments, each of Spacer C21, Spacer C22, Spacer C23, Spacer C24, and Spacer C25 may be independently a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. For example, each of the substituents may be independently =O. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In some embodiments, each of Spacer C21, Spacer C22, Spacer C23, Spacer C24, and Spacer C25 may be independently a bond, substituted or unsubstituted $C_{1-15}$ alkylene, substituted or unsubstituted $C_{1-15}$ heteroalkylene, substituted or unsubstituted $C_{2-15}$ alkenylene, substituted or unsubstituted $C_{2-15}$ heteroalkenylene, substituted or unsubstituted $C_{2-15}$ alkynylene, or substituted or unsubstituted $C_{2-15}$ heteroalkynylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. For example, each of the substituents may be independently =O. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In specific embodiments, each of Spacer C21, Spacer C22, Spacer C23, Spacer C24, and Spacer C25 may be independently a bond, substituted or unsubstituted $C_{1-10}$ alkylene, or substituted or unsubstituted $C_{1-10}$ heteroalkylene. Herein, the "substituted" indicates that one or more hydrogen atoms in a group modified by the term of "substituted" are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH. For example, each of the substituents may independently be =O. Herein, heteroalkylene, heteroalkenylene, heteroalkynylene, heterocycloalkyl, and heteroaryl each independently comprises one or more heteroatoms, wherein each of the heteroatoms may be independently selected from N, O, and S.

In specific embodiments, each of Spacer C21, Spacer C22, Spacer C23, Spacer C24, and Spacer C25 may be independently a bond, substituted or unsubstituted $C_{1-12}$ alkylene, or substituted or unsubstituted $C_{1-12}$ heteroalkylene. Herein, substituted alkylene or substituted heteroalkylene may comprise one or more substituents, wherein all of the substituents may be =O. Herein, the heteroalkylene comprises one or more heteroatoms, wherein each of the heteroatoms may be independently selected from N, O, or S.

In specific embodiments, each of Spacer C21, Spacer C22, Spacer C23, Spacer C24, and Spacer C25 may be independently a bond, substituted or unsubstituted $C_{1-10}$ alkylene, or substituted or unsubstituted $C_{1-10}$ heteroalkylene. Herein, substituted alkylene or substituted heteroalkylene may comprise one or more substituents, wherein all of the substituents may be =O. Herein, the heteroalkylene comprises one or more heteroatoms, wherein each of the heteroatoms may be independently selected from N, O, or S.

Linker C21 (L"c21) and Linker C22 (L"c22)

Each of Linker C21 and Linker C22 may be referred to as Linker C20. Furthermore, it should be understood that each of Linker C21 and Linker C22 may be independently selected. For example, Linker C21 and Linker C22 may have different structures.

Linker C20 is a trivalent linker with three sites linked to other parts. The presence of Linker C20 may allow a branched structure to be formed.

In some embodiments, the sum of the atomic masses of all atoms constituting Liker C20 may be 300 dalton, 200 dalton, 190 dalton, 180 dalton, 170 dalton, 160 dalton, 150 dalton, 140 dalton, 130 dalton, 120 dalton, 110 dalton, or 100 dalton or less. In some embodiments, Linker C20 may be any amino acid residue. For example, each of Linker C21 and Linker C22 may be independently selected from conjugated diaminopropionic acid (Dap) residue, conjugated diaminobutyric acid (Dab) residue, conjugated ornithine (Orn) residue, conjugated lysine (Lys) residue, conjugated 2,7-diaminoheptanoic acid residue, conjugated cysteine residue, and conjugated 2-aminosuberic acid residue. In specific embodiments, both Linker C21 and Linker C22 may be conjugated lysine residues. Herein, for convenience, the term of conjugated may be omitted. For example, the conjugated diaminopropionic acid residue may be referred to as diaminopropionic acid residue or diaminopropionic acid. For example, the conjugated diaminobutyric acid residue can be referred to as diaminobutyric acid residue or diaminobutyric acid. For example, the conjugated ornithine residue may be referred to as ornithine residue or ornithine. For example, the conjugated lysine residue may be referred to as lysine residue or lysine.

In some embodiments, Linker C20 may have the following structure:

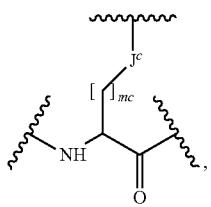

wherein mc is an integer of 1 to 5, $J^c$ is —NH—, —S—, or —C(=O)—, and

The wavy line drawn perpendicular to the bond represents the attachment point of Linker C20 to other parts.

For example, Linker C21 may have the following structure:

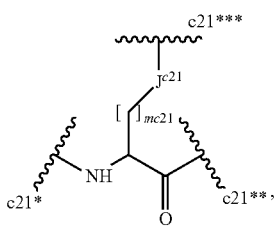

wherein mc21 is an integer of 1 to 5, $J^{c21}$ is —NH—, —S—, or —C(=O)—, and c21*, c21 and c21* represents the attachment point of Linker 21 to other parts. For example, each of c21*, c21, and c21* indicate an attachment point with Spacer C21, an attachment point with Spacer C22, and an attachment point with Spacer C23.

In specific embodiments, c21* may be an attachment point with Spacer C22, c21 may be an attachment point with Spacer C21, and c21* may be an attachment point with Spacer C23.

For example, Linker C22 may have the following structure:

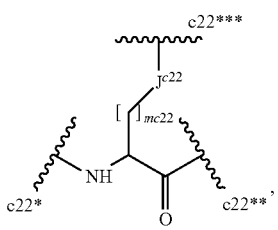

wherein mc22 is an integer of 1 to 5, $J^{c22}$ is —NH—, —S—, or —C(=O)—, and c22*, c22 and c22* represent the attachment point of Linker C22 to other parts. For example, each of c22*, c22, and c22* represents an attachment point with Spacer C23, an attachment point with PEG moiety C21, and an attachment point with PEG moiety C22.

In specific embodiments, c22* may be an attachment point with PEG moiety C21, c22 may be an attachment point with Spacer C23, and c22* may be an attachment point with PEG moiety C22.

Functional Group C21 (FG"c21), Functional Group C22 (FG"c22), and Functional Group C23 (FG"c22)

Each of Functional group C21 ($FG^{c21}$), Functional group C22 ($FG^{c22}$), and Functional group C23 ($FG^{c23}$) may be referred to as Functional group C20. Furthermore, it should be understood that each of Functional group C21, Functional group C22, and Functional group C23 may be independently selected. For example, Functional group C21 and Functional group C22 may be different. As another example, Functional group C21 and Functional group C22 may be the same.

For the description of Functional group C20, the explanation regarding the functional group in the section "Compounds comprising Fc binding unit" of the present application may be referenced. Functional group C20 comprises one or more active moieties. Hereinafter, Functional group C20 will be described in detail.

In some embodiments, the sum of the atomic masses of all atoms constituting Functional group C20 may be 5000 dalton or less, 4000 dalton or less, 3000 dalton or less, 2500 dalton or less, 2000 dalton or less, 1500 dalton or less, or 1000 dalton or less.

Functional group C20 comprises an active moiety, wherein each active moiety may comprise any one selected from, for example, a drug moiety, an imaging moiety, a radioactive moiety, a stabilizing substance, a vitamin, a nucleic acid (for example, DNA or RNA), and a PEG moiety, but is not limited thereto. In specific embodiments, the active moiety may be a drug moiety, an imaging moiety, a radioactive moiety, or a PEG moiety. In specific embodiments, the active moiety may be a drug moiety or a PEG moiety. For example, any one of Functional group C21, Functional group C22, and Functional group C23 may be a drug moiety, and the remaining two may be PEG groups. For example, any two of Functional group C21, Functional group C22, and Functional group C23 may be drug moieties, and the other one may be a PEG moiety. For example, all of Functional group C21, Functional group C22, and Functional group C23 may be drug moieties.

For example, the drug moiety may be any one selected from auristatin (for example, monomethyl auristatin), eribulin, tubulysin, geldanamycin, maytansinoid, calicheamicin, mertansine, daunomycin, doxorubicin, methotrexate, vindesine, SG2285, dolastatin, dolastatin analogs auristatin, cryptophycin, camptothecin, camptothecin analogs (for example, $S_N38$, FL118, or exatecan), rhizoxin derivative, CC 1065 analog or derivative, duocarmycin, enediyne antibiotic, esperamicin, epothilone, pyrrolobenzodiazepine (PBD) derivative, α-amanitin, toxoid, toll-like receptor 5 (TLR5) agonist, toll-like receptor 7 (TLR7) agonist, toll-like receptor 8 (TLR8) agonist, 1,4,7-triazacyclononane-1,4,7-triacetic acid (NOTA), and 1,4,7,10-tetraazacyclododecane-1,4,7,10-tetraacetic acid (DOTA), or an analog thereof.

The PEG moiety may comprise 1 to 30, 1 to 20, or 1 to 10 of ethyleneglycol units (for example, —CH$_2$OCH$_2$—, —OCH$_2$CH$_2$— or —CH$_2$CH$_2$O—).

In some embodiments, the PEG moiety may have the following structure:

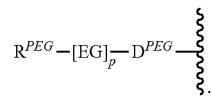

At this time, $D^{PEG}$ is a spacer of the PEG moiety and may be a group having a main chain length of 0 to 6. For example, $D^{PEG}$ is a bond, or substituted or unsubstituted $C_{1-6}$ alkylene, substituted or unsubstituted $C_{1-6}$ heteroalkylene, substituted or unsubstituted $C_{1-6}$ alkenylene, substituted or unsubstituted $C_{1-6}$ heteroalkenylene, substituted or unsubstituted alkynylene, or substituted or unsubstituted heteroalkynylene, wherein the substituted alkylene, substituted heteroalkylene, substituted alkenylene, or substituted heteroalkynylene may comprise one or more substituents, and may be selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, =O, =S, and —SH. In specific embodiments, the substituent may be selected from —$C_{1-4}$ alkyl, —C(=O)H, —C(=O)CH$_3$, —C(=O)OH, —C(=O)NH$_2$, —NH$_2$, =O, =S, —OH, —NO$_2$ and —SH. Herein, each of the heteroalkylene, the heteroalkenylene, and the heteroalkynylene independently comprises one or more heteroatoms, wherein each of the heteroatoms may be independently selected from N, O, and S. In specific embodiments, $D^{PEG}$ may be a bond, or substituted or unsubstituted $C_{1-3}$ alkylene, or substituted or unsubstituted $C_{1-3}$ heteroalkylene, wherein the substituted alkylene or the substituted heteroalkylene comprises one or more substituents, wherein the substituent is =O or $C_{1-3}$ alkyl, wherein the heteroalkylene comprises one or more heteroatoms, wherein each of the heteroatoms may be independently selected from N, O, and S.

In the structure of the PEG moiety, $R^{PEG}$ is a PEG capping group. At this time, the PEG capping group may not be present, or may be —CH$_3$, C$_2$ alkyl, C$_3$ alkyl, —NH$_2$, —CH$_2$NH$_2$, —SC(=O)CH$_3$, —SC(=O)CH$_2$CH$_3$, —CH$_2$SC(=O)CH$_3$, —CH$_2$SC(=O)CH$_2$CH$_3$, —OH, —CH$_2$OH, —SH, —CH$_2$SH, —OCH$_3$, —CH$_2$OCH$_3$, —CH$_2$OCH$_2$CH$_3$, —C(=O)CH$_3$, —C(=O)CH$_2$CH$_3$, —CH$_2$C(=O)CH$_3$, —CH$_2$C(=O)CH$_2$CH$_3$, —NHC(=O)CH$_3$, —NHC(=O)CH$_2$CH$_3$, —CH$_2$NHC(=O)CH$_3$, —CH$_2$CH$_2$NHC(=O)CH$_3$, —CH$_2$CH$_2$NHC(=O)CH$_2$CH$_3$, —CH$_2$NHC(=O)CH$_2$CH$_3$, —CH$_2$CH$_2$COOH, glucose or —O-glucose, but is not limited thereto. In specific embodiments, the PEG capping group may not be present, or may be —CH$_3$, —OCH$_3$, —CH$_2$OCH$_3$, —C(=O)CH$_3$, —CH$_2$C(=O)CH$_3$, —NHC(=O)CH$_3$, —CH$_2$NHC(=O)CH$_3$ or —CH$_2$CH$_2$COOH. In some embodiments, the sum of the atomic masses of the atoms belonging to the PEG capping group may be 300 dalton or less, 200 dalton or less, 150 dalton or less, 100 dalton or less, or 50 dalton or less, but is not limited thereto.

In the structure of the PEG moiety, p may be an integer of 1 to 30, preferably 1 to 10.

In the structure of the PEG moiety, [EG] refers to an ethyleneglycol unit (for example, —CH$_2$OCH$_2$—, —OCH$_2$CH$_2$— or —CH$_2$CH$_2$O—).

In some embodiments, Functional group C20 may further comprise a spacer of the functional group in addition to the active moiety. For example, the active moiety may be linked to parts other than the functional group through a spacer of the functional group.

In some embodiments, Functional group C20 may have the following structure:

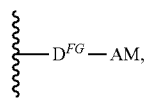

wherein $D^{FG}$ is a spacer of the functional group (spacer FG), and AM is an active moiety.

In some embodiments, the length of the spacer of the functional group ($D^{FG}$) may be 0 to 6 based on the number of atoms in the main chain.

In some embodiments, $D^{FG}$ may be a bond, or substituted or unsubstituted $C_{1-6}$ alkylene, substituted or unsubstituted $C_{1-6}$ heteroalkylene, substituted or unsubstituted $C_{2-6}$ alkenylene, substituted or unsubstituted $C_{2-6}$ heteroalkenylene, substituted or unsubstituted $C_{2-6}$ alkynylene, substituted or unsubstituted $C_{2-6}$ heteroalkynylene, substituted or unsubstituted $C_{3-8}$ cycloalkylene, substituted or unsubstituted $C_{3-8}$ heterocycloalkylene, substituted or unsubstituted $C_{3-8}$ cycloalkenylene (for example, aryl), or substituted or unsubstituted $C_{3-8}$ heterocycloalkenylene (for example, heteroaryl). Herein, the substituted indicates that one or more hydrogen atoms in a group modified by the term of substituted are substituted with one or more substituents. That is, the substituted alkylene, and the like may comprise one or more substituents. For example, each of the substituents may be independently selected from —R, =O, =S, —NO$_2$, —CR$_3$, —NR$_2$, =NR, —OR, —SR, —C(=O)R, —C(=O) CR$_3$, —C(=O)OR, and —C(=O)NR$_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —NH$_2$, =O, =S, and —SH. In specific embodiments, each of the substituents may be independently selected from —$C_{1-4}$ alkyl, —C(=O)H, —C(=O)CH$_3$, —C(=O)OH, —C(=O)NH$_2$, —NH$_2$, =O, =S, —OH, —NO$_2$ and —SH. Herein, each of the heteroalkylene, the heteroalkenylene, and the heteroalkynylene independently comprises one or more heteroatoms, wherein each of the heteroatoms may be independently selected from N, O, and S.

In specific embodiments, $D^{FG}$ may be a bond, or substituted or unsubstituted $C_{1-3}$ alkylene, substituted or unsubstituted $C_{1-3}$ heteroalkylene. At this time, the substituted alkylene or substituted heteroalkylene may comprise one or more substituents, and each of the substituents may be independently selected from —$C_{1-4}$ alkyl and =O. At this time, the heteroalkylene comprises one or more heteroatoms, wherein each of the heteroatoms may be independently selected from O, N, and S.

In specific embodiments, $D^{FG}$ may be a bond.

In the structure, labels such as c20, c21, c22, and c23 may be additionally marked to each element such as an active moiety and a spacer of the functional group, if necessary, for differentiation from other structures.

Cleavable linker C21 (CL"c21), Cleavable linker C22 (CL"c22), and Cleavable linker C23 (CL"c23)

Each of Cleavable linker C21 ($CL^{c21}$), Cleavable linker C22 ($CL^{c22}$), and Cleavable linker C23 ($CL^{c23}$) may be referred to as Cleavable linker C20. Furthermore, it should be understood that each of Cleavable linker C21 ($CL^{c21}$), Cleavable linker C22 ($CL^{c22}$), and Cleavable linker C23 ($CL^{c23}$) may be independently selected.

The payload of formula 7-1 may comprise Cleavable linker C20 (when any one of qa, qb, and qc is 1) or may not comprise Cleavable linker C20 (when all of qa, qb, and qc are 0).

Cleavable linker C20 is a "cleavable linker" optionally labeled with "C20," and Cleavable linker C20 may be referred to as a cleavable linker. Hereinafter, the cleavable linker will be described in detail.

In some embodiments, cleavable linkers may be designed such that a drug moiety or radioactive moiety can be released at a target position. For example, the cleavable linker may be a linker that can be cleaved by an in vivo or intracellular enzyme (for example, cathepsin or glucuronidase). In some embodiments, a cleavable linker may be present with a functional group including a drug moiety when the active moiety of the functional group is a drug moiety. For example, when the active moiety of the functional group is a PEG moiety, any one of qa, qb, and qc, which determines the presence or absence of a cleavable linker, may be 0 in Chemical Formula 7-1.

Examples of cleavable linkers used in the field of antibody conjugates (for example, an antibody-drug conjugate) are disclosed in detail in the document [Su, Z., Xiao, D., Xie, F., Liu, L., Wang, Y., Fan, S., . . . & Li, S. (2021). Antibody-drug conjugates: Recent advances in linker chemistry. Acta Pharmaceutica Sinica B, 11(12), 3889-3907.], the contents of which are hereby incorporated by reference in their entirety. For example, the cleavable linker may comprise a cleavage group comprising a cleavage site or a triggering site, and a self-immolative group. The cleavable linker may be referred to as, for example, a self-immolative linker.

In some embodiments, the cleavable linker may be a linker that is cleavable by cathepsin. For example, the cleavable linker may comprise the structure of any one selected from valine-citrulline, lysine-lysine, phenylalanine-lysine, valine-alanine, and alanine-alanine. In some embodiments, the cleavable linker may be a linker that is cleavable by any one of cathepsin B, cathepsin C, and cathepsin D.

In some embodiments, the cleavable linker may comprise a valine-citrulline linker (VC linker). For example, the cleavable linker may be -valine-citrulline-p-aminobenzoyloxycarbonyl-(-valine-citrulline-PAB-).

In some embodiments, the cleavable linker may comprise a beta-glucuronide linker. Beta-glucuronide linkers are described in detail in the document [U.S. Pat. No. 8,568, 728B2, Application No. U.S. Ser. No. 13/274,212], the contents of which are hereby incorporated by reference in their entirety. In some embodiments, the beta-glucuronide linker may be a linker that is cleavable by glucuronidase. In some embodiments, the beta-glucuronide linker may be a linker that is cleavable by beta-glucuronidase.

In some embodiments, the beta-glucuronide linker may have the following structure:

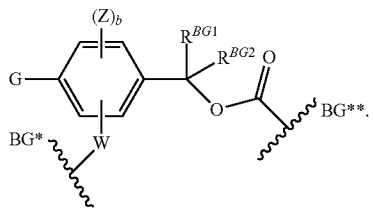

At this time, G is sugar or sugar acid. In specific embodiments, G may be glucuronic acid.

At this time, W represents an electron withdrawing group. In specific embodiments, W is —NR$^w$—, —C(=O)— or —C(=O)NR$^w$—, wherein R$^w$ may be H or $C_{1-3}$ alkyl. At this time, when W is —C(=O)NR$^w$—, the carbonyl group may be linked to the phenyl group through —NR$^w$—. At this time, when W is —C(=O)NR$^w$—, —NR$^w$— may be linked to the phenyl group through the carbonyl group.

At this time, each of R$^{BG1}$ and R$^{BG2}$ is independently selected from H and $C_{1-3}$. In specific embodiments, both R$^{BG1}$ and R$^{BG2}$ may be H.

At this time, each Z is independently H, $C_{1-3}$ alkyl, or an electron withdrawing group (for example, an amide, carboxylic acid, carboxylic acid ester, halogen, cyano, or nitro group). In specific embodiments, Z may be hydrogen. At this time, b is an integer of 1 to 3.

At this time, BG* represents an attachment point with a spacer (for example, D$^{c22}$, D$^{c24}$, or D$^{c25}$) in formula 7-1.

At this time, BG** represents an attachment point with a functional group (for example, FG$^{c21}$, FG$^{c22}$, or FG$^{c23}$) in formula 7-1.

In specific embodiments, the beta-glucuronide linker may have the following structure:

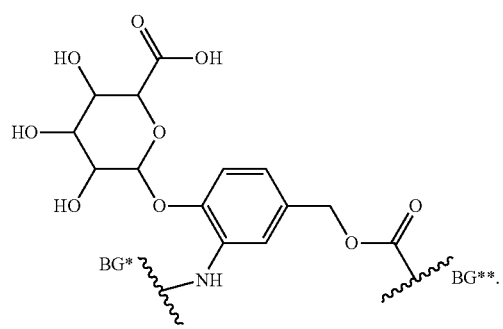 [SMILES: *Nc1cc(COC(*)=O)ccc1OC1OC(C(=O)O)C(O)C(O)C1O]

In some embodiments, when Spacer C24 (D$^{c24}$) and Spacer C25 (D$^{c25}$) are a bond, qc and qb are 0, each of Functional group C22 (FG$^{c22}$) and Functional group C23 (FG$^{c23}$) are a PEG moiety (referred to as PEG moiety C21 and PEG moiety C22 for convenience), and Functional group C21 (FG$^{c21}$) is -D$^{FG}$-AM, the payload of formula 7-1 may be represented by formula 7-2.

Some embodiments of the present application provide a payload having the structure of the following formula 7-2. Some embodiments of the present application provide a compound having the structure of the following formula 7-2:

[formula 7-2]

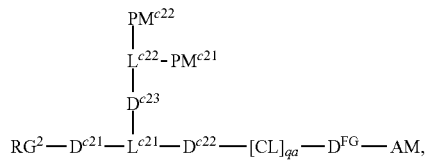

wherein

RG$^2$ is a second reactive group,

AM is an active moiety (herein, the active moiety is not a PEG moiety),

CL is a cleavable linker, qa is an integer of 0 to 1,

D$^{FG}$ is a spacer of the functional group,

D$^{c21}$, D$^{c22}$, and D$^{c23}$ are Spacer C21, Spacer C22, and Spacer C23, respectively, L$^{c21}$ and L$^{c22}$ are Liker C21 and Linker C22, respectively, and PM$^{c21}$ and PM$^{c22}$ are PEG moiety C21 and PEG moiety C22, respectively.

Each element of formula 7-2 has been described in detail in previous paragraphs, and each element is as described in previous paragraphs.

That is, the cargo moiety (CM) may have the following structure:

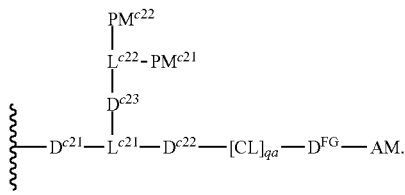

In some embodiments, each of PEG moiety C21 and PEG moiety C22 may be referred to as PEG moiety C20. Furthermore, it will be understood that each of PEG moiety C21 and PEG moiety C22 may be independently selected. For example, PEG moiety C21 and PEG moiety C22 may have different structures.

In some embodiments, PEG moiety C20 may comprise 1 to 30, 1 to 20, or 1 to 10 of ethyleneglycol units (for example, —$CH_2OCH_2$—, —$OCH_2CH_2$— or —$CH_2CH_2O$—).

In some embodiments, PEG moiety C20 may be a PEG moiety, wherein the PEG moiety may have the following structure:

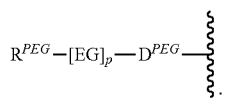

At this time, $D^{PEG}$ is a spacer of the PEG moiety and may be a group having a main chain length of 0 to 6. For example, $D^{PEG}$ is a bond, or substituted or unsubstituted $C_{1-6}$ alkylene, substituted or unsubstituted $C_{1-6}$ heteroalkylene, substituted or unsubstituted $C_{1-6}$ alkenylene, substituted or unsubstituted $C_{1-6}$ heteroalkenylene, substituted or unsubstituted alkynylene, or substituted or unsubstituted heteroalkynylene, wherein the substituted alkylene, substituted heteroalkylene, substituted alkenylene, or substituted heteroalkynylene may comprise one or more substituents, herein each of the substituents may be independently selected from —R, =O, =S, —$NO_2$, —$CR_3$, —$NR_2$, =NR, —OR, —SR, —C(=O)R, —C(=O)$CR_3$, —C(=O)OR, and —C(=O)$NR_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —$NH_2$, =O, =S, and —SH. In specific embodiments, the substituent may be selected from —$C_{1-4}$ alkyl, —C(=O)H, —C(=O)$CH_3$, —C(=O)OH, —C(=O)$NH_2$, —$NH_2$, =O, =S, —OH, —$NO_2$ and —SH. Herein, each of the heteroalkylene, the heteroalkenylene, and the heteroalkynylene independently comprises one or more heteroatoms, wherein each of the heteroatoms may be independently selected from N, O, and S. In specific embodiments, $D^{PEG}$ may be a bond, or substituted or unsubstituted $C_{1-3}$ alkylene, or substituted or unsubstituted $C_{1-3}$ heteroalkylene, wherein the substituted alkylene or the substituted heteroalkylene comprises one or more substituents, wherein the substituent is =O or $C_{1-3}$ alkyl, wherein the heteroalkylene comprises one or more heteroatoms, wherein each of the heteroatoms may be independently selected from N, O, and S.

In the structure of the PEG moiety, $R^{PEG}$ is a PEG capping group. At this time, the PEG capping group may not be present, or may be —$CH_3$, $C_2$ alkyl, $C_3$ alkyl, —$NH_2$, —$CH_2NH_2$, —SC(=O)$CH_3$, —SC(=O)$CH_2CH_3$, —$CH_2$SC(=O)$CH_3$, —$CH_2$SC(=O)$CH_2CH_3$, —OH, —$CH_2$OH, —SH, —$CH_2$SH, —$OCH_3$, —$CH_2OCH_3$, —$CH_2OCH_2CH_3$, —C(=O)$CH_3$, —C(=O)$CH_2CH_3$, —$CH_2$C(=O)$CH_3$, —$CH_2$C(=O)$CH_2CH_3$, —NHC(=O)$CH_3$, —NHC(=O)$CH_2CH_3$, —$CH_2$NHC(=O)$CH_3$, —$CH_2CH_2$NHC(=O)$CH_3$, —$CH_2CH_2$NHC(=O)$CH_2CH_3$, —$CH_2$NHC(=O)$CH_2CH_3$, —$CH_2CH_2$COOH, glucose or —O-glucose, but is not limited thereto. In specific embodiments, the PEG capping group may not be present, or may be —$CH_3$, —$OCH_3$, —$CH_2OCH_3$, —C(=O)$CH_3$, —$CH_2$C(=O)$CH_3$, —NHC(=O)$CH_3$, —$CH_2$NHC(=O)$CH_3$ or —$CH_2CH_2$COOH. In some embodiments, the sum of the atomic masses of the atoms belonging to the PEG capping group may be 300 dalton or less, 200 dalton or less, 150 dalton or less, 100 dalton or less, or 50 dalton or less, but is not limited thereto.

In the structure of the PEG moiety, p may be an integer of 1 to 30, preferably 1 to 10.

In the structure of the PEG moiety, [EG] refers to an ethyleneglycol unit, and the ethyleneglycol unit is as described above in the related paragraph.

In some embodiments, the length of the main chain of the spacer ($D^{FG}$) of the functional group (that is, the number of atoms located in the main chain) may be 0 to 6. The spacer of the functional group is a bond, or substituted or unsubstituted $C_{1-6}$ alkylene, substituted or unsubstituted $C_{1-6}$ heteroalkylene, substituted or unsubstituted $C_{1-6}$ alkenylene, substituted or unsubstituted $C_{1-6}$ heteroalkenylene, substituted or unsubstituted alkynylene, or substituted or unsubstituted heteroalkynylene, wherein the substituted alkylene, substituted heteroalkylene, substituted alkenylene, or substituted heteroalkynylene may comprise one or more substituents, and the may be selected from —R, =O, =S, —$NO_2$, —$CR_3$, —$NR_2$, =NR, —OR, —SR, —C(=O)R, —C(=O)$CR_3$, —C(=O)OR, and —C(=O)$NR_2$, wherein each R may be independently selected from H, halogen, $C_{1-6}$ alkyl, $C_{3-10}$ cycloalkyl, $C_{3-10}$ heterocycloalkyl, aryl, heteroaryl, —OH, —$NH_2$, =O, =S, and —SH. In specific embodiments, the substituent may be selected from —$C_{1-4}$ alkyl, —C(=O)H, —C(=O)$CH_3$, —C(=O)OH, —C(=O)$NH_2$, —$NH_2$, =O, =S, —OH, —$NO_2$ and —SH. Herein, each of the heteroalkylene, the heteroalkenylene, and the heteroalkynylene independently comprises one or more heteroatoms, wherein each of the heteroatoms may be independently selected from N, O, and S. In specific embodiments, $D^{FG}$ may be a bond, or substituted or unsubstituted $C_{1-3}$ alkylene, or substituted or unsubstituted $C_{1-3}$ heteroalkylene, wherein the substituted alkylene or the substituted heteroalkylene includes one or more substituents, wherein the substituent is =O or $C_{1-3}$ alkyl, wherein the heteroalkylene comprises one or more heteroatoms, wherein each of the heteroatoms may be independently selected from N, O, and S.

In some embodiments, the active moiety (AM) may be a drug moiety.

In specific embodiments, the payload may have a structure of the following formula 7-3:
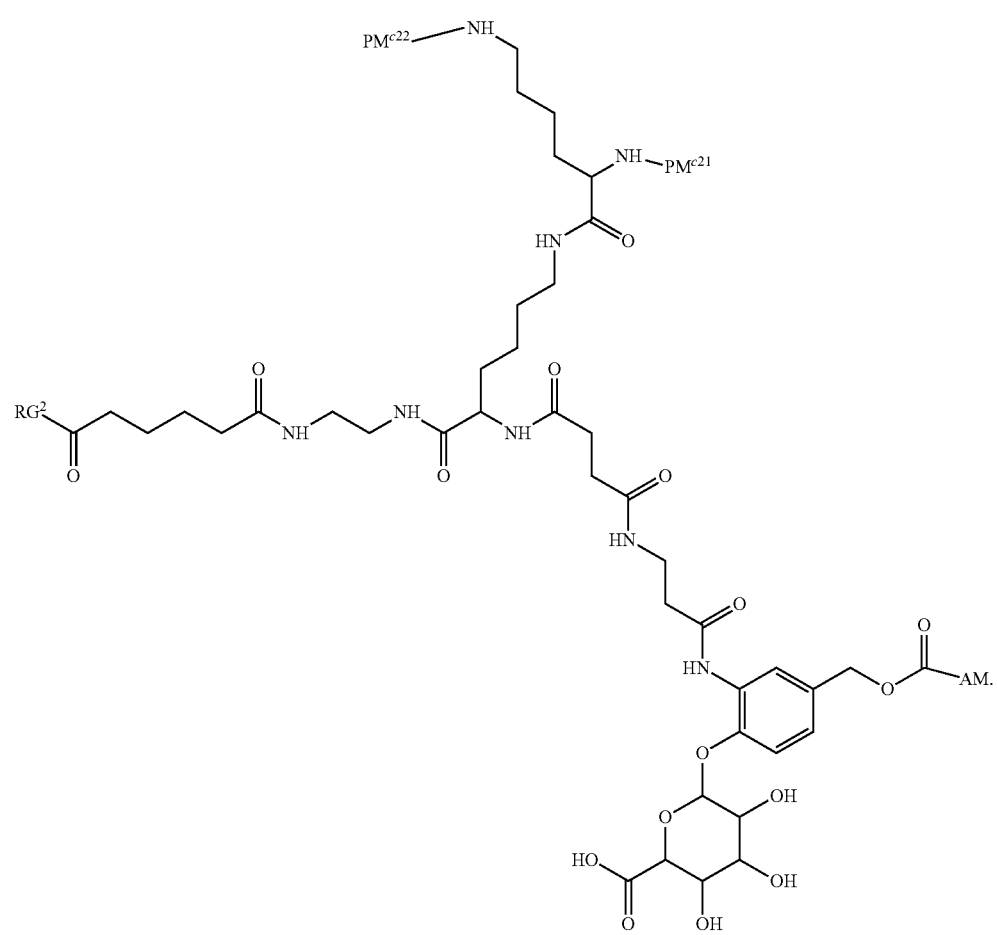
[formula 7-3]

That is, the cargo moiety may have the following structure:
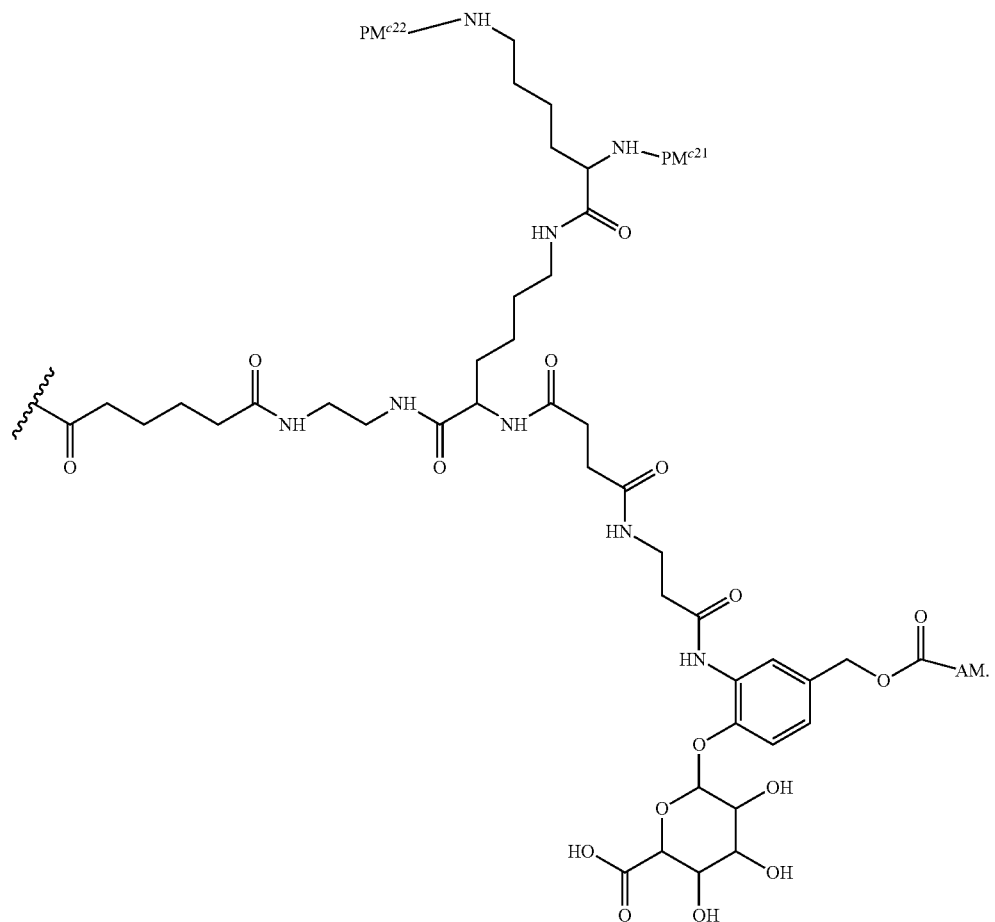
40
In specific embodiments, the payload may have a structure of the following formula 7-4:

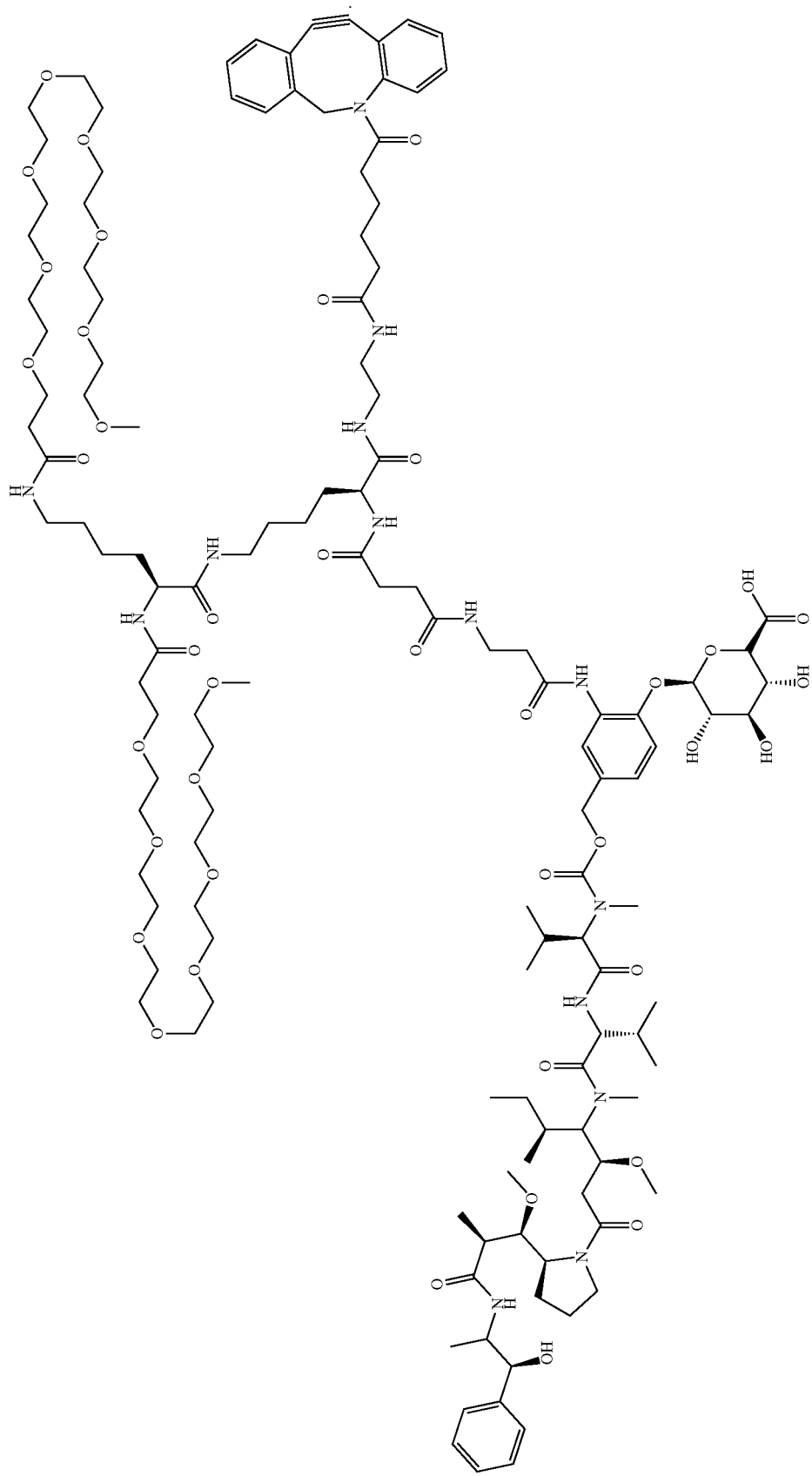

That is, the cargo moiety may have the following structure:

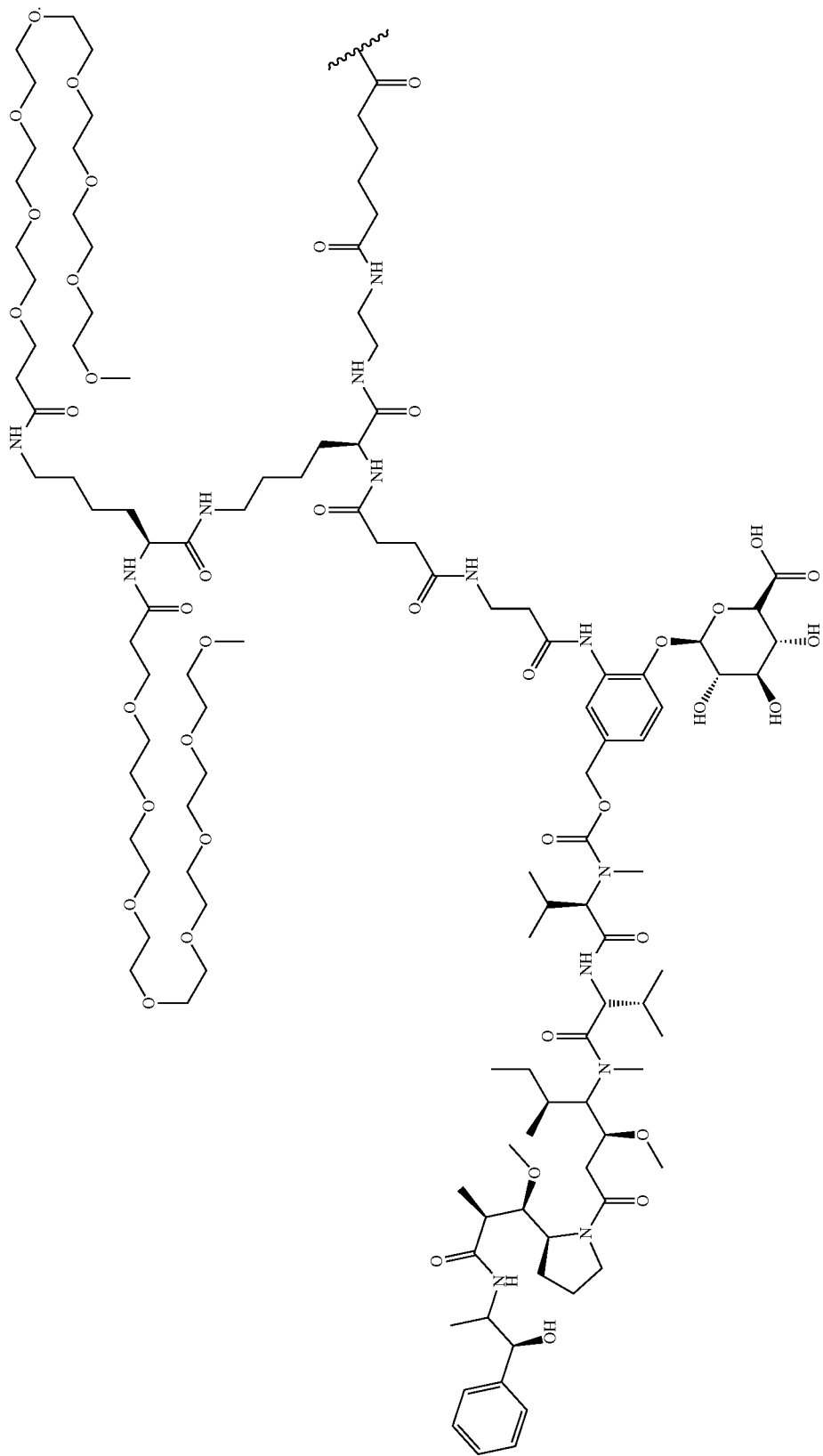

Composition or Kit Comprising Antibody Conjugate Comprising Group of Interest

Some embodiments of the present application provide a composition or kit comprising an antibody conjugate comprising a group of interest. In some embodiments, the composition or kit comprising an antibody conjugate comprising a group of interest may be used to prepare an antibody-payload conjugate to be described below.

In some embodiments, the composition or kit may further comprise an additional element in addition to the antibody conjugate comprising the group of interest. For example, the additional element included in the composition or kit may be a pharmaceutically acceptable salt, an excipient, a diluent, a stabilizer, a pH modifier, and the like, but is not limited thereto.

As described above, among the antibody conjugates comprising a group of interest, an antibody-payload conjugate may be prepared by using an antibody conjugate comprising reactive group (for example, a compound of formula 6-1). Hereinafter, a method for preparing the antibody-payload conjugate will be described in detail.

Preparation of Antibody-Payload Conjugate

Overview of Preparation of Antibody-Payload Conjugate

Some embodiments of the present application provide a method for preparing an antibody-payload conjugate.

The following two elements are used in the antibody-payload conjugate:
an antibody conjugate comprising reactive group; and
a payload.

Furthermore, since a compound comprising Fc binding unit and an antibody are used in the preparation of the antibody conjugate comprising reactive group, it can be understood that the following three elements are used in the antibody-payload conjugate:
a compound comprising Fc binding unit;
an antibody; and
a payload.

Hereinafter, a method for preparing the antibody-payload conjugate will be described in detail.

Method for Preparing Antibody-Payload Conjugate

Some embodiments of the present application provide a method for preparing an antibody-payload conjugate, the method comprising:
contacting a payload with an antibody conjugate comprising reactive group.

Herein, the term "contact" may be replaced by terms such as the term "reacting" or "mixing".

Herein, the antibody conjugate comprising reactive group is an antibody conjugate provided by the present application (for example, a compound of formula 6-1). It has been described in detail in the previous paragraphs that the antibody conjugate comprising reactive group can be prepared through contacting an antibody with a compound comprising Fc binding unit.

Herein, contacting the antibody conjugate comprising reactive group with the payload may be performed through various methods. For example, contacting may be achieved by mixing a composition comprising an antibody conjugate comprising reactive group with a composition comprising a payload. As another example, contacting may be achieved by adding an antibody conjugate comprising reactive group and a payload to a prepared solution, and is not particularly limited.

In some embodiments, an antibody-payload conjugate may be prepared by contacting a payload with an antibody conjugate comprising reactive group. At this time, in the antibody-payload conjugate, the payload may be linked to any one or more of K246 and K248 of the Fc region of the antibody. It is because the antibody-payload conjugate is prepared by a reaction of a first reactive group (a reactive group linked to any one or more selected from K246 and K248) of the antibody conjugate comprising reactive group with a second reactive group of the payload.

In some embodiments, the contact or reaction of a payload with an antibody conjugate comprising reactive group may be performed in a solution or composition.

In some embodiments, the contact or reaction of a payload with an antibody comprising reactive group may be carried out at any one pH selected from pH 4, 4.5, 5, 5.5, 6, 6.5, 7, 7.5, 8, 8.5, 9, 9.5, 10, 10.5, 11, 11.5, and 12, or at a pH within a range set by two values selected from the above-described values. In some embodiments, the contact or reaction of a payload with an antibody conjugate comprising reactive group may be performed under pH conditions of 5 to 10, 6 to 10, 7 to 10, 5 to 9, 5 to 8, 6 to 9, 6 to 8, 7 to 9, or 7 to 8, but is not limited thereto.

In some embodiments, the contact or reaction of the payload with the antibody conjugate comprising reactive group may be carried out at 10° C. to 45° C., 15° C. to 45° C., 15° C. to 40° C., 20° C. to 45° C., 20° C. to 40° C., 20° C. to 35° C., 20° C. to 30° C., 25° C. to 45° C., 25° C. to 40° C., 25° C. to 35° C., or 20° C. to 30° C. In some embodiments, the contact or reaction of a payload with an antibody conjugate comprising reactive group may be carried out at room temperature.

In some embodiments, the method for preparing an antibody-payload conjugate may further comprise incubating a solution (or a composition) comprising an antibody conjugate comprising reactive group and a payload. At this time, a process such as stirring or vortexing may be optionally performed during the incubation, but is not limited thereto. The incubation may be carried out for a period of time of about 10 minutes, 20 minutes, 30 minutes, 40 minutes, 50 minutes, 1 hour, 1.5 hours, 2 hours, 2.5 hours, 3 hours, 4 hours, 5 hours, 6 hours, 7 hours, 8 hours, 9 hours, 10 hours, 14 hours, 16 hours, 18 hours, 20 hours, 22 hours, 24 hours, 30 hours, 36 hours, 42 hours, 48 hours, 60 hours, or 72 hours, or more, and the period of time is not particularly limited.

In some embodiments, the method for preparing an antibody-payload conjugate may further comprise a process of obtaining an antibody-payload conjugate. At this time, obtaining the antibody-payload conjugate may comprise a process of purifying the antibody-payload conjugate, and the like, but is not limited thereto.

Figure 13:
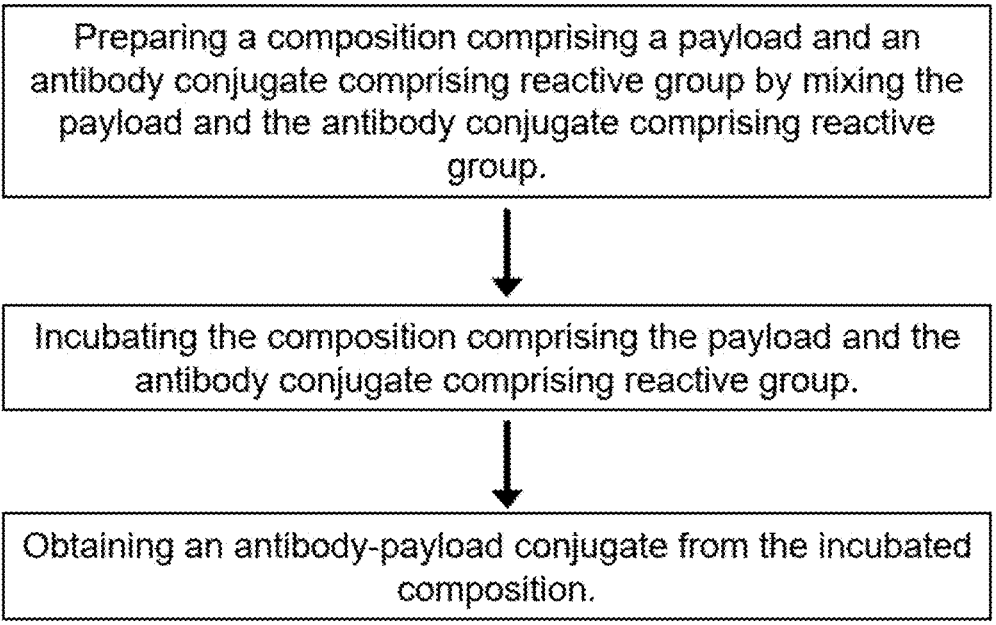
FIG. 13 relates to one embodiment of a method for preparing an antibody-payload conjugate.

Exemplarily, a method for preparing an antibody-payload conjugate may comprise (see FIG. 13):
preparing a composition comprising an antibody conjugate comprising reactive group and a payload by mixing the antibody conjugate comprising reactive group and the payload;
incubating the composition comprising the antibody conjugate comprising reactive group and the payload; and
obtaining an antibody-payload conjugate from the incubated composition.

Furthermore, it has been described in detail in previous paragraphs that the antibody conjugate comprising reactive group can be prepared by a contact or reaction of the antibody with the compound comprising Fc binding unit.

For example, the method for preparing an antibody-payload conjugate may further comprise:
preparing an antibody conjugate comprising reactive group.

Furthermore, some embodiments of the present application provide an antibody-payload conjugate, comprising:
preparing a compound-payload conjugate comprising Fc binding unit by contacting a payload with a compound comprising Fc binding unit; and
preparing an antibody-payload conjugate by contacting an antibody with the compound-payload conjugate comprising Fc binding unit.

At this time, the compound-payload conjugate comprising Fc binding unit may be formed by a reaction of a second reactive group of the payload with a reactive group of the compound comprising Fc binding unit. This example intended to form a compound-payload conjugate comprising Fc binding unit may be derived when the group of interest of the compound comprising Fc binding unit comprises a reactive group (for example, when the group of interest is a reactive group).

For another example, the method for preparing an antibody-payload conjugate may comprise: mixing a compound comprising Fc binding unit, an antibody, and a payload.

Composition or Kit for Preparing Antibody-Payload Conjugate

Some embodiments of the present application provide a composition or kit for preparing an antibody-payload conjugate. A composition or kit for preparing an antibody-payload conjugate may be used for preparing an antibody-payload conjugate.

The composition or kit for preparing an antibody-payload conjugate may comprise:
an antibody conjugate comprising reactive group and a payload; or
a compound comprising Fc binding unit, an antibody, and a payload; or
a compound-payload conjugate comprising Fc binding unit and an antibody.

In specific embodiments, the composition or kit for preparing an antibody-payload conjugate may comprise an antibody conjugate comprising reactive group and a payload.

In some embodiments, the composition or kit may further an additional element in addition to the above-described elements (for example, an antibody conjugate comprising reactive group and a payload). For example, the additional element included in the composition or kit may be a pharmaceutically acceptable salt, an excipient, a diluent, a stabilizer, a pH modifier, and the like, but is not limited thereto.

Hereinafter, the structure of the antibody-payload conjugate will be described in detail.

Antibody-Payload Conjugate

Overview of Antibody-Payload Conjugate

Some embodiments of the present application provide an antibody-payload conjugate having the structure of formula 8:

[Chemical Formula 8]

In formula 8, $L^b$ is a linker B. Linker B has been described in detail in the section "Antibody conjugate comprising group of interest" of the present application, and is as described in previous paragraphs.

In formula 8, Ab is an antibody unit. The antibody unit has been described in detail in previous paragraphs, and is as described in previous paragraphs.

In formula 8, CM is a cargo moiety. The cargo moiety has been described in detail in the section "Antibody conjugate comprising group of interest" of the present application, and is as described in previous paragraphs. For example, the cargo moiety comprises one or two or more active moieties.

In formula 8, n is an integer of 1 to 4. At this time, in formula 8, the cargo moiety may be linked to one or more of lysine residue 246 and lysine residue 248 of the Fc region of the antibody unit. For specific examples of the conjugation site and n, the subsection "Site to which group of interest is linked" of the section "Antibody conjugate comprising group of interest" of the present application is referenced.

For example, an antibody payload conjugate may comprise one cargo moiety (when n=1). In this case, the cargo moiety is linked to K246 of the first heavy chain or linked to K248 of the first heavy chain.

For example, an antibody-payload conjugate may comprise two cargo moieties (for example, a first cargo moiety and a second cargo moiety) (when n=2). In this case, for example, the first cargo moiety may be linked to K246 of the first heavy chain, and the second cargo moiety may be linked to K246 of the second heavy chain. As another example, the first cargo moiety may be linked to K246 of the first heavy chain, and the second cargo moiety may be linked to K248 of the second heavy chain. As still another example, the first cargo moiety may be linked to K248 of the first heavy chain, and the second cargo moiety may be linked to K248 of the second heavy chain.

For example, an antibody-payload conjugate may comprise three cargo moieties (for example, a first cargo moiety, a second cargo moiety, and a third cargo moiety) (when n=3).

For example, an antibody-payload conjugate may comprise four cargo moieties (for example, a first cargo moiety, a second cargo moiety, a third cargo moiety, and a fourth cargo moiety) (when n=4).

In formula 8, RG' is a structure formed by a reaction of a second reactive group (a reactive group of the payload) with a first reactive group (for example, the reactive group of the antibody conjugate comprising reactive group or the reactive group of the compound comprising Fc binding unit). Specifically, RG' comprises a structure formed by a reaction of a second reactive moiety of a second reactive group with a first reactive moiety of a first reactive group.

Hereinafter, RG', which is a structure formed by the reaction of the first reactive group with the second reactive group will be described in detail.

Structure (RG') Formed by Reaction of Second Reactive Group with First Reactive Group Herein, the first reactive group is a reactive group of an antibody conjugate comprising reactive group or a reactive group of a compound comprising Fc binding unit. The first reactive group comprises a reactive moiety (herein, the reactive moiety of the first reactive group refers to the first reactive moiety).

In some embodiments, the first reactive moiety may be a bio-orthogonal functional group (herein, the first reactive moiety refers to a first bio-orthogonal functional group when the first reactive moiety is a bio-orthogonal functional group). In some embodiments, the first reactive moiety may be a click-chemistry functional group (herein, when the first reactive moiety is a click-chemistry functional group, the first reactive moiety refers to a first click-chemistry functional group). In specific embodiments, the first reactive moiety may be azide group, terminal alkyne group, terminal alkene group, cyclooctyne group, tetrazine group, norbornene group, cyclooctene group, oxime group, and isocyanide group, wherein the cyclooctyne group may be any one selected from OCT cyclooctyne, Bicyclononyne (BCN), Dibenzocyclooctyne (DBCO), aza-dibenzocyclooctynes (DIBAC), dibenzocyclooctynol (DIBO), difluorinated cyclooctynes (DIFO), biarylazacyclooctynone (BARAC), dimethoxyazacyclooctyne (DIMAC) and difluorobenzocyclooctyne (DIFBO), wherein the cyclooctene group may be any one selected from cis-cyclooctene group and trans-cyclooctene (TCO) group. As described in the previous paragraphs, the first reactive group may further comprise a spacer of the reactive group (spacer RG; $D^{RG}$) (for example, may be referred to as a spacer of the first reactive group).

The second reactive group may be a group capable of reacting with the first reactive group. For example, the second reactive group may be referred to as a partner group of the first reactive group. In some embodiments, the second reactive group may comprise a second reactive moiety capable of reacting with the first reactive moiety. For example, the second reactive moiety may be referred to as a partner moiety of the first reactive moiety. In some embodiments, the second reactive moiety may be a second bio-orthogonal functional group. The second bio-orthogonal functional group is capable of a bio-orthogonal reaction with the first bio-orthogonal functional group. For example, the second bio-orthogonal functional group may be a bio-orthogonal chemical partner of the first bio-orthogonal functional group. In some embodiments, the second reactive moiety may be a second click-chemistry functional group. The second click-chemistry functional group may be a click-chemistry partner of the first click-chemistry functional group.

For example, when the first reactive moiety is azide, the second reactive moiety may be DBCO, DIFO, BCN, BARAC, or the like, but is not limited thereto, and may be a group capable of reacting with the azide. For another example, when the first reactive moiety is DBCO, the second reactive moiety may be azide.

For example, when the first reactive moiety is norbornene, the second reactive moiety may be tetrazine. As another example, when the first reactive moiety is tetrazine, the second reactive moiety may be TCO or norbornene, but is not limited thereto, and may be a group capable of reacting with tetrazine.

In some embodiments, the second reactive group may further comprise a spacer of the reactive group, similar to the first reactive group. At this time, the spacer of the reactive group included in the second reactive group may be referred to as a spacer of the second reactive group.

A structure RG' formed by a reaction of the first reactive group with the second reactive group may comprise a structure formed by a reaction of the first reactive moiety and the second reactive moiety. As described above, each of the first reactive group and the second reactive group may optionally further comprise a spacer of the reactive group, so that in addition to the structure formed by the reaction of the first reactive moiety and the second reactive moiety, RG' may further comprise a spacer of the first reactive group and a spacer of the second reactive group.

An exemplary structure of RG' is illustrated as follows:

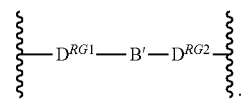

In the above structure, B' is a structure formed by the reaction of the first reactive moiety with the second reactive moiety, $D^{RG1}$ is a spacer of the first reactive group, $D^{RG2}$ is a spacer of the second reactive group, and each of the spacer of the first reactive group and the spacer of the second reactive group is independently a spacer of the reactive group. At this time, the spacer of the first reactive group is linked to $L^b$ in formula 8, and the spacer of the second reactive group is linked to CM in formula 8. The spacer of the reactive group (spacer RG; $D^{RG}$) has been described in detail in the section "Compound comprising Fc binding unit" of the present application, and is as described in the previous paragraphs. For example, $D^{RG}$ may be a bond, or substituted or unsubstituted $C_{1-3}$ alkylene, substituted or unsubstituted $C_{1-3}$ heteroalkylene. At this time, the substituted alkylene or substituted heteroalkylene may comprise one or more substituents, and each of the substituents may be independently selected from $—C_{1-4}$ alkyl and $=O$. At this time, the heteroalkylene comprises one or more heteroatoms, wherein each of the heteroatoms may be independently selected from O, N, and S.

In some embodiments, B' may have any one of the following structures:

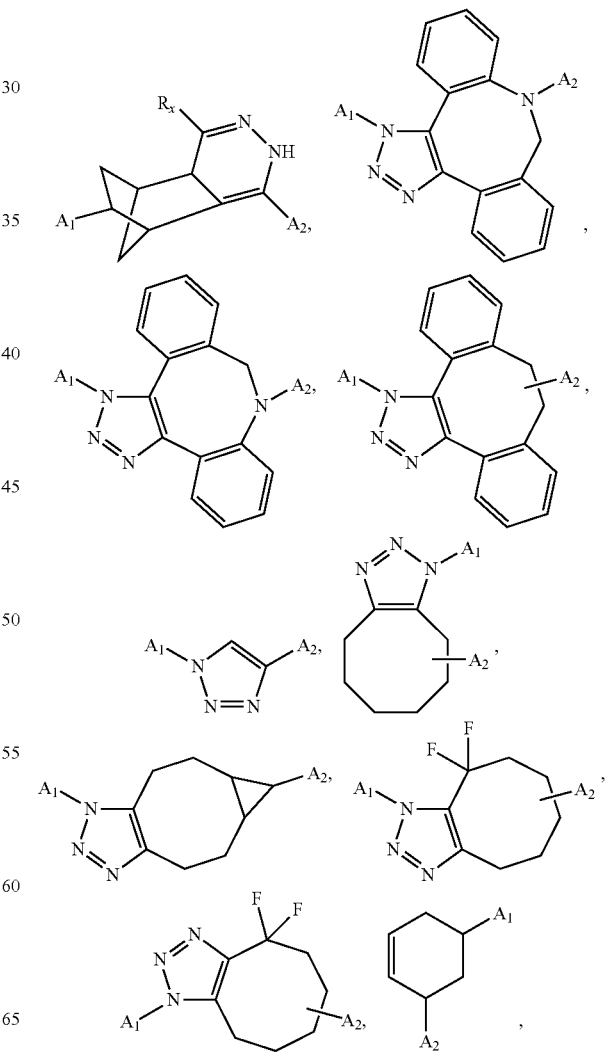

-continued

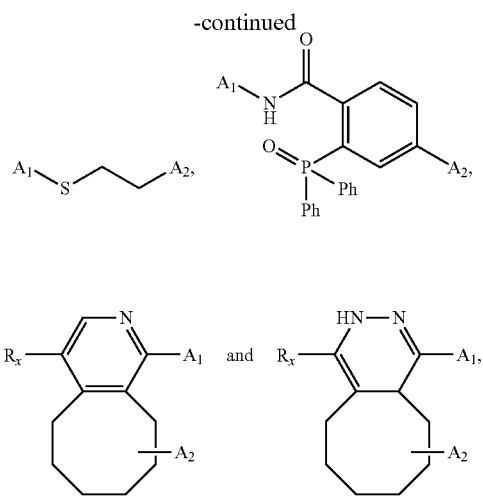

wherein $R_x$ is selected from H, halogen, and $C_{1-3}$alkyl, and each of $A_1$ and $A_2$ indicates a part (that is, an attachment point) linked to another part other than B'. In some embodiments, $A_1$ may indicate the attachment point with the spacer of the first reactive group (or when the spacer of the first reactive group is a bond, this may be described as the attachment point with $L^b$), and $A_2$ may indicate the attachment point with the spacer of the second reactive group (or when the spacer of the second reactive group is a bond, this may be described as the attachment point with CM). In some embodiments, $A_1$ may indicate the attachment point with the spacer of the second reactive group (or when the spacer of the second reactive group is a bond, this may be described as the attachment point with CM), and $A_2$ may indicate the attachment point with the spacer of the first reactive group (or when the spacer of the first reactive group is a bond, this may be described as the attachment point with $L^b$).

Specific Embodiments of Antibody-Payload Conjugate

In some embodiments, the cargo moiety (CM) may have the following structure:

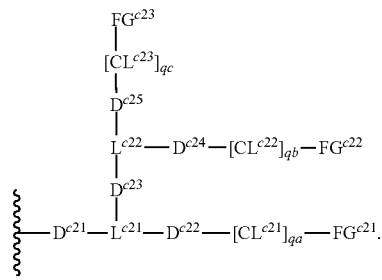

At this time, each element of the cargo moiety is as described in previous paragraphs.

In some embodiments, in the compound of formula 8, the cargo moiety (CM) may have the following structure:

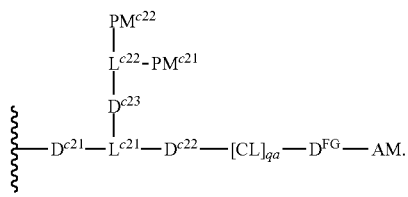

At this time, each element of the cargo moiety is as described in previous paragraphs.

In some embodiments, the antibody-payload conjugate may have a structure of the following formula 8-1:

[formula 8-1]

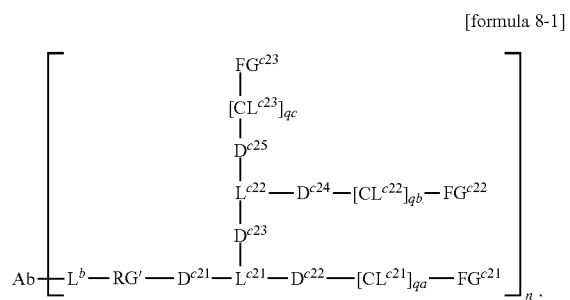

At this time, each element is as described in previous paragraphs.

In some embodiments, the antibody-payload conjugate may have a structure of the following formula 8-2:

[formula 8-2]

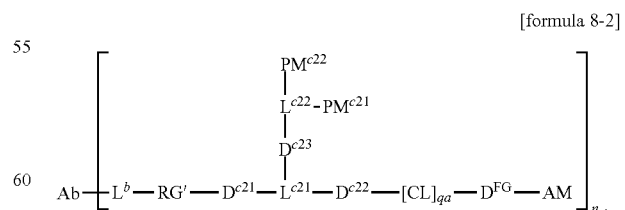

wherein each element is as described in previous paragraphs.

In specific embodiments, the antibody-payload conjugate may have a structure of the following formula 8-3:

[formula 8-3]

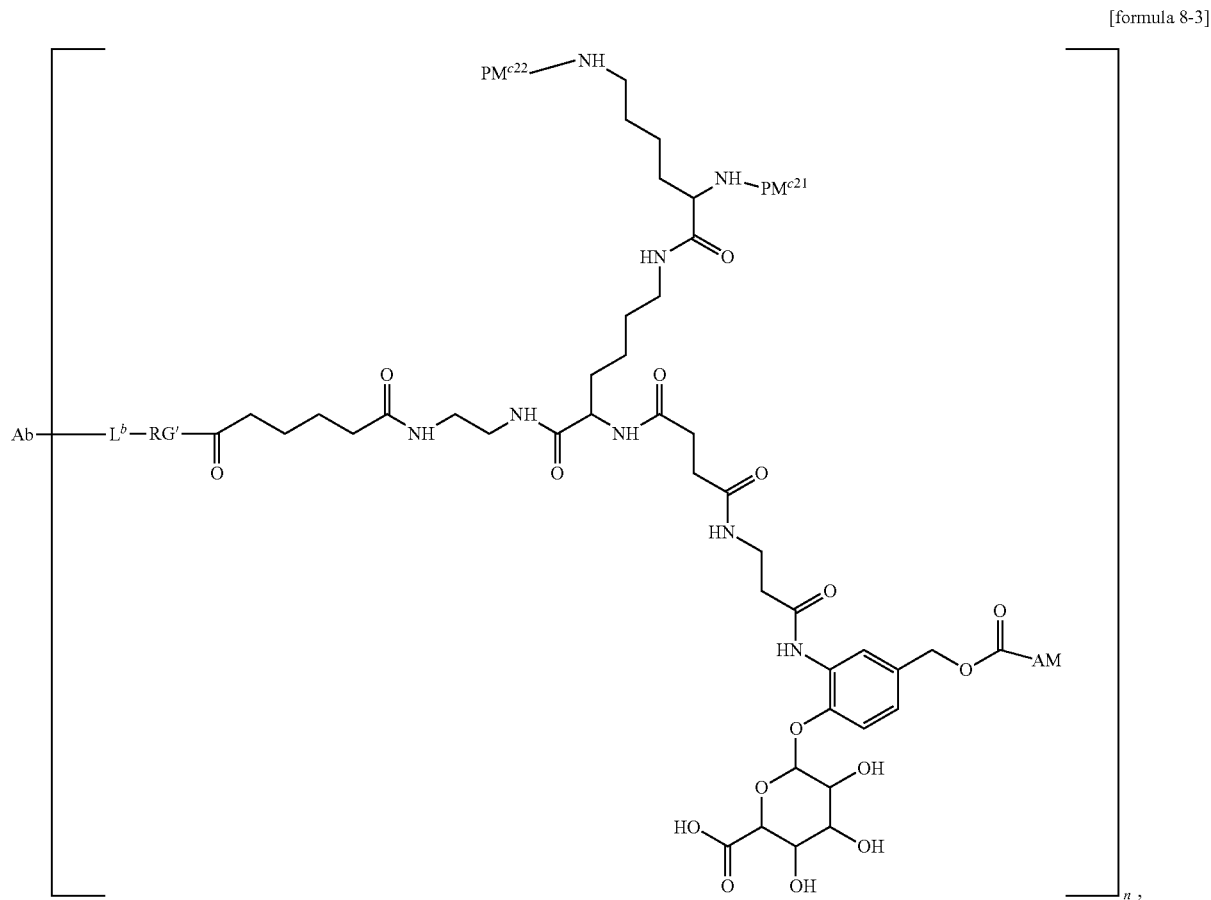

wherein each element is as described in previous paragraphs.

In some embodiments, $L^b$ (linker B) may be

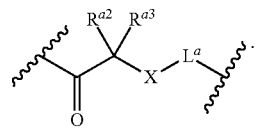

In specific embodiments, $L^b$ (linker B) may be

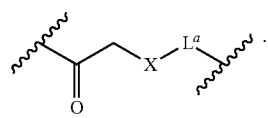

In specific embodiments, $L^b$ is

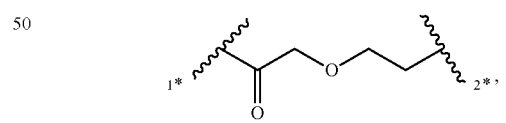

wherein 1* indicates a linking point (that is, attachment point) to the antibody unit, and 2* indicates a linking point to RG'.

In some embodiments, RG' may be

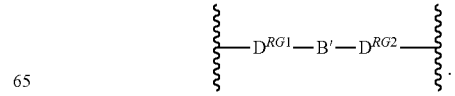

In specific embodiments, RG' is

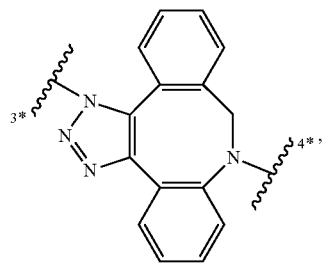 [SMILES: *N1Cc2ccccc2-c2c(nnn2*)-c2ccccc21]

wherein 3* indicates a linking point to $L^b$, and 4* indicates a linking point to a part other than $L^b$.

In specific embodiments, each of $PM^{c21}$ and $PM^{c22}$ is

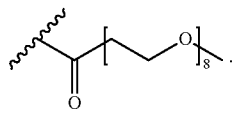

In some embodiments, AM may be a drug moiety. In specific embodiments, AM is MMAE. In specific embodiments, MMAE is

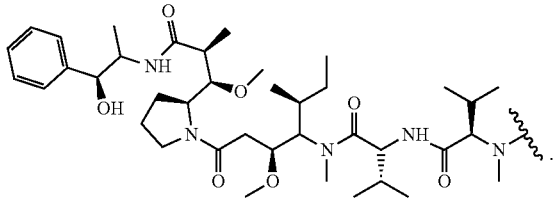

In some embodiments, n may be an integer of 1 to 4. In specific embodiments, n is 1 or 2. In specific embodiments, n is 2.

In specific embodiments, the antibody unit is an anti-CLDN18.2 antibody unit (derived from an anti-CLDN18.2 antibody). In specific embodiments, the antibody unit is derived from an anti-CLDN18.2 antibody comprising a light chain of SEQ ID NO: 26 and a heavy chain of SEQ ID NO: 25.

In specific embodiments, the antibody-payload conjugate may have a structure of the following formula 8-4:

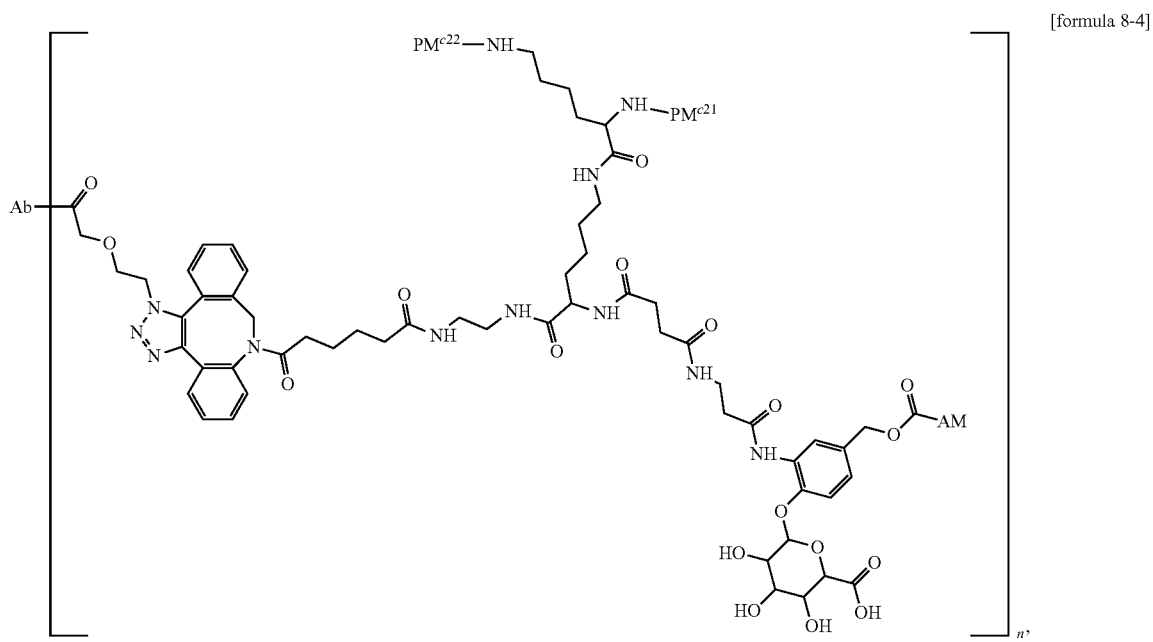

[formula 8-4]

wherein
n is 2,
Ab is an antibody unit, and the antibody unit is derived from an anti-CLDN18.2 antibody comprising a light chain of SEQ ID NO: 26 and a heavy chain of SEQ ID NO: 25,
each of PM$^{c21}$ and PM$^{c22}$ is

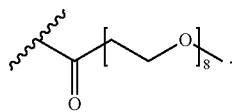

and
AM is

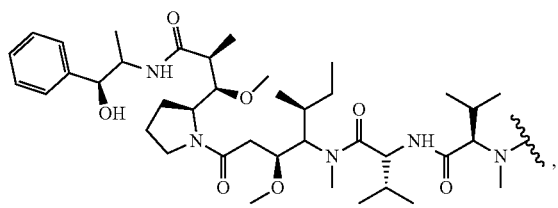

each AM is linked to any one of K246 and K248 of one heavy chain, and linked to any one of K246 and K248 of the other heavy chain of the antibody unit.

Compound-Payload Conjugate Comprising Fc-Binding Unit

As described above, it has been described that the antibody-payload conjugate may be prepared by contacting a payload with an antibody conjugate comprising a group of interest. Furthermore, as another aspect, it has been described that the antibody-payload conjugate may be prepared by contacting an antibody with a compound-payload conjugate comprising Fc binding unit. The compound comprising Fc binding unit comprises a group of interest. When the group of interest comprises a reactive group (that is, when comprising a first reactive group), the compound comprising Fc binding unit and the payload can react with each other through the first reactive group and the second reactive group, and accordingly, a compound-payload conjugate comprising Fc binding unit can be prepared. Hereinafter, the compound-payload conjugate comprising Fc binding unit will be exemplified.

Some embodiments of the present application provide a compound-payload conjugate comprising Fc binding unit, which has the structure of formula 9. Some embodiments of the present application provide a compound of formula 9:

[formula 9]

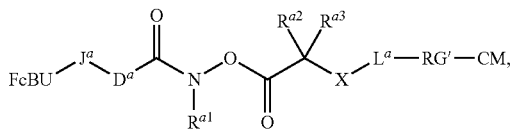

wherein each element of formula 9 is as described above.

Composition or Kit Comprising Antibody-Payload Conjugate

Some embodiments of the present application provide a composition or kit comprising an antibody-payload conjugate. In some embodiments, a composition or kit comprising an antibody-payload conjugate may be used for appropriate purposes according to the function of the antibody conjugate included in the composition or kit. For example, the functions of an antibody conjugate may be determined by the function of the antibody and/or the function of the active moiety of the payload or functional group. In some embodiments, the composition or kit may further comprise an additional element in addition to the antibody conjugate comprising the group of interest. For example, the additional element included in the composition or kit may be a pharmaceutically acceptable salt, an excipient, a diluent, a stabilizer, a pH modifier, and the like, but is not limited thereto.

Use of Antibody-Payload Conjugate

This section relates to the use of the antibody conjugate comprising an active moiety. The antibody conjugate comprising an active moiety includes, for example, an antibody conjugate comprising a functional group among antibody conjugates comprising a group of interest (when the group of interest comprises a functional group), and an antibody-payload conjugate. Hereinafter, the use of an antibody conjugate comprising an active moiety will be described in detail, using an antibody-payload conjugate as an example.

As described above, the active moiety may be, for example, a drug moiety, an imaging moiety, a radioactive moiety, or the like.

For example, when the active moiety of the antibody-payload conjugate is a radioactive moiety, the antibody-payload conjugate may be used as a radioactive contrast agent or for radioimmunotherapy.

As another example, when the active moiety of the antibody-payload conjugate is an imaging moiety, the antibody-payload conjugate may be used to detect or analyze a specific substance, or to image a specific disease. For example, the antibody-payload conjugate may be used as a label which is used for enzyme-linked immunosorbent assay (ELISA) and the like.

As still another example, when the active moiety of the antibody-payload conjugate is a drug moiety, the antibody-payload conjugate may be used to treat a disease (for example, cancer) in a subject (for example, a human).

When the active moiety is a drug moiety in an antibody conjugate comprising an active moiety (that is, a conjugate in which the active moiety is conjugated to an antibody), the composition comprising the antibody conjugate may be referred to as a pharmaceutical composition. Hereinafter, the pharmaceutical composition will be described in detail.

Pharmaceutical Composition and Use Thereof

Some embodiments of the present application provide a pharmaceutical composition comprising an antibody conjugate comprising an active moiety. Herein, the active moiety is a drug moiety. Furthermore, an antibody conjugate comprising an active moiety may be an antibody conjugate comprising a functional group or an antibody-payload conjugate. In an antibody conjugate comprising a functional group, when the functional group comprises an active moiety, an antibody conjugate comprising an active moiety is provided. Since the antibody-payload conjugate comprises an active moiety, the antibody-payload conjugate may be an antibody conjugate comprising an active moiety. When the active moiety is a drug moiety, the antibody conjugate comprising the active moiety is referred to as an antibody-drug conjugate.

Some embodiments of the present application provide a pharmaceutical composition comprising an antibody-drug conjugate. In some embodiments, the pharmaceutical composition may be a composition for treating cancer. At this time, the cancer may be any one selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, bile duct cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, genitourinary cancer, testicular germ cell cancer, thymoma, and thymus cancer. For example, the cancer may be breast cancer, gastric cancer, or pancreatic cancer. The cancer associated with the cancer treatment use of the pharmaceutical composition may be determined by the type of antibody unit (or antibody) in the antibody-drug conjugate. For example, when the antibody is trastuzumab, the cancer may be breast cancer (particularly HER2-positive breast cancer). For example, when the antibody is trastuzumab, the cancer may be HER2-positive breast cancer. For example, when the antibody is an anti-CLDN18.2 antibody, the cancer is gastric cancer (particularly claudin 18.2-positive gastric cancer), pancreatic cancer (particularly claudin 18.2-positive pancreatic cancer), colorectal cancer (particularly claudin 18.2-positive colorectal cancer), genitourinary cancer (particularly claudin 18.2-positive genitourinary cancer) or bile duct cancer (particularly claudin 18.2-positive bile duct cancer). For example, when the antibody is an anti-CLDN18.2 antibody, the cancer may be claudin 18.2-positive cancer.

Some embodiments of the present application provide a method for treating a subject (for example, a human) having cancer, comprising administering a pharmaceutical composition comprising an antibody-drug conjugate to the subject. At this time, the cancer may be any one selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, bile duct cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, genitourinary cancer, testicular germ cell cancer, thymoma, and thymus cancer. The subject to be administered or treated may be, for example, a human. The subject to be administered or treated may be, for example, a non-human animal. For example, the subject may be a dog, a horse, a cat, a mouse, a rat, a pig, a rabbit, a sheep, a monkey, a chimpanzee or a cow.

To prepare a pharmaceutical composition comprising an antibody-drug conjugate, the antibody-drug conjugate may be mixed with a pharmaceutically acceptable carrier. Furthermore, the pharmaceutical composition may further contain one or more other elements suitable for the treatment or prevention of cancer. The term of pharmaceutically acceptable carrier may be used to include an excipient, a diluent or an adjuvant. The carrier may be one or more selected from, for example, lactose, dextrose, sucrose, sorbitol, mannitol, xylitol, erythritol, maltitol, starch, gum acacia, alginate, gelatin, calcium phosphate, calcium silicate, cellulose, methylcellulose, polyvinylpyrrolidone, water, physiological saline, a buffer such as PBS, methylhydroxy benzoate, propylhydroxy benzoate, talc, magnesium stearate, and mineral oil. The carrier may comprise a filler, an anti-agglomerating agent, a lubricant, a wetting agent, a flavoring agent, an emulsifying agent, a preservative, or a combination thereof.

The pharmaceutical composition may be administered through various routes. Further, the composition of the present application may be administered by one or more routes of administration through one or more of various methods known in the related art. For example, the pharmaceutical composition may be administered orally or parenterally. Administration may be carried out, for example, by topical or dermal application, by intravenous, intraperitoneal, intracerebral, intramuscular, intraocular, intraarterial, intracerebrospinal, intralesional injection or infusion. Furthermore, the antibody-drug conjugate may be administered using a controlled or delayed release system or in a formulation for controlled or delayed release.

The pharmaceutical composition may be administered to a subject at an appropriate dose. In some embodiments, regarding the antibody-drug conjugate, a dosage administered to a subject (for example, a patient) may be 0.0001 mg/kg to 100 mg/kg (body weight of the patient), but is not limited thereto. In some embodiments, the pharmaceutical composition may be administered multiple times, wherein the intervals between administrations may be appropriately designed. For example, the pharmaceutical composition may be administered at intervals of 1 day to 6 months. Furthermore, the dosage may vary each time when the pharmaceutical composition is administered.

In some embodiments, the pharmaceutical composition may be administered in conjunction with a composition comprising another substance (for example, a therapeutic or prophylactic agent). Co-administration is not limited to administering therapies at exactly the same time. For example, co-administered therapies may be administered at appropriate time intervals or at the same time.

Specific Examples of Pharmaceutical Composition and Use Thereof

Some embodiments of the present application provide a pharmaceutical composition comprising any one antibody-payload conjugate selected from formula 8 and formulae 8-1 to 8-4. In some embodiments, the pharmaceutical composition may be used to treat cancer. At this time, the cancer may be any one selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, bile duct cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, genitourinary cancer, testicular germ cell cancer, thymoma, and thymus cancer. In some embodiments, cancer may be claudin 18.2-positive cancer. In specific embodiments, the cancer may be claudin 18.2-positive gastric cancer, claudin 18.2-positive pancreatic cancer, claudin 18.2-positive colorectal cancer, claudin 18.2-positive genitourinary cancer, or claudin 18.2-positive bile duct cancer. In specific embodiments, the cancer may be claudin 18.2-positive gastric cancer or claudin 18.2-positive pancreatic cancer.

Some embodiments of this application provide a method for treating cancer in a subject, the method comprising:
administering a pharmaceutical composition comprising any one antibody-payload conjugate selected from formula 8 and formulae 8-1 to 8-4 to the subject.

At this time, the cancer may be any one selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, bile duct cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, genitourinary cancer, testicular germ cell cancer, thymoma, and thymus cancer. In some embodiments, the cancer may be claudin 18.2-positive cancer. In specific embodiments, the cancer may be claudin 18.2-positive gastric cancer, claudin 18.2-positive pancreatic cancer, claudin 18.2-positive colorectal cancer, claudin 18.2-positive genitourinary cancer, or claudin 18.2-positive bile duct cancer. In specific embodiments, the cancer may be claudin 18.2-positive gastric cancer or claudin 18.2-positive pancreatic cancer. At this time, the subject may be a subject who has been diagnosed with claudin 18.2-positive cancer (for example, claudin 18.2-positive gastric cancer or claudin 18.2-positive pancreatic cancer).

Exemplary Embodiments of Invention Provided by Present Application

Hereinafter, specific examples of the invention provided according to some embodiments of the present application are provided. The invention provided by the present application is not limited to the following specific examples.

Exemplary embodiments of compound comprising Fc binding unit

A01. A compound comprising Fc binding unit having a structure of formula 2:

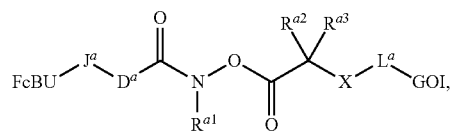

[Formula 2]

wherein $D^a$ is a spacer A, wherein the spacer A is a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H, herein the heteroalkylene, the heteroalkenylene, the heteroalkynylene, the heterocycloalkyl, or the heteroaryl comprises one or more heteroatoms, wherein each of the heteroatoms is independently selected from N, O, and S, $L^a$ is a linker A, wherein the linker A is a bond, substituted or unsubstituted $C_{1-100}$ alkylene, substituted or unsubstituted $C_{1-100}$ heteroalkylene, substituted or unsubstituted $C_{2-100}$ alkenylene, substituted or unsubstituted $C_{2-100}$ heteroalkenylene, substituted or unsubstituted $C_{2-100}$ alkynylene, or substituted or unsubstituted $C_{2-100}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H, herein heteroalkylene, heteroalkenylene, heteroalkynylene, heterocycloalkyl, or heteroaryl comprises one or more heteroatoms, wherein each of the heteroatoms is independently selected from N, O, and S, X is —CH$_2$—, —O—, or —NH—, $R^{a1}$ is H or $C_{1-6}$ alkyl, $R^{a2}$ is H or $C_{1-6}$ alkyl, $R^{a3}$ is H or $C_{1-6}$ alkyl, $J^a$ is —C(=O)—, —S—, —NH—, or —C(=NH)—, GOI is a group of interest, wherein the group of interest comprises a reactive group comprising a reactive moiety or a functional group comprising an active moiety, FcBU is a Fc binding unit, wherein the Fc binding unit has a structure of

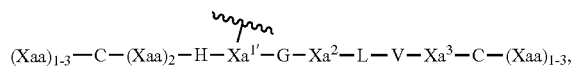

wherein each of Xaa is independently selected from any amino acid, $Xa^2$ is glutamic acid residue or asparagine residue, and $Xa^3$ is tryptophan residue, naphthylalanine residue, or phenylalanine residue, a cysteine residue adjacent to the N terminus and a cysteine residue adjacent to the C terminus are, optionally, covalently linked, $Xa^{1'}$ is

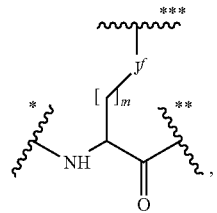

herein, m is an integer of 1 to 5, $J^f$ is —NH—, —S—, or —C(=O)—, each of * and ** indicates an attachment point of $Xa^{1'}$ with an amino acid residue adjacent to $Xa^{1'}$, and

*** indicates an attachment point of $Xa^{1'}$ with a portion, in the compound comprising Fc binding unit, that are not the Fc binding unit.

A02. The compound comprising Fc binding unit according to A01,
wherein X is —O— or —CH$_2$—.

A03. The compound comprising Fc binding unit according to any one of A01 to A02, wherein X is —O—.

A04. The compound comprising Fc binding unit according to any one of A01 to A03, wherein $R^{a1}$ is $C_{1-3}$ alkyl.

A05. The compound comprising Fc binding unit according to any one of A01 to A04, wherein $R^{a1}$ is methyl.

A06. The compound comprising Fc binding unit according to any one of A01 to A05, wherein each of $R^{a2}$ and $R^{a3}$ is independently any one selected from H and $C_{1-3}$ alkyl.

A07. The compound comprising Fc binding unit according to any one of A01 to A06, wherein both of $R^{a2}$ and $R^{a3}$ are H.

A08. The compound comprising Fc binding unit according to any one of A01 to A07, wherein $J^a$ is —C(=O)—.

A09. The compound comprising Fc binding unit according to any one of A01 to A08, wherein $D^a$ is unsubstituted $C_{1-10}$ alkylene, unsubstituted $C_{1-10}$ heteroalkylene, unsubstituted $C_{2-10}$ alkenylene, or unsubstituted $C_{2-10}$ heteroalkenylene.

A10. The compound comprising Fc binding unit according to any one of A01 to A09, wherein $D^a$ is unsubstituted $C_{1-10}$ alkylene.

A11. The compound comprising Fc binding unit according to any one of A01 to A10, wherein Fc binding unit has a structure below:

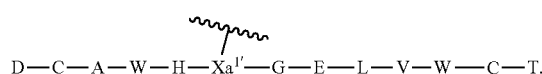

A12. The compound comprising Fc binding unit according to any one of A01 to A11, wherein $J^f$ is —NH—.

A13. The compound comprising Fc binding unit according to any one of A01 to A12, wherein m is an integer of 1 to 4.

A14. The compound comprising Fc binding unit according to any one of A01 to A13, wherein m is 3.

A15. The compound comprising Fc binding unit according to any one of A01 to A14, wherein $L^a$ is a bond, unsubstituted $C_{1-60}$ alkylene, unsubstituted $C_{1-60}$ heteroalkylene, unsubstituted $C_{2-60}$ alkenylene, or unsubstituted $C_{2-60}$ heteroalkenylene.

A16. The compound comprising Fc binding unit according to any one of A01 to A15, wherein $L^a$ is a bond, unsubstituted $C_{1-60}$ alkylene, or unsubstituted $C_{1-60}$ heteroalkylene, wherein the unsubstituted heteroalkylene comprises 0 to 20 of ethyleneglycol units.

A17. The compound comprising Fc binding unit according to any one of A01 to A16, wherein $L^a$ is a bond, unsubstituted $C_{1-30}$ alkylene, or unsubstituted $C_{1-30}$ heteroalkylene, wherein the unsubstituted heteroalkylene comprises 0 to 10 of ethyleneglycol units.

A18. The compound comprising Fc binding unit according to any one of A01 to A17, wherein $L^a$ is a bond, unsubstituted $C_{1-25}$ alkylene, or unsubstituted $C_{1-25}$ heteroalkylene, wherein the unsubstituted heteroalkylene comprises 0 to 8 of ethyleneglycol units.

A19. The compound comprising Fc binding unit according to any one of A01 to A16, wherein $L^a$ has any one selected from the following structures:

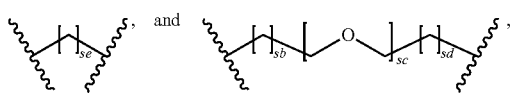

wherein
se is an integer of 0 to 15,
sb is an integer of 0 to 3,
sc is an integer of 1 to 15, and
sd is an integer of 0 to 3.

A20. The compound comprising Fc binding unit according to any one of A01 to A19, wherein the group of interest comprises a reactive group.

A21. The compound comprising Fc binding unit according to any one of A01 to A20, wherein the compound comprising Fc binding unit has a structure of the following formula 2-2:

[formula 2-2]

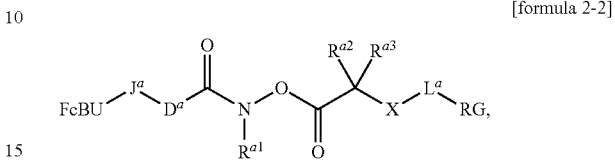

wherein RG is a reactive group.

A22. The compound comprising Fc binding unit according to any one of A01 to A21, wherein the compound comprising Fc binding unit has a structure of the following formula 2-3:

[formula 2-3]

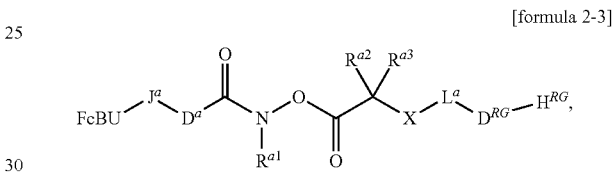

wherein
$D^{RG}$ is a spacer of the reactive group (spacer RG),
wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(=O)H, —C(=O)NH$_2$, —NH$_2$, =NH, =O, =S, —OH, —NO$_2$ and —SH, herein heteroalkylene or heteroalkenylene comprises one or more heteroatoms, wherein each of the heteroatoms is independently selected from O, N, and S,
$H^{RG}$ is the reactive moiety.

A23. The compound comprising Fc binding unit according to any one of A01 to A22, wherein the reactive moiety is a bio-orthogonal functional group.

A24. The compound comprising Fc binding unit according to any one of A01 to A23, wherein the reactive moiety has any one structure of the following structures:

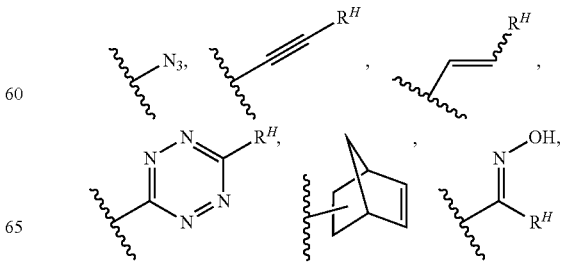

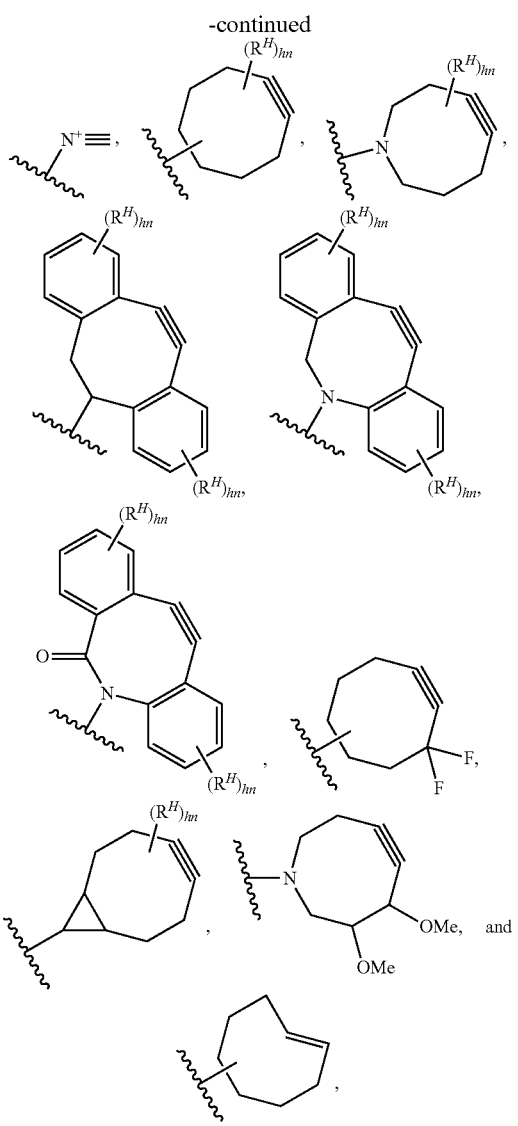

wherein,
hn is an integer of 1 to 3,
$R^H$ is, each independently, H or selected from —R, =O, =S, —NO₂, —CR₃, —NR₂, —OR, —SR, —C(=O)R, —C(=O)CR₃, —C(=O)OR, and —C(=O)NR₂, wherein R is each independently selected from H, halogen, $C_{1-6}$alkyl, $C_{3-10}$ cycloalkyl, $C_{3-10}$ heterocycloalkyl, aryl, heteroaryl, —OH, —NH₂, —COOH, =O, =S, and —SH, wherein the heterocycloalkyl or heteroaryl comprises one or more heteroatoms, wherein each heteroatom is independently selected from N, O, and S.

A25. The compound comprising Fc binding unit according to any one of A01 to A24, the reactive moiety is selected from azide group, terminal alkyne group, terminal alkene group, cyclooctyne group, tetrazine group, norbornene group, cyclooctene group, oxime group, and isocyanide group, wherein the cyclooctyne group is any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group is any one selected from cis-cyclooctene group and trans-cyclooctene group.

A26. The compound comprising Fc binding unit according to any one of A01 to A19, wherein the group of interest comprises a functional group,
wherein the functional group comprises an active moiety, and
wherein each of the active moieties is independently selected from a drug moiety, a radioactive moiety, and an affinity moiety.

A27. A compound comprising Fc binding unit having a structure of formula 2-15

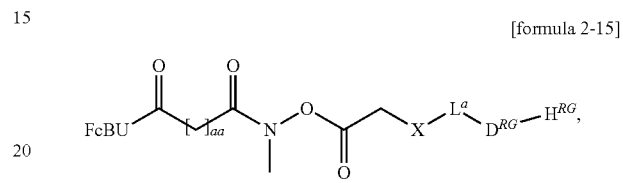

[formula 2-15]

wherein
aa is an integer of 1 to 10,
X is —O— or —CH₂—,
$L^a$ is a linker A, wherein the linker A is a bond, unsubstituted $C_{1-30}$ alkylene, or unsubstituted $C_{3-30}$ heteroalkylene comprising 1 to 10 of ethyleneglycol units,

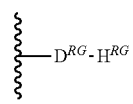

is a group of interest,
$D^{RG}$ is a spacer of the reactive group (spacer RG), wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(=O)H, —C(=O)CH₃, —C(=O)OH, —C(=O)NH₂, —NH₂, =NH, =O, =S, —OH, —NO₂ and —SH, herein, heteroalkylene or heteroalkenylene comprises one or more heteroatoms, wherein each of the heteroatoms is independently selected from N, O, and S,
$H^{RG}$ is the reactive moiety,
FcBU is a Fc binding unit, wherein the Fc binding unit has a structure of

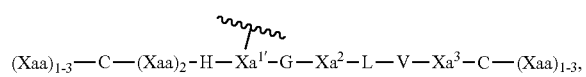

wherein
each of Xaa is independently selected from any amino acid,
$Xa^2$ is glutamic acid residue or asparagine residue, and
$Xa^3$ is tryptophan residue, naphthylalanine residue, or phenylalanine residue, a cysteine residue adjacent to the N terminus and a cysteine residue adjacent to the C terminus are, optionally, covalently linked, $Xa^{1'}$ is

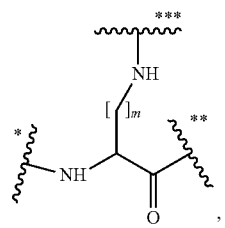

herein, m is an integer of 1 to 4, each of * and ** indicates an attachment point of $Xa^{1'}$ with an amino acid residue adjacent to $Xa^{1'}$, and

*** indicates an attachment point of $Xa^{1'}$ with a portion that are not the Fc binding unit in the compound comprising Fc binding unit.

A28. The compound comprising Fc binding unit according to A27, wherein aa is an integer of 1 to 6.

A29. The compound comprising Fc binding unit according to any one of A27 to A28, wherein aa is 3.

A30. The compound comprising Fc binding unit according to any one of A27 to A29, wherein Fc binding unit has the following structure:

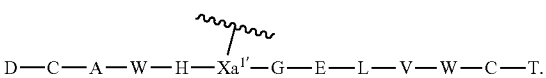

A31. The compound comprising Fc binding unit according to any one of A27 to A30, wherein m is 3.

A32. The compound comprising Fc binding unit according to any one of A27 to A31, wherein the reactive moiety is a bio-orthogonal functional group.

A33. The compound comprising Fc binding unit according to any one of A27 to A32, wherein the reactive moiety has any one structure of the following structures:

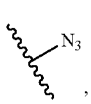

,
,
,
,
,
,
,
,
,

-continued

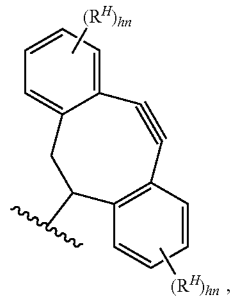

,
,
,
,
,
, and
, wherein hn is an integer of 1 to 3, $R^H$ is, each independently, H or selected from —R, ═O, ═S, —$NO_2$, —$CR_3$, —$NR_2$, —OR, —SR, —C(═O)R, —C(═O)$CR_3$, —C(═O)OR, and —C(═O)$NR_2$, wherein R is each independently selected from H, halogen, $C_{1-6}$ alkyl, $C_{3-10}$ cycloalkyl, $C_{3-10}$ heterocycloalkyl, aryl, heteroaryl, —OH, —$NH_2$, —COOH, ═O, ═S, and —SH, wherein the heterocycloalkyl or heteroaryl comprises one or more heteroatoms, wherein each heteroatom is independently selected from N, O, and S.

A34. The compound comprising Fc binding unit according to any one of A27 to A33, the reactive moiety is selected from azide group, terminal alkyne group, terminal alkene group, cyclooctyne group, tetrazine group, norbornene group, cyclooctene group, oxime group, and isocyanide group, wherein the cyclooctyne group is any one selected from OCT cyclooctyne, BCN (Biclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group is any one selected from cis-cyclooctene group and trans-cyclooctene group.

Exemplary Embodiments of Method for Preparing Antibody Conjugate Comprising Group of Interest B01. A method for preparing an antibody conjugate comprising a group of interest, wherein the method comprises:
contacting a compound comprising Fc binding unit with an antibody,
wherein the compound comprising Fc binding unit has a structure of the following formula 2:

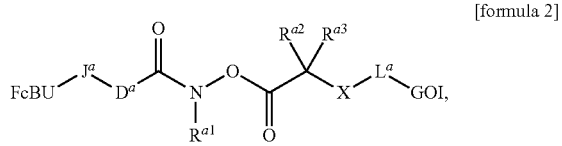

[formula 2]

wherein
$D^a$ is a spacer A, wherein the spacer A is a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H,
$L^a$ is a linker A, wherein the linker A is a bond, substituted or unsubstituted $C_{1-100}$ alkylene, substituted or unsubstituted $C_{1-100}$ heteroalkylene, substituted or unsubstituted $C_{2-100}$ alkenylene, substituted or unsubstituted $C_{2-100}$ heteroalkenylene, substituted or unsubstituted $C_{2-100}$ alkynylene, or substituted or unsubstituted $C_{2-100}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H,
wherein each of the heteroalkylene, the heteroalkenylene, the heteroalkynylene, the heterocycloalkyl, and the heteroaryl independently comprises one or more heteroatoms, wherein each of the heteroatoms is independently selected from N, O, and S,
X is —CH$_2$—, —O—, or —NH—,
$R^{a1}$ is H or $C_{1-6}$ alkyl,
$R^{a2}$ is H or $C_{1-6}$ alkyl,
$R^{a3}$ is H or $C_{1-6}$ alkyl,
$J^a$ is —C(=O)—, —S—, —NH—, or —C(=NH)—,
GOI is a group of interest, wherein the group of interest comprises a reactive group comprising a reactive moiety or a functional group comprising an active moiety, FcBU is a Fc binding unit, wherein the Fc binding unit has a structure of

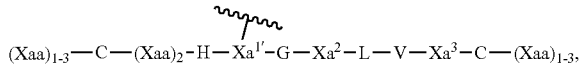

$(Xaa)_{1-3}$—C—$(Xaa)_2$—H—$Xa^{1'}$-G—$Xa^2$—L—V—$Xa^3$—C—$(Xaa)_{1-3}$, wherein
each of Xaa is independently selected from any amino acid,
$Xa^2$ is glutamic acid residue or asparagine residue, and
$Xa^3$ is tryptophan residue, naphthylalanine residue, or phenylalanine residue,
a cysteine residue adjacent to the N terminus and a cysteine residue adjacent to the C terminus are, optionally, covalently linked,
$Xa^{1'}$ is

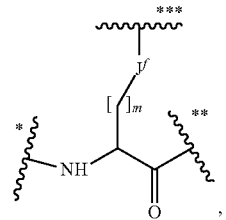

herein, m is an integer of 1 to 5,
$J'$ is —NH—, —S—, or —C(=O)—,
each of * and ** indicates an attachment point of $Xa^{1'}$ with an amino acid residue adjacent to $Xa^{1'}$, and
*** indicates an attachment point of $Xa^{1'}$ with a portion that are not the Fc binding unit in the compound comprising Fc binding unit.

B02. A method for preparing an antibody conjugate comprising a group of interest, wherein the method comprises: contacting a compound comprising Fc binding unit according to any one of A01 to A34 with an antibody.

B03. The method according to any one of B01 to B02, wherein the antibody is an IgG.

B04. The method according to any one of B01 to B03, wherein the antibody is an IgG, wherein the IgG is human IgG, humanized IgG, or chimeric IgG.

B05. The method according to any one of B01 to B03, wherein the antibody is an IgG, wherein the IgG is IgG1, IgG2, or IgG4.

B06. The method according to any one of B01 to B03, wherein the antibody is an IgG, wherein the IgG is human IgG1, humanized IgG1, chimeric IgG1, human IgG2, humanized IgG2, chimeric IgG2, human IgG4, humanized IgG4, or chimeric IgG4.

B07. The method according to any one of B01 to B02, wherein a Fc region of the antibody comprises an amino acid sequence of SEQ ID NO: 14 or an amino acid sequence having 80% or more sequence identity thereof, wherein the Fc region of the antibody comprises an amino acid sequence of KPKDTLM (SEQ ID NO: 10) and an amino acid sequence of MHEALHNH (SEQ ID NO: 11).

B08. The method according to any one of B01 to B02, wherein a Fc region of the antibody comprises an amino acid sequence of SEQ ID NO: 14 or an amino acid sequence having 80% or more sequence identity thereof, wherein the Fc region of the antibody comprises an amino acid sequence of KPKDTLM (SEQ ID NO: 10) and an amino acid sequence of MHEALHNHY (SEQ ID NO: 12).

B09. The method according to any one of B01 to B08, wherein, according to contacting the compound comprising Fc binding unit with the antibody, a group of interest is transferred to one or more of K246 and K248 of the Fc region of the antibody.

B10. The method according to any one of B01 to B09, wherein the method further comprises obtaining the antibody conjugate comprising a group of interest.

B111. The method according to any one of B01 to B110, wherein, according to contacting the compound comprising Fc binding unit with the antibody, a group of interest is transferred to K246 and K248 of the Fc region of the antibody.

B12. The method according to any one of B01 to B111, wherein, according to contacting the compound comprising Fc binding unit with the antibody, the antibody conjugate comprising a group of interest is prepared,
wherein in the antibody conjugate comprising a group of interest, the group of interest is linked to any one or more of K246 and K248 of the antibody.

B13. The method according to any one of B01 to B12, wherein, according to contacting the compound comprising Fc binding unit with the antibody, the antibody conjugate comprising a group of interest is prepared,
wherein the antibody conjugate comprising the group of interest comprises 1 to 4 of groups of interest.

B14. The method according to any one of B01 to B13, wherein, according to contacting the compound comprising Fc binding unit with the antibody, the antibody conjugate comprising a group of interest is prepared,
wherein the antibody conjugate comprising the group of interest two groups of interest,
wherein each of the two groups of interest is linked to first K246 and second K246 of the antibody, respectively, or is linked to first K248 and second K248 of the antibody, respectively.

B15. The method according to any one of B01 to B14, wherein contacting the compound comprising Fc binding unit with the antibody is achieved by a method comprising:
mixing a composition comprising the compound comprising Fc binding unit with a composition comprising the antibody.

B16. The method according to any one of B01 to B14, wherein contacting the compound comprising Fc binding unit with the antibody is achieved by a method comprising:
preparing a composition for preparing an antibody conjugate comprising a group of interest by mixing a composition comprising a compound comprising Fc binding unit with a composition comprising an antibody; and
incubating the composition for preparing an antibody conjugate comprising a group of interest.

B17. The method according to any one of B15 to B16, wherein the mixing of the composition comprising the compound comprising Fc binding unit with the composition comprising the antibody is performed under conditions of pH 6 to pH 8.5.

B18. The method according to B16, wherein the mixing of the composition comprising the compound comprising Fc binding unit with the composition comprising the antibody and the incubating the composition for preparing an antibody conjugate comprising a group of interest are performed under conditions of pH 6 to pH 8.5.

B19. The method according to any one of B01 to B18, wherein the antibody conjugate comprising the group of interest has a structure of the following formula 6:

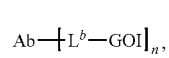

[formula 6]

wherein
n is an integer of 1 to 4,
Ab is an antibody unit,
GOI is a group of interest,
$L^b$ is a linker B, wherein the linker B is

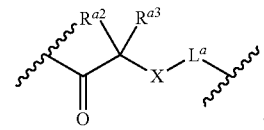

Exemplary Embodiments of Compound Comprising Fc Binding Unit Comprising Reactive Group C01. A compound comprising Fc binding unit having a structure of formula 2-2:

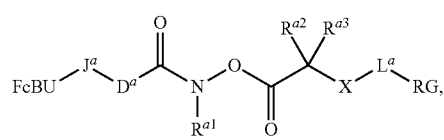

[formula 2-2]

wherein
$D^a$ is a spacer A, wherein the spacer A is a bond, substituted or unsubstituted $C_{1-20}$ alkylene, substituted or unsubstituted $C_{1-20}$ heteroalkylene, substituted or unsubstituted $C_{2-20}$ alkenylene, substituted or unsubstituted $C_{2-20}$ heteroalkenylene, substituted or unsubstituted $C_{2-20}$ alkynylene, or substituted or unsubstituted $C_{2-20}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, $C_{1-6}$ alkyl, $C_{3-10}$ cycloalkyl, $C_{3-10}$ heterocycloalkyl, aryl, heteroaryl, —OH, —NH$_2$, —COOH, =O, =S, and —SH, herein the substituent is not H,
$L^a$ is a linker A, wherein the linker A is a bond, substituted or unsubstituted $C_{1-100}$ alkylene, substituted or unsubstituted $C_{1-100}$ heteroalkylene, substituted or unsubstituted $C_{2-100}$ alkenylene, substituted or unsubstituted $C_{2-100}$ heteroalkenylene, substituted or unsubstituted $C_{2-100}$ alkynylene, or substituted or unsubstituted $C_{2-100}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)

R, —C(═O)CR$_3$, —C(═O)OR, and —C(═O)NR$_2$, wherein each R is independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, ═O, ═S, and —SH, herein the substituent is not H, wherein each of the heteroalkylene, the heteroalkenylene, the heteroalkynylene, the heterocycloalkyl, and the heteroaryl independently comprises one or more heteroatoms, wherein each of the heteroatoms is independently selected from N, O, and S, X is —CH$_2$—, —O—, or —NH—, $R^{a1}$ is H or C$_{1-6}$ alkyl, $R^{a2}$ is H or C$_{1-6}$ alkyl, $R^{a3}$ is H or C$_{1-6}$ alkyl, $J^a$ is —C(═O)—, —S—, —NH—, or —C(═NH)—, RG is a reactive group, wherein the reactive group comprises a reactive moiety, FcBU is a Fc binding unit, wherein the Fc binding unit has a structure of

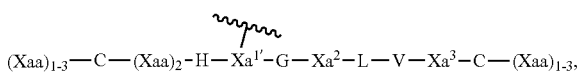

(Xaa)$_{1-3}$—C—(Xaa)$_2$-H—Xa$^{1'}$-G—Xa$^2$-L—V—Xa$^3$-C—(Xaa)$_{1-3}$, wherein each of Xaa is independently selected from any amino acid, Xa$^2$ is glutamic acid residue or asparagine residue, and Xa$^3$ is tryptophan residue, naphthylalanine residue, or phenylalanine residue, a cysteine residue adjacent to the N terminus and a cysteine residue adjacent to the C terminus are, optionally, covalently linked, Xa$^{1'}$ is

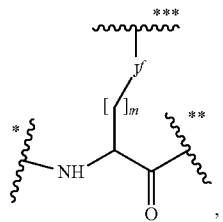

herein, m is an integer of 1 to 5, $J^f$ is —NH—, —S—, or —C(═O)—, each of * and ** indicates an attachment point of Xa$^{1'}$ with an amino acid residue adjacent to Xa$^{1'}$, and

*** indicates an attachment point of Xa$^{1'}$ with a portion that are not the Fc binding unit in the compound comprising Fc binding unit.

C02. The compound comprising Fc binding unit according to C01, wherein X is —O— or —CH$_2$—.

C03. The compound comprising Fc binding unit according to any one of C01 to

[formula 2-3]

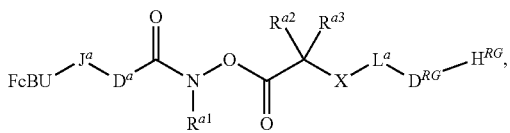

wherein $D^{RG}$ is a spacer of the reactive group (spacer RG), wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(=O)H, —C(=O)CH$_3$, —C(=O)NH$_2$, —NH$_2$, =NH, =O, =S, —OH, —NO$_2$ and —SH, herein heteroalkylene or heteroalkenylene comprises one or more heteroatoms, wherein each of the heteroatoms is independently selected from O, N, and S, $H^{RG}$ is the reactive moiety.

C21. The compound comprising Fc binding unit according to any one of C01 to C20, wherein the reactive moiety is a bio-orthogonal functional group.

C22. The compound comprising Fc binding unit according to any one of C01 to C21, wherein the reactive moiety has any one structure of the following structures:

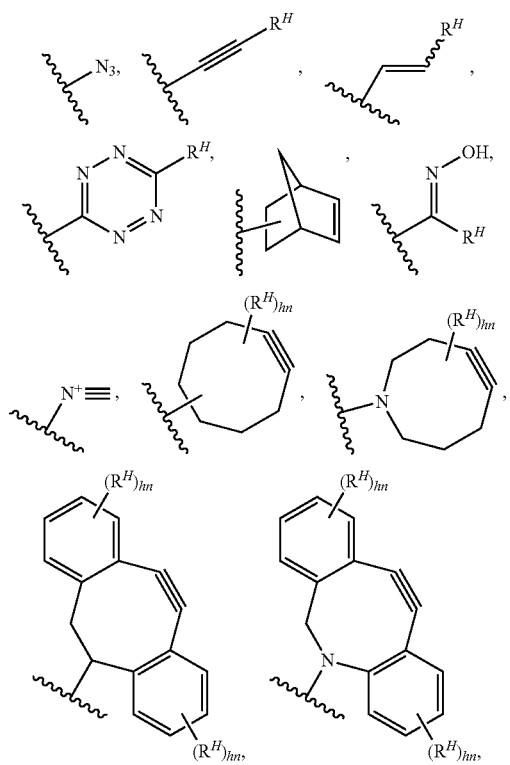

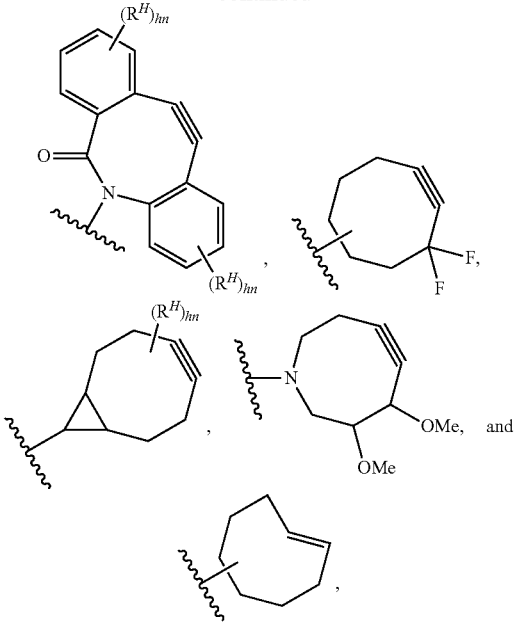

wherein
hn is an integer of 1 to 3,
$R^H$ is, each independently, H or selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein R is each independently selected from H, halogen, $C_{1-6}$alkyl, $C_{3-10}$ cycloalkyl, $C_{3-10}$ heterocycloalkyl, aryl, heteroaryl, —OH, —NH$_2$, —COOH, =O, =S, and —SH, wherein the heterocycloalkyl or heteroaryl comprises one or more heteroatoms, wherein each heteroatom is independently selected from N, O, and S.

C23. The compound comprising Fc binding unit according to any one of C01 to C20, the reactive moiety is selected from azide group, terminal alkyne group, terminal alkene group, cyclooctyne group, tetrazine group, norbornene group, cyclooctene group, oxime group, and isocyanide group, wherein the cyclooctyne group is any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group is any one selected from cis-cyclooctene group and trans-cyclooctene group.

C24. A compound comprising Fc binding unit having a structure of formula 2-15

[formula 2-15]

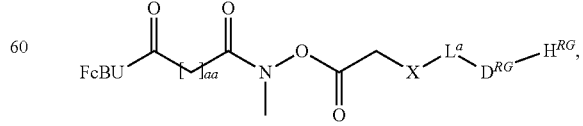

wherein
aa is an integer of 1 to 10,
X is —O— or —CH$_2$—, $L^a$ is a linker A, wherein the linker A is a bond, unsubstituted $C_{1-30}$ alkylene, or unsubstituted $C_{3-30}$ heteroalkylene comprising 1 to 10 of ethyleneglycol units,

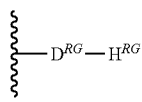

is a reactive group, $D^{RG}$ is a spacer of the reactive group (spacer RG), wherein the spacer of the reactive group is a bond, substituted or unsubstituted $C_{1-6}$ alkylene, substituted or unsubstituted $C_{1-6}$ heteroalkylene, substituted or unsubstituted $C_{2-6}$ alkenylene, or substituted or unsubstituted $C_{2-6}$ heteroalkenylene, herein the substituted indicates that one or more hydrogen atoms in a group modified by the term of substituted are substituted with one or more substituents, herein each of the substituents is independently selected from —$C_{1-4}$ alkyl, —C(═O)H, —C(═O)$CH_3$, —C(═O)OH, —C(═O)$NH_2$, —$NH_2$, =NH, ═O, ═S, —OH, —$NO_2$ and —SH, herein, heteroalkylene or heteroalkenylene comprises one or more heteroatoms, wherein each of the heteroatoms is independently selected from O, N, and S, $H^{RG}$ is the reactive moiety, FcBU is a Fc binding unit, wherein the Fc binding unit has a structure of

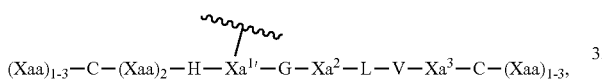

wherein each of Xaa is independently selected from any amino acid, $Xa^2$ is glutamic acid residue or asparagine residue, and $Xa^3$ is tryptophan residue, naphthylalanine residue, or phenylalanine residue, a cysteine residue adjacent to the N terminus and a cysteine residue adjacent to the C terminus are, optionally, covalently linked,

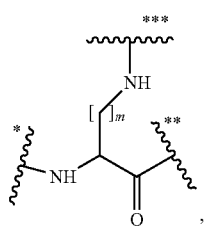

$Xa^{1'}$ is O herein, m is an integer of 1 to 4, each of * and ** indicates an attachment point of $Xa^{1'}$ with an amino acid residue adjacent to $Xa^{1'}$, and

*** indicates an attachment point of $Xa^{1'}$ with a portion that are not the Fc binding unit in the compound comprising Fc binding unit.

C25. The compound comprising Fc binding unit according to C24, wherein aa is an integer of 1 to 6.

C26. The compound comprising Fc binding unit according to any one of C24 to C25, wherein aa is 3.

C27. The compound comprising Fc binding unit according to any one of C24 to C26, wherein Fc binding unit has the following structure:

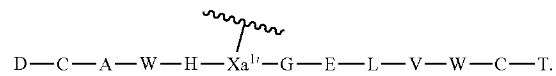

C28. The compound comprising Fc binding unit according to any one of C24 to C27, wherein m is 3.

C29. The compound comprising Fc binding unit according to any one of C24 to C28, wherein the reactive moiety is a bio-orthogonal functional group.

C30. The compound comprising Fc binding unit according to any one of C24 to C28, wherein the reactive moiety has any one structure of the following structures:

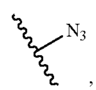

, 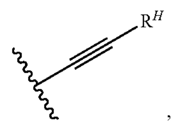 , 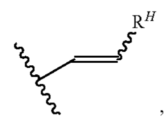 , 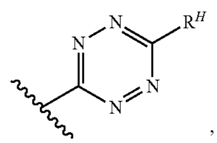 , 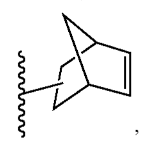 , , 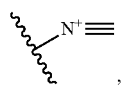 , 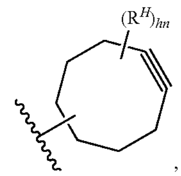 , 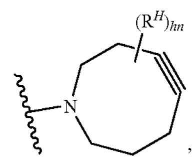 , , , 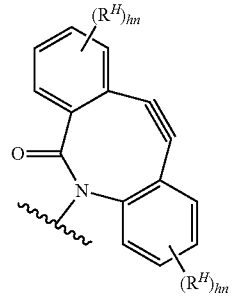 , 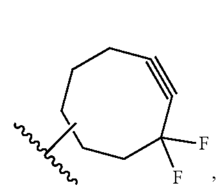 , , 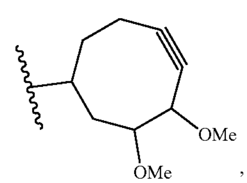 , and

-continued

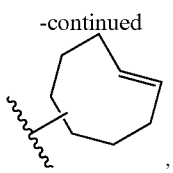

wherein
hn is an integer of 1 to 3,
$R^H$ is, each independently, H or selected from —R, =O, =S, —NO$_2$, —CR$_3$, —NR$_2$, —OR, —SR, —C(=O)R, —C(=O)CR$_3$, —C(=O)OR, and —C(=O)NR$_2$, wherein R is each independently selected from H, halogen, C$_{1-6}$alkyl, C$_{3-10}$ cycloalkyl, C$_{3-10}$ heterocycloalkyl, aryl, heteroaryl, —OH, —NH$_2$, —COOH, =O, =S, and —SH, wherein the heterocycloalkyl or heteroaryl comprises one or more heteroatoms, wherein each heteroatom is independently selected from N, O, and S.

C31. The compound comprising Fc binding unit according to any one of C24 to C28, the reactive moiety is selected from azide group, terminal alkyne group, terminal alkene group, cyclooctyne group, tetrazine group, norbornene group, cyclooctene group, oxime group, and isocyanide group, wherein the cyclooctyne group is any one selected from OCT cyclooctyne, BCN (Bicyclononyne), DBCO (Dibenzocyclooctyne), DIBAC (aza-dibenzocyclooctynes), DIBO (dibenzocyclooctynol), DIFO (difluorinated cyclooctynes), BARAC (biarylazacyclooctynone), DIMAC (dimethoxyazacyclooctyne) and DIFBO (difluorobenzocyclooctyne), wherein the cyclooctene group is any one selected from cis-cyclooctene group and trans-cyclooctene group.

Exemplary Embodiments of Method for Preparing Antibody Conjugate Comprising Reactive Group D01. A method for preparing an antibody conjugate comprising reactive group, wherein the method comprises:
contacting a compound comprising Fc binding unit with an antibody,
wherein the compound having Fc binding unit has a structure of the following formula 2-2:

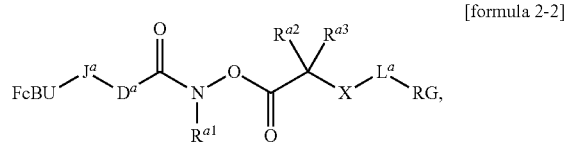

[formula 2-2]

wherein
$D^a$ is a spacer A, wherein the spacer A is a bond, substituted or unsubstituted C$_{1-20}$ alkylene, substituted or unsubstituted C$_{1-20}$ heteroalkylene, substituted or unsubstituted C$_{2-20}$ alkenylene, substituted or unsubstituted C$_{2-20}$ heteroalkenylene, substituted or unsubstituted C$_{2-20}$ alkynylene, or substituted or unsubstituted C$_{2-20}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH, herein the substituent is not H, $L^a$ is a linker A, wherein the linker A is a bond, substituted or unsubstituted C$_{1-100}$ alkylene, substituted or unsubstituted C$_{1-100}$ heteroalkylene, substituted or unsubstituted C$_{2-100}$ alkenylene, substituted or unsubstituted C$_{2-100}$ heteroalkenylene, substituted or unsubstituted C$_{2-100}$ alkynylene, or substituted or unsubstituted C$_{2-100}$ heteroalkynylene, herein the substituted indicates that one or more hydrogen atoms in a group modified by the term of substituted are substituted with one or more substituents, herein each of the substituents is independently selected from —R, =O, =S, —NO$_2$, —CR$_3$, —NR$_2$, =NR, —OR, —SR, —C(=O)R, —C(=O)CR$_3$, —C(=O)OR, and —C(=O)NR$_2$, wherein each R is independently selected from H, halogen, C$_{1-6}$ alkyl, C$_{3-10}$ cycloalkyl, C$_{3-10}$ heterocycloalkyl, aryl, heteroaryl, —OH, —NH$_2$, —COOH, =O, =S, and —SH, herein the substituent is not H, wherein each of the heteroalkylene, the heteroalkenylene, the heteroalkynylene, the heterocycloalkyl, and the heteroaryl independently comprises one or more heteroatoms, wherein each of the heteroatoms is independently selected from N, O, and S, X is —CH$_2$—, —O—, or —NH—,
$R^{a1}$ is H or C$_{1-6}$ alkyl,
$R^{a2}$ is H or C$_{1-6}$ alkyl,
$R^{a3}$ is H or C$_{1-6}$ alkyl,
$J^a$ is —C(=O)—, —S—, —NH—, or —C(=NH)—,
RG is a reactive group, wherein the reactive group comprises a reactive moiety,
FcBU is a Fc binding unit, wherein the Fc binding unit has a structure of

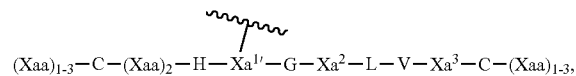

$(Xaa)_{1-3}$—C—$(Xaa)_2$—H—$Xa^{1'}$—G—$Xa^2$—L—V—$Xa^3$—C—$(Xaa)_{1-3}$, wherein
each of Xaa is independently selected from any amino acid,
$Xa^2$ is glutamic acid residue or asparagine residue, and
$Xa^3$ is tryptophan residue, naphthylalanine residue, or phenylalanine residue,
a cysteine residue adjacent to the N terminus and a cysteine residue adjacent to the C terminus are, optionally, covalently linked,

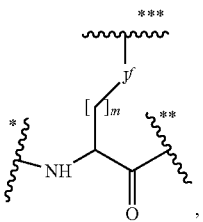

$Xa^{1'}$ is 0
herein, m is an integer of 1 to 5,
$J^f$ is —NH—, —S—, or —C(=O)—,
each of * and ** indicates an attachment point of $Xa^{1'}$ with an amino acid residue adjacent to $Xa^{1'}$, and

*** indicates an attachment point of $Xa^{1\prime}$ with a portion that are not the Fc binding unit in the compound comprising Fc binding unit.

D02. A method for preparing an antibody conjugate comprising reactive group, wherein the method comprises: contacting a compound comprising Fc binding unit according to any one of C01 to C31 with an antibody.

D03. The method according to any one of D01 to D02, wherein the antibody is an IgG.

D04. The method according to any one of D01 to D03, wherein the antibody is an IgG,
wherein the IgG is human IgG, humanized IgG, or chimeric IgG.

D05. The method according to any one of D01 to D03, wherein the antibody is an IgG,
wherein the IgG is IgG1, IgG2, or IgG4.

D06. The method according to any one of D01 to D03, wherein the antibody is an IgG,
wherein the IgG is human IgG1, humanized IgG1, chimeric IgG1, human IgG2, humanized IgG2, chimeric IgG2, human IgG4, humanized IgG4, or chimeric IgG4.

D07. The method according to any one of D01 to D02, wherein a Fc region of the antibody comprises an amino acid sequence of SEQ ID NO: 14 or an amino acid sequence having 80% or more sequence identity thereof, wherein the Fc region of the antibody comprises an amino acid sequence of KPKDTLM (SEQ ID NO: 10) and an amino acid sequence of MHEALHNH (SEQ ID NO: 11).

D08. The method according to any one of D01 to D02, wherein a Fc region of the antibody comprises an amino acid sequence of SEQ ID NO: 14 or an amino acid sequence having 80% or more sequence identity thereof, wherein the Fc region of the antibody comprises an amino acid sequence of KPKDTLM (SEQ ID NO: 10) and an amino acid sequence of MHEALHNHY (SEQ ID NO: 12).

D09. The method according to any one of D01 to D08, wherein, according to contacting the compound comprising Fc binding unit with the antibody, a reactive group is transferred to one or more of K246 and K248 of the Fc region of the antibody.

D10. The method according to any one of D01 to D09, wherein the method further comprises obtaining the antibody conjugate comprising reactive group.

D11. The method according to any one of D01 to D10, wherein, according to contacting the compound comprising Fc binding unit with the antibody, the reactive group is transferred to K246 or K248 of the Fc region of the antibody.

D12. The method according to any one of D01 to D11, wherein, according to contacting the compound comprising Fc binding unit with the antibody, the antibody conjugate comprising reactive group is prepared,
wherein in the antibody conjugate comprising reactive group, the reactive group is linked to any one or more of K246 and K248 of the antibody.

D13. The method according to any one of D01 to D12, wherein, according to contacting the compound comprising Fc binding unit with the antibody, the antibody conjugate comprising reactive group is prepared,
wherein the antibody conjugate comprising reactive group comprises 1 to 4 of reactive groups.

D14. The method according to any one of D01 to D13, wherein, according to contacting the compound comprising Fc binding unit with the antibody, the antibody conjugate comprising reactive group is prepared,
wherein the antibody conjugate comprising reactive group comprises two reactive groups,
wherein each of the reactive groups is linked to first K246 and second K246 of the antibody, respectively, or is linked to first K248 and second K248 of the antibody, respectively.

D15. The method according to any one of D01 to D14, wherein contacting the compound comprising Fc binding unit with the antibody is achieved by a method comprising:
mixing a composition comprising the compound comprising Fc binding unit with a composition comprising the antibody.

D16. The method according to any one of D01 to D14, wherein contacting the compound comprising Fc binding unit with the antibody is achieved by a method comprising:
preparing a composition for preparing an antibody conjugate comprising reactive group by mixing a composition comprising the compound comprising Fc binding unit with a composition comprising the antibody; and
incubating the composition for preparing an antibody conjugate comprising reactive group.

D17. The method according to any one of D15 to D16, wherein the mixing of the composition comprising the compound comprising Fc binding unit with the composition comprising the antibody is performed under conditions of pH 6 to pH 8.5.

D18. The method according to D16, wherein the mixing of the composition comprising the compound comprising Fc binding unit with the composition comprising the antibody and the incubating the composition for preparing an antibody conjugate comprising reactive group are performed under conditions of pH 6 to pH 8.5.

D19. The method according to any one of D01 to D18, wherein the antibody conjugate comprising reactive group has a structure of the following formula 6-1:

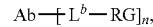
[formula 6-1]

wherein
n is an integer of 1 to 4,
Ab is an antibody unit,
RG is a reactive group,

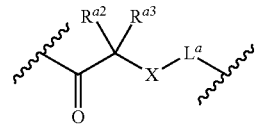

$L^b$ is a linker B, wherein the linker B is O

Exemplary Embodiments of Method for Preparing Antibody-Payload Conjugate

E01. A method for preparing an antibody-payload conjugate, wherein the method comprises:
preparing an antibody conjugate comprising reactive group according to a method for preparing an antibody conjugate comprising the reactive group according to D01 to D19; and
contacting the antibody conjugate comprising reactive group with a payload,
wherein the payload has a structure of the following formula 7:

$CM-RG^2$ [formula 7]

wherein

CM is a cargo moiety (CM) comprising an active moiety, and $RG^2$ is a second reactive group.

E02. The method according to E01, wherein the second reactive group is a group capable of reacting with the reactive group (a first reactive group) of an antibody conjugate comprising reactive group.

E03. The method according to any one of E01 to E02, wherein the second reactive group comprises a second reactive moiety, wherein the second reactive moiety is a moiety capable of reacting with a reactive moiety (a first reactive moiety) of the first reactive group.

E04. The method according to E03, wherein the second reactive moiety is a bio-orthogonal partner of the first reactive moiety.

E05. The method according to E03, wherein the second reactive moiety is a click-chemistry partner of the first reactive moiety.

E06. The method according to any one of E01 to E05, wherein the active moiety is any one selected from a drug moiety, a radioactive moiety, and an imaging moiety.

E07. The method according to any one of E01 to E06, wherein the active moiety is a drug moiety, wherein the drug moiety is any one selected from auristatin, eribulin, tubulysin, geldanamycin, maytansinoid, calicheamicin, mertansine, daunomycin, doxorubicin, methotrexate, vindesine, SG2285, dolastatin, dolastatin analogs auristatin, cryptophycin, camptothecin, camptothecin analogs (for example, SN38, FL118, or exatecan), rhizoxin derivatives, CC 1065 analogs or derivatives, duocarmycin, enediyne antibiotics, esperamicin, epothilone, pyrrolobenzodiazepine (PBD) derivatives, α-amanitin, toxoid, toll-like receptor 5 (TLR5) agonist, toll-like receptor 7 (TLR7) agonist, toll-like receptor 8 (TLR8) agonist, 1,4,7-triazacyclononane-1,4,7-triacetic acid (NOTA), and 1,4,7,10-tetraazacyclododecane-1,4,7,10-tetraacetic acid (DOTA), or an analog thereof.

E08. The method according to E07, wherein the drug moiety is monomethyl auristatin e (MMAE).

Exemplary Embodiments of Antibody-Payload Conjugate

F01. An antibody-payload conjugate having a structure of the following formula 8-3:

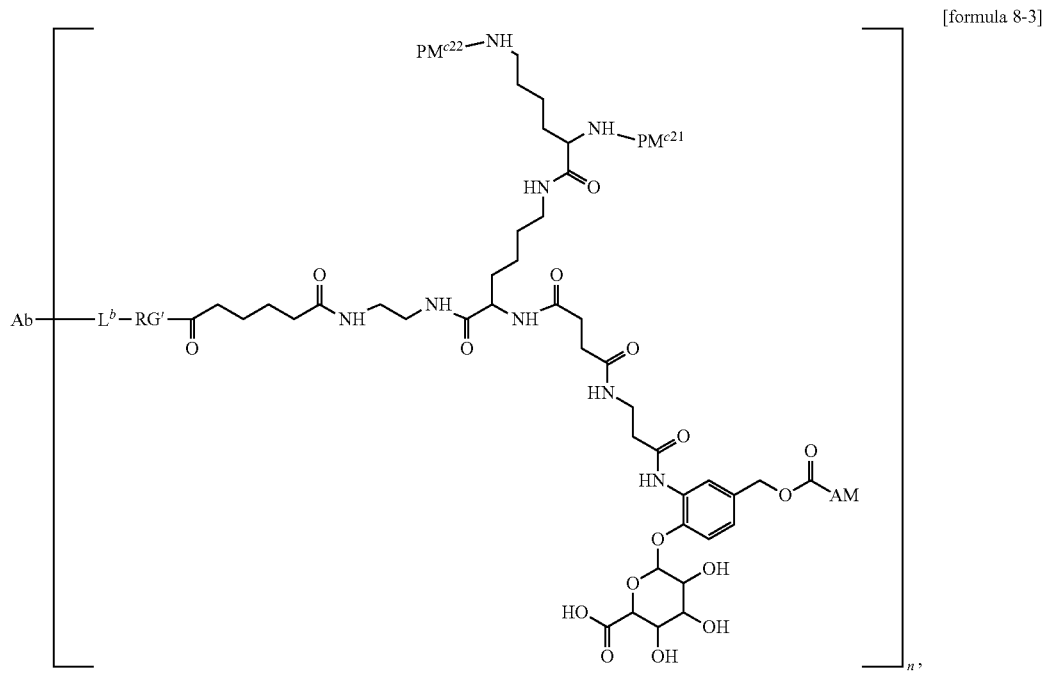

[formula 8-3]

wherein n is an integer of 1 to 4, $L^b$ is

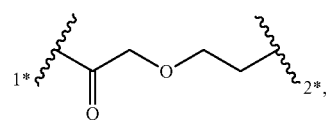 [SMILES: *CCOCC(*)=O]

wherein 1* indicates a linking point (that is, attachment point) to the antibody unit, and 2* indicates a linking point to RG', RG' is

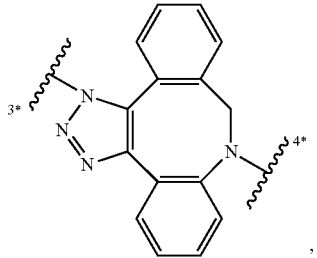 [SMILES: *N1Cc2ccccc2-c2c(nnn2*)-c2ccccc21]

wherein 3* indicates a linking point to $L^b$, and 4* indicates a linking point to another part which is not $L^b$, each of $PM^{c21}$ and $PM^{c22}$ is

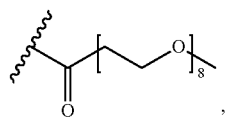

AM is an active moiety, and
Ab is an antibody unit.

F02. The antibody-payload conjugate according to F01, wherein AM is any one selected from a drug moiety, a radioactive moiety, and an imaging moiety.

F03. The antibody-payload conjugate according to any one of F01 to F02, wherein AM is MMAE.

F04. The antibody-payload conjugate according to any one of F01 to F02,

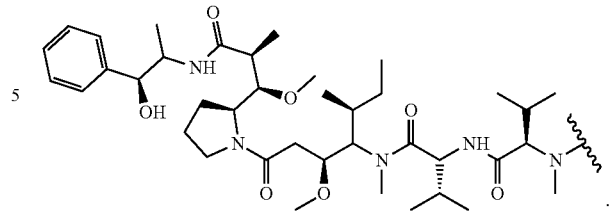

wherein AM is 0

F05. The antibody-payload conjugate according to any one of F01 to F04, wherein the antibody unit is derived from an anti-claudin 18.2 antibody.

F06. The antibody-payload conjugate according to F05, wherein the anti-claudin 18.2 antibody comprises a light chain having a sequence of SEQ ID NO: 26 and a heavy chain having a sequence of SEQ ID NO: 25.

F07. The antibody-payload conjugate according to any one of F01 to F06, wherein each AM is linked to any one or more of K246 and K248 of the antibody unit.

F08. The antibody-payload conjugate according to any one of F01 to F06, wherein n is 2.

F09. The antibody-payload conjugate according to F08, wherein each AM is linked to K248 of one heavy chain (first K248 of the Fc region) and K248 of the other heavy chain (second K248 of the Fc region) of the antibody unit.

F10. The antibody-payload conjugate according to F08, wherein each AM is linked to K246 of one heavy chain (first K246 of the Fc region) and K246 of the other heavy chain (second K246 of the Fc region) of the antibody unit.

F11. An antibody-payload conjugate having a structure of the following formula 8-3:

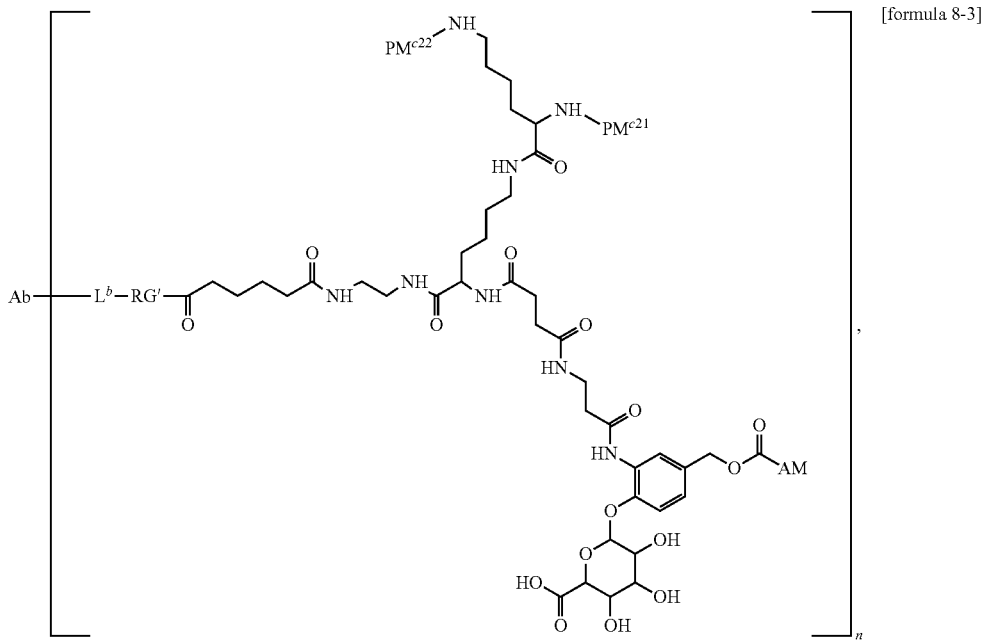

[formula 8-3]

wherein n is 2, $L^b$ is

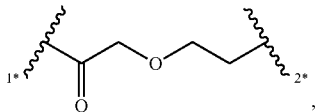

wherein 1* indicates a linking point (that is, attachment point) to the antibody unit, and 2* indicates a linking point to RG', RG' is

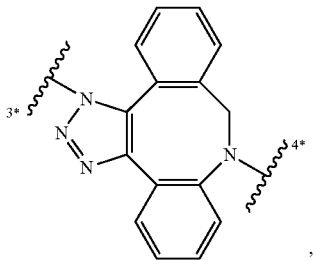 [SMILES: *N1Cc2ccccc2-c2c(nnn2*)-c2ccccc21]

wherein 3* indicates a linking point to $L^b$, and 4* indicates a linking point to a part other than $L^b$, each of $PM^{c21}$ and $PM^{c22}$ is

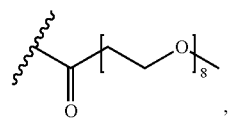

AM is MMAE, and

Ab is an antibody unit, wherein the antibody unit is an anti-claudin 18.2 antibody, wherein a heavy chain of the anti-claudin 18.2 antibody comprises CDRH1 represented by an amino acid sequence of SEQ ID NO: 19, CDRH2 represented by an amino acid sequence of SEQ ID NO: 20, and CDRH3 represented by an amino acid sequence of SEQ ID NO: 21, wherein a light chain of the anti-claudin 18.2 antibody comprises CDRL1 represented by an amino acid sequence of SEQ ID NO: 22, CDRL2 represented by an amino acid sequence of SEQ ID NO: 23, and CDRL3 represented by an amino acid sequence of SEQ ID NO: 24, wherein the anti-claudin 18.2 antibody is an IgG1-type antibody, wherein each AM is linked to any one of K246 and K248 of one heavy chain, and to any one of K246 and K248 of the other heavy chain of the antibody unit.

F12. The antibody-payload conjugate according to F11, wherein the anti-claudin 18.2 antibody comprises a light chain having a sequence of SEQ ID NO: 26 and a heavy chain having a sequence of SEQ ID NO: 25.

Exemplary Embodiments of Pharmaceutical Composition and Method for Treating Cancer in Subject G01. A pharmaceutical composition for treating cancer, comprising the antibody-payload conjugate according to any one of F11 to F12.

G02. The pharmaceutical composition according to G01, wherein the cancer is claudin 18.2-positive gastric cancer, claudin 18.2-positive pancreatic cancer, claudin 18.2-positive colorectal cancer, claudin 18.2-positive genitourinary cancer, or claudin 18.2-positive bile duct cancer.

H01. A method for treating cancer in a subject, wherein the method comprises: administering the pharmaceutical composition according to G01 to the subject.

H02. The method according to H01, wherein the cancer is claudin 18.2-positive gastric cancer, claudin 18.2-positive pancreatic cancer, claudin 18.2-positive colorectal cancer, claudin 18.2-positive genitourinary cancer, or claudin 18.2-positive bile duct cancer.

Hereinafter, the invention provided by the present specification will be described in more detail through experimental examples and examples. These examples are provided for illustrating the content disclosed by the present application, and the scope of the content disclosed by the present application is not limited by these examples.

EXAMPLES

Materials and Equipment

Materials

Materials used in the synthesis or preparation and analysis of the compounds, payloads, and conjugates of examples were purchased from commercial suppliers and used without further purification. Ammonium sulfate ($(NH_4)_2SO_4$), N-Boc-ethylenediamine, triisopropylsilane (TIS), 1,2-ethanedithiol (EDT), O-benzylhydroxylamine, HATU, tetrahydrofuran, LiOH, triethylamine and TSTU were purchased from Sigma-Aldrich (St. Louis, MO, USA). 4-Methyltetrazine NHS ester, NHS ester-PEG4-$N_3$(1-azido-16-methyl-14,17-dioxo-3,6,9,12,15-pentaoxa-16-azahenicosan-21-oic acid), and NHS ester-PEG8-$N_3$(2,5-dioxopyrrolidin-1-yl 26-azido-3,6,9,12,15,18,21,24-octaoxahexacosanoate) were purchased from Broadpharm Inc. (San Diego, CA, USA). Fmoc-PEG8-OH was purchased from Quanta Biodesign (Plain City, OH, USA). DBCO-C6-NHS was purchased from Lumiprobe (Hong Kong). All amino acids, rink amide resin, and coupling reagents were purchased from Aapptec (Louisville, KY, USA), GL Biochem Ltd. (Shanghai, China), and Combi-Blocks (San Diego, CA, USA). Solvents were used without distillation. Trifluoroacetic acid (TFA), N,N-diisopropylethylamine (DIPEA), ammonium hydroxide (ammonia solution), diethylamine, $Na_2HPO_4$, N,N-dimethylformamide (DMF), dichloromethane (DCM), methanol (MeOH), hexane (Hex), ethyl acetate (EA), and diethyl ether were obtained from Daejung (Siheung, Korea). High performance liquid chromatography (HPLC)-grade acetonitrile (ACN), isopropanol, and water were purchased from Thermo Fisher Scientific (Waltham, MA, USA). 5-Ethoxy-5-oxopentanoic acid was purchased from Ambeed Inc. (IL, USA).

Cells and Plasma

A MIA PaCa-2-CLDN18.2 cell line (C3002) was purchased from Accurus Biosciences. A PATU8988S cell line (ACC204) was purchased from DSMZ. A MIA PaCa-2 (CLDN18.2-) cell line (CRL-1420) was purchased from ATCC. An SNU 601 cell line (00601) was purchased from KCLB. A NUGC-4 cell line (ABC-TC0862) was purchased from Accegen. An AGS cell line (21739) was purchased from KCLB.

Human plasma was purchased from BIO IVT. Monkey plasma was purchased from GENIA. Rat plasma was purchased from QuBest Bio. Mouse plasma was purchased from QuBest Bio.

Antibodies and ADC

Human IgG antibodies (Sigma-Aldrich, 14506) were purchased from Sigma-Aldrich (St. Louis, MO, USA).

Trastuzumab was purchased from Roche (Basel, Switzerland).

An anti-Claudin 18.2 antibody (Anti-CLDN18.2 mAb) (antibody-A) is an antibody comprising a light chain having an amino acid sequence of SEQ ID NO: 26 and a heavy chain having an amino acid sequence of SEQ ID NO: 25 (herein, anti-CLDN18.2 antibody has two light chains and two heavy chains, similar to the generally known antibody structure). Information on the antibody is disclosed in the document [Korean Patent Application No. 10-2021-7023724 (Publication No. 10-2021-0110339)]. The anti-claudin 18.2 antibody was obtained from GenScript ProBio, and a method for preparing the anti-claudin 18.2 antibody is disclosed in detail in "Example 3" of the document [Korean Patent Application No. 10-2021-7023724 (Publication No. 10-2021-0110339)] which is incorporated herein by reference.

Zolbetuximab (antibody-B) was purchased from Biointron. Zolbetuximab is an antibody that binds to claudin 18.2.

Meanwhile, the anti-claudin 18.2 antibodies mentioned in the following Examples 1 to 10 are all the aforementioned antibody-A (an antibody comprising a light chain of SEQ ID NO: 26 and a heavy chain of SEQ ID NO: 25).

Human IgG antibody (antibody-C) (Sigma-Aldrich, 14506) was purchased from Sigma-Aldrich (St. Louis, MO, USA).

ADC-A is MMAE conjugated with antibody-A, and was produced through the process of Example 11.

ADC-B is MMAE conjugated with antibody-B, and was prepared by commissioning Abzena. For the method for preparing ADC-B, the content disclosed in the document [US 2018/0117174 (Korean Patent Application No. U.S. Ser. No. 15/565,848)] was referenced.

ADC-C is MMAE conjugated with antibody-C, and was produced through the process of Example 11. At this time, the only difference from Example 11 is that the antibody-C was used rather than antibody-A.

Equipment and Conditions

Equipment

All peptides and compounds comprising a payload were characterized using HPLC (Waters, XBridge©, C18, 4.6× 250 mm, 5 µm).

For HPLC, an HPLC Alliance system (2996 PAD detector and 2695 separations module) manufactured by Waters was used.

As a mass spectrometer used for analysis of all small molecular substances such as peptides and compounds, an LC/MS equipped with Quatro Premier XE equipment of Waters and an Acquity Waters LC system was used.

All antibodies comprising antibody conjugates (for example, ADC and the like) were characterized using HIC-HPLC (Thermo Fisher Scientific, MAbPac™, HIC-butyl, 4.6×100 mm, 5 µm), size-exclusion chromatography (SEC)-HPLC (Thermo Fisher Scientific, MAbPac™, SEC-1, 300 Å 4×300 mm, 5 µm) and a UV spectrometer (Thermo Fisher Spectrophotometer, MULTISKAN GO/MicroDrop™ plate use, N12391).

A Fleta 4 centrifuge (Hanil, Korea) was used for centrifugation in spin desalting.

A UV-Vis spectrometer (Thermo Fisher, 4661030N) was used to measure the OD values in all ELISA experiments.

GloMax® Discover (Promega, GM3000) was used to measure cell viability in cytotoxicity experiments.

An S3 Live Cell Analysis Instrument (SARTORIUS, Incucyte® S3) was used for real-time internalization analysis.

As a centrifuge, Smart R17 Plus (Hanil, SM-R17PL) was used.

Characterization of Peptides, Compounds, and the Like Using C18-HPLC

C18-HPLC was carried out at a flow rate of 1 mL/min. All compounds were analyzed using the same elution conditions [initial 80% mobile phase A (0.1% TFA in $H_2O$) for 1 min followed by a 20-80% gradient of mobile phase B (0.075% TFA in ACN) in A for 15 min]. The chromatograms of peptides and compounds were acquired at 280 nm (marked separately when acquired at 254 nm), and the chromatograms of payloads were acquired at 254 nm.

Characterization of Antibodies and the Like Using HIC-HPLC

HIC-HPLC was carried out at a flow rate of 1 mL/min. All antibodies and the like were performed under the same conditions [initial 100% mobile phase A (1.5 M $(NH_4)_2SO_4$, 50 mM $Na_2HPO_4$ at pH 7.0, 5% isopropanol) for 1 min followed by a 0-100% gradient of mobile phase B (50 mM sodium phosphate at pH 7.0, 20% isopropanol) in A for 15 min]. All chromatograms were acquired at 280 nm.

Characterization of Antibodies and the Like Using SEC-HPLC

SEC-HPLC was carried out at a flow rate of 0.2 mL/min. All antibodies and the like were analyzed under the same conditions [isocratic mobile phase D (1×PBS) for 20 min]. All chromatograms were acquired at 280 nm.

Measurement of OD Values of ELISA Experiments Using UV-Vis Spectrometer

For the measurement of OD values through ELISA, absorbance at 450 nm was measured using a UV-Vis spectrometer.

Measurement of Cell Viability to Confirm Cytotoxicity

To measure cell viability in cytotoxicity experiments, the measurement of luminescence using GloMax® Discover was used, and the measurement method was according to the equipment manual.

Real-Time Internalization Analysis

Real-time internalization measurements were performed according to the reagent and equipment manual.

Process of Pretreating Plasma Sample and PK Sample Using Centrifuge

Centrifugation in the pretreatment process was carried out under the conditions of 13,000 rpm, 4° C., and 10 min.

Example 1. Preparation of Fc Binding Substance, Compound, and the Like

Preparation of Fc Binding Substance

The inventors of the present application referred to the content disclosed in the document [WO2020/184944 (Application No. PCT/KR2020/003282)] to prepare an Fc binding substance represented by FcBP (Orn) below. FcBP (Orn) may be represented by PEG8-DCAWHOrnGELVWCT-$NH_2$, and the structure thereof is as follows:

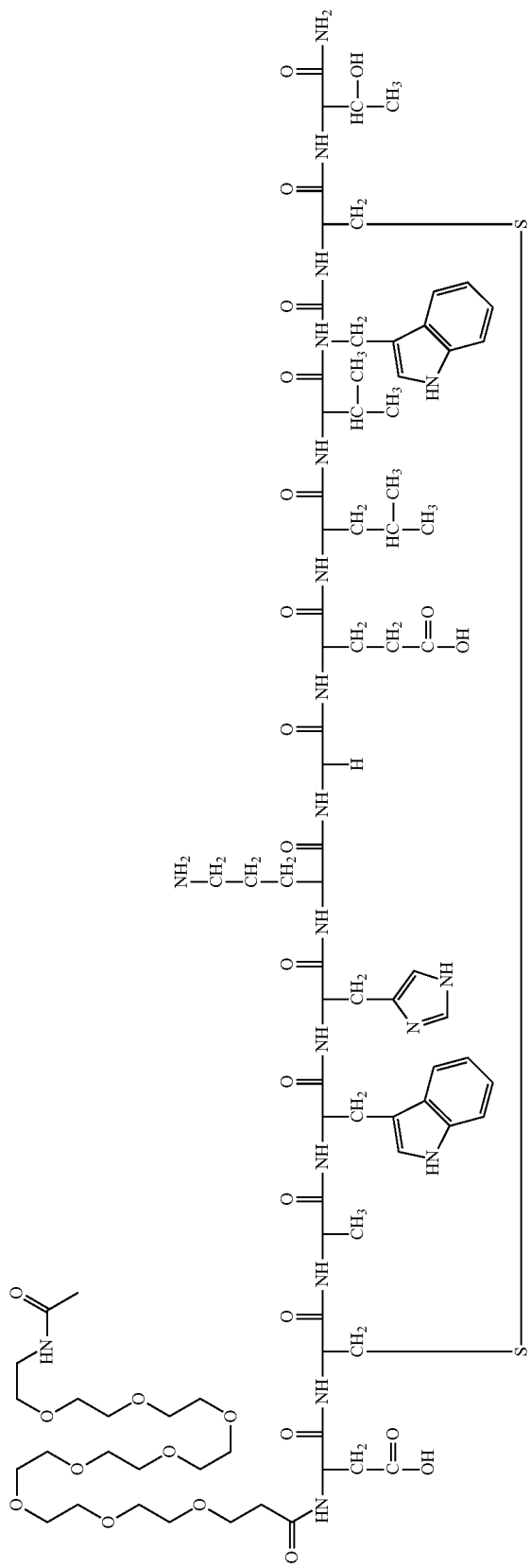

The inventors of the present application prepared FcBP (Orn) using solid-phase peptide synthesis (SPPS).

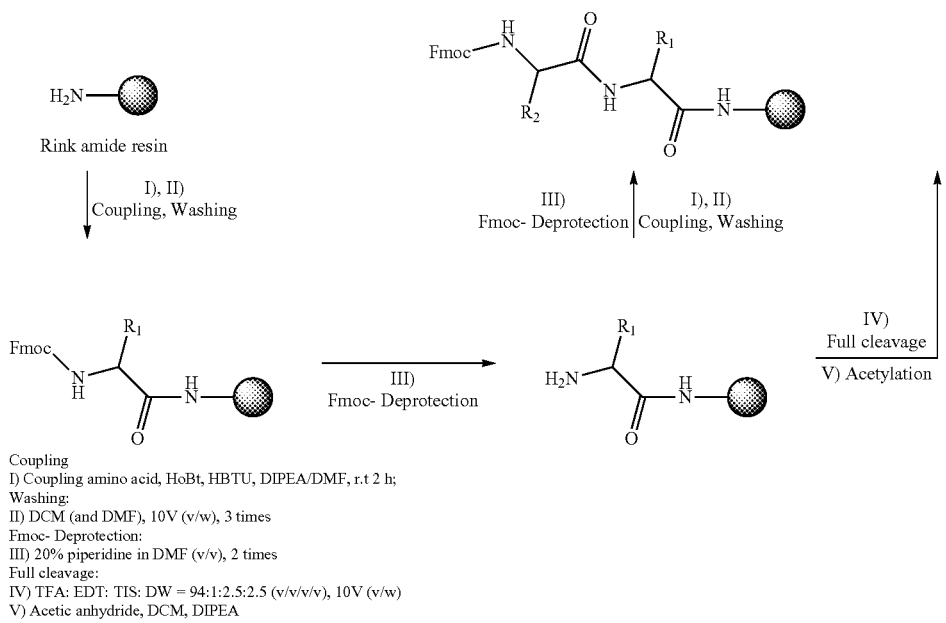

Coupling
I) Coupling amino acid, HoBt, HBTU, DIPEA/DMF, r.t 2 h;
Washing:
II) DCM (and DMF), 10V (v/w), 3 times
Fmoc- Deprotection:
III) 20% piperidine in DMF (v/v), 2 times
Full cleavage:
IV) TFA: EDT: TIS: DW = 94:1:2.5:2.5 (v/v/v/v), 10V (v/w)
V) Acetic anhydride, DCM, DIPEA List of Fmoc Amino Acids Used and Order of Introduction
Fmoc-L-Thr(tBu)-OH, Fmoc-Cys(Trt)-OH, Fmoc-L-Trp (Boc)-OH, Fmoc-L-Val-OH, Fmoc-L-Leu-OH, Fmoc-L-Glu(OtBu)-OH, Fmoc-Gly-OH, Fmoc-Orn(Boc)-OH, Fmoc-L-His(Trt)-OH, Fmoc-L-Trp(Boc)-OH Fmoc-Ala-OH, Fmoc-Cys(Trt)-OH, Fmoc-Asp(tBu)-OH.

Fmoc-Lys(Boc)-OH is used instead of Fmoc-Orn(Boc)-OH in the preparation of PEG8-DCAWHLysGELVWCT-NH$_2$. Fmoc-Dab(Boc)-OH is used instead of Fmoc-Orn (Boc)-OH in the preparation of PEG8-DCAWHDabGELVWCT-NH$_2$. Fmoc-Dap(Boc)-OH is used instead of Fmoc-Orn(Boc)-OH in the preparation of PEG8-DCAWHDabGELVWCT-NH$_2$. A specific preparation method is described in detail in the document [WO 2020/184944 (Application No. PCT/KR2020/003282)] which is incorporated herein by reference.

Introduction of Amino Acids
The amount of reagent used in the following process was based on 0.25 mmol. 0.5 g of a rink amide resin (0.48 mmol/g, Peptides International, USA) was put into a synthesis reactor, and 1 mmol of each Fmoc-amino acid block was weighed and prepared in the order of the peptide amino acid sequence from the C-terminal to the N-terminal.

A reaction of attaching the activated residue to the clear amide resin by activating the Fmoc-amino acid was carried out sequentially from the C-terminal amino acid.

The removal of Fmoc was performed in 20% piperidine-containing DMF, and for the activation and introduction of the residue, amino acids prepared according to the sequence were mixed with 2 mL of a 0.5 M HOBt-containing DMF solution, 2 mL of a 0.5 M HBTU-containing DMF solution, and 174 µL of DIPEA for 5 minutes, and then the resulting mixture was poured into a reactor containing a resin and was mixed with the resin for 2 hours.

The confirmation of the introduction reaction was performed by the Kaiser test method, and when it was confirmed that there was no reaction the introduction reaction was repeated once more, or capping was performed with a 20% Ac2O-containing DMF solution. The resin was sufficiently washed with DMF and DCM before moving on to the next step in each introduction reaction and Fmoc removal process. Such a process was performed repeatedly until a target peptide sequence was completed.

Introduction of H-PEG8-OH
To introduce H-PEG8-OH at the N-terminal after all amino acids had been introduced, 1 mL of 0.5 M Fmoc-N-amido-dPEG8-acid in a DMF solution, 1 mL of a 0.5 M HBTU-containing DMF solution, 1 mL of a 0.5 M HOBt-containing DMF solution, and 87 µL of DIPEA were mixed for 5 minutes, and then the resulting mixture was poured into a reactor containing a resin and was mixed with the resin for 2 hours.

The progress of the reaction was confirmed by the Kaiser test method, and when it was determined that unreacted amines remained, the reaction time was further extended by 1 to 3 hours, or the reaction solution was emptied and the aforementioned reaction process was repeated again. After the removal of the N-terminal Fmoc protecting group was performed using 20% piperidine-containing DMF, the resin was sufficiently washed with a solution of DMF and DCM, and then capping was performed with a 20% Ac2O-containing DMF solution. After capping, the resin to which the peptide was attached was dried with a solution of DCM and diethyl ether, and the weight was measured.

The peptide was cleaved from the resin by stirring 250 mg of the resin to which the peptide prepared during the process of introducing amino acids was attached with 2 mL of a mixed solution of TFA, TIS, water and EDT (94:1.0:2.5:2.5) at room temperature for 120 minutes. The cleavage mixture was filtered, the filtrate was concentrated by about half with nitrogen gas, and then diethyl ether was poured to precipitate the peptide. The precipitated peptide was further washed three times with diethyl ether and dried with nitrogen gas. After the dried precipitate was dissolved in 0.1% TFA-30% ACN-containing water, the resulting solution was stirred for 6 hours, and then concentrated.

After the concentrate was dissolved in a 0.01 M ammonium acetate buffer (pH 6.5) solution containing 5%-DMSO-20%-ACN at a concentration of 0.1 mg/mL, the resulting solution was stirred for 3 days while exposed to air. The progress of a disulfide bond formation reaction was observed by HPLC, and when it was determined that the reaction did not proceed any further, the reaction solution was lyophilized to obtain a peptide precipitate.

Purification

A peptide precipitate obtained by performing lyophilization in the process was purified by prep-LC and then lyophilized. The purity of the obtained peptide was confirmed to be 90% or higher using analytical HPLC, and the molecular weight of the synthesized peptide was confirmed using a LC/MS mass spectrometer.

LC/MS analysis results: [M/3+H]=666.26; [M/2+H]=999.38

HPLC analysis results: 9.004 min, purity: 99.9%

Preparation of Compound 1

The inventors of the present application prepared Compound 1, which is a compound comprising Fc binding unit disclosed in the prior document [Korean Patent Application No. 10-2020-0091826 (Application No. 10-2020-0009162)].

(Compound 1)

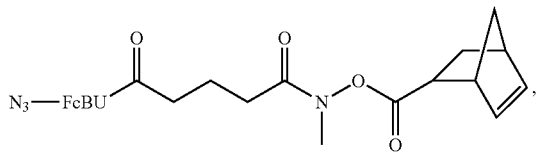

Herein, $N_3$-FcBU is $N_3$-PEG8-DCAWHOrn'GELVWCT-$NH_2$, and Orn' is conjugated ornithine. The structure of $N_3$-PEG8-DCAWHOrn'GELVWCT-$NH_2$ ($N_3$-FcBU) is illustrated as follows:

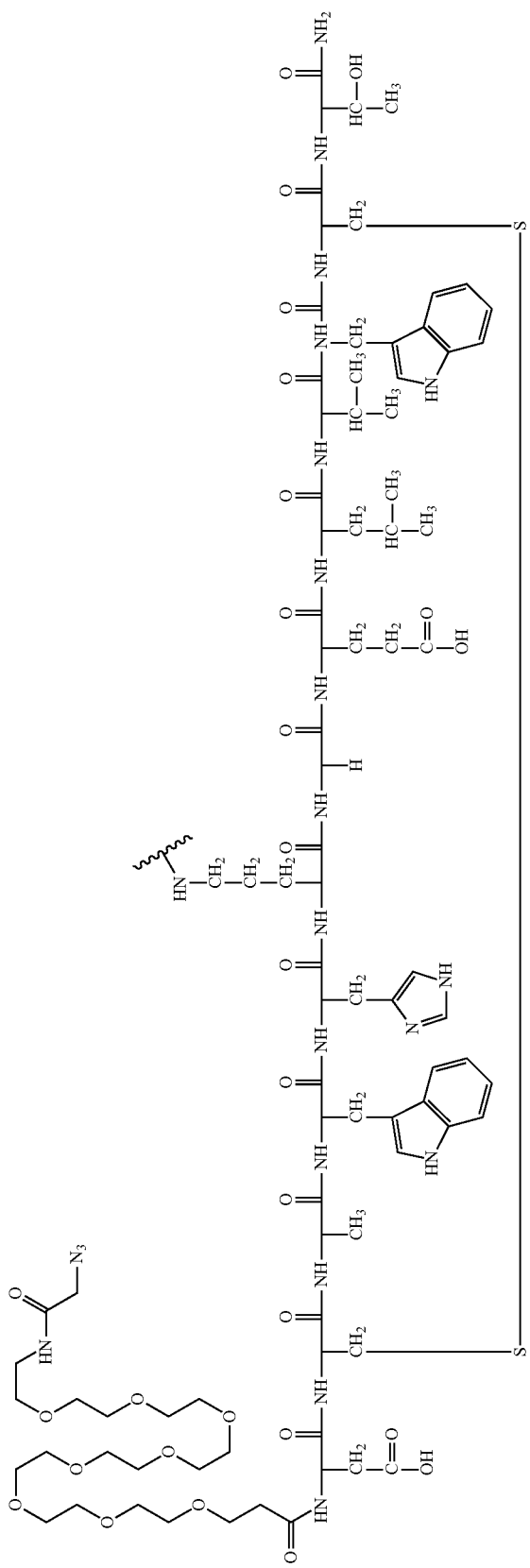

The preparation process of Compound 1 will be described through the following reaction processes.

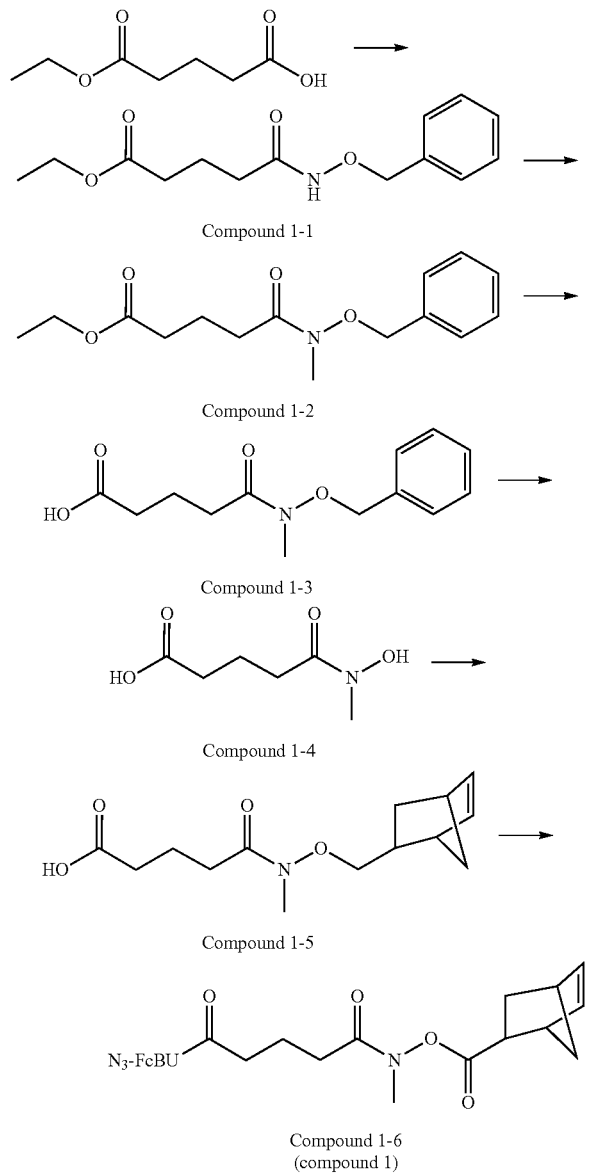

The following process was performed to obtain Compound 1-1. Hexafluorophosphate azabenzotriazole tetramethyl uranium (HATU) and O-benzylhydroxylamine were each added to a solution of a compound 5-ethoxy-5-oxopentanoic acid in dichloromethane (DCM). The reaction mixture was stirred at room temperature under an N2 atmosphere for 3 hours. Thereafter, the solvent was removed under reduced pressure, and the resulting residue was washed with 10% citric acid. The desired product (Compound 1-1) was extracted with ethyl acetate (50*3). The collected solvent was removed under reduced pressure, and the product was purified by MPLC (Hex:EA=1:1).

The following process was performed to obtain Compound 1-2. $K_2CO_3$ and methyl iodide were added to a solution of Compound 1-1 in N,N-dimethylformamide (DMF). The reaction mixture was stirred at room temperature for 18 hours. The solvent was removed under reduced pressure, and the resulting residue was washed with 10% citric acid. The desired product (Compound 1-2) was extracted with ethyl acetate (100*3). The collected solvent was removed under reduced pressure, and the product was purified by MPLC (HEX:EA=1:1) (hexane; HEX) (Ethyl acetate; EA).

The following process was performed to obtain Compound 1-3. 1 N NaOH was added to a solution of Compound 1-2 in MeOH. The reaction mixture was stirred at room temperature for 1 hour. The solvent was removed under reduced pressure and the resulting residue was washed with 10% citric acid. The desired product (Compound 1-3) was extracted with ethyl acetate (100*3). The collected solvent was removed under reduced pressure, and the product was used in the next step without further purification.

The following processes were performed to obtain Compound 1-4. Pd/C was added to a solution of Compound 1-3 in EtOH. The reaction mixture was stirred under H2 gas for 3 hours. The product was poured into Celite545 to remove Pd/C. The filtered product was evaporated under reduced pressure and used in the next step without further purification.

The following process was performed to obtain Compound 1-5. Triethylamine (TEA) and norbornene acid chloride were each added to a solution of Compound 1-4 in DCM. The reaction mixture was stirred at room temperature for 3 hours. The solvent was removed under reduced pressure, and the resulting residue was washed with 10% citric acid. The desired product was extracted with ethyl acetate (50*3). The collected solvent was removed under reduced pressure, and the product was purified by MPLC. (Hex:EA=2:1)

The following process was performed to obtain Compound 1-6 (Compound 1). N,N-diisopropylethylamine (DIPEA) and $N_3$-FcBP (Orn) were added to a solution of Compound 1-5 in DMF. Herein, $N_3$-FcBP (Orn) is $N_3$-PEG8-DCAWHOrnGELVWCT-$NH_2$. The reaction mixture was stirred at room temperature for 2 hours. The solvent was removed under reduced pressure, and the resulting residue was purified by prep-HPLC.

Thereafter, the obtained Compound 1 was analyzed through mass spectrometry and HPLC, and the results are as follows:

LC/MS analysis results: [M/2+H]=1151.48 (Exact Mass: 2299.0289)

HPLC analysis results: 14.959 min, purity 99.99%

Preparation of Compound 2

The inventors of the present application attempted to prepare a compound (Compound 2) in which the norbornene group of Compound 1 was changed to azide.

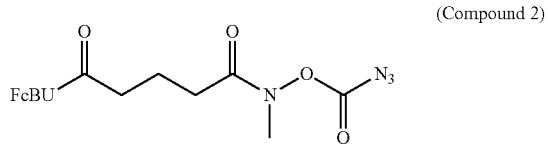

(Compound 2)

However, it was not possible to confirm that Compound 2 had been prepared, either because Compound 2 could not be prepared, or because the stability of Compound 2 was extremely low even though Compound 2 was prepared.

For reference, a schematic view of the preparation process used for the preparation of Compound 2 is attached.

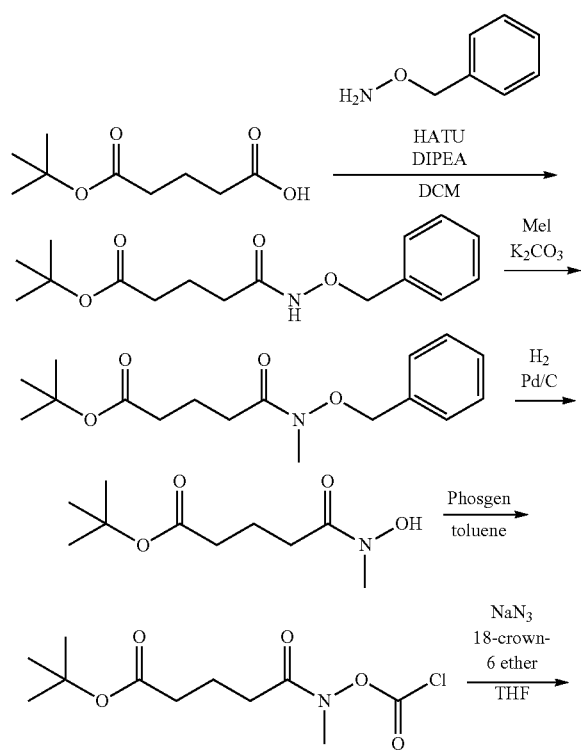

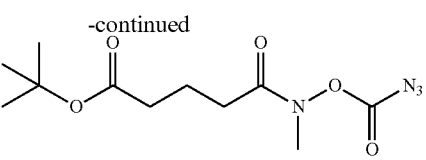

No products were observed in the last step, which is the azide introduction reaction step using NaN₃, and it is assumed that the product degraded before observation due to poor reactivity or due to being an extremely unstable product.

Preparation of Compound 3

The inventors of the present application prepared a compound (Compound 3) in which a peptide linker (Val-Gly peptide linker) is introduced between an azide group and a carbonyl group in Compound 2.

(Compound 3)

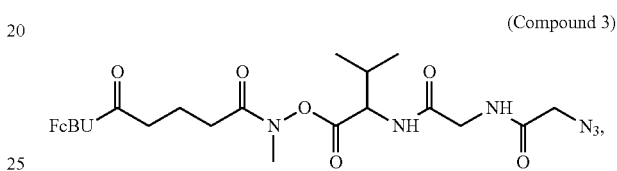

wherein FcBU is PEG8-DCAWHOrn'GELVWCT-NH₂, and Orn' is conjugated ornithine. The structure of PEG8-DCAWHOrn'GELVWCT-NH₂ (FcBU) is illustrated as follows:

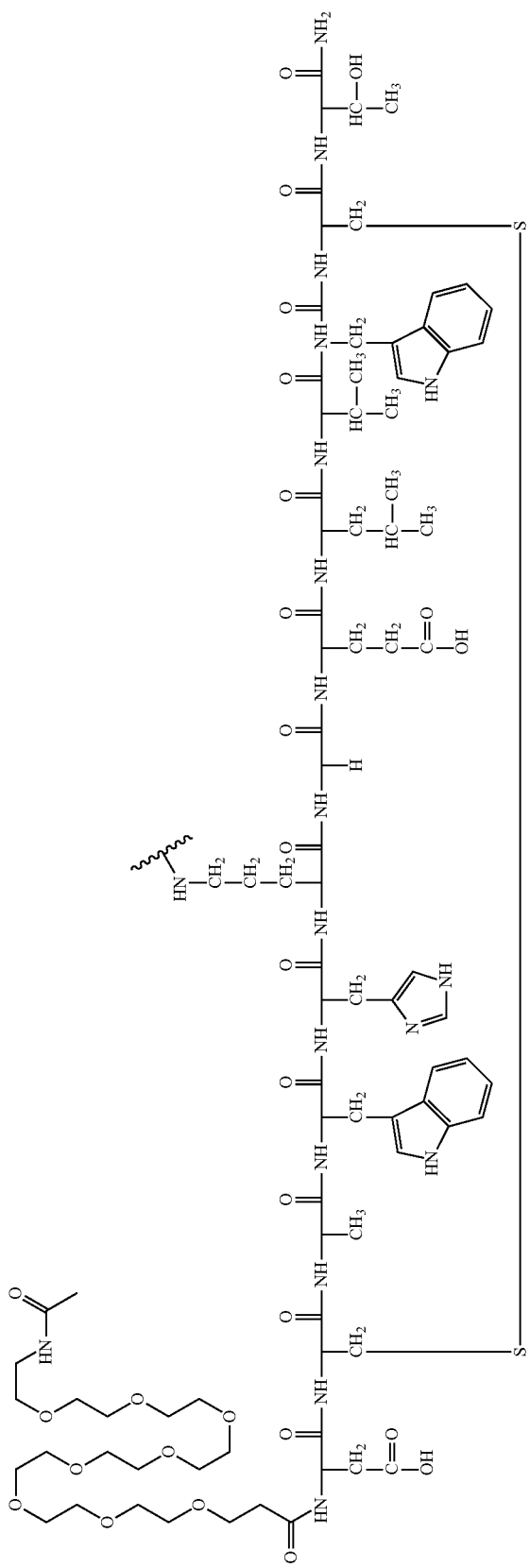

Furthermore, all FcBUs of the following compounds (Compounds 4 to 12 and Compound 14) are FcBU represented by PEG8-DCAWHOrn'GELVWCT-NH$_2$.

The preparation process of Compound 3 will be described through the following reaction processes.

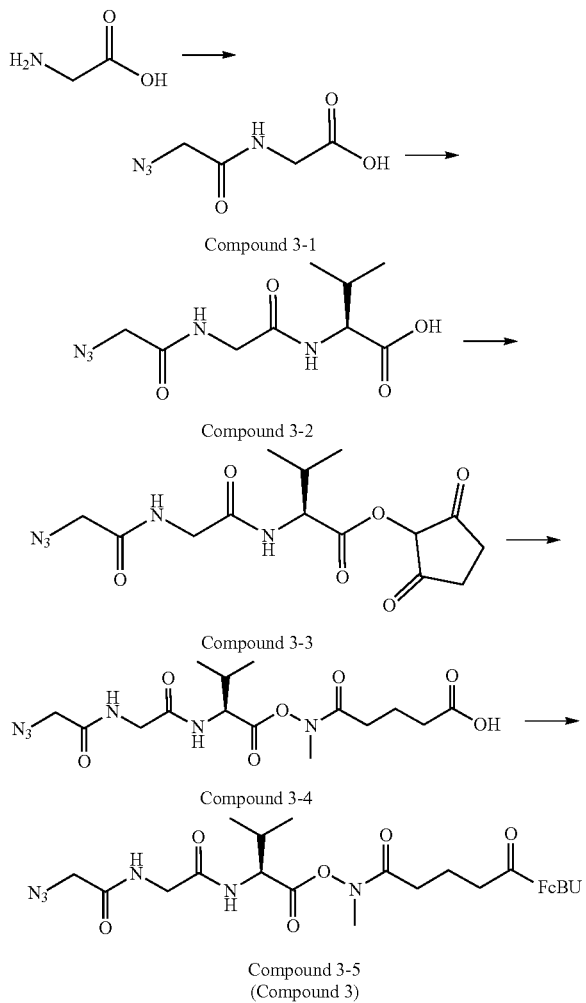

The following process was performed to obtain Compound 3-1. TEA and 2-azidoacetyl chloride were added to a solution of glycine in tetrahydrofuran (THF). The reaction mixture was stirred at room temperature for 2 hours. The solvent was removed under reduced pressure, and the resulting residue was washed with 10% citric acid. The desired product was extracted with ethyl acetate (50*3). The collected solvent was removed under reduced pressure, and the product was purified by MPLC (DCM:MeOH=10:1).

The following process was performed to obtain Compound 3-2. Tert-butyl-L-valine, HATU, and DIPEA were added to a solution of Compound 3-1 in DMF. The reaction mixture was stirred at room temperature under an N2 atmosphere for 2 hours. The solvent was removed under reduced pressure, and the resulting residue was washed with 10% citric acid. A product was extracted with ethyl acetate (50*3). The collected organic solvent was evaporated under reduced pressure. A crude product was dissolved in DCM, and TFA was slowly added thereto. After 1 hour, the solvent was removed under reduced pressure, and the product was purified by MPLC (DCM:MeOH=15:1).

The following process was performed to obtain Compound 3-3. TEA and N,N,N',N'-tetramethyl-O—(N-succinimidyl)uronium tetrafluoroborate (TSTU) were each added to a solution of Compound 3-2 in DCM. The reaction mixture was stirred at room temperature under an N$_2$ atmosphere for 3 hours. The solvent was removed under reduced pressure, and the resulting residue was purified by MPLC (HEX:EA=1:3).

The following process was performed to obtain Compound 3-4. TEA and 5-(hydroxy(methyl)amino)-5-oxopentanoic acid were each added to a solution of Compound 3-3 in DCM. The reaction mixture was stirred at room temperature under N2 atmosphere for 3 hours. The solvent was removed under reduced pressure, and the resulting residue was purified by MPLC (HEX:EA=1:2).

The following process was performed to obtain Compound 3-5 (Compound 3). 4-(4,6-dimethoxy-1,3,5-triazin-2-yl)-4-methyl-morpholinium chloride (DMTMM), DIPEA, and FcBP (Orn) were added to a solution of Compound 3-4 in DCM. Here, FcBP (Orn) is PEG8-DCAWHOrn-GELVWCT-NH$_2$, and the same also applies below. The reaction mixture was stirred at room temperature under an N2 atmosphere for 2 hours. The solvent was removed under reduced pressure, and the resulting residue was purified by prep-HPLC.

Thereafter, the obtained Compound 3 was analyzed through mass spectrometry and HPLC, and the results are as follows:

LC/MS analysis results: [M/2+H]=1190.3 (Exact Mass: 2377.0719)

HPLC analysis results: 13.759 min, purity 99.1%.

Preparation of Compound 4

The inventors of the present application prepared a compound (Compound 4) in which a peptide linker (Gly-Ala peptide linker) was introduced between an azide group and a carbonyl group in Compound 2.

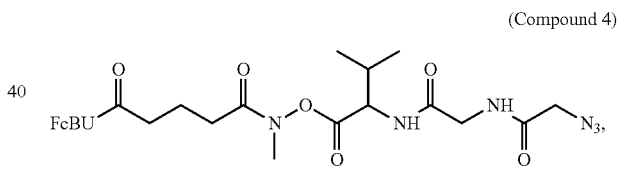

(Compound 4)

wherein FcBU is PEG8-DCAWHOrn'GELVWCT-NH$_2$, and Orn' is conjugated ornithine.

The preparation process of Compound 4 will be described through the following reaction processes.

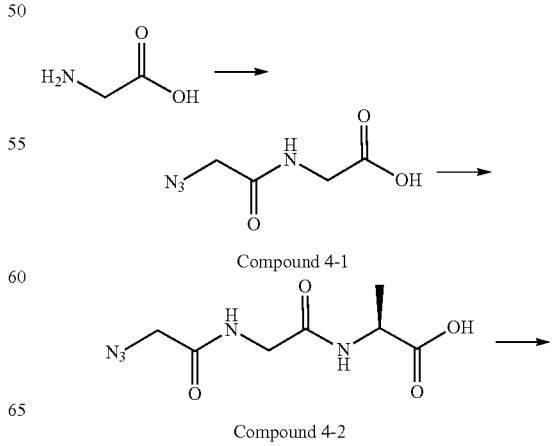

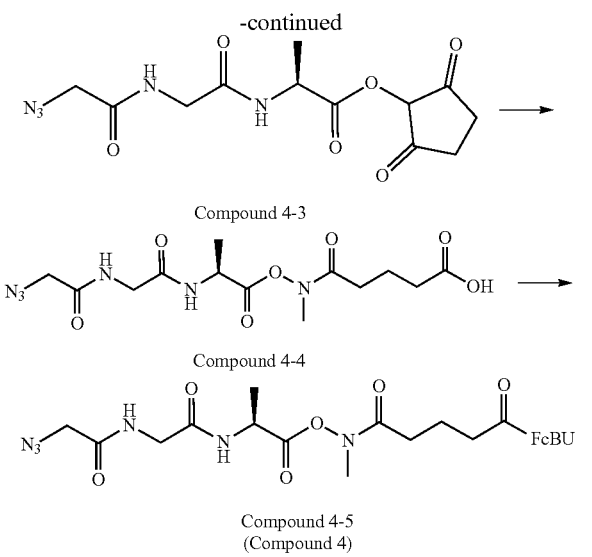

Compound 4-3

Compound 4-4

Compound 4-5
(Compound 4)

The following process was performed to obtain Compound 4-1. TEA and 2-azidoacetyl chloride were added to a solution of glycine in THF. The reaction mixture was stirred at room temperature for 2 hours. The solvent was removed under reduced pressure, and the resulting residue was washed with 10% citric acid. The desired product was extracted, and extracted with ethyl acetate (50*3). The collected solvent was removed under reduced pressure, and the product was purified by MPLC (DCM:MeOH=10:1).

The following process was performed to obtain Compound 4-2. Tert-butyl-L-alanine, HATU, and DIPEA were added to a solution of Compound 4-1 in DMF. The reaction mixture was stirred at room temperature under an $N_2$ atmosphere for 2 hours. The solvent was removed under reduced pressure, and the resulting residue was washed with 10% citric acid. A product was extracted with ethyl acetate (50*3). The collected solvent was evaporated under reduced pressure. A crude product was dissolved in DCM, and TFA was slowly added thereto. After 1 hour, the solvent was removed under reduced pressure, and the product was purified by MPLC (DCM:MeOH=15:1).

The following process was performed to obtain Compound 4-3. TEA and TSTU were each added to a solution of Compound 4-2 in DCM. The reaction mixture was stirred at room temperature under an N2 atmosphere for 3 hours. The solvent was removed under reduced pressure, and the resulting residue was purified by MPLC (HEX:EA=1:2).

The following process was performed to obtain Compound 4-4. TEA and 5-(hydroxy(methyl)amino)-5-oxopentanoic acid were each added to a solution of Compound 4-3 in DCM. The reaction mixture was stirred at room temperature under $N_2$ atmosphere for 3 hours. The solvent was removed under reduced pressure, and the resulting residue was purified by MPLC (HEX:EA=1:2).

The following process was performed to obtain Compound 4-5 (Compound 4). DMTMM, DIPEA, and FcBP (Orn) were each added to a solution of Compound 4-4 in DMF. The solvent was removed under reduced pressure, and the resulting residue was purified by prep-HPLC.

Thereafter, the obtained Compound 4 was analyzed through mass spectrometry and HPLC, and the results are as follows:

LC/MS analysis results: [M/2+H]=1176.20 (Exact Mass: 2350.6060)

HPLC analysis results: 13.114 min, purity 99.9%.

Preparation of Compounds 5 to 8

The inventors of the present application prepared Compound 5 (C1), Compound 6 (C2), Compound 7 (C3), and Compound 8 (C4).

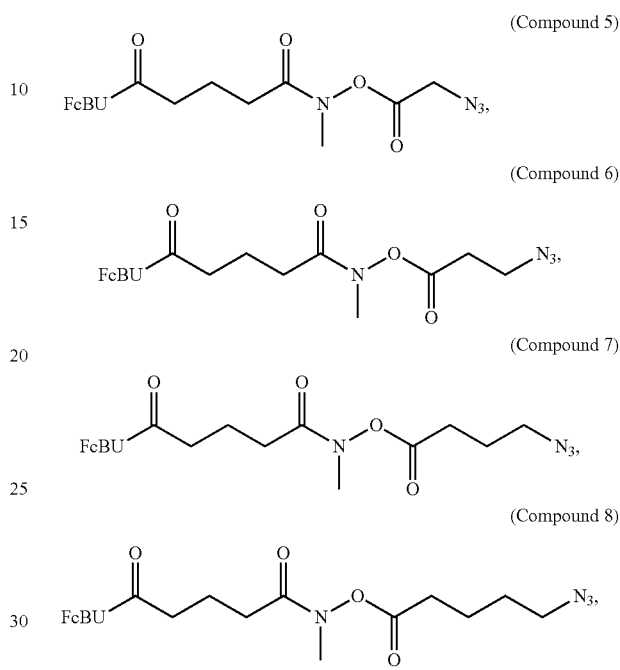

(Compound 5)

(Compound 6)

(Compound 7)

(Compound 8)

wherein FcBU is PEG8-DCAWHOrn'GELVWCT-NH$_2$, and Orn' is conjugated ornithine.

The preparation process of Compound 8 will be described with reference to the following reaction processes.

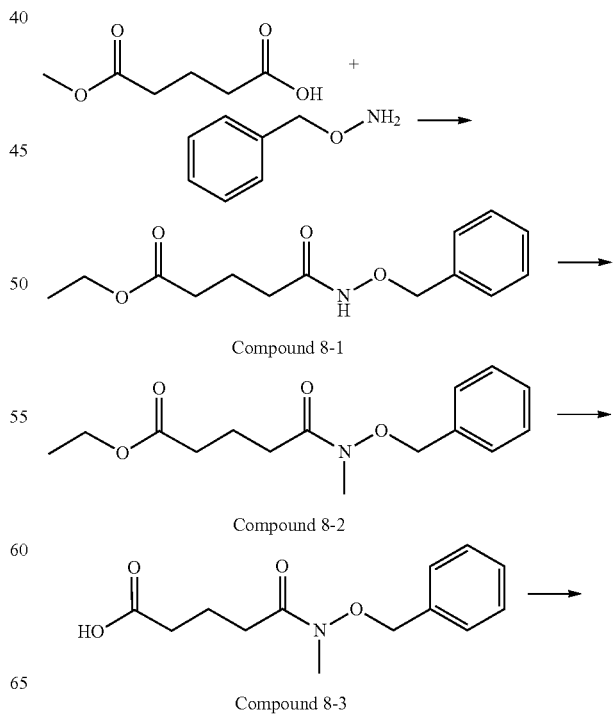

Compound 8-1

Compound 8-2

Compound 8-3

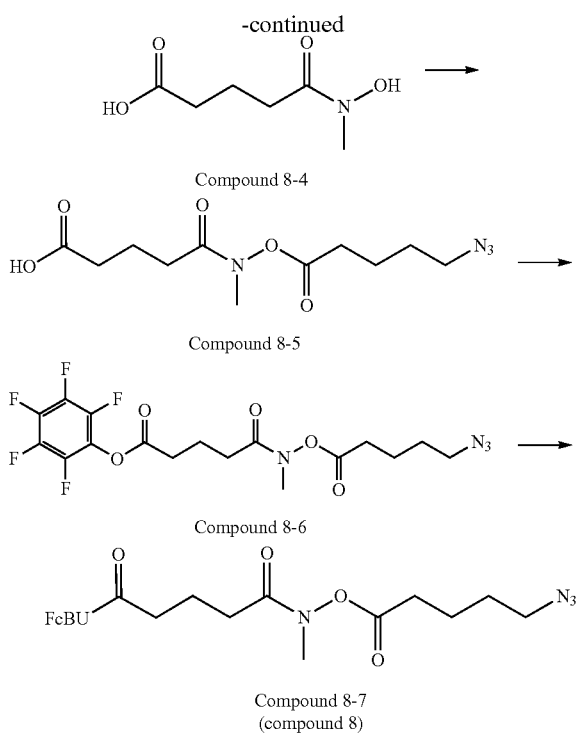

Compound 8-4

Compound 8-5

Compound 8-6

Compound 8-7
(compound 8)

1 g (6.2434 mmol, 1 eq) of ethyl hydrogen glutarate was put into a reaction vessel, DCM was added thereto, and the resulting mixture was stirred. Next, 1.1963 mL (6.8677 mmol, 1.1 eq) of DIPEA and 3.5609 g (9.3650 mmol, 1.5 eq) of HATU were sequentially added thereto. Thereafter, 0.8074 g (6.5555 mmol, 1.05 eq) of O-benzylhydroxylamine was added thereto, and a reaction was carried out at room temperature overnight. After the reaction, the solution was filtered and then the pressure was reduced to obtain Compound 8-1.

After assuming that the reaction to obtain Compound 8-1 had been performed 100%, 1.6564 g (6.2434 mmol, 1 eq) of the obtained Compound 8-1 was put into a reaction vessel, DMF was added thereto, and the resulting mixture was stirred. Thereafter, 1.8982 g (13.7352 mmol, 2.2 eq) of $K_2CO_3$ and 1.5547 mL (24.9731 mmol, 4 eq) of iodomethane were sequentially added thereto, and the resulting mixture was reacted at room temperature for 3 hours. After the reaction, ethyl acetate (EA) and water were each added to the mixture in an amount three-fold the volume of DMF and mixed, and then the EA phase was separated. The separated EA phase was depressurized to obtain Compound 8-2.

After assuming that the reaction to obtain Compound 8-2 had been performed 100%, 1.7440 g (6.2433 mmol, 1 eq) of the obtained Compound 8-2 was put into a reaction vessel, EtOH was added thereto, and the resulting mixture was stirred. Thereafter, 0.2243 g (9.3649 mmol, 1.5 eq) of LiGH and a small amount of water were added thereto, and the resulting mixture was reacted at room temperature for 3 hours. After the reaction, the mixture was depressurized and then subjected to acidic workup to separate the EA phase. The separated EA phase was depressurized and purified by prep-HPLC to obtain Compound 8-3.

500 mg (0.3980 mmol, 1 eq) of Compound 8-3 was put into a reaction vessel, EtOH was added thereto, and the resulting mixture was stirred. Thereafter, 25 mg (5% w/w) of Pd/C was added thereto, and then the resulting mixture was purged with hydrogen and allowed to react at room temperature for 3 hours. After the reaction, the mixture was filtered and depressurized to obtain Compound 8-4.

100 mg (0.6986 mmol, 1 eq) of 5-aziopentanoic acid was put into a reaction vessel, DCM was added thereto, and the resulting mixture was stirred. The reaction vessel was transferred to an ice bath, and then purged with nitrogen, and 0.089 mL (1.0479 mmol, 1.5 eq) of oxalyl chloride and a small amount of DMF were added thereto, and the resulting mixture was reacted at low temperature for 2 hours. After the reaction, the mixture was depressurized to obtain Compound 8-5'. 0.1464 g (0.9081 mmol, 1.3 eq) of Compound 8-4 was put into a reaction vessel, DCM was added thereto, and the resulting mixture was stirred. After the stirred solution was transferred to an ice bath, 0.1899 mL (1.3622 mmol, 1.95 eq) of TEA and Compound 8-5' were sequentially added thereto, and the resulting mixture was reacted for 2 hours. After the reaction, the pressure was reduced to obtain Compound 8-5.

After assuming that the reaction to obtain Compound 8-5 had been performed 100%, 200 mg (0.6986 mmol, 1 eq) of the obtained Compound 8-5 was put into a reaction vessel, DCM was added thereto, and the resulting mixture was stirred. 0.107 mL (0.7685 mmol, 1.1 eq) of TEA and 413 mg (1.0479 mmol, 1.5 eq) of bis(pentafluorophenyl)carbonate were sequentially added to the stirred solution, and the resulting mixture was reacted at room temperature for 2 hours. After the reaction, the solution was depressurized and purified by prep-HPLC to obtain Compound 8-6.

286.2 mg (0.1434 mmol, 1.3 eq) of FcBP (Orn) was put into a reaction vessel, DCM was added thereto, and the resulting mixture was stirred. Here, FcBP (Orn) is PEG8-DCAWHOrnGELVWCT-NH$_2$. 0.026 mL (0.1864 mmol, 1.69 eq) of TEA and 50 mg (0.1103 mmol, 1 eq) of Compound 8-6 were sequentially added to the stirred solution, and the resulting mixture was reacted for 2 hours. After the reaction, the reaction solution was purified by prep-HPLC to obtain Compound 8-7 (Compound 8).

Compounds 5 to 7 were prepared in a similar manner to Compound 8. Specifically, 1 mmol (0.143 g, 1 eq) of 5-azidopentanoic acid was used in order to introduce an azide group in the preparation process of Compound 8, but azido acetic acid (1 mmol, 0.101 g) was used instead of 5-azidopentanoic acid in the preparation of Compound 5, 3-azido propionic acid (1 mmol, 0.115 g) was used instead of 5-azidopentanoic acid in the preparation of Compound 6, and 4-azido butyric acid (1 mmol, 0.13 g) was used instead of 5-azidopentanoic acid in the preparation of Compound 7. The other processes are the same as for the preparation of Compound 8.

Thereafter, the obtained Compounds 5 to 8 were analyzed through mass spectrometry and HPLC, and the results are as follows:

[Compound 5]
LC/MS analysis results: $[M/2+H]^+=1112.36$ (Exact Mass: 2222.48)
HPLC analysis results: 12.94 min, purity 39.21%

[Compound 6]
LC/MS analysis results: $[M/2+H]^+=1119.28$ (Exact Mass: 2236.50)
HPLC analysis results: 13.97 min, purity 93.03%

[Compound 7]
LC/MS analysis results: $[M/2+H]^+=1126.28$ (Exact Mass: 2250.53)
HPLC analysis results: 13.47 min, purity 94.36%

[Compound 8]
LC/MS analysis results: $[M/3+H]=755.73$; $[M/2+H]=1133.25$ (Exact Mass: 2264.56)

HPLC analysis results: 14.068 min, Purity 97.76%

Preparation of Compound 9

The inventors of the present application prepared Compound 9.

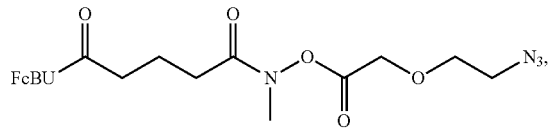

(Compound 9)

wherein FcBU is PEG8-DCAWHOrn'GELVWCT-NH₂ derived from FcBP (Orn), and Orn' is conjugated ornithine.

The preparation process of Compound 9 will be described with reference to the following reaction processes.

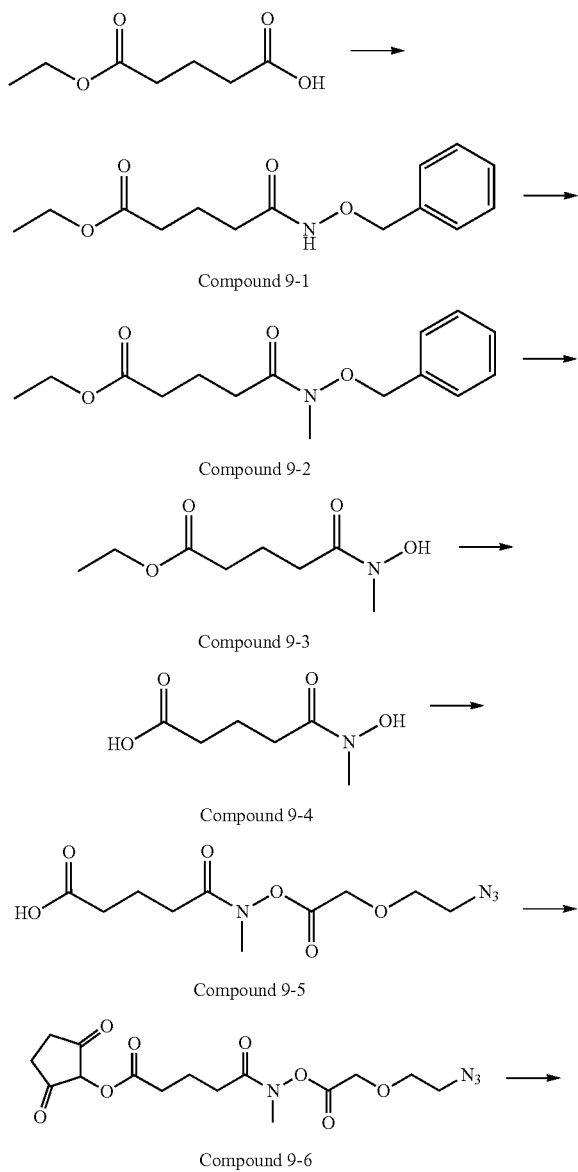

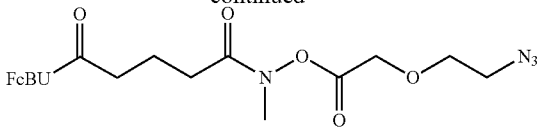

Compound 9-7
(compound 9)

After 5-ethoxy-5-oxopentanoic acid (10 g, 68.4 mmol) was dissolved in 240 mL of dichloromethane and 9.6 mL of N,N-dimethylformamide, O-benzylhydroxylamine (6.5 g, 52.7 mmol), HATU (23.7 g, 62.3 mmol), and DIPEA (17.6 mL, 100.6 mmol) were added thereto, and the resulting mixture was stirred at room temperature for 18 hours. Ethyl acetate (EtOAC) and distilled water were added to extract the organic layer. The collected organic layer was dried over anhydrous magnesium sulfate. After filtration, the resulting product was concentrated and purified by column chromatography to obtain Compound 9-1 (11.4 g, 95%).

After Compound 9-1 (5.4 g, 21.5 mmol) was dissolved in 180 mL of N,N-dimethylformamide, potassium carbonate ($K_2CO_3$, 6.5 g, 47.3 mmol) and iodomethane (5.4 mL, 86.0 mmol) were added thereto, and the resulting mixture was stirred at room temperature for 3 hours. Ethyl acetate and distilled water were added to extract the organic layer. The collected organic layer was dried over anhydrous magnesium sulfate ($MgSO_4$). After filtration, the resulting product was concentrated and purified by column chromatography to obtain Compound 9-2 (5.0 g, 87.7%).

After Compound 9-2 (1 g, 3.7 mmol) was dissolved in 24 mL of tetrahydrofuran, lithium hydroxide (LiOH, 0.23 g in 8 mL of water) was added thereto, and the resulting mixture was reacted at room temperature for 3 hours. Water and ethyl acetate were added thereto, and the water was extracted. The aqueous layer was acidified to pH 3 using 4 N HCl. Ethyl acetate was added to extract the organic layer. The collected organic layer was dried over magnesium sulfate ($MgSO_4$). After filtration, the resulting product was concentrated and purified by column chromatography to obtain Compound 9-3 (0.7 g, 74.7%).

After Compound 9-3 (0.85 g, 3.4 mmol) was dissolved in 13 mL methanol, Pd/C (0.05 g) was added thereto, and the resulting mixture was stirred under a hydrogen atmosphere. The reaction solution was filtered through Celite, and then concentrated under reduced pressure to obtain Compound 9-4 (0.46 g, quantitative yield) without purification.

After Compound 9-4 (1 g, 6.208 mmol) was dissolved in 4 mL of dichloromethane, triethylamine (1.77 mL, 13.0368 mmol) and 2-(2-azidoethoxy)acetyl chloride (1.13 g, 6.828 mmol) were added thereto, and the resulting mixture was stirred at room temperature under a nitrogen gas atmosphere for 3 hours. After concentration, ethyl acetate and a 10% citric acid solution were added to extract the organic layer. After concentration, the resulting product was purified by column chromatography to obtain Compound 9-5 (1.65 mg, 92.2%).

After Compound 9-5 (200 mg, 0.694 mmol) was dissolved in 6.8 mL of dichloromethane, triethylamine (0.1015 mL, 0.728 mmol) and N,N,N',N'-tetramethyl-O—(N-succinimidyl)uronium tetrafluoroborate (TSTU, 229.8 mg, 0.8634 mmol) were added thereto, and the resulting mixture was reacted at room temperature under an argon atmosphere for 3 hours. After concentration, the resulting product was purified by column chromatography to obtain Compound 9-6. (221.8 mg, 83%)

After FcBP (Orn) (200 mg, 0.1002 mmol) was dissolved in 0.5 mL of N,N-dimethylformamide, N,N-diisopropylethylamine (0.07 mL) and Compound 9-6 (40.51 mg) were added thereto, and the resulting mixture was stirred at room temperature under an argon atmosphere for 2 hours. After concentration, the resulting product was purified by reverse phase column chromatography to obtain Compound 9-7 (Compound 9) (226.9 mg, 64.8%).

Thereafter, the obtained Compound 9 was analyzed through mass spectrometry and HPLC, and the results are as follows:

LC/MS analysis results: [M/2+H]=1134.35; [M+H]=2268.37 (Exact mass: 2265.0082)

HPLC analysis results: 13.379 min, purity 98.16% (254 nm)

Preparation of Compounds 10 and 11

The structures of Compounds 10 and 11 are as follows.

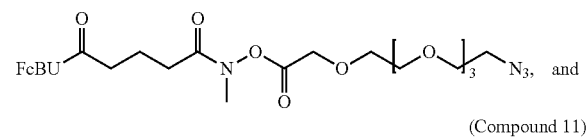
(Compound 10)

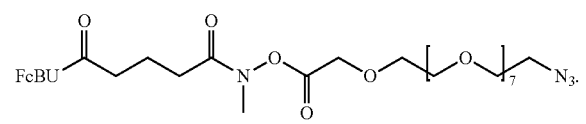
(Compound 11)

At this time, FcBU is PEG8-DCAWHOrn'GELVWCT-NH$_2$, and Orn' is conjugated ornithine.

The preparation process of Compounds 10 and 11 will be described with reference to the following reaction processes.

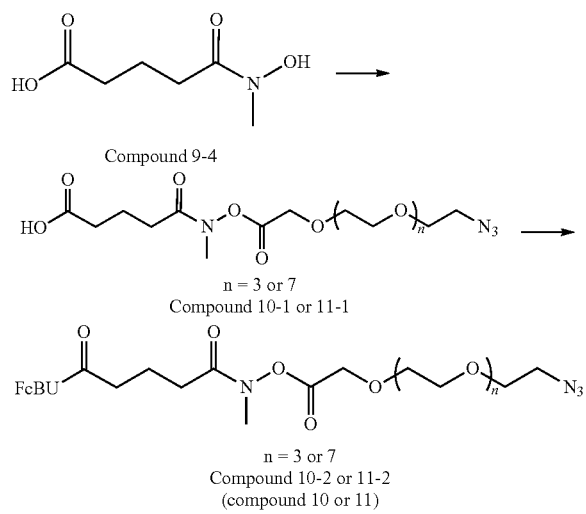

After Compound 9-4 (100 mg, 0.62 mmol) was dissolved in 3 mL of dichloromethane, triethylamine (0.093 μL, 0.68 mmol) and 2,5-dioxopyrrolidin-1-yl 14-azido-3,6,9,12-tetraoxatetradecanoate (0.232 g, 0.62 mmol) were added thereto, and the resulting mixture was stirred at room temperature under a nitrogen gas atmosphere for 3 hours. After concentration, ethyl acetate and a 10% citric acid solution were added to extract the organic layer. After concentration, the resulting product was purified by column chromatography to obtain Compound 10-1 (220 mg, 84.6%).

After Compound 10-1 (10 mg, 0.0237 mmol) was dissolved in 2.3 mL of N,N-dimethylformamide, N,N-diisopropylethylamine (0.0046 mL, 0.026 mmol) and 4-(4,6-dimethoxy-1,3,5-triazin-2-yl)-4-methylmorpholinium chloride (DMTMM, 68.8 mg, 0.2488 mmol) were added thereto, and the resulting mixture was stirred at room temperature under a nitrogen atmosphere for 1 hour. After 10 minutes had passed, FcBP (Orn) (47.4 mg, 0.0237 mmol) was added thereto, and the resulting mixture was stirred at room temperature under a nitrogen atmosphere for 1 hour. After concentration, the resulting product was purified by reverse phase column chromatography to obtain Compound 10-2 (30 mg, 67.3%).

Compound 11 was prepared through a process similar to Compound 10. Specifically, NHS ester-PEG4-N$_3$ (2,5-dioxopyrrolidin-1-yl 14-azido-3,6,9,12-tetraoxatetradecanoate) (0.232 g, 0.62 mmol) was added to a solution of Compound 9-4 in dichloromethane in order to obtain Compound 10-1 in the preparation of Compound 10, but NHS ester-PEG8-N3 (2,5-dioxopyrrolidin-1-yl 26-azido-3,6,9,12,15,18,21,24-octaoxahexacosanoate)(0.24 g, 0.62 mmol) was added to a solution of Compound 9-4 in dichloromethane instead of NHS ester-PEG4-N3 in order to obtain Compound 11-1 in the preparation of Compound 11 (the other processes are the same).

Thereafter, the obtained Compounds 10 and 11 were analyzed through mass spectrometry and HPLC, and the results are as follows:

[Compound 10]
LC/MS analysis results: [M/2+H]=1200.62
HPLC analysis results: 14.186 min, 99.8%

[Compound 11]
LC/MS analysis results: [M/2+H]=1288.75
HPLC analysis results: 14.236 min, 99.9%

Preparation of Compound 12

The structure of Compound 12 is as follows.

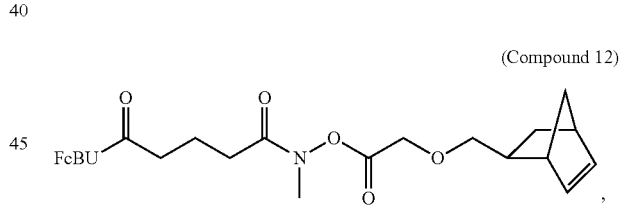
(Compound 12)

wherein FcBU is PEG8-DCAWHOrn'GELVWCT-NH$_2$, and Orn' is conjugated ornithine.

The preparation process of Compound 12 will be described with reference to the following reaction processes.

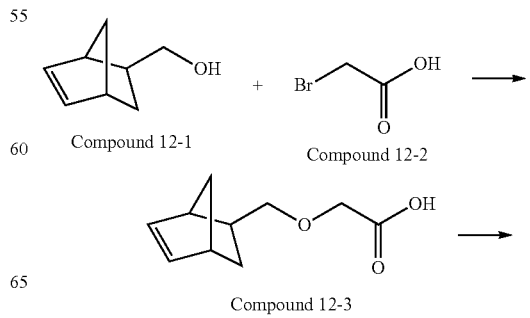

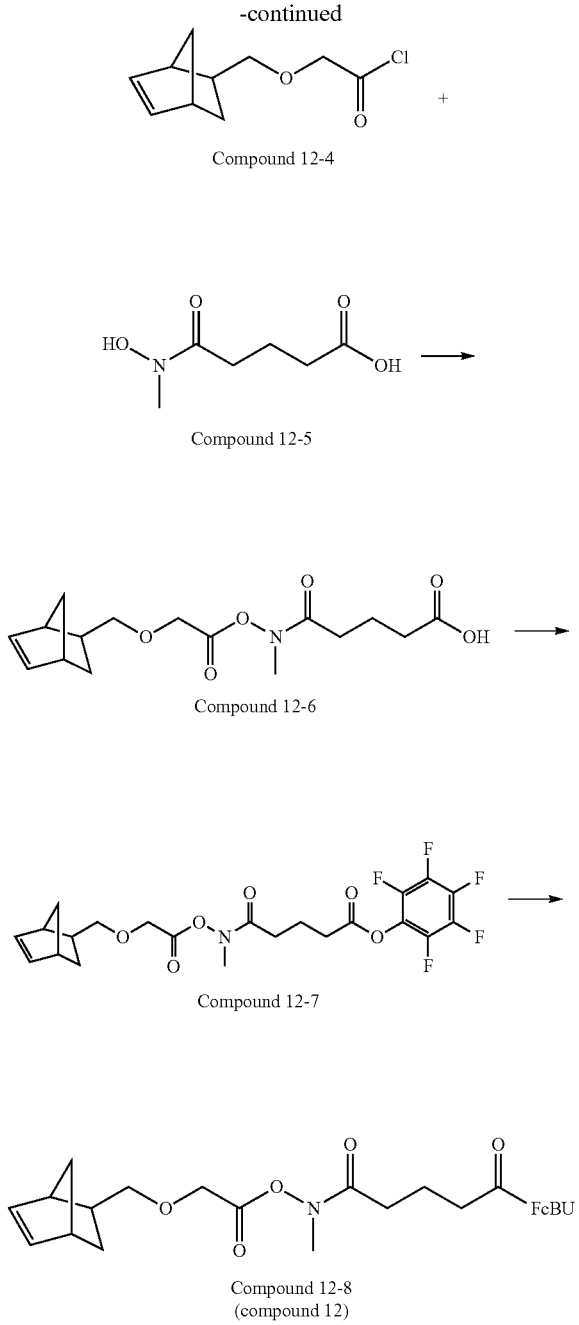

Compound 12-4

Compound 12-5

Compound 12-6

Compound 12-7

Compound 12-8
(compound 12)

After NaH (110 mg, 4.6 mmol) was washed twice with hexane, THF (5 ml) was slowly added thereto and dissolved, Compound 12-1 (150 mg, 1.21 mmol) dissolved in THF (2 ml) was slowly added thereto, and the resulting mixture was stirred at room temperature for 1 hour. Compound 12-2 (168 mg, 1.21 mmol) dissolved in THF (2 ml) was slowly added thereto, and the resulting mixture was stirred at room temperature overnight. The solvent was evaporated, and the resulting residue was acidified using an aqueous hydrochloric acid solution. Extraction was performed with dimethyl ether, and the extract was washed with water and brine.

Thereafter, the washed extract was purified by silica under the conditions of DCM:MeOH=9:1 to obtain Compound 12-3 (110 mg, 50%).

Compound 12-3 (40 mmg, 0.22 mmol) was dissolved in DCM (2 ml). Thereafter, thionyl chloride (0.024 ml, 0.33 mmol) was added thereto, and the resulting mixture was stirred at room temperature for 2 hours. Thereafter, the solvent was evaporated and Compound 12-4 in the form of a mixture was obtained.

Compound 12-4 in the form of a mixture was dissolved in DCM (2 ml). Thereafter, Compound 12-5 (35 mg, 0.22 mmol) and TEA (0.061 ml, 0.44 mmol) were added thereto, and the resulting mixture was stirred at room temperature for 2 hours. The organic layer was washed with water and brine, and purified by silica under the conditions of DCM: MeOH=9:1 to obtain Compound 12-6 (45 mg, 62%).

Compound 12-6 (10 mg, 0.03 mmol) was dissolved in DCM (0.2 ml). Bis(pentafluorophenyl) carbonate (12 mg, 0.03 mmol) and DIPEA (0.005 ml, 0.03 mmol) were added thereto, and the resulting mixture was stirred at room temperature for 2 hours. The organic layer was washed with water and brine, and purified by silica under the conditions of hexane:ethyl acetate=1:1 to obtain Compound 12-7 (12 mg, 81%).

Compound 12-7 (12 mg, 0.024 mmol) was dissolved in DMF (0.2 ml). FcBP (Orn) (49 mg, 0.024 mmol) and DIPEA (0.006 ml, 0.036 mmol) were added thereto, and the resulting mixture was stirred at room temperature for 2 hours. After reverse-phase purification using Prep-HPLC, the resulting product was lyophilized to obtain Compound 12-8 (Compound 12) (22 mg, 40%).

Thereafter, the obtained Compound 12 was analyzed through mass spectrometry and HPLC, and the results are as follows:

LC/MS analysis results: $[M/2+H]^+=1152.99$
HPLC analysis results: 15.194 min, purity 99.9%
Preparation of Compound 13 (Payload 1)
Preparation of Compound 13-1

40 mL of dichloromethane was added to a 2-chlorotrityl chloride resin (1.4 mmol/g, 1 g) (1 eq), and the resulting mixture was stirred for 30 minutes or more. Thereafter, the solution was removed, ethylene-di-amine (5.6 mmol, 4 eq) and diisopropylethylamine (N,N'-diisopropylethylamine) (5.6 mmol, 4 eq) were mixed with dichloromethane, and the resulting mixture was mixed with the resin. After the mixture was stirred at room temperature for 2 hours or more, the reaction solution was removed. Compound 13-1 was prepared by washing the resin at least three times with sufficient amounts of dichloromethane and dimethylformamide, respectively, in order to remove the residual reaction solution.

(Compound 13-1)

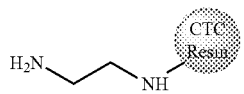

Preparation of Compound 13-2

N-alpha-fluorenylmethoxycarbonyl-N-epsilon-allyl-oxy-carbonyl-L-lysine (Fmoc-Lys(alloc)-OH) (2.8 mmol, 2 eq), N,N'-diisopropylcarbodiimide (2.8 mmol, 2 eq), hydroxybenzotriazole (5.6 mmol, 4 eq), and dimethylformamide were sufficiently mixed, and the resulting mixture was added to the resin. After the resulting mixture was stirred at room temperature for 2 hours or more, the reaction solution was removed. Compound 13-2 was prepared by washing the resin at least three times with sufficient amounts of dichloromethane and dimethylformamide, respectively, in order to remove the residual reaction solution. The preparation of Compound 13-2 was confirmed by the Kaiser test.

(Compound 13-2)

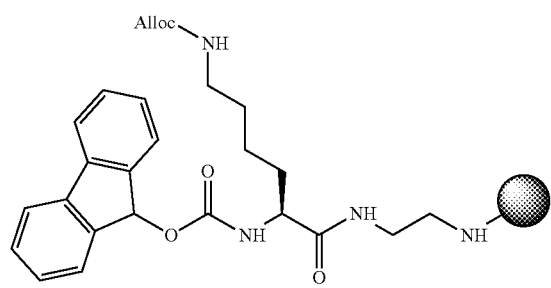

Preparation of Compound 13-3

A 20% piperidine solution dissolved in dimethylformamide was prepared and stirred at room temperature for 10 minutes, and then the reaction solution was removed. The above process was performed a total of two times. Compound 13-3 was prepared by washing the resin at least three times with sufficient amounts of dichloromethane and dimethylformamide, respectively, in order to remove the residual reaction solution.

(Compound 13-3)

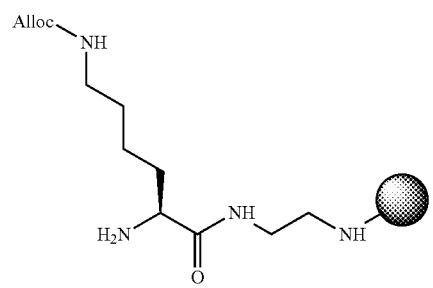

Preparation of Compound 13-4

Mono-tert-butyl succinate (2.8 mmol, 2 eq), N,N'-diisopropylcarbodiimide (2.8 mmol, 2 eq), hydroxybenzotriazole (5.6 mmol, 4 eq), and dimethylformamide were sufficiently mixed, and the resulting mixture was added to the resin. After the resulting mixture was stirred at room temperature for 2 hours or more, the reaction solution was removed. Compound 13-4 was prepared by washing the resin at least three times with sufficient amounts of dichloromethane and dimethylformamide, respectively, in order to remove the residual reaction solution.

(Compound 13-4)

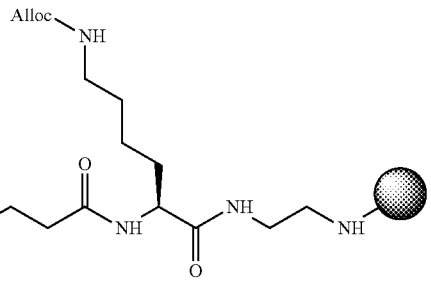

Preparation of Compound 13-5

The remaining resin was washed three times or more with a sufficient amount of dichloromethane. Tetrakis(triphenylphosphine palladium) (0.7 mmol, 0.5 eq), 1,3-dimethylbarbituric acid (14 mmol, 10 eq), and dichloromethane were sufficiently mixed, and the resulting mixture was added to the resin. After the resulting mixture was stirred at room temperature for about 1 hour, the reaction solution was removed. Compound 13-5 was prepared by washing the resin at least three times with sufficient amounts of dichloromethane and dimethylformamide, respectively, in order to remove the residual reaction solution.

(Compound 13-5)

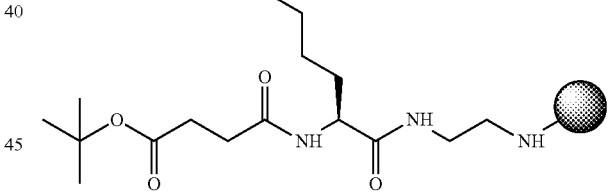

Preparation of Compound 13-6

N-alpha-N-epsilon-bis(9-fluorenylmethyloxycarbonyl)-L-lysine (Fmoc-Lys(fmoc)-OH)(2.8 mmol, 2 eq), N,N'-diisopropylcarbodiimide)(2.8 mmol, 2), hydroxybenzotriazole (5.6 mmol, 4 eq), and dimethylformamide were sufficiently mixed, and the resulting mixture was added to the resin. After the resulting mixture was stirred at room temperature for 2 hours or more, the reaction solution was removed. Compound 13-6 was prepared by washing the resin at least three times with sufficient amounts of dichloromethane and dimethylformamide, respectively, in order to remove the residual reaction solution. The preparation of Compound 13-6 was confirmed by the Kaiser test.

(Compound 13-6)

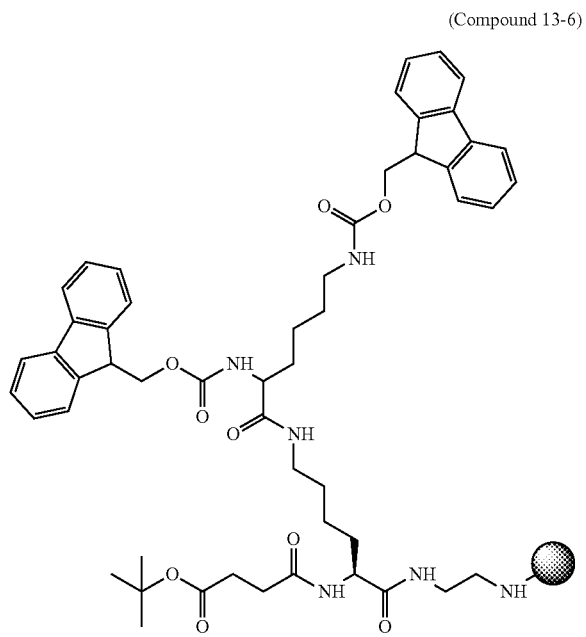 [SMILES: CNCCNC(=O)[C@H](CCCCNC(=O)C(CCCCNC(=O)OCC1c2ccccc2-c2ccccc21)NC(=O)OCC1c2ccccc2-c2ccccc21)NC(=O)CCC(=O)OC(C)(C)C]

(Compound 13-7)

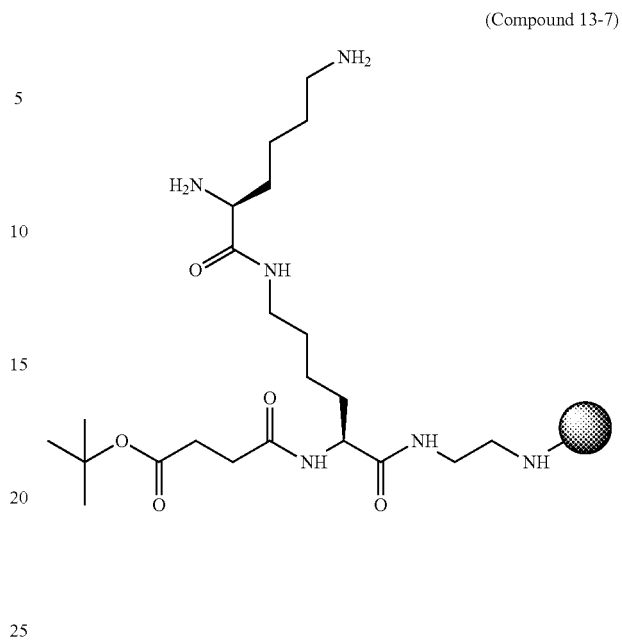

Preparation of Compound 13-7

A 20% piperidine solution dissolved in dimethylformamide was prepared and stirred at room temperature for 10 minutes, and then the reaction solution was removed. The above process was performed a total of two times. Compound 13-7 was prepared by washing the resin at least three times with sufficient amounts of dichloromethane and dimethylformamide, respectively, in order to remove the residual reaction solution.

Preparation of Compound 13-8

2,5,8,11,14,17,20,23-octaoxahexacosan-26-oic-acid (m-PEG8-acid)(2.8 mmol, eq), N,N'-diisopropylcarbodiimide (2.8 mmol, 2 eq), hydroxybenzotriazole (5.6 mmol, 4 eq), and dimethylformamide were sufficiently mixed, and the resulting mixture was added to the resin. After the resulting mixture was stirred at room temperature for 2 hours or more, the reaction solution was removed. Compound 13-8 was prepared by washing the resin at least three times with sufficient amounts of dichloromethane and dimethylformamide, respectively, in order to remove the residual reaction solution.

(Compound 13-8)

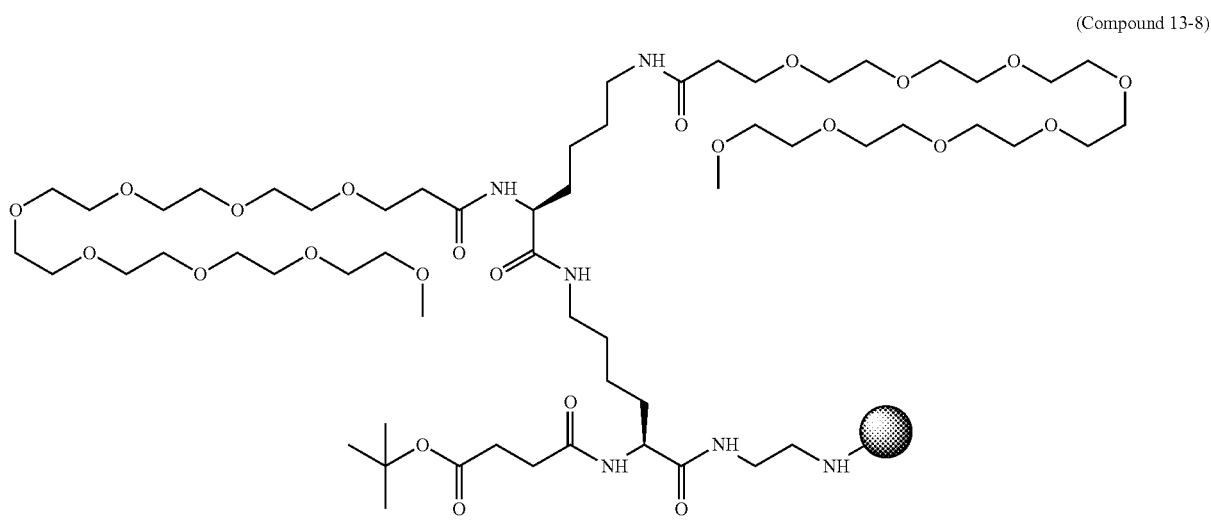 [SMILES: CNCCNC(=O)[C@H](CCCCNC(=O)[C@H](CCCCNC(=O)CCOCCOCCOCCOCCOCCOCCOCCOC)NC(=O)CCOCCOCCOCCOCCOCCOCCOCCOC)NC(=O)CCC(=O)OC(C)(C)C]

Preparation of Compound 13-9

A mixture of trifluoroacetic acid and distilled water was prepared at a ratio of 95:5, a sufficient amount of the mixture was added to the resin, and the resulting mixture was stirred at room temperature for 2 hours. After stirring, the solution and the resin were separated. A sufficient amount of 0° C. diethyl ether was added to the separated solution and mixed, and the resulting mixture was left to stand at 0° C. for 2 hours or more to ensure sufficient precipitation. Compound 13-9 was prepared by centrifugation and drying. The preparation of Compound 13-9 was confirmed by mass and HPLC analysis. ([M/2+H]=603.38; [M+H]=1206.21 (Exact mass: 1204.72))

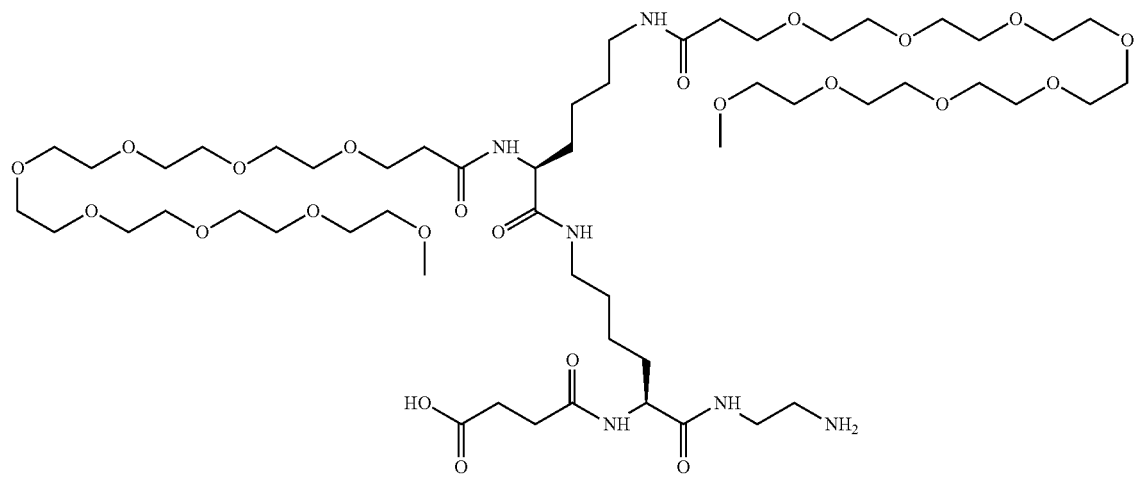

(Compound 13-9)

Preparation of Compound 13-10

After 1 g (0.83 mmol) of the product obtained in the previous process was dissolved in dimethylformamide, DBCO-C6-NHS (0.995 mmol, 1.2 eq) and N,N'-diisopropylethylamine (1.659 mmol, 2 eq) were added thereto, and the resulting mixture was stirred at room temperature for 1 hour or more. After the reaction was completed, the reaction solution was purified by prep-HPLC (C18) and lyophilized to obtain a product (0.394 mmol, 47.5%). The preparation of Compound 13-10 was confirmed by mass and HPLC analysis. ([M/2+H]=761.09 (Exact mass: 1519.84))

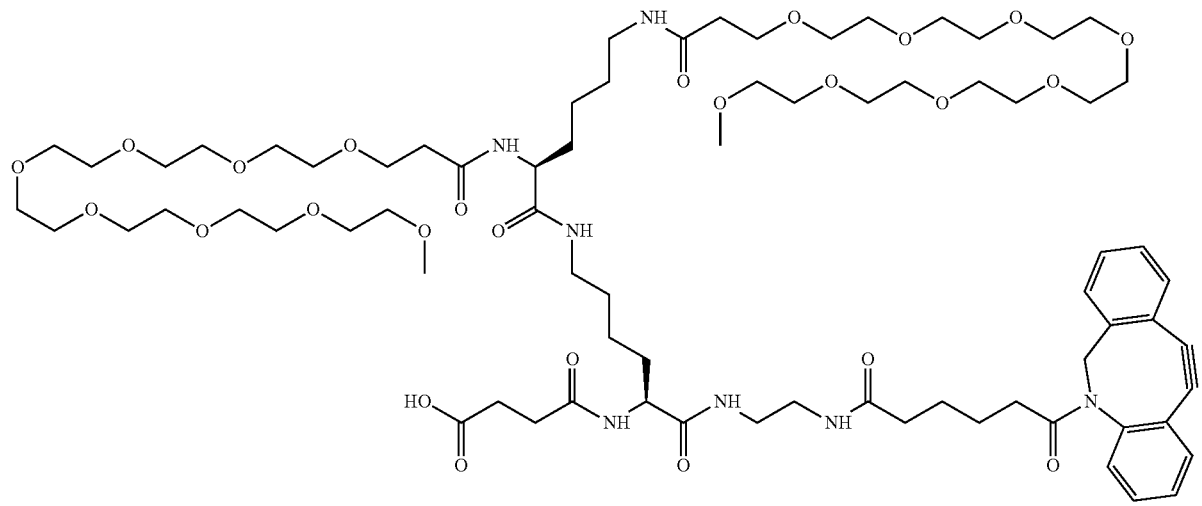

(Compound 13-10)

Preparation of Compound 13-11

After the product (0.394 mmol) obtained in the previous process was dissolved in dimethylformamide, tetramethyl-O—(N-succinimidyl)uronium tetrafluoroborate)(0.788 mmol, 2 eq) and N,N'-diisopropylethylamine (0.788 mmol, 2 eq) were added thereto, and the resulting mixture was stirred at room temperature for 1 hour. After the reaction was completed, the reaction solution was purified by prep-HPLC (C18) and lyophilized to obtain a product (0.138 mmol, 35%). The preparation of Compound 13-11 was confirmed by mass and HPLC analysis. ([M/2+H]=809.67 (Exact mass: 1616.86))

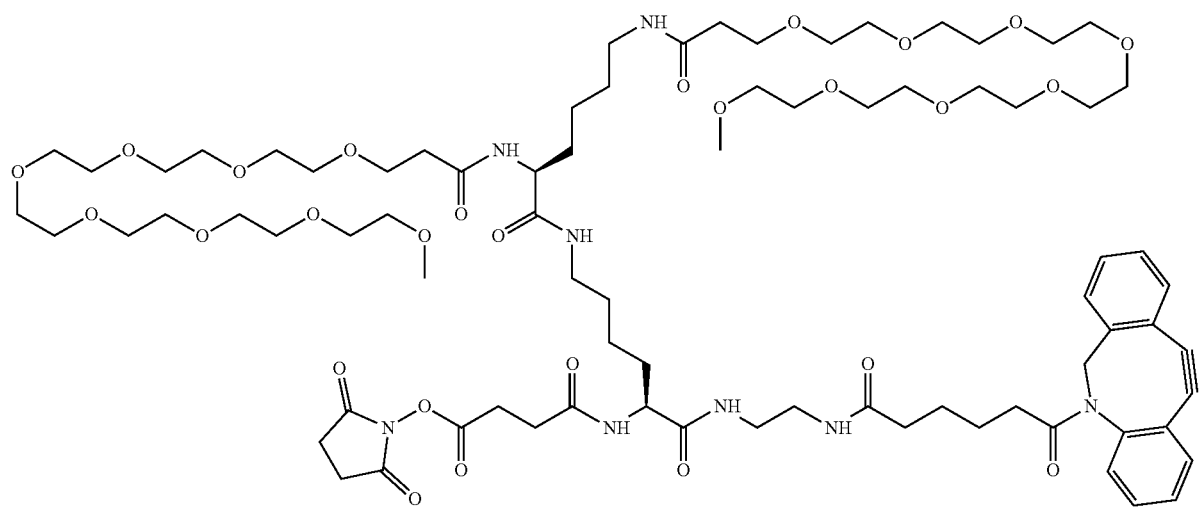

(Compound 13-11)

Preparation of Compound 13-12 (Compound 13, Payload 1)

After the product (0.138 mmol) obtained in the previous process was dissolved in dimethylformamide, H2N-BG-MMAE (0.152 mmol, 1.1 eq) prepared in advance and N,N'-diisopropylethylamine (0.276 mmol, 2 eq) were added thereto, and the resulting mixture was stirred at room temperature for 1 hour. After the reaction was completed, the reaction solution was purified by Prep-HPLC (C18) and lyophilized to obtain a product DBCO-(PEG8)2-BG-MMAE (Compound 13, Payload 1). (0.065 mmol, 47.5%)

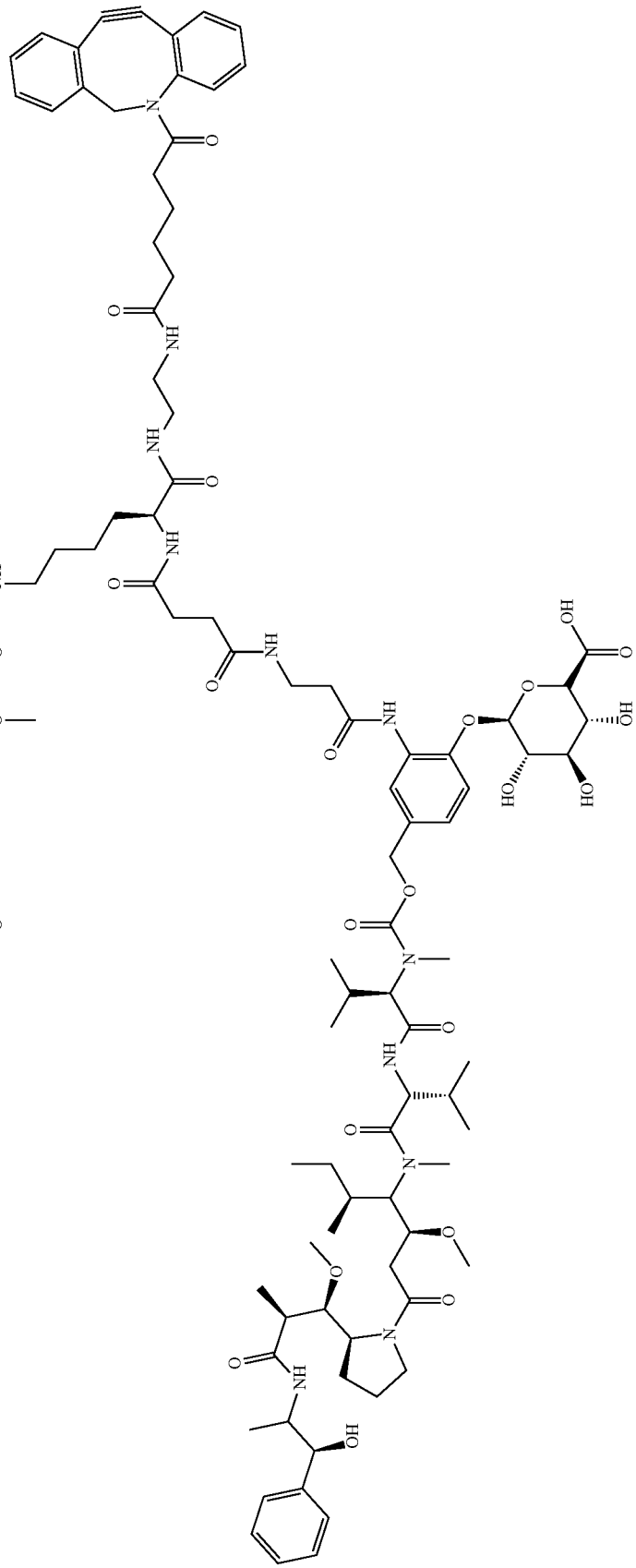
(Compound 13, Payload 1)

Thereafter, the obtained Compound 13 was analyzed through mass spectrometry and HPLC, and the results are as follows:

LC/MS analysis results: [M/2+H]=1318.06; [M+H]=2635.38 (Exact mass: 2631.45)

HPLC analysis results: 16.721 min, purity 100%

The inventors of the present application confirmed the conjugation efficiency of the compound comprising Fc binding unit. The conjugation efficiency may be understood as the efficiency of reaction with an antibody or the efficiency of transfer of a group of interest to an antibody.

The conjugate efficiency was measured as follows:

reacting an antibody with a compound comprising Fc binding unit to prepare an antibody conjugate comprising reactive group; reacting a payload with the antibody conjugate comprising reactive group to prepare an antibody-payload conjugate; and confirming the conjugation yield of the antibody-payload conjugate. In the experiments of the present application, since a payload comprising one drug was used, the antibody-payload conjugate to which one payload is conjugated is referred to as drug to antibody ratio 1 (DAR1), and an antibody-payload conjugate to which two payloads are conjugated is referred to as drug to antibody ratio 2 (DAR2). The yield of the antibody-payload conjugate (or conjugation efficiency of the compound) was calculated based on the area of the peak corresponding to the antibody-payload conjugate from a data derived through HIC-HPLC.

Example 2. Confirmation of Conjugation Efficiency of Conventional Compound 1

The inventors of the present application confirmed the conjugation efficiency of conventional Compound 1.

Compound 1 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 3 hours using a tube rotator. After stirring, an unreacted linker was removed using a Zeba spin desalting column. Tetrazine-PEG8-DM1 (Payload 2) (1 mM 27.4 µL) used in the example of the document [Korean Patent Application No. 10-2020-0091826 (Application No. 10-2020-0009162)] in the related art was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 14:
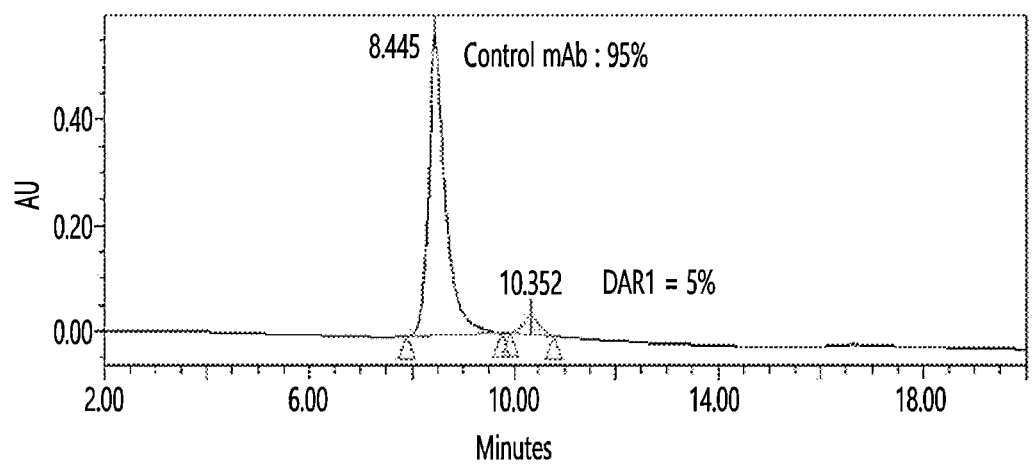
FIG. 14 shows the results of confirming the conjugation efficiency of Compound 1.

The conjugation efficiency confirmation results of Compound 1 are disclosed in FIG. 14. As disclosed in FIG. 14, as a result of reacting the antibody with conventional Compound 1 for 3 hours, it was confirmed that 5% of a DAR1 antibody-payload conjugate was prepared. Thus, it was confirmed that conventional Compound 1 had a very low conjugation efficiency. As described above, since conventional Compound 1 has a very low conjugation efficiency, it is determined that it is difficult to use conventional Compound 1 for transferring a group of interest to an antibody, and furthermore, it is determined that conventional Compound 1 is not suitable for preparing an antibody-payload conjugate.

Example 3. Confirmation of Conjugation Efficiency of Compound 3

The inventors of the present application confirmed the conjugation efficiency of Compound 3.

Compound 3 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 48 hours using a tube rotator. After 48 hours, unreacted linkers were removed using a Zeba spin desalting column. DBCO-(PEG8)2-BG-MMAE (Compound 13, Payload 1) (1 mM 27.4 µL) was added to the antibody-linker intermediate (antibody conjugate comprising reactive group), and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 15:
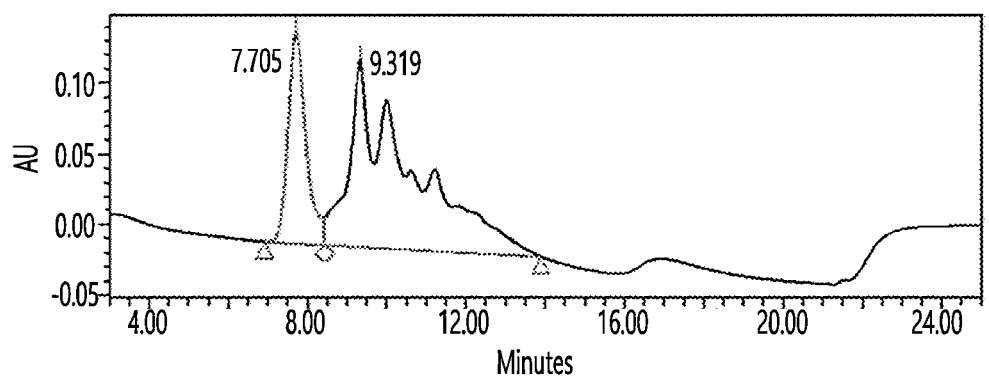
FIG. 15 shows the results of confirming the conjugation efficiency of Compound 3.

The conjugation efficiency confirmation results of Compound 3 are disclosed in FIG. 15. As illustrated in FIG. 15, when an antibody conjugate comprising reactive group and an antibody-payload conjugate are prepared using Compound 3, it appears that a desired antibody-payload conjugate was not prepared, which is presumed to be due to an irregular reaction of Compound 3 and the antibody.

Example 4. Confirmation of Conjugation Efficiency of Compound 4

The inventors of the present application confirmed the conjugation efficiency of Compound 4.

Compound 4 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 48 hours using a tube rotator. After 48 hours, unreacted linkers were removed using a Zeba spin desalting column. DBCO-(PEG8)2-BG-MMAE (Payload 1) (1 mM 27.4 µL) was added to an antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 16:
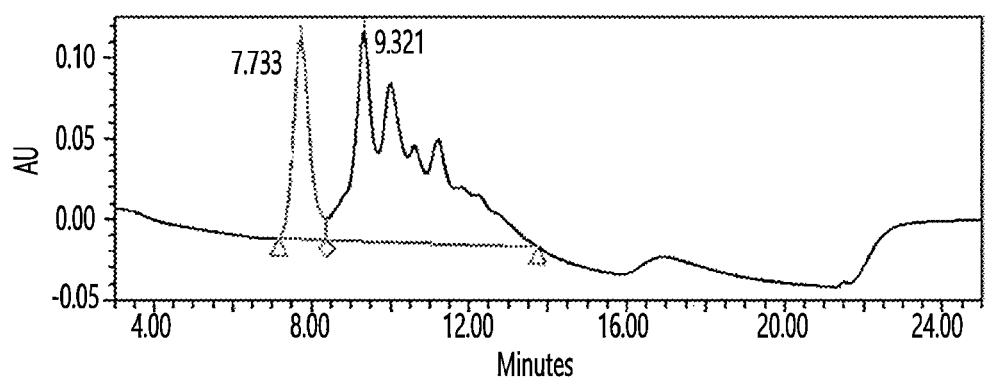
FIG. 16 shows the results of confirming the conjugation efficiency of Compound 4.

The conjugation efficiency confirmation results of Compound 4 are disclosed in FIG. 16. As illustrated in FIG. 16, when an antibody conjugate comprising reactive group and an antibody-payload conjugate are prepared using Compound 4, it appears that a desired antibody-payload conjugate was not prepared, which is presumed to be due to an irregular reaction of Compound 4 and the antibody.

As described above, in order to improve the conjugation efficiency of conventional Compound 1, the inventors of the present application prepared a compound comprising Fc binding unit, in which a peptide linker was introduced between the group of interest (herein, azide) and a reaction site with the antibody. However, as shown in the results, it is determined that Compounds 3 and 4 are not suitable for the preparation of the antibody-payload conjugate.

Example 5. Confirmation of Conjugation Efficiency of Compound 5

The inventors of the present application confirmed the conjugation efficiency of Compound 5.

Compound 5 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 30 minutes, 1 hour, and 3 hours using a tube rotator. After stirring, unreacted linkers were removed using a Zeba spin desalting column. DBCO-(PEG8)2-BG-MMAE (Payload 1) (1 mM 27.4 µL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 17:
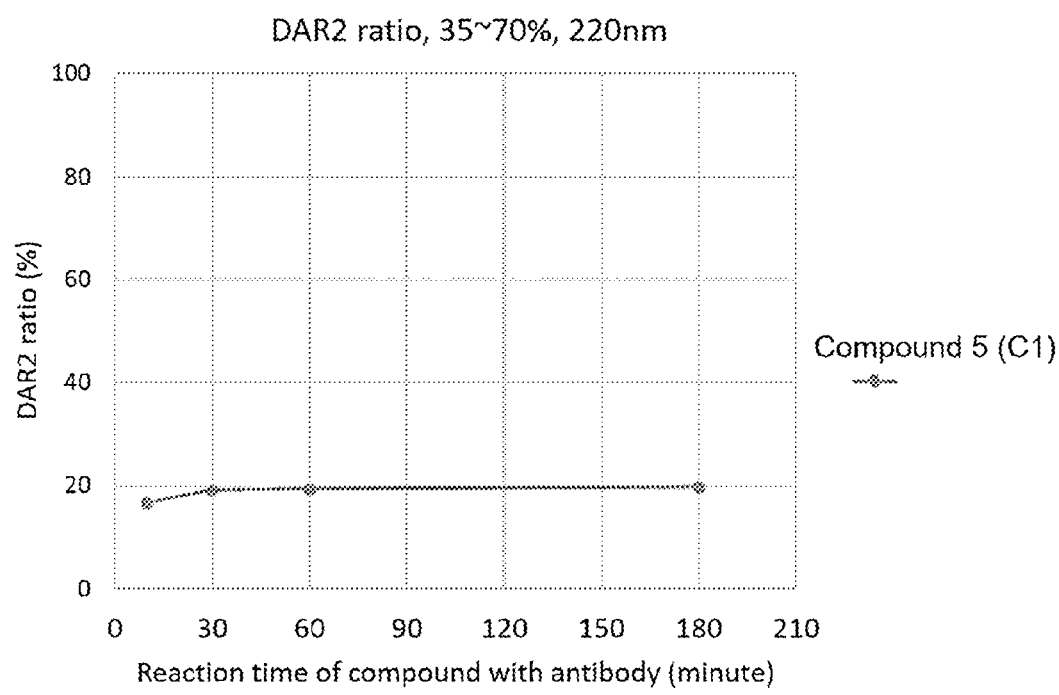
FIG. 17 shows the results of confirming the conjugation efficiency of Compound 5.

The conjugation efficiency confirmation results of Compound 5 are disclosed in FIG. 17. As illustrated in FIG. 17, as a result of reacting the antibody with Compound 5 in which methylene is introduced between a group of interest and a reaction site with an antibody for 3 hours, it was confirmed that about 20% of a DAR2 antibody-payload conjugate was prepared.

Furthermore, the inventors of the present application confirmed the stability of Compound 5 which was observed to have low conjugation efficiency. Compound 5 in the form of a powder was dissolved in DMSO so as to be a 10 mM stock. 180 µL of 1×PBS was put into an analytical vial, and 20 µL of the 10 mM stock of Compound 5 was added thereto (DMSO content 10%). Thereafter, stability was analyzed every 30 min using a C18-HPLC apparatus while slowly rotating the vial using a rotator. As a result of analysis, it was confirmed that only about 7.5% of Compound 5 remained 30 minutes after dissolving the stock in DMSO, and it was confirmed that about 2.2% of Compound 5 remained after 1 hour. Furthermore, after Compound 5 was dissolved in DMSO, almost no Compound 5 was observed at 2 hours and most of Compound 5 was observed to be degraded. In the case of Compound 5, it is observed that the compound has poor conjugation efficiency and is rapidly degraded, confirming that the compound is not suitable to be used for the preparation of an antibody conjugate comprising reactive group or an antibody-payload conjugate.

Example 6. Confirmation of Conjugation Efficiency of Compounds 6 to 8

Confirmation of Conjugation Efficiency of Compounds 6 and 7

The inventors of the present application confirmed the conjugation efficiency of Compounds 6 to 8.

Each of Compounds 6 and 7 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 30 minutes, 1 hour, and 3 hours using a tube rotator. After stirring, unreacted linkers were removed using a Zeba spin desalting column. DBCO-(PEG8)2-BG-MMAE (Payload 1) (1 mM 27.4 µL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 18:
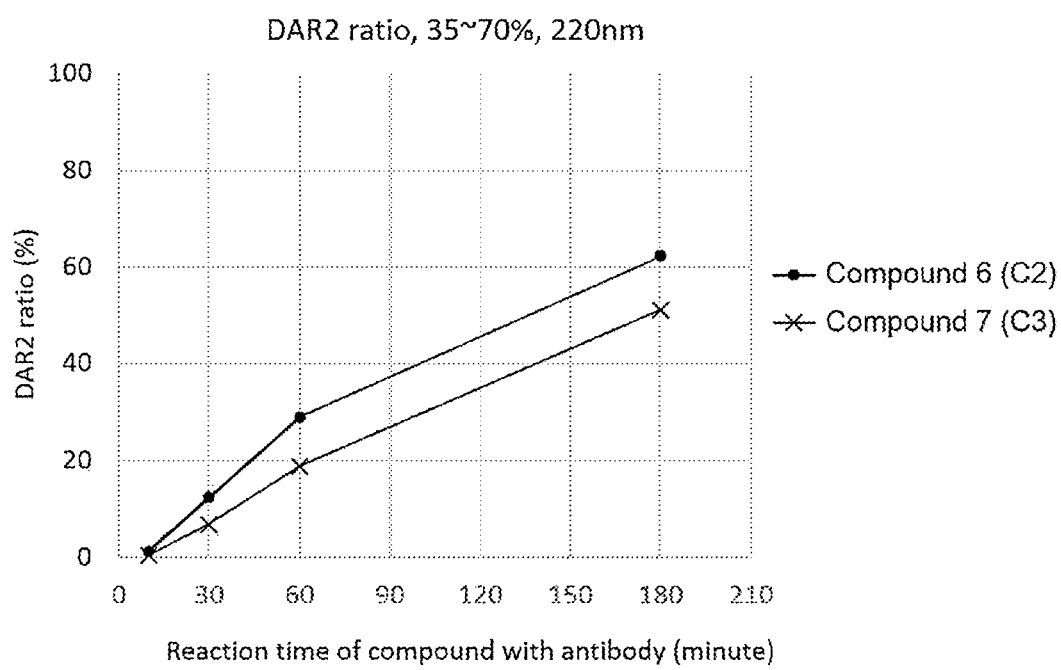
FIG. 18 shows the results of confirming the conjugation efficiency of each of Compounds 6 and 7.

The conjugation efficiency confirmation results of Compounds 6 and 7 are disclosed in FIG. 18. As disclosed in FIG. 18, as a result of reacting the antibody with Compound 6 for 3 hours, it was confirmed that about 60% of a DAR2 antibody-payload conjugate was prepared, and as a result of reacting the antibody with Compound 7 for 3 hours, it was confirmed that about 70% of a DAR2 antibody-payload conjugate was prepared.

Confirmation of Conjugation Efficiency of Compound 8

The inventors of the present application confirmed the conjugation efficiency of Compound 8.

Compound 8 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 10 minutes, 30 minutes, 1 hour, and 3 hours using a tube rotator. After stirring, unreacted linkers were removed using a Zeba spin desalting column. DBCO-(PEG8)2-BG-MMAE (Payload 1) (1 mM 27.4 µL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 19:
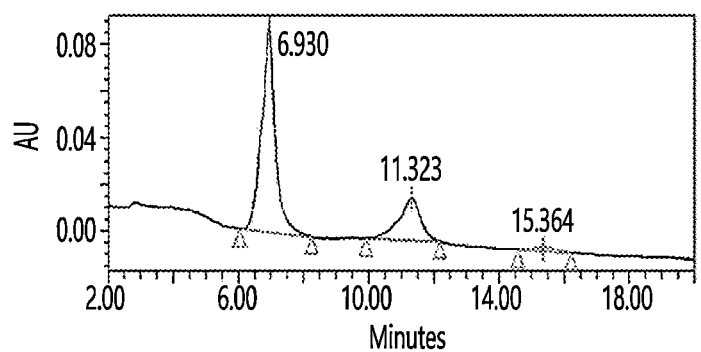
FIGS. 19 and 20 show the results of confirming the conjugation efficiency of Compound 8.
Figure 19:
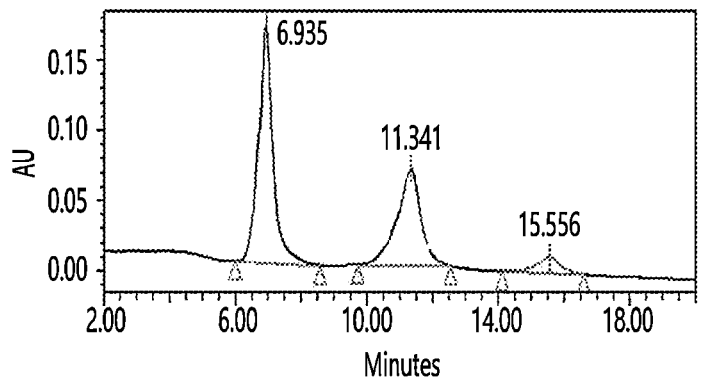
Figure 20:
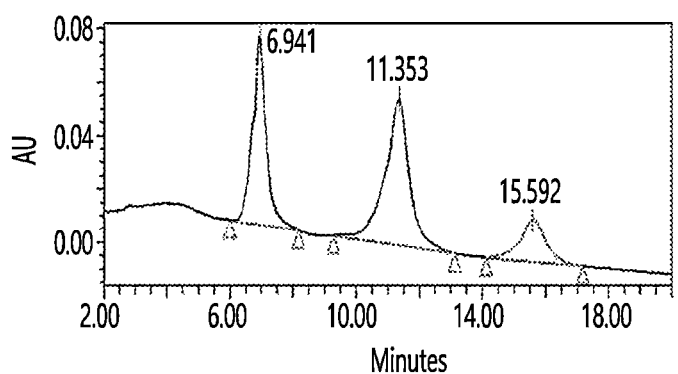
Figure 20:
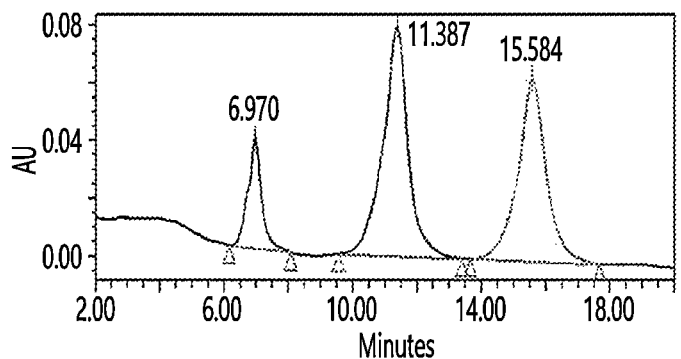

The conjugation efficiency confirmation results of Compound 8 are disclosed in FIGS. 19 to 20. As disclosed in FIGS. 19 to 20, as a result of reacting the antibody with Compound 8 for 3 hours, it was confirmed that about 41% of a DAR2 antibody-payload conjugate was prepared.

Confirmation of Conjugation Efficiency of Compounds 6 to 8 (Long Reaction Time)

The inventors of the present application confirmed the conjugation efficiency of Compounds 6 to 8 by setting a longer reaction time between each of Compounds 6 to 8 and the antibody.

Each of Compounds 6 to 8 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 10 minutes to 48 hours using a tube rotator. After stirring, unreacted linkers were removed using a Zeba spin desalting column. DBCO-(PEG8)2-BG-MMAE (Payload 1) (1 mM 27.4 µL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 21:
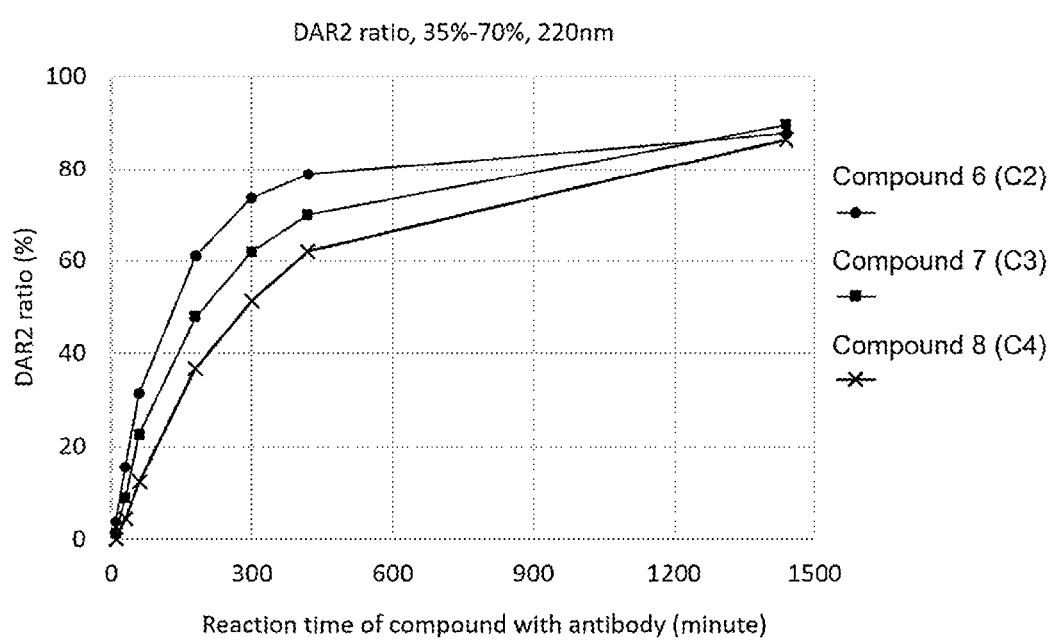
FIG. 21 shows the results of confirming the conjugation efficiency of each of Compounds 6 to 8 according to long-time reaction.
Figure 22:
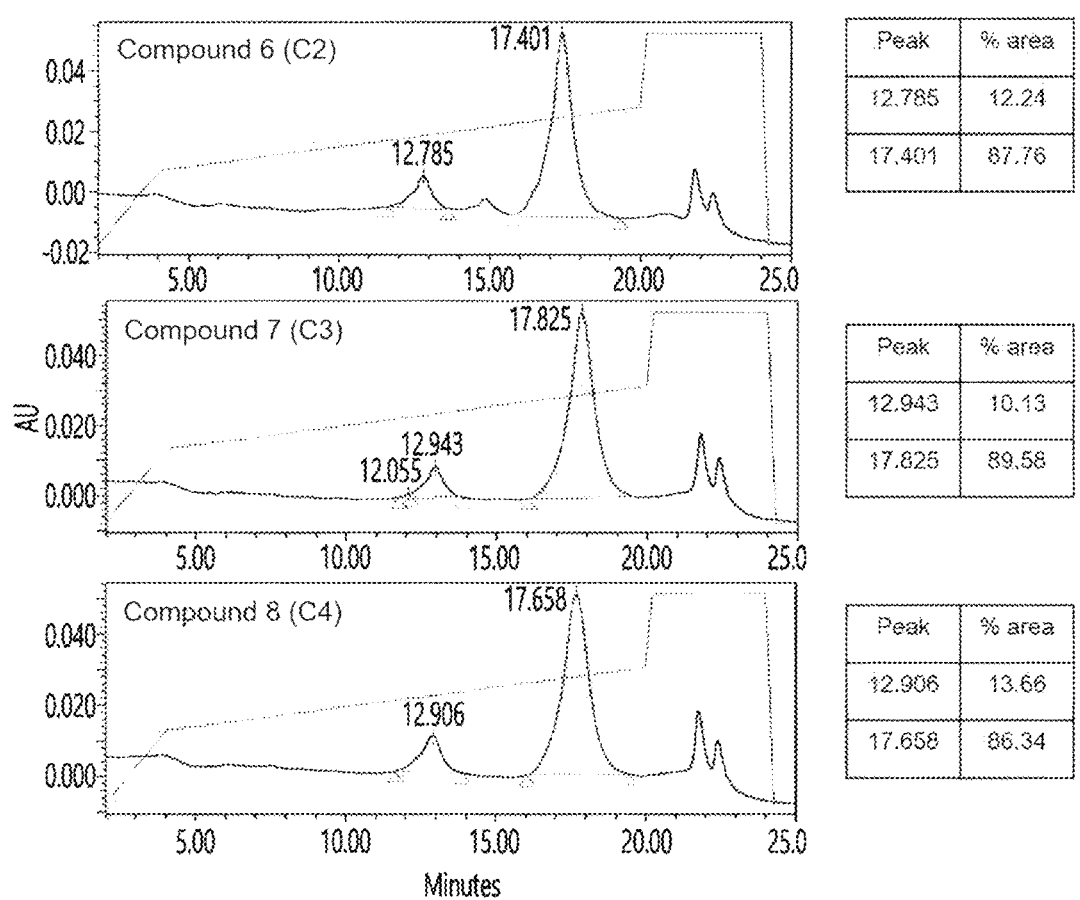
FIG. 22 shows the results of confirming the conjugation efficiency of each compound when the reaction time between the compound (Compounds 6 to 8) and the antibody is 48 hours.

The conjugation efficiency confirmation results of Compounds 6 to 8 are disclosed in FIG. 21. As disclosed in FIGS. 21 to 22, as a result of reacting the antibody with Compound 6 for 7 hours, it was confirmed that about 78% of a DAR2 antibody-payload conjugate was prepared, and as a result of reacting the antibody with Compound 6 for 48 hours, it was confirmed that about 87% of a DAR2 antibody-payload conjugate was prepared (see FIGS. 21 and 22). As a result of reacting the antibody with Compound 7 for 7 hours, it was confirmed that about 70% of a DAR2 antibody-payload conjugate was prepared, and as a result of reacting the antibody with Compound 7 for 48 hours, it was confirmed that about 89% of a DAR2 antibody-payload conjugate was prepared (see FIGS. 21 and 22). As a result of reacting the antibody with Compound 8 for 7 hours, it was confirmed that about 62% of a DAR2 antibody-payload conjugate was prepared, and as a result of reacting the antibody with Compound 8 for 48 hours, it was confirmed that about 86% of a DAR2 antibody-payload conjugate was prepared (see FIGS. 21 and 22). Thus, it was confirmed that Compounds 6 to 8 exhibited high conjugation efficiency.

Example 7. Confirmation of Conjugation Efficiency of Compound 9

The inventors of the present application confirmed the conjugation efficiency of Compound 9.

Figure 23:
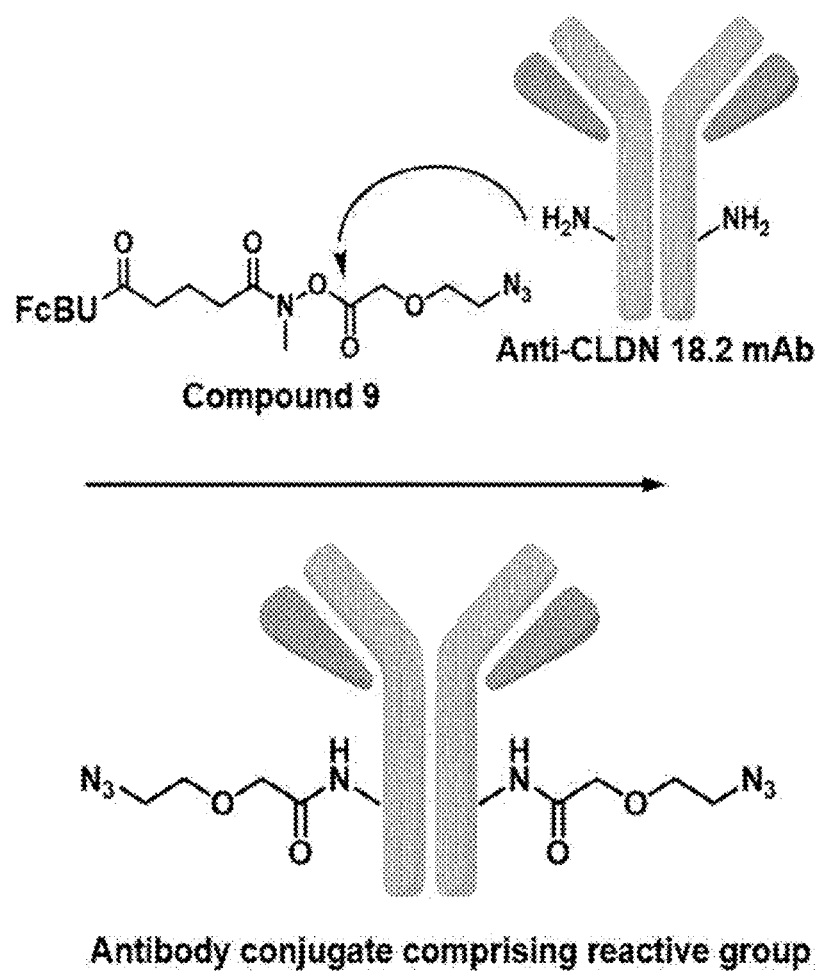
FIGS. 23 to 24 show a schematic view of the preparation of an antibody-payload conjugate using Compound 9, anti-CLDN18.2 mAb, and Payload 1.
Figure 24:
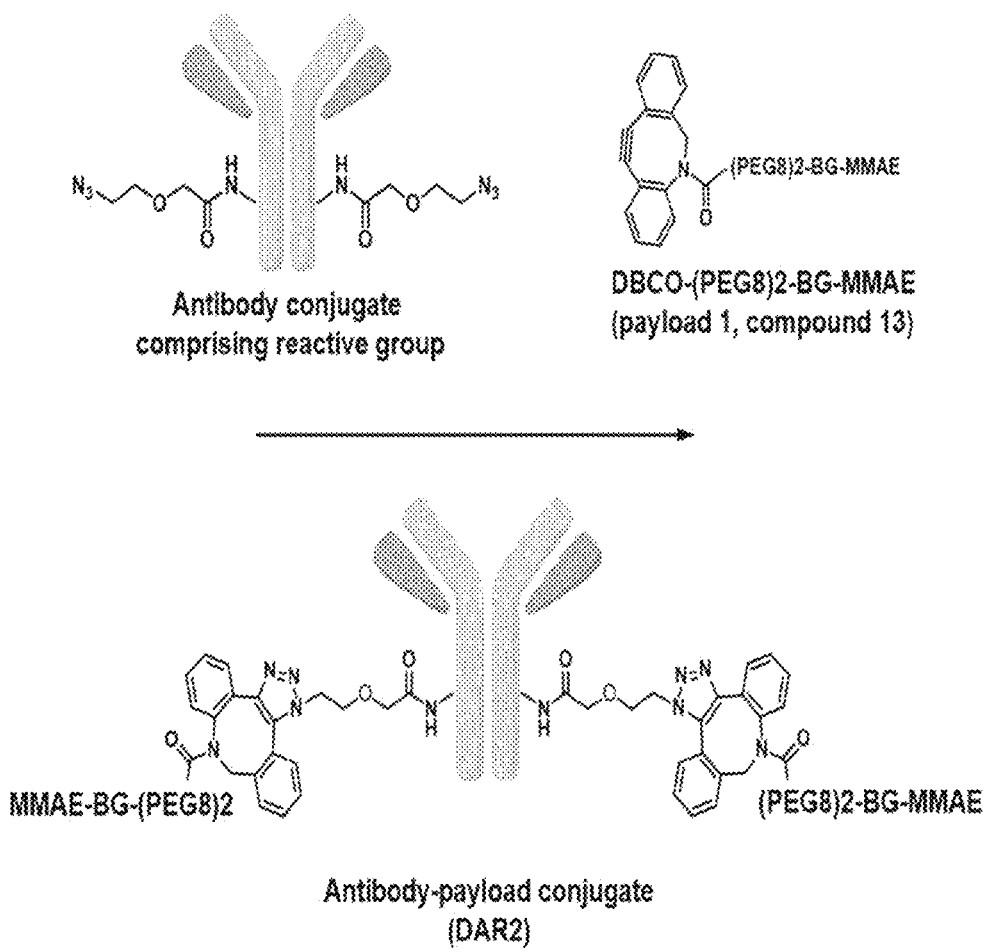
Figure 25:
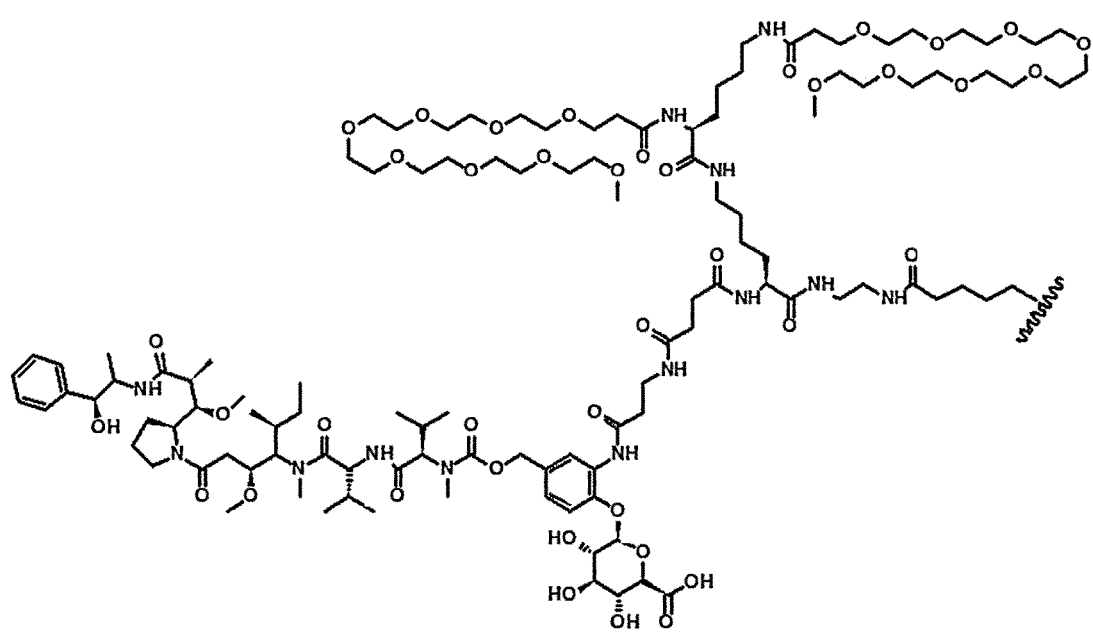
FIG. 25 specifically illustrates the (PEG8)2-BG-MMAE moiety of the antibody-payload conjugate (DAR2) of FIG. 24.

Compound 9 (1 mM stock solution in DMSO 27.4 µL, 27.4 nmol) was diluted in 72.6 µL of DMSO (total DMSO content 10%) and then added to anti-CLDN18.2 mAb (1 mg/mL, 1 mL, 6.85 µM), and the resulting mixture was slowly stirred at room temperature for 10 minutes, 30 minutes, 1 hour, and 3 hours using a tube rotator. After stirring, unreacted linkers were removed using a Zeba spin desalting column. DBCO-(PEG8)2-BG-MMAE (Payload 1) (1 mM 27.4 μL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus. For reference, a schematic view of the preparation of an antibody-payload conjugate using Compound 9, anti-CLDN18.2mAb, and Payload 1 is provided through FIGS. 23 and 24. The schematic views of the preparation in FIGS. 23 and 24 were created based on the DAR2 antibody-payload conjugate. FIG. 25 illustrates the specific structure of the (PEG8)2-BG-MMAE portion of the antibody-payload conjugate (DAR2) of FIG. 24.

Figure 26:
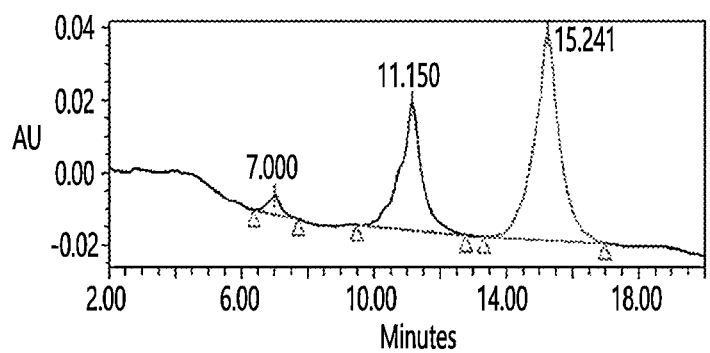
FIGS. 26 and 27 show the results of confirming the conjugation efficiency of Compound 9.
Figure 26:
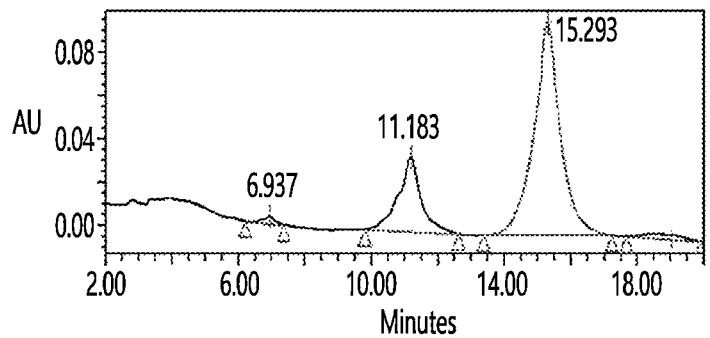
Figure 27:
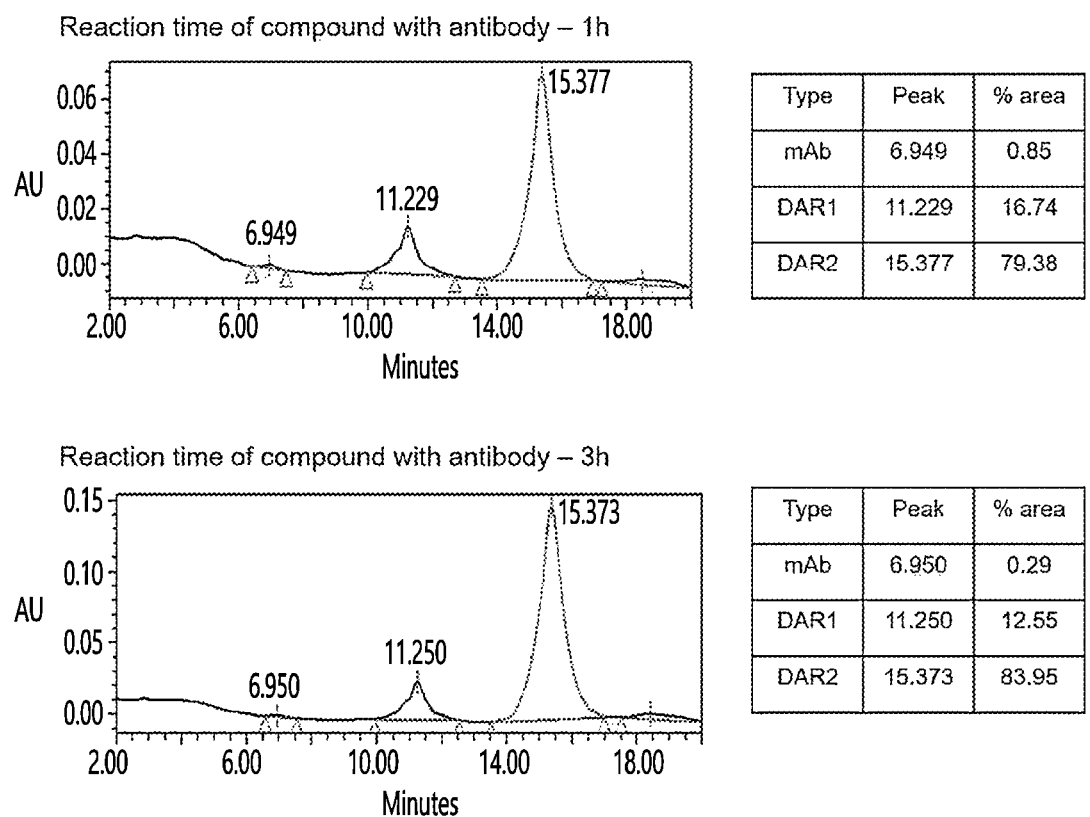

The conjugation efficiency confirmation results of Compound 9 are disclosed in FIGS. 26 to 27. As disclosed in FIGS. 26 to 27, as a result of reacting the antibody with Compound 9 for 3 hours, it was confirmed that about 84% of the DAR2 antibody-payload conjugate was prepared. As described above, it was confirmed that Compound 9 exhibited high conjugation efficiency. Furthermore, the inventors of the present application repeated the experiment on Compound 9 in the same manner as described above, and the results of the repeated experiment are disclosed in FIG. 28.

Example 8. Confirmation of Conjugation Efficiency of Compounds 10 and 11

The inventors of the present application confirmed the conjugation efficiency of Compounds 10 and 11.

Each of Compounds 10 to 11 (1 mM stock solution in DMSO 27.4 μL, 27.4 nmol) was diluted in 72.6 μL of DMSO (total DMSO content 10%) and then added to anti-CLDN18.2 mAb (1 mg/mL, 1 mL, 6.85 μM), and the resulting mixture was slowly stirred at room temperature for 30 minutes, 1 hour, and 3 hours using a tube rotator. After stirring, unreacted linkers were removed using a Zeba spin desalting column. DBCO-(PEG8)2-BG-MMAE (Payload 1) (1 mM 27.4 μL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 29:
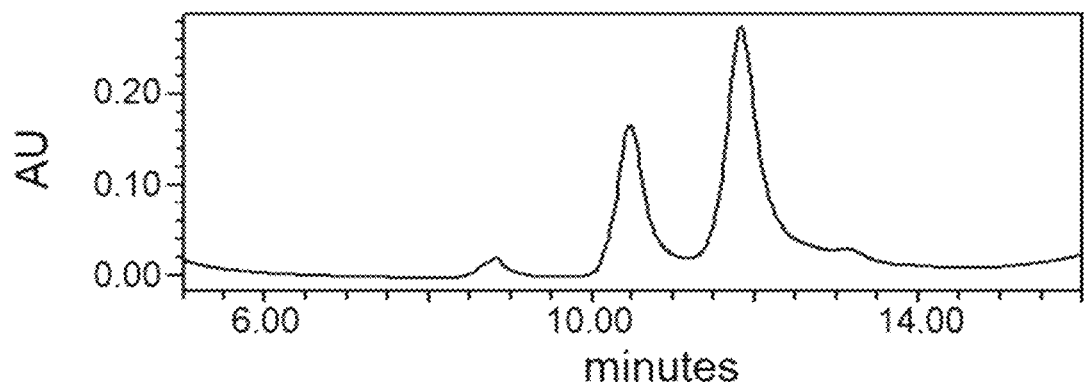
FIG. 29 shows the results of confirming the conjugation efficiency of Compound 10.
Figure 29:
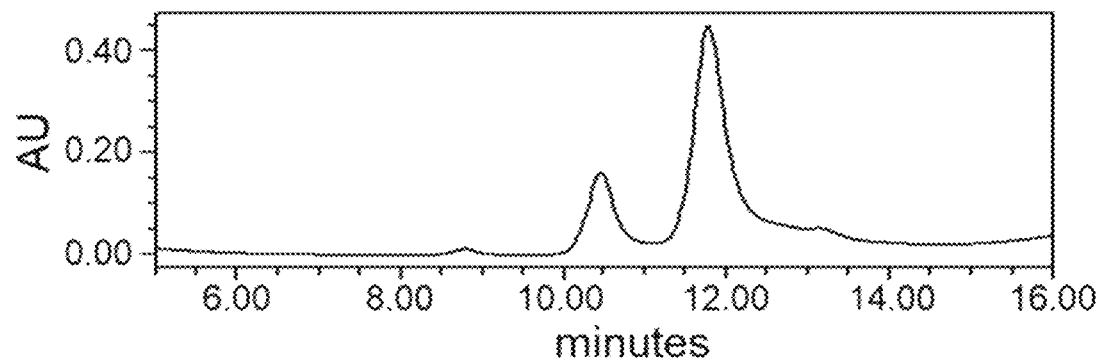
Figure 29:
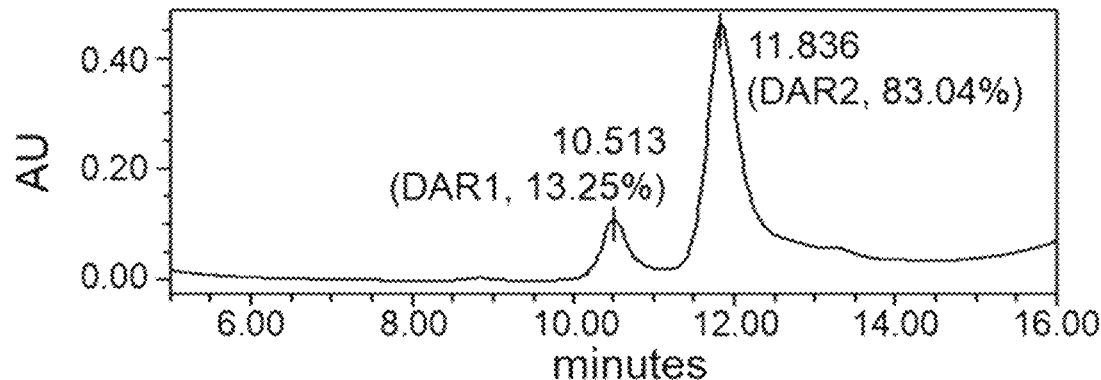

The conjugation efficiency confirmation results of Compound 10 are disclosed in FIG. 29. As disclosed in FIG. 29, as a result of reacting the antibody with Compound 10 for 3 hours, it was confirmed that about 83% of a DAR2 antibody-payload conjugate was prepared. As described above, it was confirmed that Compound 10 exhibited high conjugation efficiency.

Figure 30:
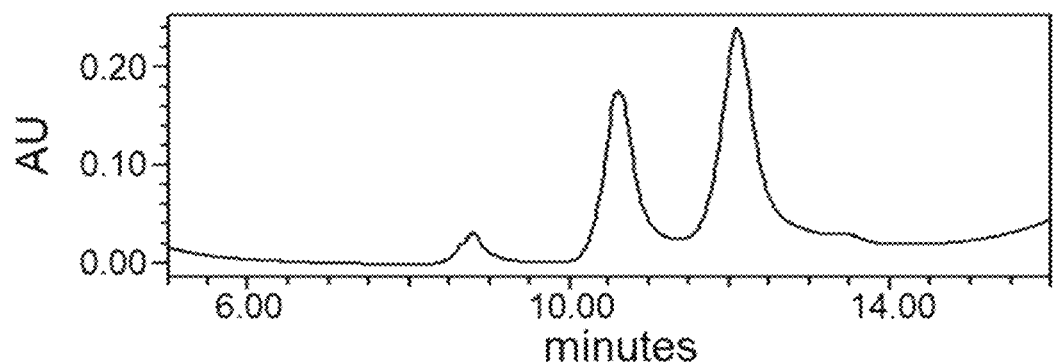
FIG. 30 shows the results of confirming the conjugation efficiency of Compound 11.
Figure 30:
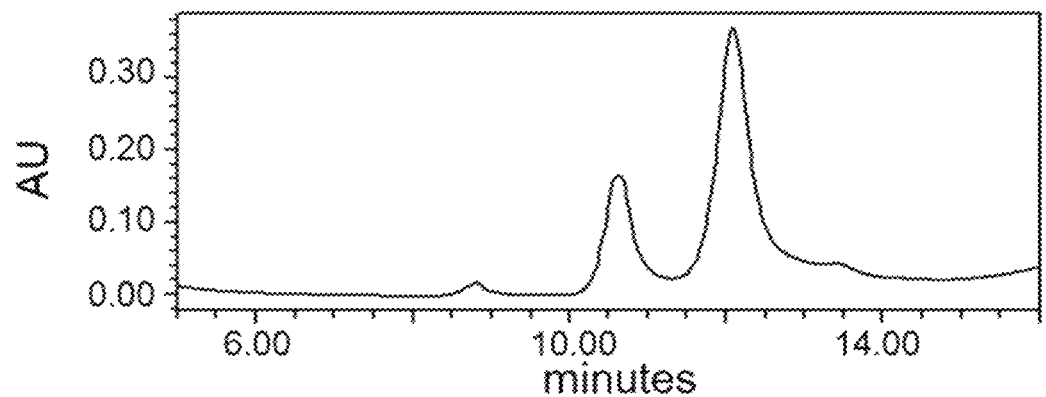
Figure 30:
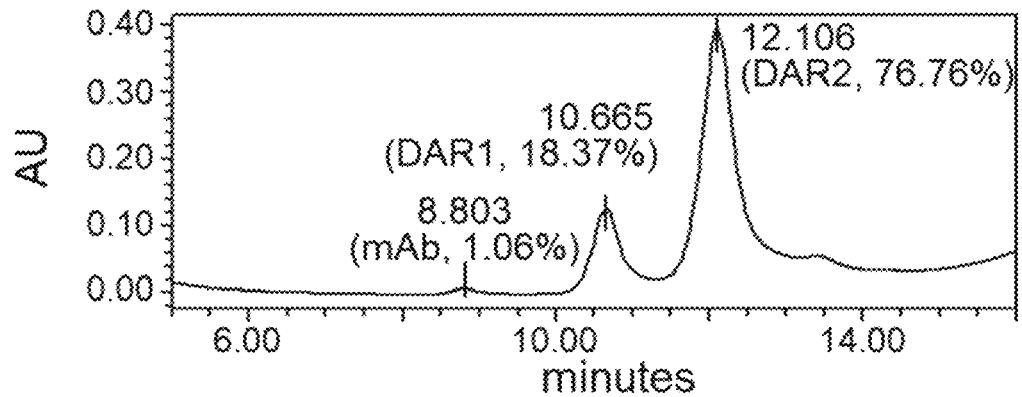

The conjugation efficiency confirmation results of Compound 11 are disclosed in FIG. 30. As a result of reacting the antibody with Compound 11 for 3 hours, it was confirmed that about 78% of a DAR2 antibody-payload conjugate was prepared. Thus, it was confirmed that Compound 11 exhibited high conjugation efficiency.

Example 9. Confirmation of Conjugation Efficiency of Compound 12

The inventors of the present application confirmed the conjugation efficiency of Compound 12.

Compound 12 (1 mM stock solution in DMSO 27.4 μL, 27.4 nmol) was diluted in 72.6 μL of DMSO (total DMSO content 10%) and then added to anti-CLDN18.2 mAb (1 mg/mL, 1 mL, 6.85 μM), and the resulting mixture was slowly stirred at room temperature for 10 minutes, 30 minutes, 1 hour, and 3 hours using a tube rotator. After stirring, unreacted linkers were removed using a Zeba spin desalting column. Tetrazine-PEG8-DM1 (Payload 2) (1 mM 27.4 μL) was added to the antibody-linker intermediate, and the resulting mixture was slowly stirred at room temperature for 24 hours using a tube rotator. Thereafter, unreacted drugs were removed using a Zeba spin desalting column, and conjugation efficiency was analyzed using a HIC-HPLC apparatus.

Figure 31:
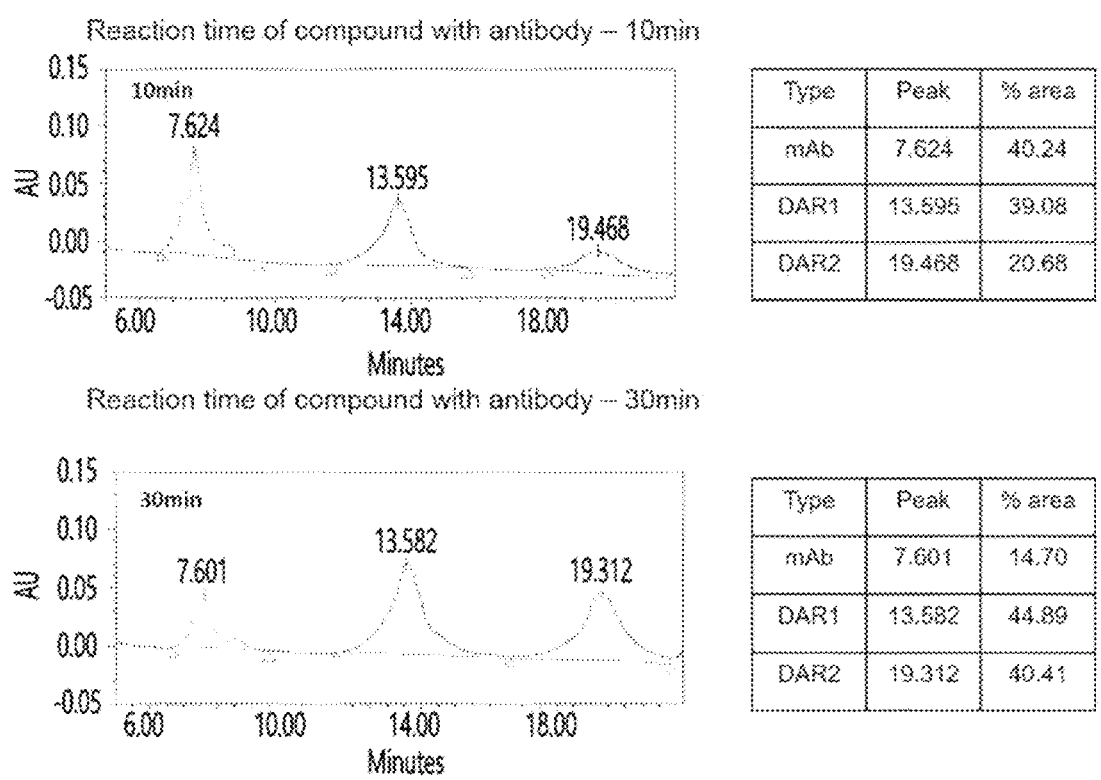
FIGS. 31 and 32 show the results of confirming the conjugation efficiency of Compound 12.
Figure 32:
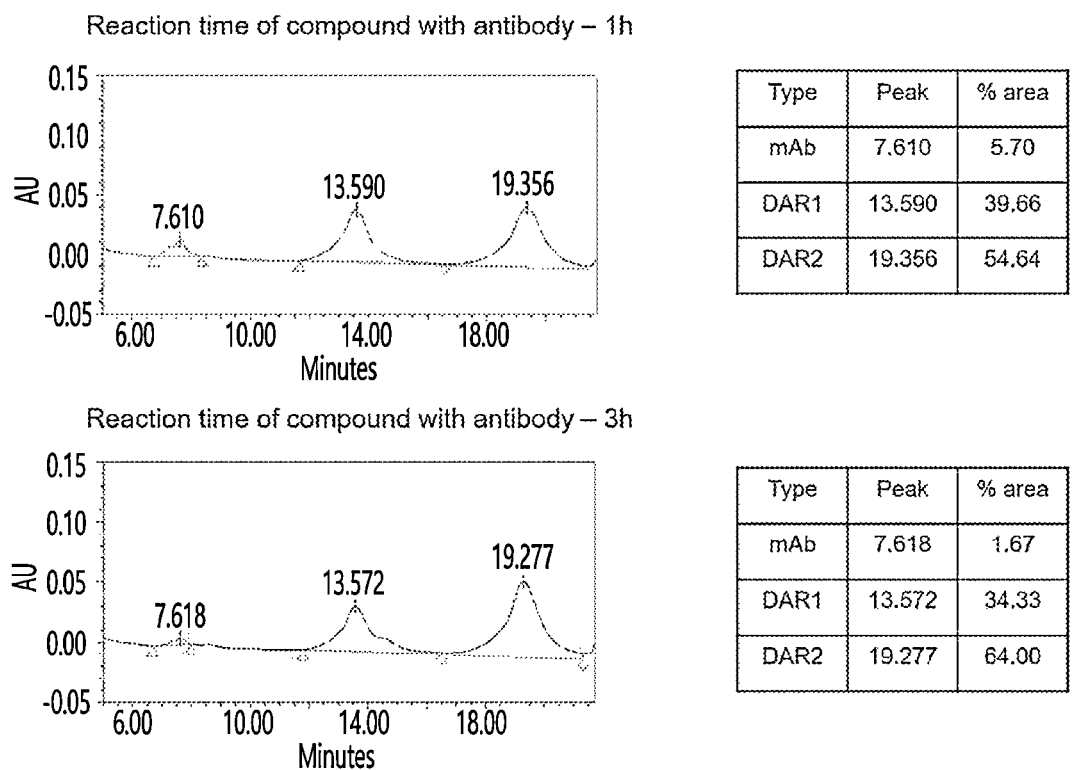

The conjugation efficiency confirmation results of Compound 12 are disclosed in FIGS. 31 to 32. As disclosed in FIGS. 31 and 32, as a result of reacting the antibody with Compound 12 for 3 hours, it was confirmed that about 64% of the DAR2 antibody-payload conjugate was prepared. Thus, it was confirmed that Compound 12 exhibited high conjugation efficiency.

Example 10. Synthesis and Stability Confirmation of NHS-Ester-Based Compound

The inventors of the present application prepared a compound whose reaction site with an antibody is NHS-ester (hereinafter, referred to as an NHS-ester-based compound).

(Compound 14, an NHS-ester-based compound)

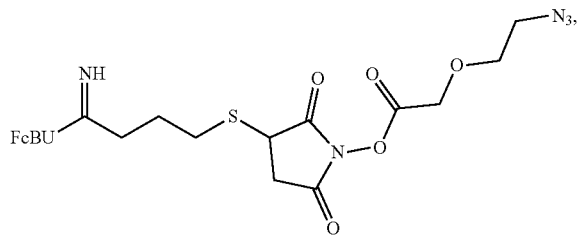

wherein FcBU is PEG8-DCAWHOrn'GELVWCT-NH$_2$, and Orn' is conjugated ornithine.

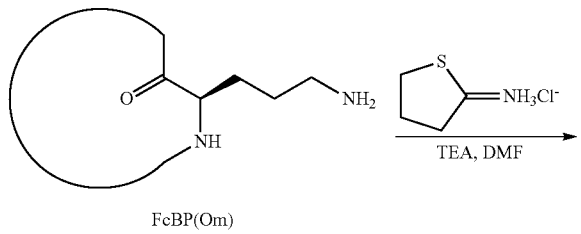

FcBP(Orn)

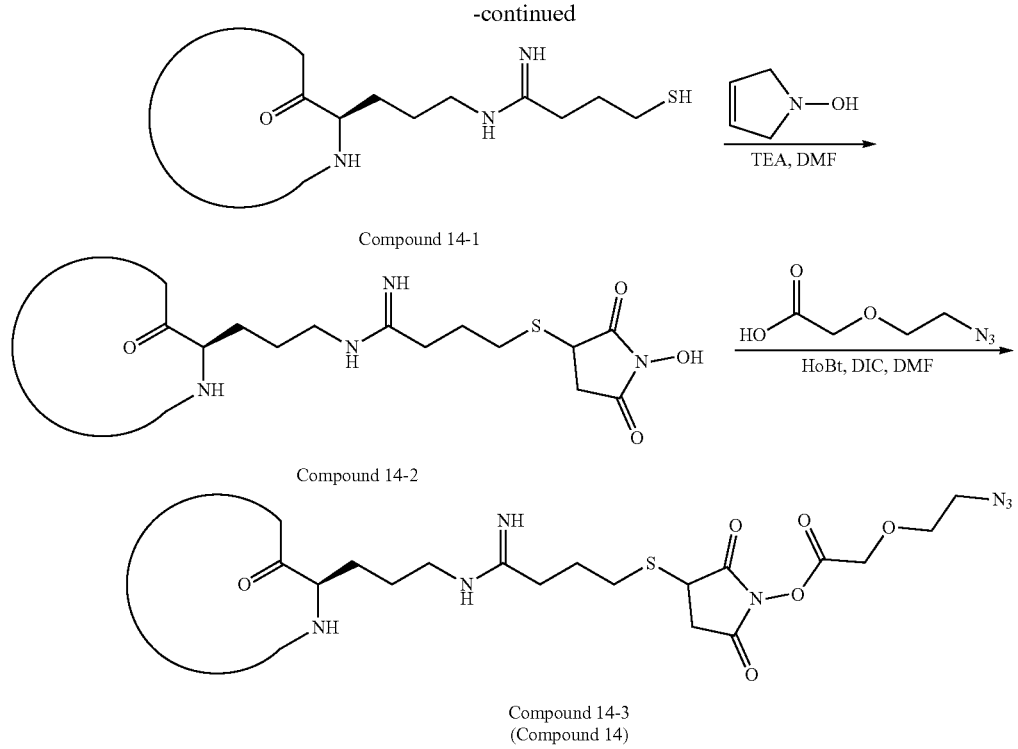

Compound 14-1

Compound 14-2

Compound 14-3
(Compound 14)

In order to prepare Compound 14-1, after FcBP (Orn) (101.6 mg, 0.051 mmol) was dissolved in 5 mL of N,N-dimethylformamide, 2-iminothiolane (70.0 mg, 0.51 mmol) was added thereto, triethylamine (132.9 μL, 0.763 mmol) as an organic base was added thereto, and the resulting mixture was stirred at room temperature for 1 hour. The monitoring of the reaction was performed through HPLC and mass analysis.

For the preparation of Compound 14-2, after monitoring the reaction of Compound 14-1 previously prepared, 2 equivalents (11.5 mg, 0.102 mmol) of N-hydroxymaleimide to be used in the next reaction were added in situ, and stirred for 0.5 hours, and the reaction was monitored through HPLC and mass analysis. After the reaction was completed, the target substance was purified using Prep-LC and then lyophilized to obtain Compound 14-2.

In order to prepare Compound 14-3, 35 mg of Compound 14-2, 2-(2-azidoethoxy)acetic acid (51 mg, 0.351 mmol), 1-hydroxybenzotriazole hydrate (67 mg, 0.496 mmol), and N,N'-diisopropylcarbodiimide (52 μL, 0.332 mmol) were dissolved in 5 mL of N,N-dimethylformamide, and then the resulting solution was stirred at room temperature for 1 hour. The 14-3 substance obtained after stirring was purified by Prep-LC without any special treatment to obtain the final product.

Figure 33:
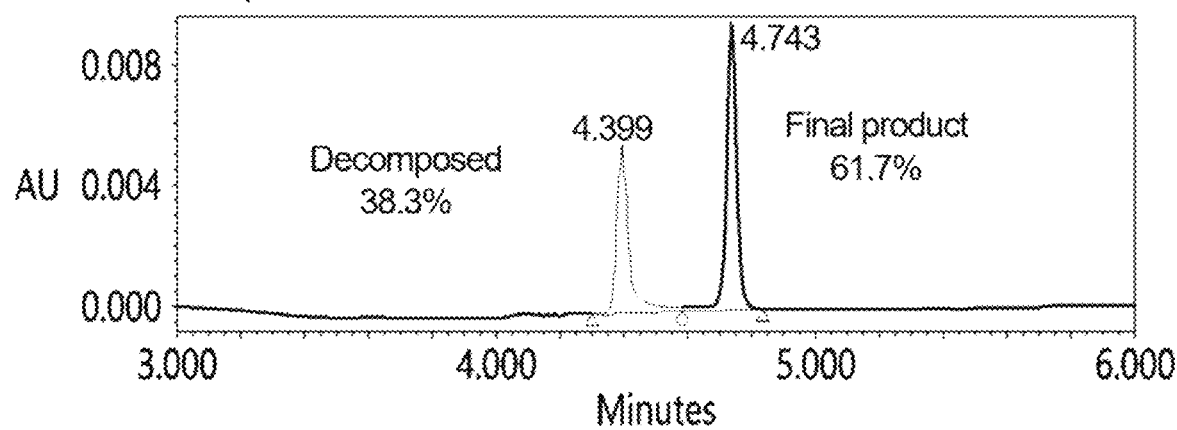
FIG. 33 shows the results of confirming the stability of Compound 14.
Figure 33:
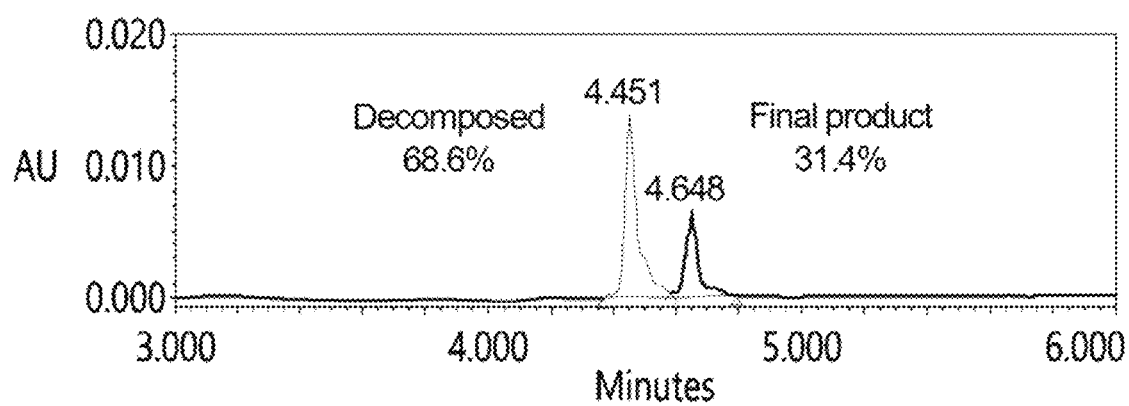
Figure 33:
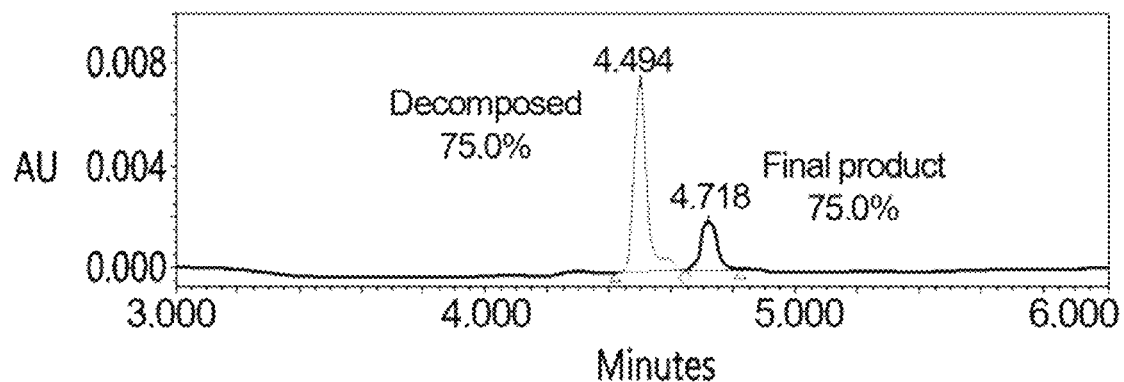

Thereafter, the stability of Compound 14-3 was confirmed. Compound 14-3 obtained immediately after the Prep-LC process is in a state of being dissolved in an approximately 60% acetonitrile solution and 40% solution of 0.1% TFA contained in water. The above acidic solution containing TFA is used as a solution of mobile phase in the Prep-LC process, and is an environment in which the hydration reaction of the obtained Compound 14-3 can be suppressed. The solution of Compound 14-3 obtained in the corresponding environment was immediately subjected to mass analysis and HPLC analysis. As a result of analysis using a solution of Compound 14-3 after Prep-LC purification as it is, it was confirmed that 38.3% was degraded 2 minutes after purification, it was confirmed that about 68% was degraded 15 minutes after purification, and it was confirmed that 75% was degraded 30 minutes after purification (FIG. 33). The degraded substance was confirmed to have the structure of Compound 14-2, and such degradation is expected to be caused by the instability of the NHS-ester group.

Example 11. Preparation of ADC-A

The inventors of the present application prepared ADC-A, in which a drug (MMAE) is conjugated to an anti-claudin 18.2 antibody (antibody-A). The structure of ADC-A is the same as the antibody-payload conjugate illustrated in FIGS. 24 and 25.

At this time, ADC-A comprises an antibody comprising two heavy chains, a payload is linked to lysine residue 246 or 248 of any one of the heavy chains, and a payload is linked to lysine residue 246 or 248 of the other heavy chain. At this time, the structures in which the payload is linked to each heavy chain are the same.

Compound 9 was prepared at a concentration of 10 mM in a DMSO solvent. The prepared Compound 9 (277.8 μL, 2,778 nmol, 4.0 eq) was mixed with 101.4 mg of antibody-A (Anti-CLDN18.2 mAb) (146 kDa, 5.2 mg/mL, 19.5 mL, 694.5 nmol). The mixture was mixed with 1×PBS (pH 7.4) and allowed to react for 3 hours. The final DMSO product was fixed at 10%. The reaction (cross-linking of compound 9 and antibody-A) was monitored by HIC-HPLC analysis. After the reaction was completed, the Compound 9 that did not react with antibody-A was removed using a spin desalting column (Zeba™ spin desalting columns, 40 K molecular weight cut-off, 10 mL, 1000 g-force) and size-exclusion chromatography. As a result, an antibody conjugate comprising reactive group was obtained.

Payload 1 (Compound 13) was prepared at a concentration of 10 mM in a DMSO solvent. The prepared Payload 1 (416.7 μL, 4,167 nmol, 6 eq) was mixed with 101.4 mg of an antibody conjugate comprising reactive group (146 kDa, 5.2 mg/mL, 19.5 mL, 694.5 nmol). The mixture was mixed in 1×PBS (pH 7.4) and incubated at 25° C. for 24 hours. The reaction was monitored through HIC-HPLC.

After the reaction was completed, the unreacted conjugate comprising reactive group and unreacted Payload 1 were removed using a spin desalting column (Zeba™ spin desalting columns, 40 K molecular weight cut-off, 10 mL, 1000 g-force) and a dialysis technique (pH 7.4, 1×PBS, 4 h, 4 h, 12 h, 3 times). As a result, crude ADC-A (DAR 2) was obtained. For the structure of ADC-A, reference may be made to the antibody-payload conjugates (DAR 2) of FIGS. 24 and 25.

optical density (OD) values were measured. At this time, the measured values are illustrated in FIGS. 34 to 36.

The measured results were used for regression analysis in GraphPad PRISM® 9.0 software to calculate EC50 and Bmax. The cell binding strength of antibody-A and ADC-A was evaluated based on the calculated values. At this time, the calculated values are listed in Table 1.

Example 12.1.2 Experimental Results

Figure 34:
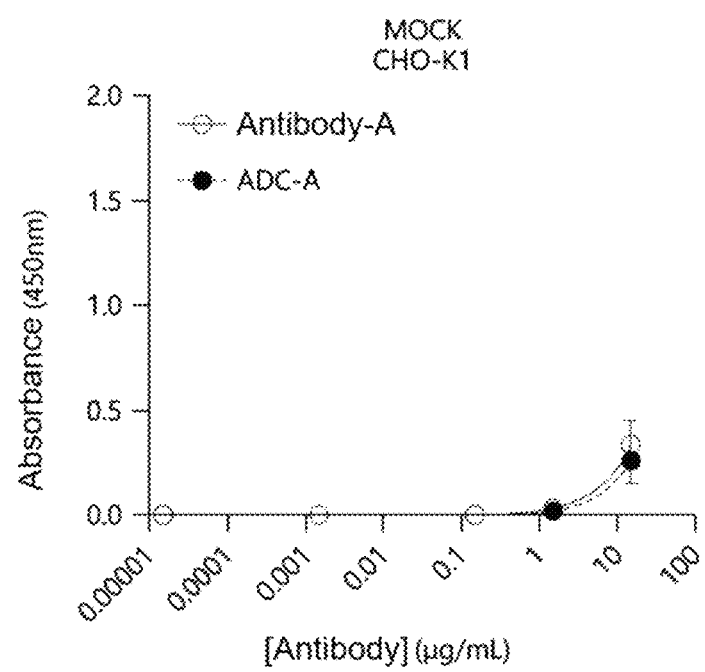
FIG. 34 is a graph showing the absorbance measured after treating antibody-A and ADC-A respectively to a CHO-K1 cell line (MOCK CHO-K1) to which only a MOCK vector (empty vector) was transiently transfected.
Figure 35:
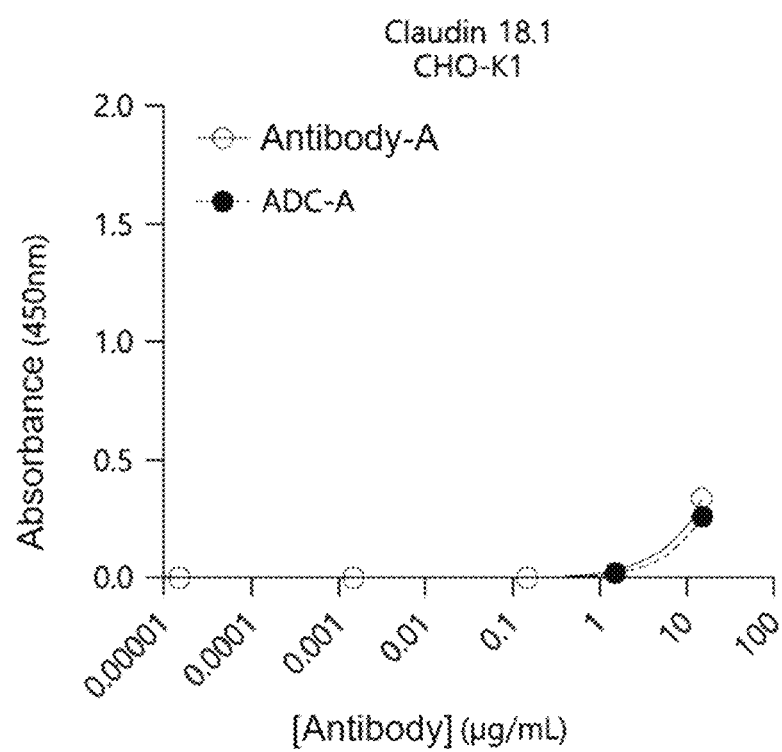
FIG. 35 is a graph showing the absorbance measured after treating antibody-A and ADC-A respectively to a CHO-K1 cell line (Claudin 18.1 CHO-K1) to which a gene (SEQ ID NO: 29) encoding Claudin 18.1 protein (CLDN18.1) was transiently transfected.
Figure 36:
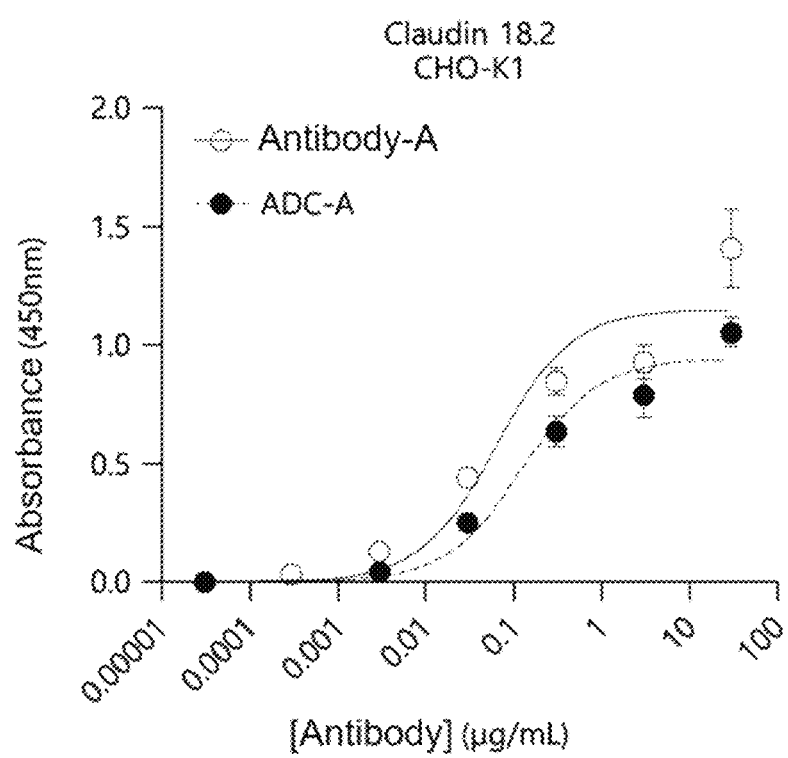
FIG. 36 is a graph showing the absorbance measured after treating antibody-A and ADC-A respectively to a CHO-K1 cell line (Claudin 18.2 CHO-K1) to which a gene (SEQ ID NO: 30) encoding Claudin 18.2 protein (CLDN18.2) was transiently transfected.

Through FIGS. 34 to 36, it was confirmed that antibody-A and ADC-A do not bind to the negative control MOCK CHO-K1 cell line and Claudin 18.1 CHO-K1 cell line, and specifically bind to only the Claudin 18.2 CHO-K1 cell line in which CLDN 18.2 is expressed.

Through Table 1, it was confirmed that the EC50 and binding maximum (Bmax) indicating the maximum binding strength of ADC-A were almost identical to those of antibody-A. That is, it can be seen that although a linker and a drug (payload) were conjugated to antibody-A, the binding strength of an antibody to an antigen was not significantly affected.

TABLE 1

| Sample | MOCK-CHO-K1 | | CLDN18.1~CHO-K1 | | CLDN18.2-CHO-K1 | |
| --- | --- | --- | --- | --- | --- | --- |
| | Antibody-A | ADC-A | Antibody-A | ADC-A | Antibody-A | ADC-A |
| Bmax | — | — | — | — | 1.149 | 0.9386 |
| Kd | — | — | — | — | 0.06363 μg/ml | 0.1230 μg/ml |
| | | | | | 0.4242 nM | 0.82 nM |

Example 12. Verification of Efficacy of ADC-A

Example 12.1 Target Specificity Verification 1—Confirmation of Binding to Antigen-Expressing Cells The inventors of the present application conducted an experiment according to Example 12.1.1 in order to confirm whether antibody-A and ADC-A can specifically bind to the claudin 18.2 protein (CLDN18.2), and the results are as described in Example 12.1.2.

Example 12.1.1 Experimental Method

A CHO-K1 cell line into which a gene (SEQ ID NO: 29) encoding the claudin 18.1 protein (CLDN18.1) was transiently transfected (hereinafter, referred to as "Claudin 18.1 CHO-K1"), a CHO-K1 cell line into which a gene (SEQ ID NO: 30) encoding the claudin 18.2 protein (CLDN18.2) was transiently transfected (hereinafter, referred to as "Claudin 18.2 CHO-K1"), and a CHO-K1 cell line into which only a MOCK vector (empty vector) was transiently transfected (hereinafter, referred to as "MOCK CHO-K1") were prepared. At this time, a pcDNA3.1 vector was used in the case of Claudin 18.1 CHO-K1, and a pcDNA3.1(+) vector was used in the case of Claudin 18.2 CHO-K1.

The CHO-K1 cell lines were prepared by the following processes.

The CHO-K1 cell lines were cultured in RPM11640 containing 10% FBS and 1% penicillin/streptomycin in an incubator under the conditions of 37° C. and 5% C02.

Transient transfection was performed according to the TransIT2020 manual, the transfected cells were plated on a 96-well plate for culture, and then treated with antibody-A and ADC-A, respectively, and then cell-based enzyme-linked immunosorbent assay (ELISA) was performed, and Example 12.2 Target Specificity Verification 2—Confirmation of Binding to Antigen Protein The inventors of the present application conducted an experiment according to Example 12.2.1 in order to confirm whether antibody-A and ADC-A can bind to the claudin 18.2 protein (CLDN18.2), and the results are as described in Example 12.2.2.

Example 12.2.1 Experimental Method

To confirm the binding strength to an antigen, a CLDN18.2 virus-like particle (VLP) in which the claudin 18.2 protein (CLDN18.2) was expressed was prepared. At this time, CLDN18.2~VLP is CSB-MP005498HU (A5) from CUSABIO TECHNOLOGY LLC.

After a 96-well plate was coated with the CLDN18.2 VLP for ELISA and treated with antibody-A and ADC-A, respectively, indirect ELISA was performed to measure OD values. At this time, the measured values are illustrated in FIG. 37.

The measured results were used for regression analysis in GraphPad PRISM@ 9.0 software to calculate EC50 and Bmax. The antigen binding strengths of antibody-A, ADC-A, antibody-B, and ADC-B were evaluated based on the calculated values. At this time, the calculated values are listed in Table 2.

Example 12.2.2 Experimental Results

Figure 37:
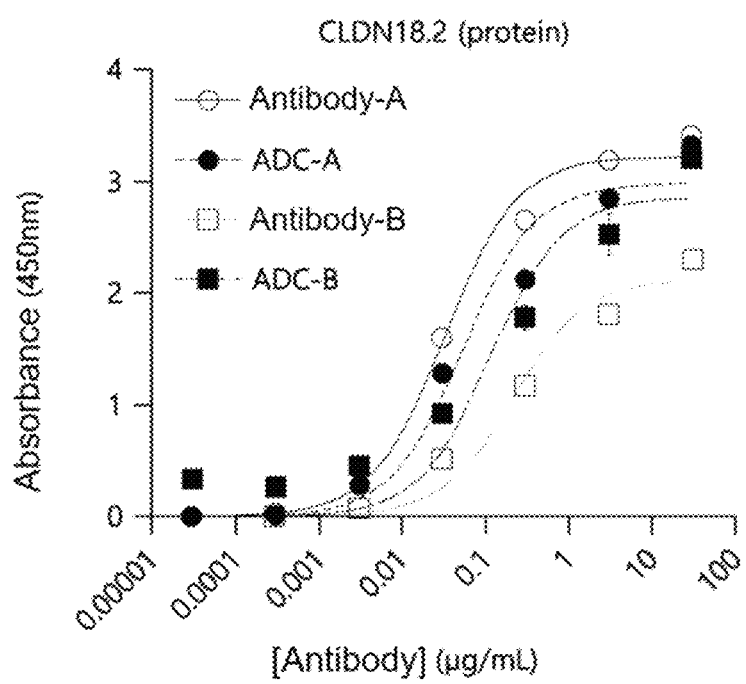
FIG. 37 is a graph showing the absorbance measured after treating antibody-A and ADC-A respectively to a CLDN18.2~virus-like particle (VLP) in which Claudin 18.2 protein (CLDN18.2) is expressed.
Figure 38:
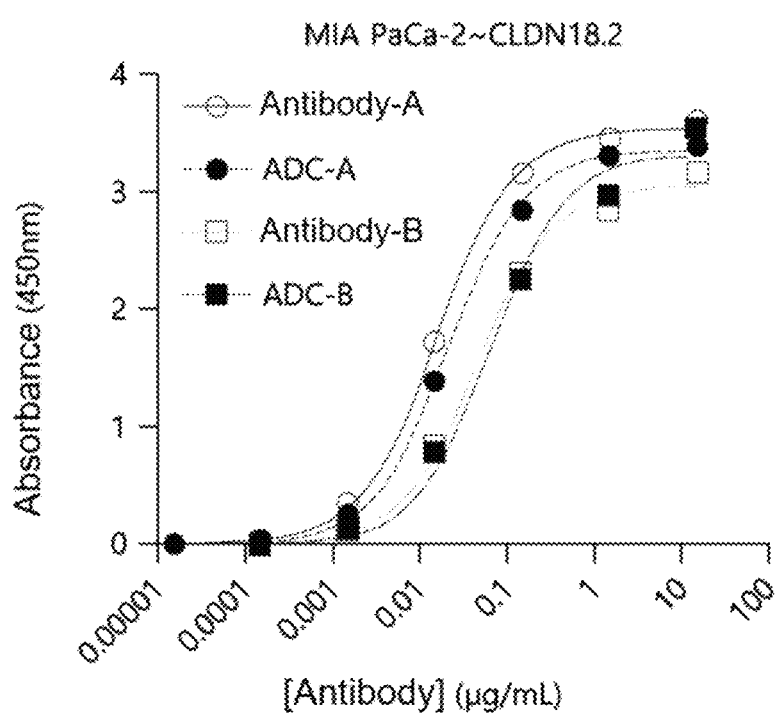
FIG. 38 is a graph showing the absorbance measured after treating antibody-A, ADC-A, antibody-B, and ADC-B respectively to MIA PaCa-2~CLDN18.2 cell line.
Figure 39:
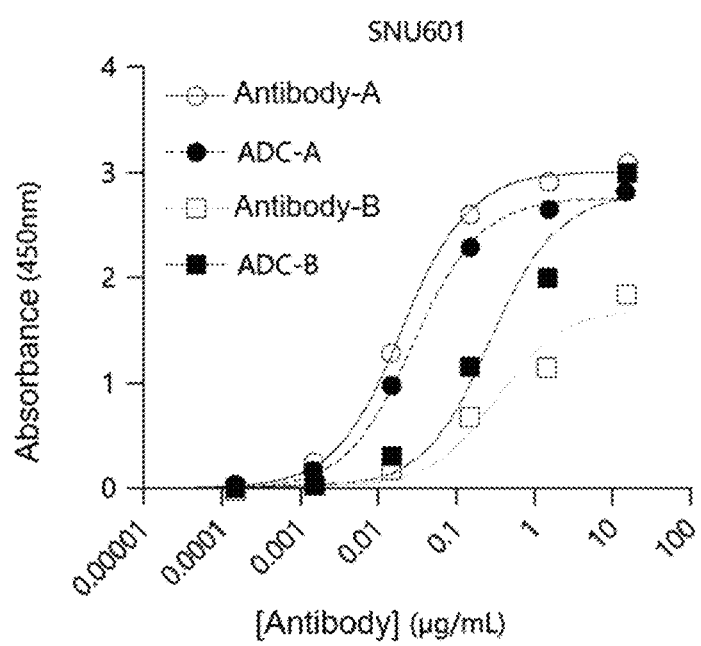
FIG. 39 is a graph showing the absorbance measured after treating antibody-A, ADC-A, antibody-B, and ADC-B respectively to SNU601 cell line.
Figure 40:
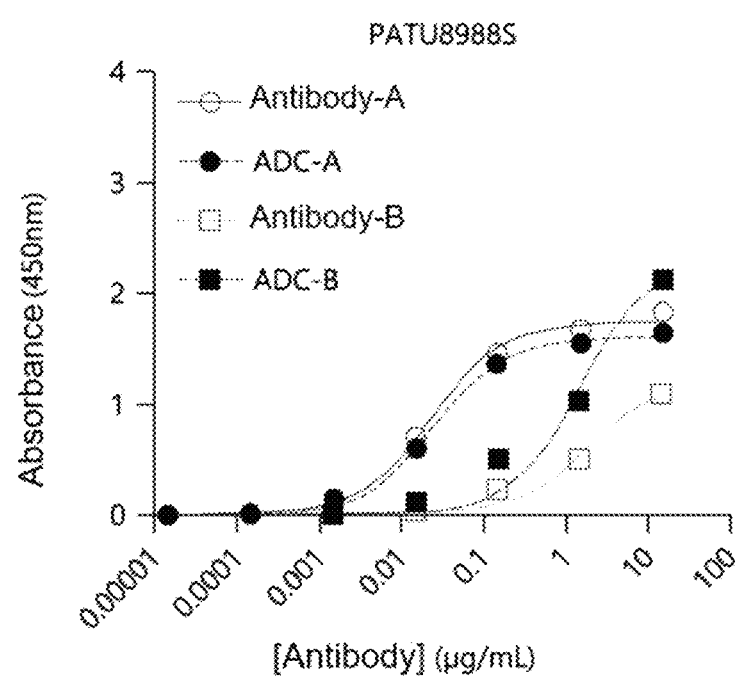
FIG. 40 is a graph showing the absorbance measured after treating antibody-A, ADC-A, antibody-B, and ADC-B, respectively to PATU8988S cell line.
Figure 41:
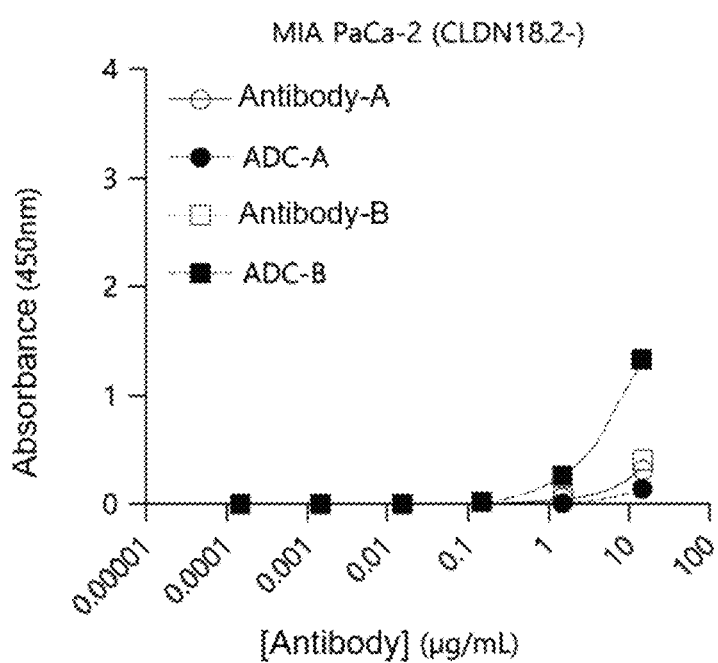
FIG. 41 is a graph showing the absorbance measured after treating antibody-A, ADC-A, antibody-B, and ADC-B, respectively to MIA PaCa-2 (CLDN18.2-) cell line.

Through FIG. 37 and Table 2, it can be confirmed that the binding strength of each test substance to the CLDN18.2 VLP was measured to be higher in the order of antibody-A, ADC-A, ADC-B, and antibody-B. These results mean that antibody-A and ADC-A have better binding strength to antigens than ADC-B and antibody-B.

TABLE 2

| | CLDN18.2 (antigen protein) | | | |
|---|---|---|---|---|
| Sample | Antibody-A | ADC-A | Antibody-B | ADC-B |
| Bmax | 3.229 | 2.995 | 2.134 | 2.869 |
| Kd | 0.03186 µg/ml | 0.05272 µg/ml | 0.02154 µg/ml | 0.1138 µg/ml |
| | 0.2124 nM | 0.3515 nM | 1.436 nM | 0.7587 nM |

Example 12.3 Target Specificity Verification 3—Confirmation of Binding to Antigen-Expressing Cancer Cells The inventors of the present application conducted an experiment according to Example 12.3.1 in order to confirm whether antibody-A and ADC-A can bind to cancer cells (CLDN18.2-positive cancer cells) expressing the claudin 18.2 protein (CLDN18.2), and the results are as described in Example 12.3.2.

Example 12.3.1 Experimental Method

Four types of cell lines (MIA PaCa-2-CLDN18.2, PATU8988S, parental MIA PaCa-2 (CLDN18.2-), and SNU601) were prepared. At this time, MIA PaCa-2-CLDN18.2 and PATU8988S are CLDN18.2-positive pancreatic cancer cell lines. MIA PaCa-2 (CLDN18.2-) is a CLDN18.2-negative pancreatic cancer cell line. SNU601 is a CLDN18.2-positive gastric cancer cell line.

The prepared cell lines were cultured in DMEM containing 10% FBS and 1% penicillin/streptomycin (MIA PaCa-2-CLDN18.2, MIA PaCa-2 (CLDN18.2-)), RPM11640 containing 10% FBS and 1% penicillin/streptomycin (SNU601), and DMEM comprising 5% FBS, 5% horse serum, 1% penicillin/streptomycin, and 2 mL L-glutamine (PATU8988S) in an incubator under the conditions of 37° C. and 5% C02.

The prepared cell lines were plated on 96-well culture plates, treated with antibody-A, ADC-A, antibody-B, and ADC-B, respectively, and then cell-based ELISA was performed, and OD values were measured. At this time, the measured values are illustrated in FIGS. 38 to 41.

The measured results were used for regression analysis in GraphPad PRISM® 9.0 software to calculate EC50 and Bmax. The cell binding strengths of antibody-A, ADC-A, antibody-B, and ADC-B to each cell line were evaluated based on the calculated values. At this time, the calculated values are listed in Table 3.

Example 12.3.2 Experimental Results

Through FIGS. 38 to 41 and Table 3, it can be seen that the binding strength to pancreatic cancer and gastric cancer cell lines was measured to be higher in the order of antibody-A, ADC-A, ADC-B, and antibody-B.

In addition, it was confirmed for all test substances (antibody-A, ADC-A, ADC-B, and antibody-B) that the binding strength was higher in the order of MIA PaCa-2-CLDN18.2, SNU601, and PATU8988S, and it was confirmed that all test substances did not bind to parental MIA PaCa-2, which is a CLDN 18.2-negative cell line. Such experimental results mean that the expression level of CLDN18.2 is higher in the order of MIAPaCa-2-CLDN18.2, SNU601, and PATU8988S.

TABLE 3

| | Antibody-A | | ADC-A | | Antibody-B | | ADC-B | |
|---|---|---|---|---|---|---|---|---|
| Sample | Kd | Bmax | Kd | Bmax | Kd | Bmax | Kd | Bmax |
| MIA PaCa-2 (CLDN18.2+) | 0.016 µg/ml 0.107 nM | 3.534 | 0.022 µg/ml 0.146 nM | 3.354 | 0.045 µg/ml 0.3 nM | 3.053 | 0.065 µg/ml 0.433 nM | 3.326 |
| SNU601 (CLDN18.2+) | 0.020 µg/ml 0.133 nM | 3.002 | 0.028 µg/ml 0.187 nM | 2.752 | 0.032 µg/ml 0.213 nM | 1.701 | 0.027 µg/ml 0.18 nM | 2.800 |
| PATU8988S (CLDN18.2+) | 0.23 µg/ml 0.153 nM | 1.743 | 0.026 µg/ml 0.173 nM | 1.607 | 1.87 µg/ml 12.467 nM | 1.214 | 1.57 µg/ml 10.467 nM | 2.326 |
| MIA PaCa-2 (CLDN18.2-) | — | — | — | — | — | — | — | — |

Example 12.4 Cellular Internalization Verification

The inventors of the present application conducted an experiment according to Example 12.4.1 in order to confirm the cellular internalization effect of ADC-A, and the results are as described in Example 12.4.2.

Example 12.4.1 Experimental Method

In order to confirm intracellular uptake (internalization) of antibody-A and ADC-A according to the presence or absence of CLDN18.2 expression, a MIA PaCa (CLDN18.2-) cell line which does not express CLDN18.2 and MIA PaCa-2-CLDN18.2 and SNU601 cell lines expressing CLDN18.2 were prepared.

The prepared cell lines were cultured in DMEM containing 10% FBS and 1% penicillin/streptomycin (MIA PaCa-2-CLDN18.2, MIA PaCa-2 (CLDN18.2-)) and RPM11640 containing 10% FBS and 1% penicillin/streptomycin (SNU601) in an incubator under the conditions of 37° C. and 5% CO₂. 96-well plates were plated with MIA PaCa (CLDN18.2-), MIA PaCa-2-CLDN18.2, and SNU601 cell lines at 3,000 to 5,000 cells/well.

Samples for internalization verification antibody-A and ADC-A were prepared according to the Incucyte® Fabfluor-pH reagent manual.

Finally, antibody-A and ADC-A were diluted to 8, 4, and 2 µg/mL, respectively, and were treated to designated wells 50 µL of each. The plates mixed with the sample were measured every hour using the Incucyte® Live-Cell Analysis System to measure the internalization levels. The measured values are illustrated in FIGS. 42 to 44.

Example 12.4.2 Experimental Results

Figure 42:
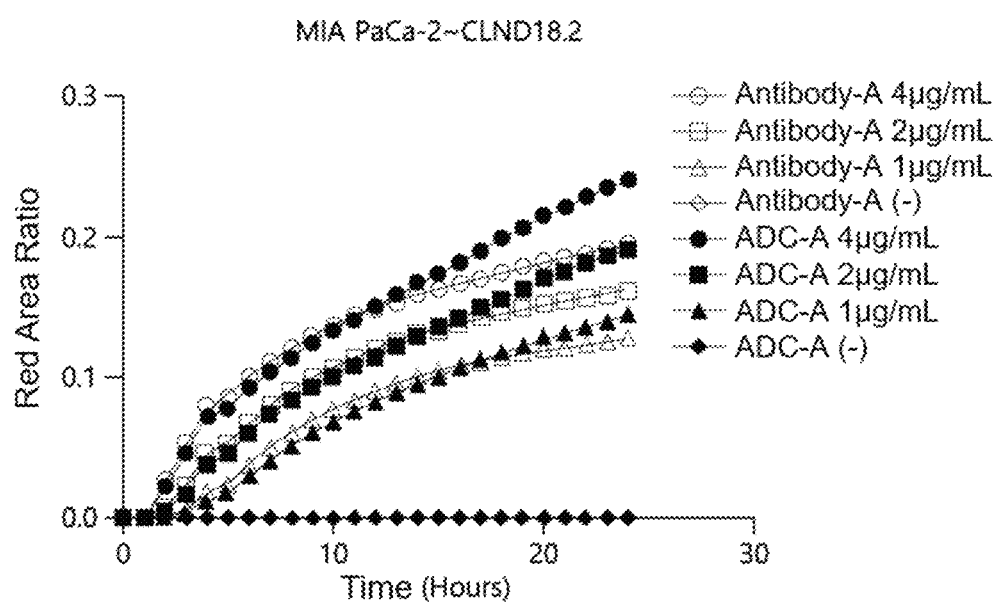
FIG. 42 is a graph showing the level of internalization measured every hour after MIA PaCa-2~CLDN18.2 cell line was treated with antibody-A and ADC-A, respectively. At this time, the proportion of the red area of the cell axis means the proportion of the area of antibody-A or ADC-A that has permeated into the cells (area measured as the red dot) in the total area occupied by the cells.
Figure 43:
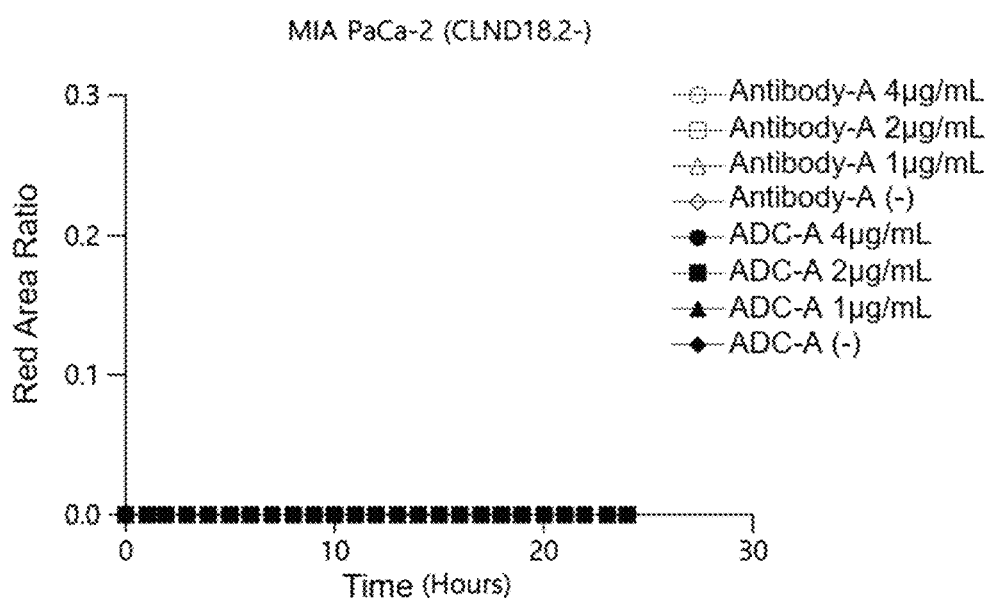
FIG. 43 is a graph showing the level of internalization measured every hour after MIA PaCa-2 (CLDN18.2-) cell line was treated with antibody-A and ADC-A, respectively. In this case, the proportion of the red area of the cell axis means the proportion of the area of antibody-A or ADC-A that has permeated into the cells (area measured as the red dot) in the total area occupied by the cells.
Figure 44:
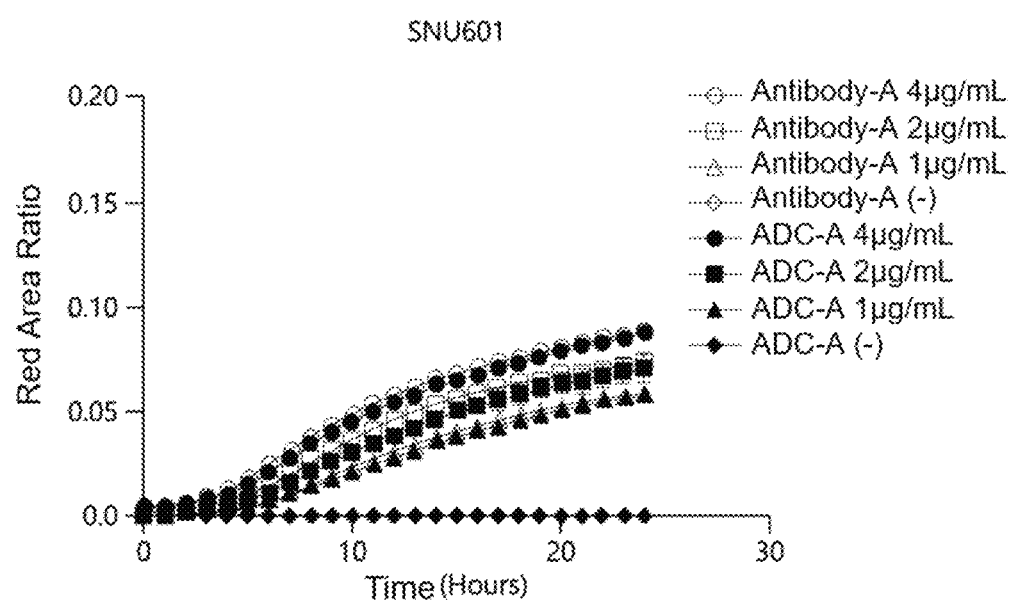
FIG. 44 is a graph showing the level of internalization measured every hour after SNU601 cell line was treated with antibody-A and ADC-A, respectively. At this time, the proportion of the red area of the cell axis means the proportion of the area of antibody-A or ADC-A that has permeated into the cells (area measured as the red dot) in the total area occupied by the cells.
Figure 45:
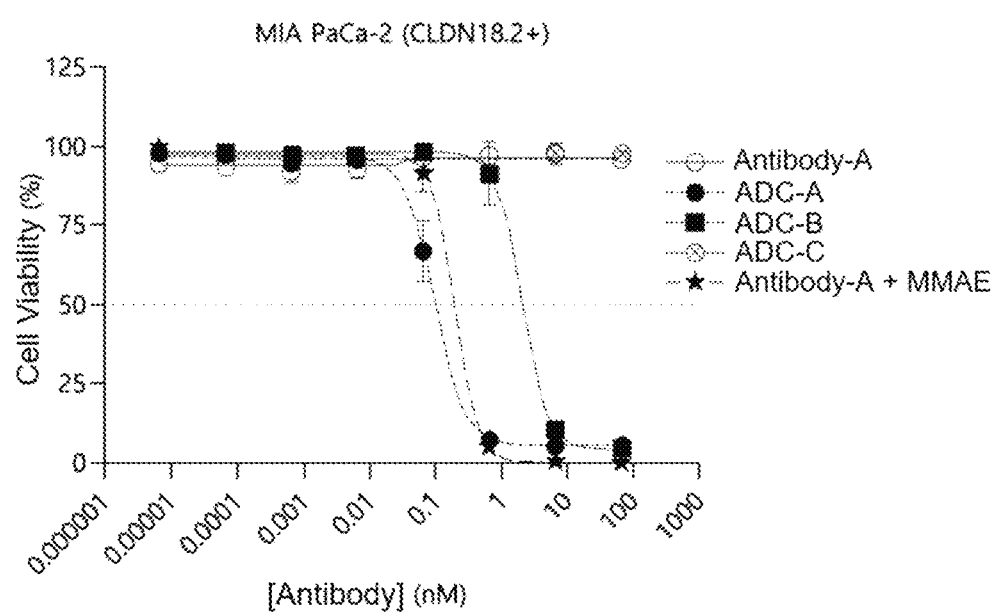
FIG. 45 is a graph showing the changes in cell viability after MIA PaCa-2~CLDN18.2 cell line was treated with antibody-A, ADC-A, antibody-B, ADC-B and a combination of antibody-A and MMAE at various concentrations.
Figure 46:
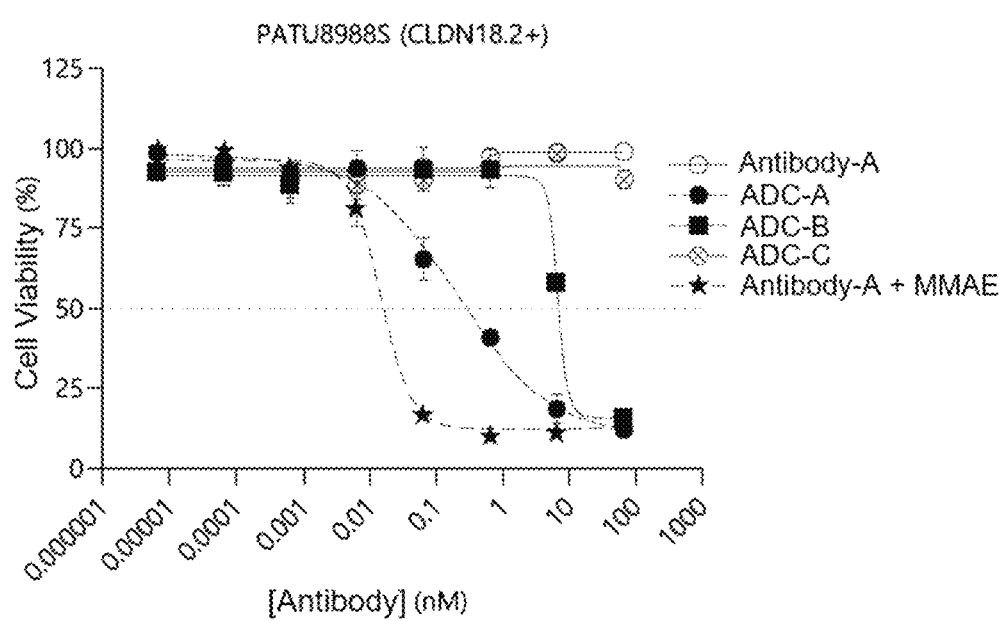
FIG. 46 is a graph showing the changes in cell viability after PATU8988S cell line was treated with antibody-A, ADC-A, antibody-B, ADC-B and a combination of antibody-A and MMAE at various concentrations.
Figure 47:
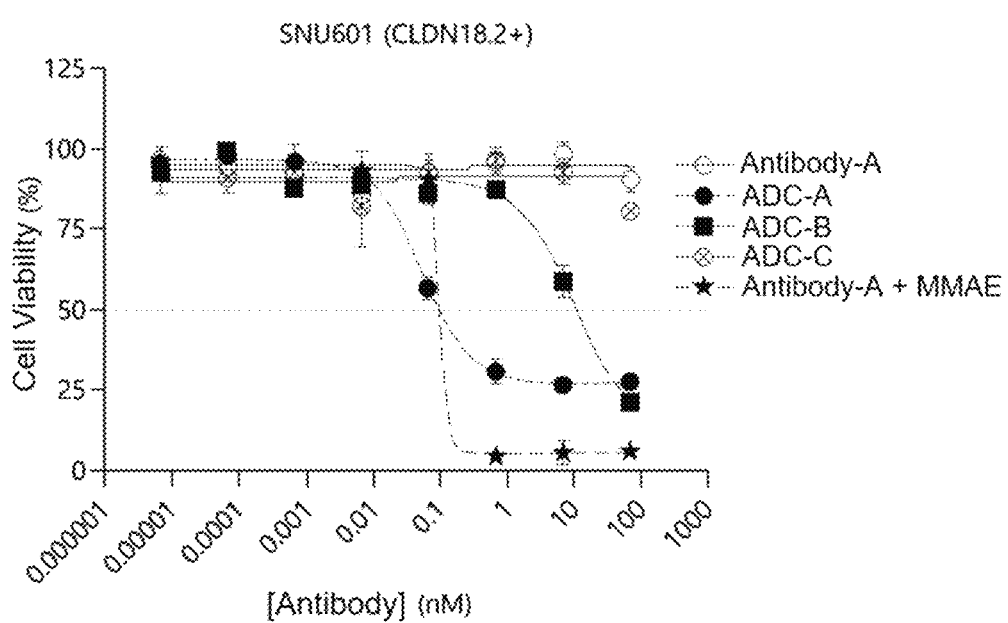
FIG. 47 is a graph showing the changes in cell viability after SNU601 cell line was treated with antibody-A, ADC-A, antibody-B, ADC-B and a combination of antibody-A and MMAE at various concentrations.
Figure 48:
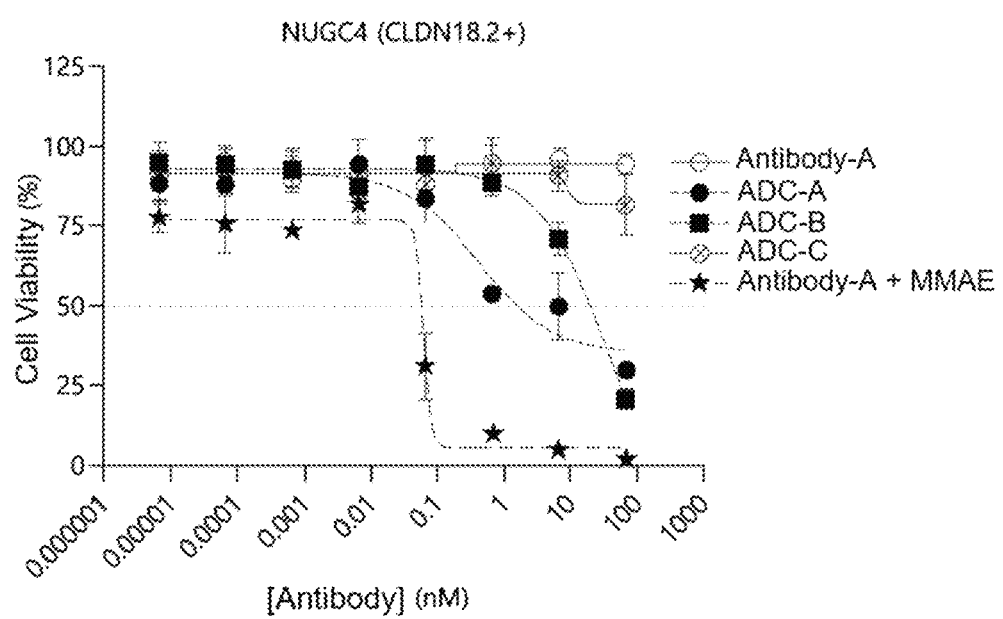
FIG. 48 is a graph showing the changes in cell viability after NUGC4 cell line was treated with antibody-A, ADC-A, antibody-B, ADC-B and a combination of antibody-A and MMAE at various concentrations.
Figure 49:
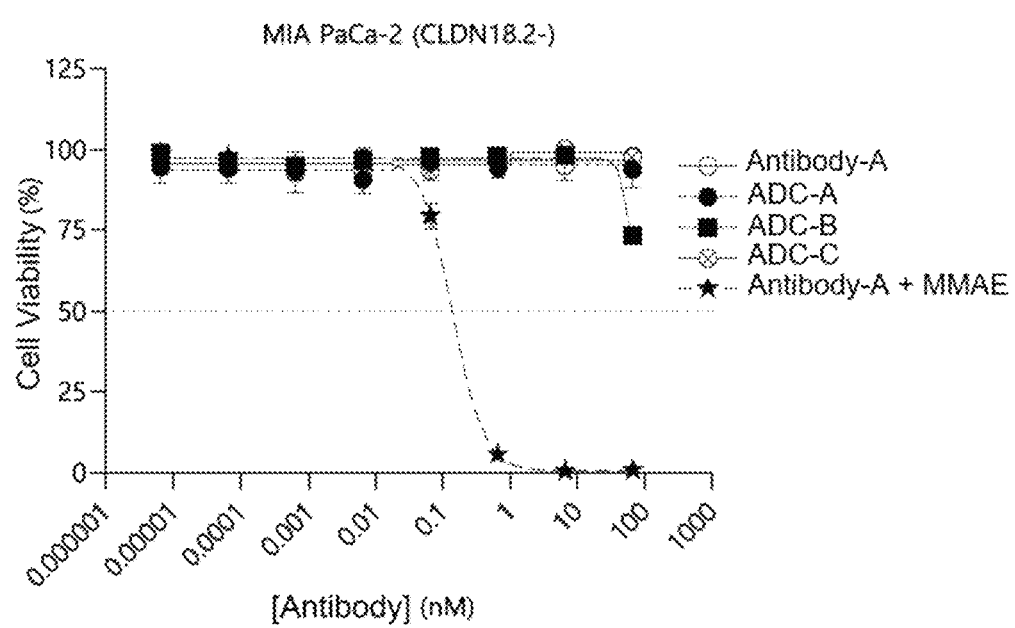
FIG. 49 is a graph showing the changes in cell viability after MIA PaCa-2 (CLDN18.2-) cell line was treated with antibody-A, ADC-A, antibody-B, ADC-B and a combination of antibody-A and MMAE at various concentrations.
Figure 50:
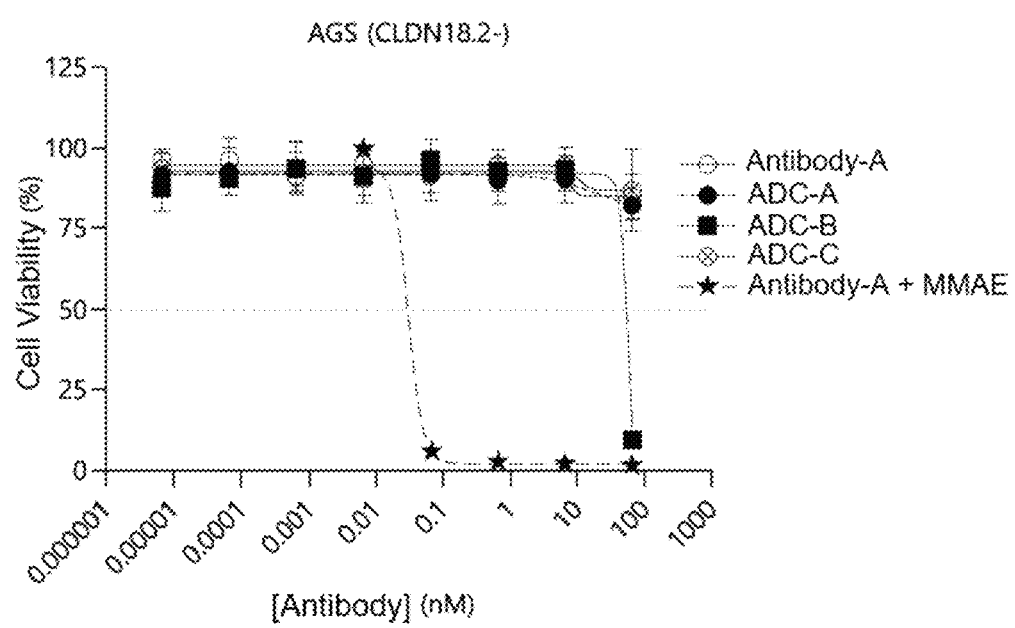
FIG. 50 is a graph showing the changes in cell viability after AGS cell line was treated with antibody-A, ADC-A, antibody-B, ADC-B and a combination of antibody-A and MMAE at various concentrations.
Figure 51:
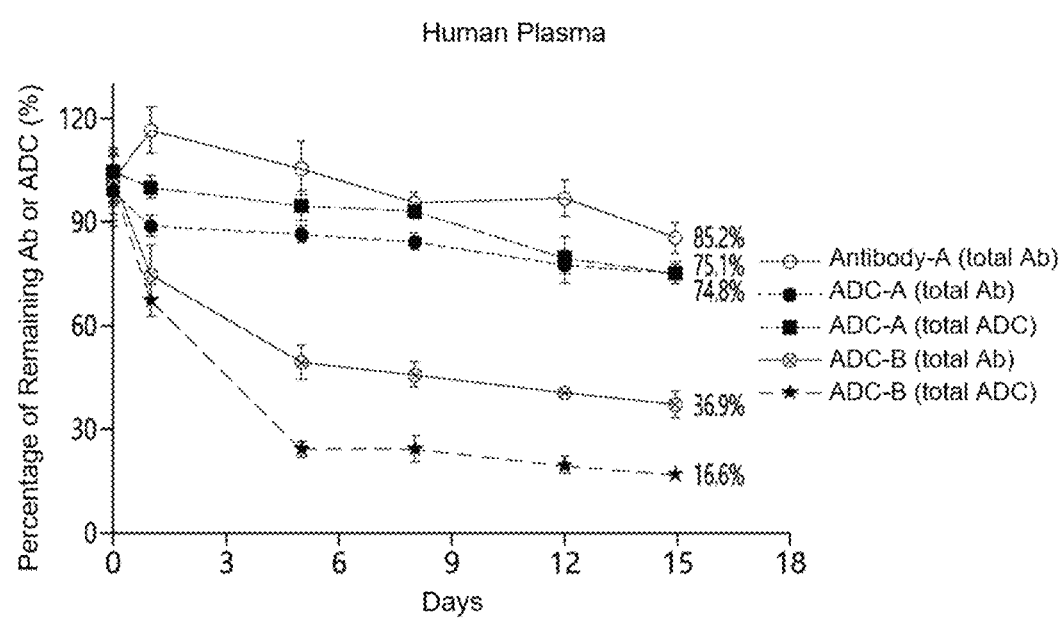
FIG. 51 is a graph showing the relative proportion of total antibodies or total ADC measured after human plasma was treated with antibody-A, ADC-A and ADC-B, respectively, and the supernatant was extracted from samples incubated for various periods of time.
Figure 52:
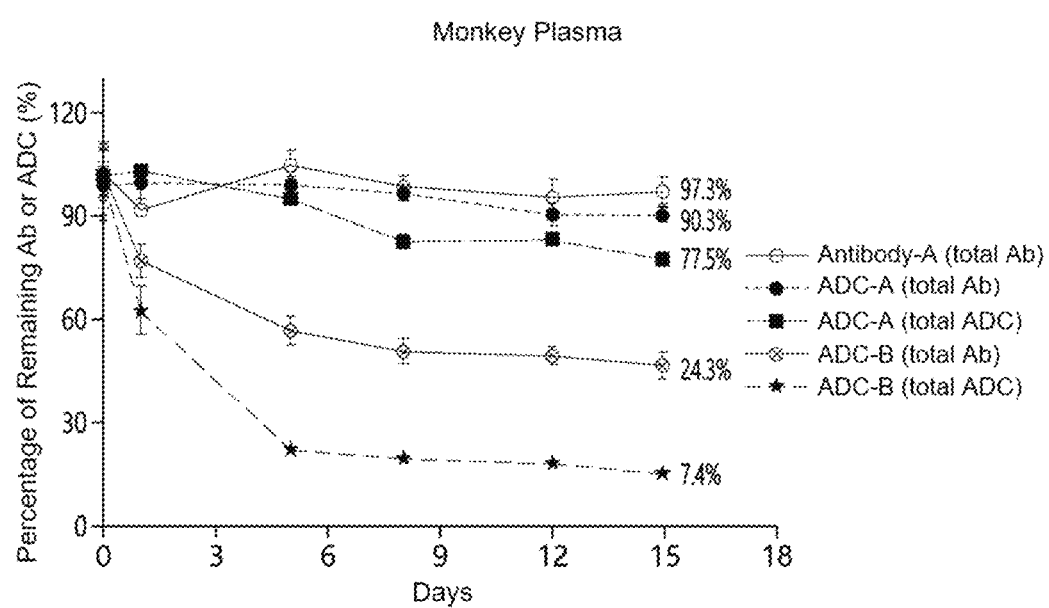
FIG. 52 is a graph showing the relative proportion of total antibodies or total ADC measured after monkey plasma was treated with antibody-A, ADC-A and ADC-B, respectively, and the supernatant was extracted from samples incubated for various periods of time.
Figure 53:
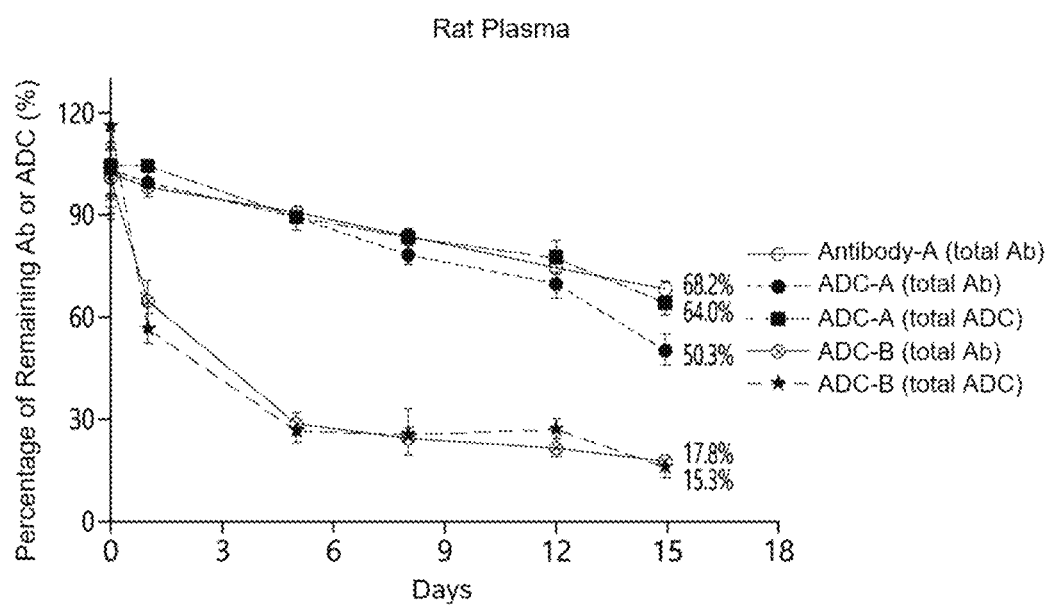
FIG. 53 is a graph showing the relative proportion of total antibodies or total ADC measured after rat plasma was treated with antibody-A, ADC-A and ADC-B, respectively, and the supernatant was extracted from samples incubated for various periods of time.
Figure 54:
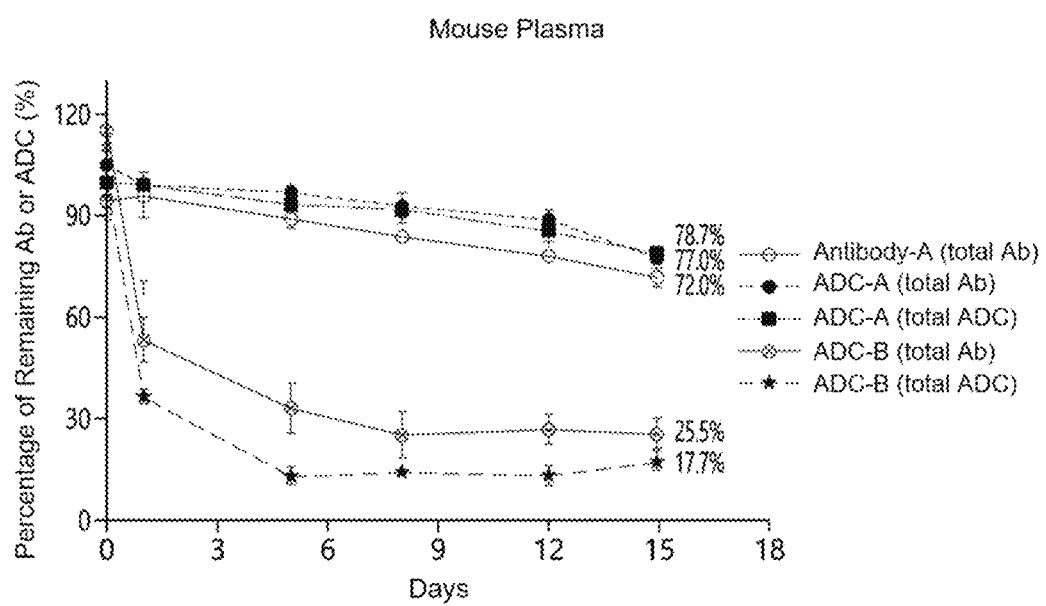
FIG. 54 is a graph showing the relative proportion of total antibodies or total ADC measured after mouse plasma was treated with antibody-A, ADC-A and ADC-B, respectively, and the supernatant was extracted from samples incubated for various periods of time.

Through FIGS. 42 to 44, it was confirmed that antibody-A and ADC-A were rapidly internalized in MIA PaCa-2-

CLDN18.2 and SNU601 cell lines expressing CLDN18.2 within 20 hours. In contrast, it was confirmed that antibody-A and ADC-A were not internalized in MIA PaCa-2 (CLDN18.2-), which does not express CLDN18.2. Further, antibody-A and ADC-A showed similar internalization efficiency at almost all concentrations. It was confirmed that a linker and a drug (payload) that make up ADC-A do not affect cell internalization compared to antibody-A, and internalization is determined by whether or not the antigen CLDN18.2 is expressed in the cell line.

Example 12.5 Cytotoxicity Evaluation

The inventors of the present application conducted an experiment according to Example 12.5.1 in order to evaluate the cytotoxicity of ADC-A, and the results are as described in Example 12.5.2.

Example 12.5.1 Experimental Method

Four types of cell lines (MIA PaCa-2-CLDN18.2, PATU8988S, parental MIA PaCa-2 (CLDN18.2-), SNU601, NUGC-4, and AGS) were prepared. MIA PaCa-2-CLDN18.2 and PATU8988S are CLDN18.2-positive pancreatic cancer cell lines. MIA PaCa-2 (CLDN18.2-) is a CLDN18.2-negative pancreatic cancer cell line. SNU601 and NUGC-4 are CLDN18.2-positive gastric cancer cell lines. AGS is a CLDN18.2-negative gastric cancer cell line.

The prepared cell lines were cultured in DMEM comprising 10% FBS and 1% penicillin/streptomycin (MIA PaCa-2-CLDN18.2, and MIA PaCa-2 (CLDN18.2-)), RPM11640 containing 10% FBS and 1% penicillin/streptomycin (SNU601, NUGC-4, and AGS), and DMEM comprising 5% FBS, 5% horse serum, 1% penicillin/streptomycin, and 2 mL L-glutamine (PATU8988S) in an incubator under the conditions of 37° C. and 5% $CO_2$.

96-well plate for cultures were plated with the prepared cell lines at 500 to 5,000 cells/well, and then treated with each test substance (antibody-A, ADC-C, ADC-A, antibody-B, ADC-C, and a combination of antibody-A and MMAE) serially diluted 10-fold (10000, 1000, 100, 10, 1, 0.1, 0.01, 0.001, and 0 ng/mL). At this time, the combination of antibody-A and MMAE means that antibody-A and MMAE are co-treated, and the concentration of MMAE is the same molar concentration as MMAE included in other ADCs (for example, ADC-A).

Changes in cell viability according to treatment of each test substance were measured using a method which is the same as the CellTiter-Glo manual. At this time, the measured values are illustrated in FIGS. 45 to 50.

The measured results were used for regression analysis in GraphPad PRISM® 9.0 software to calculate IC50. The cytotoxicity of each test substance was evaluated based on the calculated values. At this time, the calculated values are listed in Table 4.

Example 12.5.2 Experimental Results

Through FIGS. 45 to 50 and Table 4, it was confirmed that ADC-A exhibited anticancer activity in CLDN18.2-positive cancer cell lines regardless of cancer type. Furthermore, it was confirmed that the IC50 value of ADC-A was 10 to 35-fold lower than that of ADC-B, which is a control. In particular, in the MIA PaCa-2-CLDN18.2 cell line, ADC-A showed a lower IC50 than the antibody-A and MMAE co-administration group, and PATU8988S and SNU601 also showed an IC50 of 1 nM or less. Furthermore, in the CLDN18.2-negative cell lines, it was confirmed that ADC-A had almost no toxicity up to the highest treatment concentration, but ADC-B, the control group, was observed to be toxic.

TABLE 4

| Cell Line | MIA PaCa-2 (CLDN18.2+) | PATU8988S (CLDN18.2+) | SNU601 (CLDN18.2+) | NUGC4 (CLDN18.2+) | MIA PaCa-2 (CLDN18.2-) | AGS (CLDN18.2-) |
|---|---|---|---|---|---|---|
| Disease | pancreatic cancer | pancreatic cancer | gastric cancer | gastric cancer | pancreatic cancer | gastric cancer |
| Analyzed Value | | | $IC_{50}$ (nM) | | | |
| Antibody-A | —* | — | — | — | — | — |
| ADC-C | — | — | — | — | — | — |
| ADC-A | 0.1009 | 0.2785 | 0.0950 | 1.595 | — | — |
| ADC-B | 2.121 | 7.194 | 10.42 | 20.01 | — | 54.31 |
| Antibody-A + MMAE** | 0.1955 | 0.0167 | 0.0971 | 0.0580 | 0.1416 | 0.0302 |

*$IC_{50}$ value cannot be derived.

Example 12.6 Plasma Stability Evaluation

The inventors of the present application conducted an experiment according to Example 12.6.1 in order to evaluate the plasma stability of ADC-A, and the results are as described in Example 12.6.2.

Example 12.6.1 Experimental Method

Human, monkey, rat, and mouse plasma were prepared. After the prepared plasma was treated with the test substances (antibody-A, ADC-A and ADC-B), the plasma was incubated at a temperature of 37° C. for 5 minutes, 1 day, 5 days, 8 days, 12 days and 15 days (a total of 108 samples were prepared).

Only the supernatant was taken from the prepared samples using a centrifuge each time, and this was used for analysis. The plasma stability of the test substances over time was confirmed by ELISA analysis. After an ELISA plate was coated with CLDN18.2 virus-like particles (VLPs), plasma was diluted 5000-fold and the ELISA plate was treated with the diluted plasma, and then treated with antibody-A, ADC-A, and ADC-B, respectively. An anti-human IgG antibody (Promega, W4031) was used to analyze the amount of total antibodies (total Ab), and an anti-MMAE antibody (an antibody produced in-house through ABFRONTIER) was used to analyze the amount of total ADC. At this time, total Ab comprises not only an antibody to which a linker is not conjugated, such as antibody-A, but also a substance to which a linker is conjugated, such as ADC-A. A total ADC comprises only a substance such as ADC-A or ADC-B to which a linker is conjugated and does not comprise an antibody to which a linker is not conjugated. For example, a case where the linker is cleaved in ADC-A is not included in total ADC.

The amount of total antibodies or total ADC over time was converted into a relative proportion based on day 0 (5 minutes). The converted results are illustrated in FIGS. 51 to 54.

Example 12.6.2 Experimental Results

The following results can be seen from FIGS. 51 to 54.

For 15 days in human plasma, the total Ab for antibody-A was maintained at 85.2%, the total Ab for ADC-A was maintained at 74.8%, the total ADC for ADC-A was maintained at 75.1%, the total antibody for ADC-B was maintained at 36.9%, and the total ADC for ADC-B was maintained at 16.6%.

For 15 days in monkey plasma, the total Ab for antibody-A was maintained at 97.3%, the total Ab for ADC-A was maintained at 90.3%, the total ADC for ADC-A was maintained at 77.5%, the total Ab for ADC-B was maintained at 24.3%, and the total ADC for ADC-B was maintained at 7.4%.

For 15 days in rat plasma, the total Ab for antibody-A was maintained at 68.2%, the total Ab for ADC-A was maintained at 64.0%, the total ADC for ADC-A was maintained at 50.3%, the total Ab for ADC-B was maintained at 17.8%, and the total ADC for ADC-B was maintained at 15.3%.

For 15 days in mouse plasma, the total Ab for antibody-A was maintained at 72.0%, the total Ab for ADC-A was maintained at 78.7%, the total ADC for ADC-A was maintained at 77.0%, the total Ab for ADC-B was maintained at 25.5%, and the total ADC for ADC-B was maintained at 17.7%.

The stability of antibody-A and ADC-A in plasma showed similar levels and trends in all types of plasma for 15 days. In contrast, the total Ab and the total ADC for ADC-B showed a pattern of a rapid decrease over time. Since ADC-A showed the same values as antibody-A in plasma over time, it may be interpreted that phenomena such as aggregation or degradation, according to a linker and drug conjugated to the antibody, do not occur in ADC-A. Therefore, it can be seen that ADC-A exhibits stability comparable to that of an antibody in in vitro plasma, and that the linker and drug conjugated to the antibody in ADC-A do not affect the stability of ADC.

Example 12.7 Evaluation of In Vivo Drug Efficacy

The inventors of the present application conducted experiments according to Examples 12.7.1 to 12.7.4 in order to evaluate the in vivo efficacy of ADC-A, and the results are as described in Example 12.7.5.

Example 12.7.1 Cell Culture

The SNU601 cell line, which is a CLDN18.2-positive gastric cancer cell line, was cultured in an RPMI culture solution containing 10% FBS and 1% penicillin/streptomycin in an incubator under the conditions of 37° C. and 5% $CO_2$. The SNU601 cell line was regularly subcultured once a week through trypsin-EDTA treatment.

Example 12.7.2 Tumor Inoculation and Drug Administration

For tumor development, an SNU601 cell line ($1 \times 10^7$) was mixed with serum-free medium and Matrigel and the resulting mixture was inoculated subcutaneously into the left flank of each BALB/c nude mouse (purchased from Charles River Laboratories Japan Inc.). Each mouse was randomly assigned to eight groups (G1 to G8) on the basis that the average tumor volume in each group reached about 155 $mm^3$. Thereafter, drugs were administered to each group as shown in Table 5.

TABLE 5

| Group | Treatment | Drug dosage (mg/kg) | Number of administrations and timing | Administration Route | Number of mice (n) |
|---|---|---|---|---|---|
| G1 | Saline solution | — | 1 time/Day1 | Intravenous Injection | 8 |
| G2 | Antibody-A | 2 | 1 time/Day1 | Intravenous Injection | 8 |
| G3 | ADC-C | 1 | 1 time/Day1 | Intravenous Injection | 8 |
| G4 | ADC-A | 1 | 1 time/Day1 | Intravenous Injection | 8 |
| G5 | ADC-A | 1 | 2 times/Day1, Day7 | Intravenous Injection | 8 |
| G6 | ADC-A | 1.5 | 1 time/Day1 | Intravenous Injection | 8 |
| G7 | ADC-A | 1.75 | 1 time/Day1 | Intravenous Injection | 8 |
| G8 | ADC-A | 2 | 1 time/Day1 | Intravenous Injection | 8 |

Example 12.7.3 Observation and Measurement of Tumors

All animals were observed twice a day for mortality, abnormal symptoms, pain and signs of stress, and once a day for clinical signs. The change in body weight and the tumor volume were measured three times a week, and the tumor weight was determined after autopsy.

The tumor volume, tumor difference, and tumor growth inhibition were calculated as follows:

Tumor volume $(mm^3)$ = (Length of major axis × length of minor $axis^2$)/2

Tumor difference, % = $\left(\text{Tumor weight}_{test\ group} - \text{Tumor weight}_{control\ (G1)}\right)$ /Tumor weight$_{control\ (G1)}) \times 100$ Tumor growth inhibition (%) =

$100 - \left(\left((T_f/T_i)_{test\ group}\right)/\left((T_f/T_i)_{control}\right)\right) \times 100.$ $T_f$ is the last tumor volume measured before autopsy, and $T_i$ is the first tumor volume measured.

Figure 55:
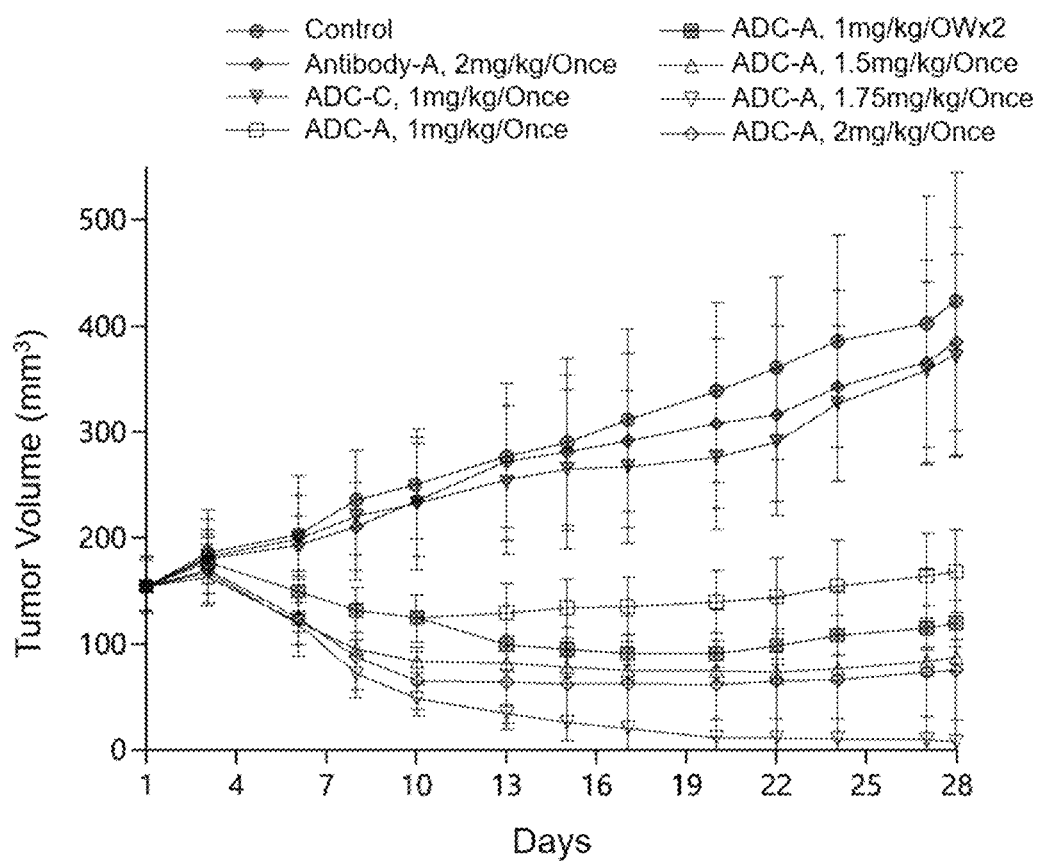
FIG. 55 is a graph showing the tumor volume measured after antibody-A, ADC-A, and ADC-C were intravenously injected into tumor model mice under various conditions (G1 to G8 groups), respectively.
Figure 56:
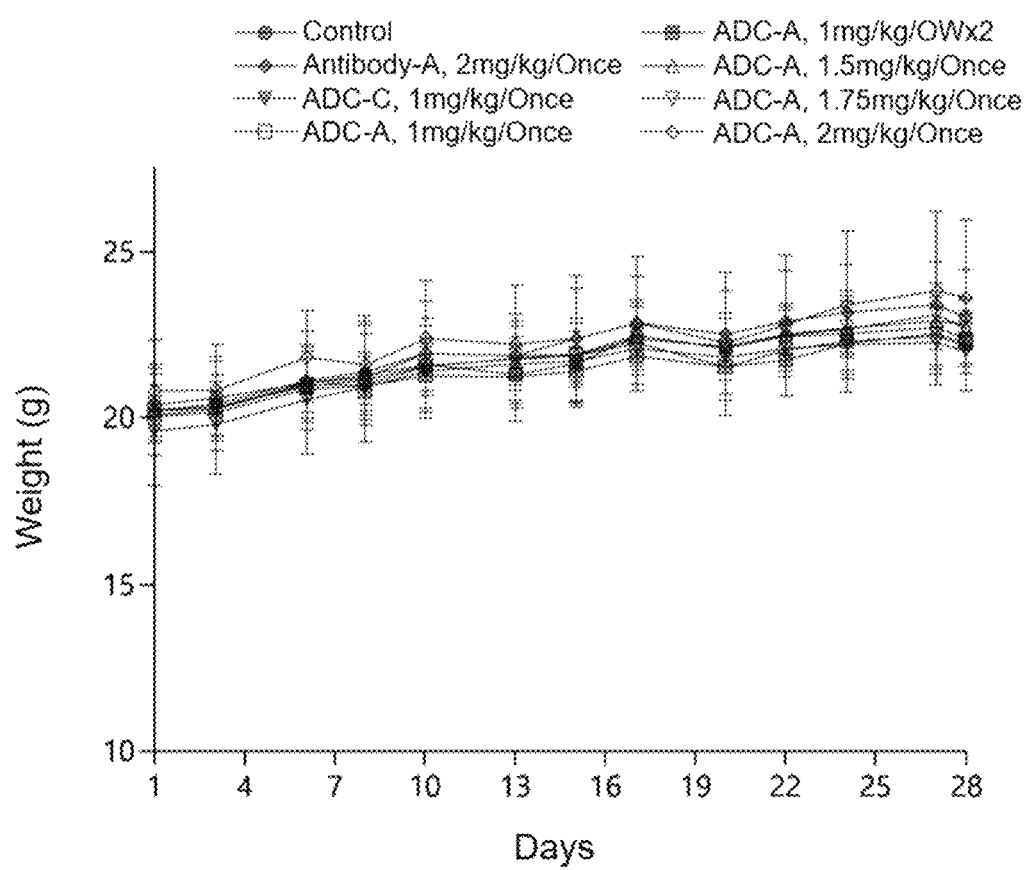
FIG. 56 is a graph showing the body weight measured after antibody-A, ADC-A, and ADC-C were intravenously injected into tumor model mice under various conditions (G1 to G8 groups), respectively.
Figure 57:
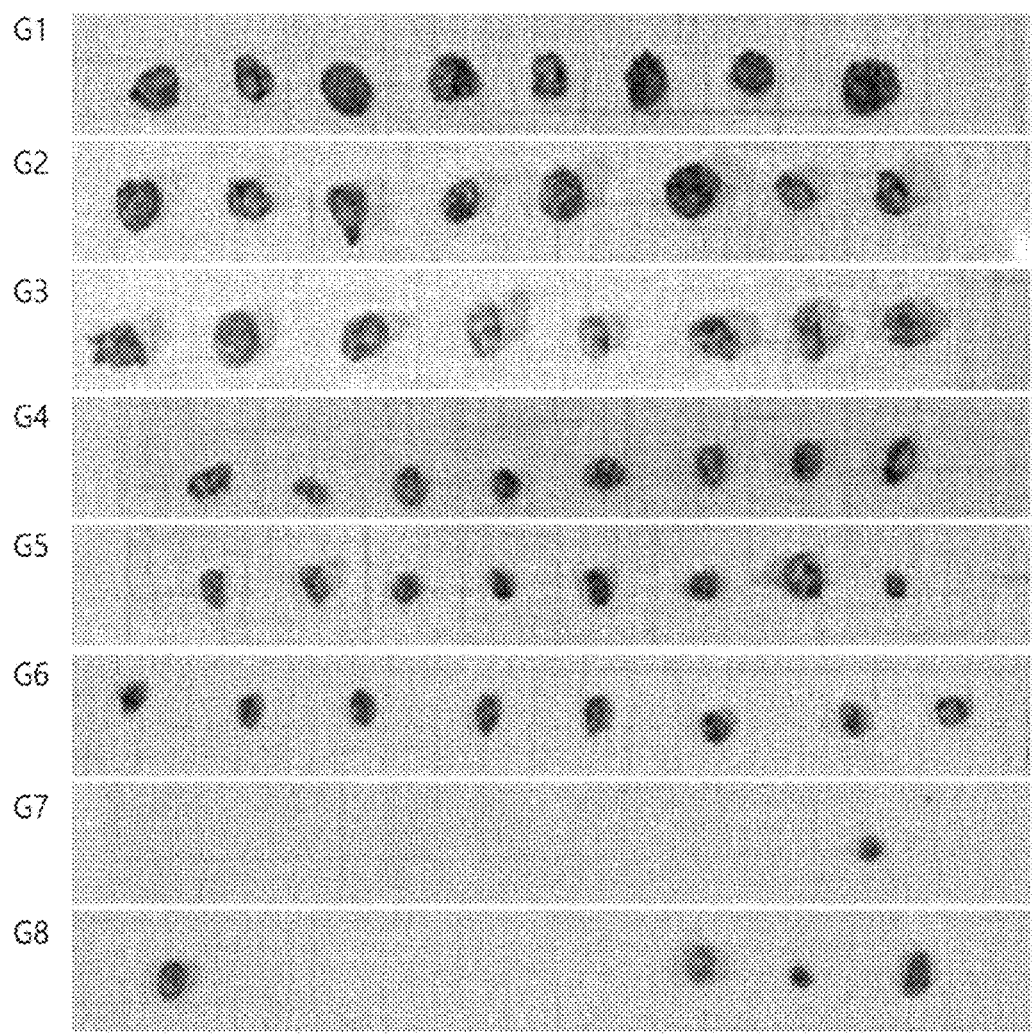
FIG. 57 shows a comparative photograph of tumors autopsied 28 days after antibody-A, ADC-A, and ADC-C were intravenously injected into tumor model mice under various conditions (G1 to G8 groups), respectively.
Figure 58:
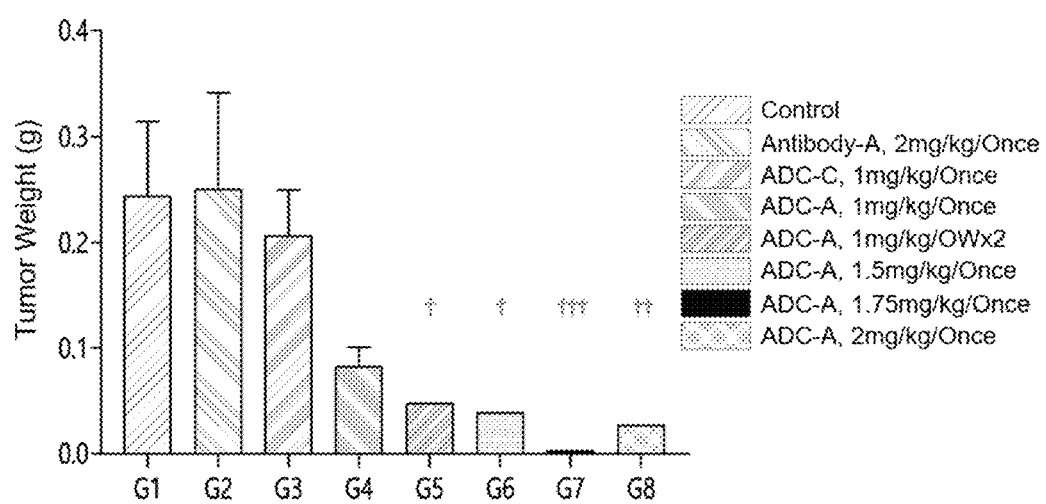
FIG. 58 is a graph showing that the weights of tumors autopsied 28 days after antibody-A, ADC-A, and ADC-C were intravenously injected into tumor model mice under various conditions (G1 to G8 groups), respectively.

At this time, the measured tumor volumes are illustrated in FIG. 55. The measured body weights are illustrated in FIG. 56. The shape of the tumors after autopsy was the same as that in FIG. 57. The tumor weights determined after autopsy is illustrated in FIG. 58.

Example 12.7.4 Statistical Analysis

Numerical data regarding the performance of the study was calculated as mean and standard deviation. Group variances were compared using the Bartlett's test at a 0.05 significance level for each parameter. When the difference between group variances was not significant, a parametric one-way analysis of variance (ANOVA) was performed. When a significant difference between means was indicated by ANOVA (p≤0.05), group mean comparisons between the control and each treatment group were performed using Dunnett's test. All considered groups were compared using the non-parametric Kruskal-Wallis test whenever the Bartlett's test showed a heterogeneous group variance (p≤0.05). When significance was identified by the Kruskal-Wallis test (p≤0.05), the significance of the difference between the control and each treatment group was assessed using the Dunn's multiple comparison test. Significance was reported at the 0.05, 0.01 and 0.001 levels for the comparison of each group. All statistical analyses were performed using Graph-Pad PRISM® Version 5.0.

Example 12.7.5 Experimental Results

No unscheduled deaths were observed during the study period.

There were no effects associated with test substances (antibody-A, ADC-A and ADC-C) on the changes in body weight during the study period. The average change in the body weight of each group is shown in Table 6 and FIG. 56.

TABLE 6

| Group | Weight (g) (Average ± Standard Deviation) | |
|---|---|---|
| | Day 1 | Day 28 |
| G1 | 20.4 ± 1.2 | 22.4 ± 1.1 |
| G2 | 20.2 ± 1.3 | 23.0 ± 1.5 |
| G3 | 19.6 ± 1.7 | 22.0 ± 1.2 |
| G4 | 20.2 ± 0.8 | 22.2 ± 0.9 |
| G5 | 20.0 ± 1.0 | 22.3 ± 0.7 |
| G6 | 20.1 ± 0.6 | 22.8 ± 1.0 |
| G7 | 20.4 ± 1.2 | 22.6 ± 1.0 |
| G8 | 20.8 ± 1.5 | 23.6 ± 2.3 |

On day 28, it was confirmed that the average tumor volumes in groups G7 and G8 were statistically significantly lower than that in the control. The average tumor volume and tumor growth inhibition of each group during the study period are shown in Table 7 and FIG. 55. The average tumor weight after autopsy in each group is shown in Table 8 and FIG. 58.

TABLE 7

| Group | Tumor Volume (mm$^3$) (Average ± Standard Deviation) | | | | | TGI* (%) |
|---|---|---|---|---|---|---|
| | Day 1 | Day 8 | Day 15 | Day 22 | Day 28 | Day 28 |
| G1 | 155.6 ± 26.6 | 234.0 ± 50.2 | 290.3 ± 79.0 | 359.8 ± 85.9 | 423.0 ± 122.0 | — |
| G2 | 155.8 ± 26.3 | 211.3 ± 41.7 | 280.4 ± 73.3 | 316.8 ± 82.7 | 384.3 ± 108.2 | 9.3 |
| G3 | 155.8 ± 26.1 | 220.7 ± 61.6 | 264.3 ± 74.8 | 289.8 ± 68.3 | 372.1 ± 94.8 | 12.2 |

TABLE 7-continued

| Group | Tumor Volume (mm$^3$) (Average ± Standard Deviation) | | | | | TGI* (%) |
|---|---|---|---|---|---|---|
| | Day 1 | Day 8 | Day 15 | Day 22 | Day 28 | Day 28 |
| G4 | 155.9 ± 25.5 | 131.7 ± 21.4 | 132.8 ± 28.1 | 145.0 ± 36.7 | 169.2 ± 39.4 | 60.1 |
| G5 | 155.7 ± 25.2 | 132.1 ± 19.9 | 95.3 ± 25.7 | 97.7 ± 47.8 | 119.3 ± 60.6 | 71.8 |
| G6 | 155.2 ± 24.2 | 95.6 ± 20.3 † | 78.8 ± 29.7 | 73.8 ± 33.4 | 87.7 ± 42.0 | 79.2 |
| G7 | 155.2 ± 24.5 | 72.8 ± 15.4 ††† | 26.5 ± 6.9 ††† | 11.1 ± 18.5 ††† | 7.3 ± 20.5 ††† | 98.3 |
| G8 | 155.9 ± 24.5 | 88.0 ± 38.9 †† | 62.2 ± 53.2 †† | 66.2 ± 76.5 | 75.2 ± 100.9 † | 82.2 |

TGI: Tumor Growth Inhibition
†: P < 0.05;
††: P < 0.01;
†††: P < 0.001. vs G1.
Significance was calculated by the Kruskal-Wallis test and the Dunn's multiple comparison test.

TABLE 8

| Group | Tumor Weight (g) (Average ± Standard Deviation) 28th day after first administration |
|---|---|
| G1 | 0.243 ± 0.070 |
| G2 | 0.250 ± 0.092 |
| G3 | 0.205 ± 0.044 |
| G4 | 0.082 ± 0.020 |
| G5 | 0.047 ± 0.033 † |
| G6 | 0.038 ± 0.012 † |
| G7 | 0.002 ± 0.006 ††† |
| G8 | 0.027 ± 0.035 †† |

†: P < 0.05;
††: P < 0.01;
†††: P < 0.001. vs G1.

Significance was calculated by the Kruskal-Wallis test and the Dunn's multiple comparison test.

In this example, an SNU601 gastric cancer tumor model was created using BALB/c nude mice, and the anticancer efficacy of antibody-A, ADC-A, and ADC-C was evaluated. In all ADC-A treatment groups, tumor volumes were measured to be lower than the control, and the tumor growth inhibition (TGI) was measured to be 60.1 to 98.3%. In particular, when ADC-A was administered at 1.75 mg/kg (G7), TGI was 98.3%, showing a very strong anticancer effect.

No unscheduled deaths occurred in any of the animals, and no significant changes in the change in body weight were observed. The histological gastric lesions associated with the antibody-A and ADC-A administration groups were not observed even in the highest concentration administration group, G8. In conclusion, ADC-A showed high anti-cancer efficacy in a gastric cancer model without weight loss or histological gastric lesions.

Example 12.8 Pharmacokinetics Evaluation

The inventors of the present application conducted an experiment according to Example 12.8.1 in order to evaluate the pharmacokinetics of ADC-A, and the results are as described in Example 12.8.2.

Example 12.8.1 Experimental Method

Figure 59:
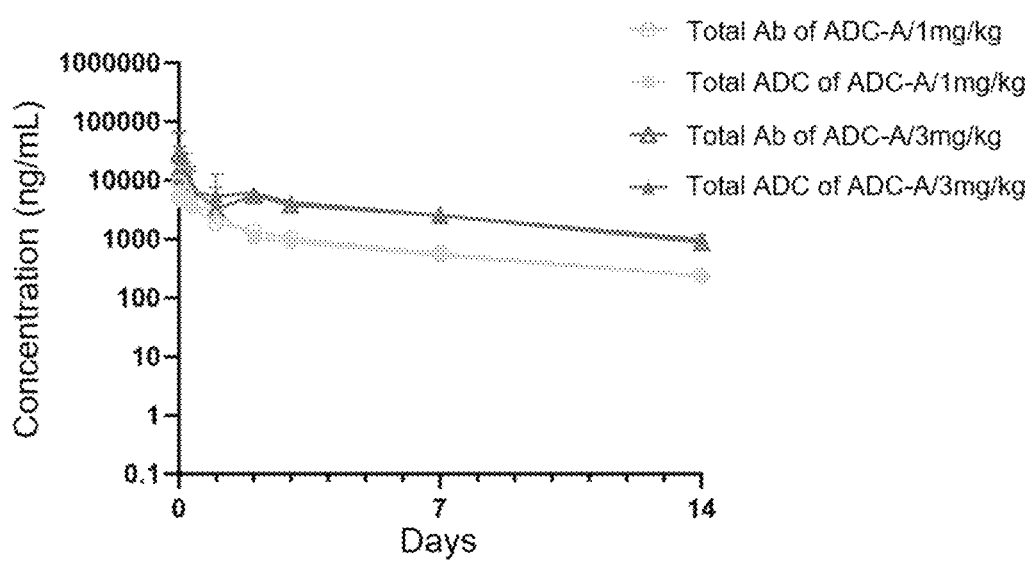
FIG. 59 is a graph showing the concentrations of total antibody and total ADC measured after a certain period of time after ADC-A was intravenously administered to rats at various concentrations.

After a single administration of ADC-A at doses of 1 and 3 mg/kg to rats (purchased from SAMTAKO Bio Korea Co., Ltd.) through the tail vein, blood was collected for a certain period of time and analyzed to compare and evaluate the pharmacokinetic profile. The supernatant was obtained from the plasma using a centrifuge, and the concentration of ADC-A in the plasma was analyzed using the ELISA method. Parameters were calculated by performing pharmacokinetic analysis in a non-compartmental manner using Phoenix® WinNonlin® software. The calculated values are illustrated in FIG. 59.

Example 12.8.2 Experimental Results

As a result of a single intravenous administration of the test substance to rats, it could be confirmed that all animals were exposed to the test substance, and the pharmacokinetic profile according to the administered dose was evaluated. After a single intravenous administration of ADC-A to rats at doses of 1 and 3 mg/kg, as a result of measuring the concentration of total antibodies (total Ab) in blood, the half-life (t1/2) was determined to be 4.5 and 4.7 days, and the total clearance was determined to be 2.9 and 2.8 mL/hr/kg, respectively. As a result of measuring the concentration of total ADC, the half-life (t1/2) was determined to be 5.2 and 4.9 days, and the total clearance was determined to be 3.0 and 2.5 mL/hr/kg, respectively. Through the corresponding analysis, it was confirmed that the blood concentrations of total Ab and total ADC for ADC-A over time were similar.

What is claimed is:

1. A compound comprising Fc binding unit having a structure of formula 2-2:

[formula 2-2]

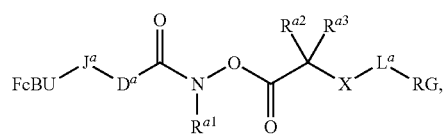

wherein,

D$^a$ is a spacer A, wherein the spacer A is unsubstituted C$_3$ alkylene,

L$^a$ is linker A, wherein the linker A is a bond, unsubstituted C$_{1-30}$ alkylene, or unsubstituted C$_{1-30}$ heteroalkylene, wherein the heteroalkylene comprises one or more heteroatoms, and wherein each of heteroatoms is independently selected from N, O, and S, X is —CH$_2$— or —O—, R$^{a1}$ is methyl, both of R$^{a2}$ and R$^{a3}$ are H, J$^a$ is —C(═O)—, RG is a reactive group, wherein the reactive group has one of the following structures:

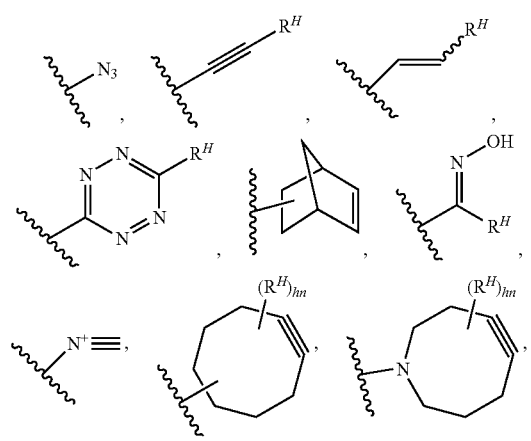

wherein, hn is integer of 1 to 3, and each of RH is independently selected from —R, ═O, ═S, —NO$_2$, —CR$_3$, —NR$_2$, ═NR, —OR, —SR, —C(═O)R, —C(═O)CR$_3$, —C(═O) OR, and —C(═O)NR$_2$, wherein each of R is independently selected from H, halogen, C$_{1-6}$alkyl, C$_{3-10}$ cycloalkyl, C$_{3-10}$ heterocycloalkyl, aryl, heteroaryl, —OH, —NH$_2$, —COOH, ═O, ═S, and —SH, and FcBU is a Fc binding unit, wherein the Fc binding unit consists of a Fc binding peptide or a modified Fc binding peptide, wherein the Fc binding peptide has the following structure:

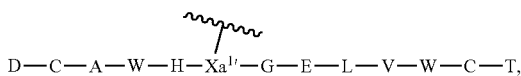

D—C—A—W—H—Xa$^{1'}$—G—E—L—V—W—C—T, wherein Xa$^{1'}$ is

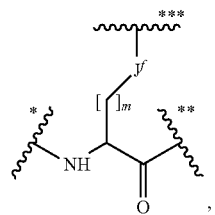

wherein,
m is 3,
J$^f$ is —NH—,
each of * and ** indicates an attachment point of Xa$^{1'}$ with the amino acid residue adjacent to Xa$^{1'}$, and
*** indicates an attachment point with J$^a$, and
wherein two cysteine residues of the Fc binding peptide are optionally covalently linked to each other, and
wherein the modified Fc binding peptide is a peptide which is modified by modifying the Fc binding peptide by at least one of followings:
a) amidation of C terminal of the Fc binding peptide, and
b) conjugation of a polyethylene glycol moiety (PEG moiety) to N terminal of the Fc binding peptide.

2. The compound of claim 1, wherein the reactive group is azide group, norbornene group, or Dibenzocyclooctyne (DBCO).

3. The compound of claim 1, wherein the reactive group is azide group.

4. The compound of claim 1, wherein the linker A is -L$^{a1}$-L$^{a2}$-L$^{a3}$-,
wherein L$^{a1}$ is a bond or unsubstituted C$_{1-10}$ alkylene,
wherein L$^{a2}$ is a bond or -[EG]$_x$-, wherein [EG] is ethyleneglycol unit which is [CH$_2$OCH$_2$], [OCH$_2$CH$_2$], or [CH$_2$CH$_2$O], wherein x is an integer of 1 to 10, and
wherein L$^{a3}$ is a bond or unsubstituted C$_{1-10}$ alkylene, provided that there are no case that all of L$^{a1}$, L$^{a2}$ and L$^{a3}$ are bonds.

5. The compound of claim 1, wherein the linker A is unsubstituted C$_{1-30}$ heteroalkylene, wherein unsubstituted C$_{1-30}$ heteroalkylene comprises 0 to 10 ethylene glycol units, and
wherein ethyleneglycol unit is —[CH$_2$OCH$_2$]—, —[OCH$_2$CH$_2$]— or —[CH$_2$CH$_2$O]—.

6. The compound of claim 1, wherein the linker A is a bond or unsubstituted C$_{1-2}$ alkylene.

7. The compound of claim 1, wherein the PEG moiety has the following structure:

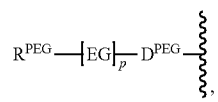

wherein,
DPEG is bond, or substituted or unsubstituted C$_{1-6}$ alkylene, substituted or unsubstituted C$_{1-6}$ heteroalkylene, or substituted or unsubstituted C$_{1-6}$ alkenylene, or substituted or unsubstituted C$_{1-6}$ heteroalkenylene,
wherein the heteroalkylene or the heteroalkenylene comprises one or more heteroatoms, and the heteroatoms are each independently selected from O, N, and S, and
wherein the substituted group comprises one or more substituents, wherein the substituents are each independently selected from —C$_{1-4}$ alkyl, —C(=O) H, —C(=O) CH$_3$, —C(=O) OH, —C(=O) NH$_2$, —NH$_2$, =O, =S, —OH, —NO$_2$ and —SH,
[EG] is [CH$_2$OCH$_2$], [OCH$_2$CH$_2$] or [CH$_2$CH$_2$O],
p is an integer of 2 to 20, and
R$^{PEG}$ is absent or —CH$_3$, C$_2$ alkyl, C$_3$ alkyl, —NH$_2$, —CH$_2$NH$_2$, —SC(=O) CH$_3$, —SC(=O) CH$_2$CH$_3$, —CH$_2$SC(=O) CH$_3$, —CH$_2$SC(=O) CH$_2$CH$_3$, —OH, —CH$_2$OH, —SH, —CH$_2$SH, —OCH$_3$, —CH$_2$OCH$_3$, —CH$_2$OCH$_2$CH$_3$, —C(=O) CH$_3$, —C(=O) CH$_2$CH$_3$, —CH$_2$C(=O) CH$_3$, —CH$_2$C(=O) CH$_2$CH$_3$, —NHC(=O) CH$_3$, —NHC(=O) CH$_2$CH$_3$, —CH$_2$NHC(=O) CH$_3$, —CH$_2$CH$_2$NHC(=O) CH$_3$, —CH$_2$CH$_2$NHC(=O) CH$_2$CH$_3$, —CH$_2$NHC(=O) CH$_2$CH$_3$, or —CH$_2$CH$_2$COOH.

8. The compound of claim 1, wherein two cysteine residues of the Fc binding peptide is covalently linked to each other through a disulfide bond.

* * * * *

```
                        SEQUENCE LISTING

Sequence total quantity: 30
SEQ ID NO: 1            moltype = AA  length = 17
FEATURE                 Location/Qualifiers
source                  1..17
                        mol_type = protein
                        note = amino acid sequence of Fc binding substance
                        organism = synthetic construct
SITE                    1
                        note = X is absent or any amino acid residue
SITE                    2
                        note = X is absent or any amino acid residue
SITE                    3
                        note = X is any amino acid residue
SITE                    5
                        note = X is any amino acid residue
SITE                    6
                        note = X is any amino acid residue
SITE                    8
                        note = X is a group having structure Xa1
SITE                    10
                        note = X is glutamic acid residue or asparagine residue
SITE                    13
                        note = X is tryptophan residue, naphthylalanine residue, or
                         phenylalanine residue
SITE                    15
                        note = X is any amino acid residue
SITE                    16
                        note = X is absent or any amino acid residue
SITE                    17
                        note = X is absent or any amino acid residue
SEQUENCE: 1
XXXCXXHXGX LVXCXXX                                                                  17

SEQ ID NO: 2            moltype = AA  length = 15
FEATURE                 Location/Qualifiers
source                  1..15
                        mol_type = protein
                        note = amino acid sequence of Fc binding substance
                        organism = synthetic construct
SITE                    1
                        note = X is L-proline residue
SITE                    4
                        note = X is any amino acid residue
SITE                    5
                        note = X is any amino acid residue
SITE                    7
                        note = X is a group having structure Xa1
SITE                    9
                        note = X is glutamic acid residue or asparagine residue
SITE                    12
                        note = X is tryptophan residue, naphthylalanine residue, or
                         phenylalanine residue
SITE                    15
                        note = X is D-proline residue
SEQUENCE: 2
XDCXXHXGXL VXCTX                                                                    15

SEQ ID NO: 3            moltype = AA  length = 15
FEATURE                 Location/Qualifiers
```

-continued

```
source                  1..15
                        mol_type = protein
                        note = amino acid sequence of Fc binding substance
                        organism = synthetic construct
SITE                    4
                        note = X is any amino acid residue
SITE                    5
                        note = X is any amino acid residue
SITE                    7
                        note = X is a group having structure Xa1
SITE                    9
                        note = X is glutamic acid residue or asparagine residue
SITE                    12
                        note = X is tryptophan residue, naphthylalanine residue, or
                         phenylalanine residue
SEQUENCE: 3
CDCXXHXGXL VXCTC                                                            15

SEQ ID NO: 4            moltype = AA  length = 13
FEATURE                 Location/Qualifiers
source                  1..13
                        mol_type = protein
                        note = amino acid sequence of Fc binding substance
                        organism = synthetic construct
SITE                    3
                        note = X is any amino acid residue
SITE                    4
                        note = X is any amino acid residue
SITE                    6
                        note = X is a group having structure Xa1
SITE                    8
                        note = X is glutamic acid residue or asparagine residue
SITE                    11
                        note = X is tryptophan residue, naphthylalanine residue, or
                         phenylalanine residue
SEQUENCE: 4
DCXXHXGXLV XCT                                                              13

SEQ ID NO: 5            moltype = AA  length = 13
FEATURE                 Location/Qualifiers
source                  1..13
                        mol_type = protein
                        note = amino acid sequence of Fc binding substance
                        organism = synthetic construct
SITE                    6
                        note = X is a group having structure Xa1
SEQUENCE: 5
DCAWHXGELV WCT                                                              13

SEQ ID NO: 6            moltype = AA  length = 13
FEATURE                 Location/Qualifiers
source                  1..13
                        mol_type = protein
                        note = amino acid sequence of Fc binding substance
                        organism = synthetic construct
SITE                    6
                        note = X is diaminopropionic acid
SEQUENCE: 6
DCAWHXGELV WCT                                                              13

SEQ ID NO: 7            moltype = AA  length = 13
FEATURE                 Location/Qualifiers
source                  1..13
                        mol_type = protein
                        note = amino acid sequence of Fc binding substance
                        organism = synthetic construct
SITE                    6
                        note = X is diaminobytyric acid
SEQUENCE: 7
DCAWHXGELV WCT                                                              13

SEQ ID NO: 8            moltype = AA  length = 13
FEATURE                 Location/Qualifiers
source                  1..13
                        mol_type = protein
                        note = amino acid sequence of Fc binding substance
                        organism = synthetic construct
SITE                    6
                        note = X is ornithine residue
```

```
SEQUENCE: 8
DCAWHXGELV WCT                                                         13

SEQ ID NO: 9            moltype = AA  length = 13
FEATURE                 Location/Qualifiers
source                  1..13
                        mol_type = protein
                        note = amino acid sequence of Fc binding substance
                        organism = synthetic construct
SEQUENCE: 9
DCAWHKGELV WCT                                                         13

SEQ ID NO: 10           moltype = AA  length = 7
FEATURE                 Location/Qualifiers
source                  1..7
                        mol_type = protein
                        note = amino acid sequence in IgG Fc region
                        organism = synthetic construct
SEQUENCE: 10
KPKDTLM                                                                 7

SEQ ID NO: 11           moltype = AA  length = 8
FEATURE                 Location/Qualifiers
source                  1..8
                        mol_type = protein
                        note = amino acid sequence in IgG Fc region
                        organism = synthetic construct
SEQUENCE: 11
MHEALHNH                                                                8

SEQ ID NO: 12           moltype = AA  length = 9
FEATURE                 Location/Qualifiers
source                  1..9
                        mol_type = protein
                        note = amino acid sequence in IgG Fc region
                        organism = synthetic construct
SEQUENCE: 12
MHEALHNHY                                                               9

SEQ ID NO: 13           moltype = AA  length = 16
FEATURE                 Location/Qualifiers
source                  1..16
                        mol_type = protein
                        note = amino acid sequence in IgG Fc region
                        organism = synthetic construct
SEQUENCE: 13
GPSVFLFPPK PKDTLM                                                      16

SEQ ID NO: 14           moltype = AA  length = 208
FEATURE                 Location/Qualifiers
source                  1..208
                        mol_type = protein
                        note = amino acid sequence in CH2-CH3 domain of human IgG1
                         Fc region
                        organism = synthetic construct
SEQUENCE: 14
GPSVFLFPPK PKDTLMISRT PEVTCVVVDV SHEDPEVKFN WYVDGVEVHN AKTKPREEQY       60
NSTYRVVSVL TVLHQDWLNG KEYKCKVSNK ALPAPIEKTI SKAKGQPREP QVYTLPPSRE      120
EMTKNQVSLT CLVKGFYPSD IAVEWESNGQ PENNYKTTPP VLDSDGSFFL YSKLTVDKSR      180
WQQGNVFSCS VMHEALHNHY TQKSLSLS                                         208

SEQ ID NO: 15           moltype = AA  length = 208
FEATURE                 Location/Qualifiers
source                  1..208
                        mol_type = protein
                        note = amino acid sequence in CH2-CH3 domain of human IgG2
                         Fc region
                        organism = synthetic construct
SEQUENCE: 15
GPSVFLFPPK PKDTLMISRT PEVTCVVVDV SHEDPEVQFN WYVDGVEVHN AKTKPREEQF       60
NSTFRVVSVL TVVHQDWLNG KEYKCKVSNK GLPAPIEKTI SKTKGQPREP QVYTLPPSRE      120
EMTKNQVSLT CLVKGFYPSD IAVEWESNGQ PENNYKTTPP MLDSDGSFFL YSKLTVDKSR      180
WQQGNVFSCS VMHEALHNHY TQKSLSLS                                         208

SEQ ID NO: 16           moltype = AA  length = 208
FEATURE                 Location/Qualifiers
```

```
source                  1..208
                        mol_type = protein
                        note = amino acid sequence in CH2-CH3 domain of human IgG3
                         Fc region
                        organism = synthetic construct
SEQUENCE: 16
GPSVFLFPPK PKDTLMISRT PEVTCVVVDV SHEDPEVQFK WYVDGVEVHN AKTKPREEQY    60
NSTFRVVSVL TVLHQDWLNG KEYKCKVSNK ALPAPIEKTI SKTKGQPREP QVYTLPPSRE   120
EMTKNQVSLT CLVKGFYPSD IAVEWESSGQ PENNYNTTPP MLDSDGSFFL YSKLTVDKSR   180
WQQGNIFSCS VMHEALHNHF TQKSLSLS                                      208

SEQ ID NO: 17           moltype = AA  length = 208
FEATURE                 Location/Qualifiers
source                  1..208
                        mol_type = protein
                        note = amino acid sequence in CH2-CH3 domain of human IgG4
                         Fc region
                        organism = synthetic construct
SEQUENCE: 17
GPSVFLFPPK PKDTLMISRT PEVTCVVVDV SQEDPEVQFN WYVDGVEVHN AKTKPREEQF    60
NSTYRVVSVL TVLHQDWLNG KEYKCKVSNK GLPSSIEKTI SKAKGQPREP QVYTLPPSQE   120
EMTKNQVSLT CLVKGFYPSD IAVEWESNGQ PENNYKTTPP VLDSDGSFFL YSRLTVDKSR   180
WQEGNVFSCS VMHEALHNHY TQKSLSLS                                      208

SEQ ID NO: 18           moltype = AA  length = 208
FEATURE                 Location/Qualifiers
source                  1..208
                        mol_type = protein
                        note = amino acid sequence in CH2-CH3 domain of Herceptin
                         Fc region
                        organism = synthetic construct
SEQUENCE: 18
GPSVFLFPPK PKDTLMISRT PEVTCVVVDV SHEDPEVKFN WYVDGVEVHN AKTKPREEQY    60
NSTYRVVSVL TVLHQDWLNG KEYKCKVSNK ALPAPIEKTI SKAKGQPREP QVYTLPPSRD   120
ELTKNQVSLT CLVKGFYPSD IAVEWESNGQ PENNYKTTPP VLDSDGSFFL YSKLTVDKSR   180
WQQGNVFSCS VMHEALHNHY TQKSLSLS                                      208

SEQ ID NO: 19           moltype = AA  length = 5
FEATURE                 Location/Qualifiers
source                  1..5
                        mol_type = protein
                        note = CDRH1 of anti-CLDN18.2 antibody
                        organism = synthetic construct
SEQUENCE: 19
TYGVH                                                                 5

SEQ ID NO: 20           moltype = AA  length = 16
FEATURE                 Location/Qualifiers
source                  1..16
                        mol_type = protein
                        note = CDRH2 of anti-CLDN18.2 antibody
                        organism = synthetic construct
SEQUENCE: 20
VIWAGGSTNY NSALMS                                                    16

SEQ ID NO: 21           moltype = AA  length = 10
FEATURE                 Location/Qualifiers
source                  1..10
                        mol_type = protein
                        note = CDRH3 of anti-CLDN18.2 antibody
                        organism = synthetic construct
SEQUENCE: 21
AAYYGNGLDY                                                           10

SEQ ID NO: 22           moltype = AA  length = 17
FEATURE                 Location/Qualifiers
source                  1..17
                        mol_type = protein
                        note = CDRL1 of anti-CLDN18.2 antibody
                        organism = synthetic construct
SEQUENCE: 22
KSSQTLLNSG NQKNYLT                                                   17

SEQ ID NO: 23           moltype = AA  length = 7
FEATURE                 Location/Qualifiers
source                  1..7
                        mol_type = protein
                        note = CDRL2 of anti-CLDN18.2 antibody
                        organism = synthetic construct
```

```
SEQUENCE: 23
WASTGES                                                                      7

SEQ ID NO: 24            moltype = AA  length = 9
FEATURE                  Location/Qualifiers
source                   1..9
                         mol_type = protein
                         note = CDRL3 of anti-CLDN18.2 antibody
                         organism = synthetic construct
SEQUENCE: 24
QNAYFYPFT                                                                    9

SEQ ID NO: 25            moltype = AA  length = 448
FEATURE                  Location/Qualifiers
source                   1..448
                         mol_type = protein
                         note = anti-CLDN 18.2 antibody Heavy chain
                         organism = synthetic construct
SEQUENCE: 25
QVQLVESGGG VVQPGRSLRL SCAASGFSLT TYGVHWVRQA PGKGLEWVAV IWAGGSTNYN         60
SALMSRFTIS RDNSKNTLYL QMNSLRAEDT AVYYCARAAY YGNGLDYWGQ GTMVTVSSAS        120
TKGPSVFPLA PSSKSTSGGT AALGCLVKDY FPEPVTVSWN SGALTSGVHT FPAVLQSSGL        180
YSLSSVVTVP SSSLGTQTYI CNVNHKPSNT KVDKRVEPKS CDKTHTCPPC PAPELLGGPS        240
VFLFPPKPKD TLMISRTPEV TCVVVDVSHE DPEVKFNWYV DGVEVHNAKT KPREEQYNST        300
YRVVSVLTVL HQDWLNGKEY KCKVSNKALP APIEKTISKA KGQPREPQVY TLPPSRDELT        360
KNQVSLTCLV KGFYPSDIAV EWESNGQPEN NYKTTPPVLD SDGSFFLYSK LTVDKSRWQQ        420
GNVFSCSVMH EALHNHYTQK SLSLSPGK                                           448

SEQ ID NO: 26            moltype = AA  length = 220
FEATURE                  Location/Qualifiers
source                   1..220
                         mol_type = protein
                         note = anti-CLDN 18.2 antibody Light chain
                         organism = synthetic construct
SEQUENCE: 26
DIVMTQSPLS LPVTPGEPAS ISCKSSQTLL NSGNQKNYLT WYLQKPGQSP QLLIYWASTG         60
ESGVPDRFSG SGSGTDFTLK ISRVEAEDVG VYYCQNAYFY PFTFGGGTKV EIKRTVAAPS        120
VFIFPPSDEQ LKSGTASVVC LLNNFYPREA KVQWKVDNAL QSGNSQESVT EQDSKDSTYS        180
LSSTLTLSKA DYEKHKVYAC EVTHQGLSSP VTKSFNRGEC                              220

SEQ ID NO: 27            moltype = AA  length = 5
FEATURE                  Location/Qualifiers
source                   1..5
                         mol_type = protein
                         note = Target region
                         organism = synthetic construct
SEQUENCE: 27
PKPKD                                                                        5

SEQ ID NO: 28            moltype =    length =
SEQUENCE: 28
000

SEQ ID NO: 29            moltype = DNA  length = 783
FEATURE                  Location/Qualifiers
source                   1..783
                         mol_type = other DNA
                         note = nucleic acid sequence encoding CLDN 18.1
                         organism = synthetic construct
SEQUENCE: 29
atgtccacca ccacatgcca agtggtggcg ttcctcctgt ccatcctggg gctggccggc         60
tgcatcgcgg ccaccgggat ggacatgtgg agcacccagg acctgtacga caacccgtc         120
acctccgtgt tccagtacga agggctctgg aggagctgcg tgaggcagag ttcaggcttc        180
accgaatgca ggccctattt caccatcctg gacttccag ccatgctgca ggcagtgcga        240
gccctgatga tcgtaggcat cgtcctgggt gccattggcc tcctggtatc catctttgcc        300
ctgaaatgca tccgcattgg cagcatggag gactctgcca aagccaacat gacactgacc        360
tccgggatca tgttcattgt ctcaggtctt tgtgcaattg ctggagtgtc tgtgtttgca        420
aacatgctgg tgactaactt ctggatgtcc acagctaaca tgtacaccgg catgggtggg        480
atggtcagaa ctgttcagac caggtacaca tttgggtgcg gctctgttcgt gggctgggtc       540
gctggaggcc tcacactaat ggggtgtgtg atgatgtgca tcgcctgccg gggcctggca        600
ccagaagaaa ccaactacaa agccgtttct tatcatgcct caggcacag tgttgcctac        660
aagcctggag gcttcaaggc cagcactggc ttgggtcca acaccaaaaa caagaagata        720
tacgatggag gtgcccgcac agaggacgag gtacaatctt atccttccaa gcacgactat        780
gtg                                                                      783

SEQ ID NO: 30            moltype = DNA  length = 786
FEATURE                  Location/Qualifiers
```

-continued

```
source          1..786
                mol_type = other DNA
                note = nucleic acid sequence encoding CLDN 18.2
                organism = synthetic construct
SEQUENCE: 30
atggccgtga ctgcctgtca gggcttgggg ttcgtggttt cactgattgg gattgcgggc    60
atcattgctg ccacctgcat ggaccagtgg agcacccaag acttgtacaa caacccgta    120
acagctgttt tcaactacca ggggctgtgg cgctcctgtg tccgagagag ctctggcttc   180
accgagtgcc ggggctactt caccctgctg gggctgccag ccatgctgca ggcagtgcga   240
gccctgatga tcgtaggcat cgtcctgggt gccattggcc tcctggtatc catctttgcc   300
ctgaaatgca tccgcattgg cagcatggag gactctgcca aagccaacat gacactgacc   360
tccgggatca tgttcattgt ctcaggtctt tgtgcaattg ctggagtgtc tgtgtttgcc   420
aacatgctgg tgactaactt ctggatgtcc acagctaaca tgtacaccgg catgggtggg   480
atggtgcaga ctgttcagac caggtacaca tttggtgggg ctctgttcgt gggctgggtc   540
gctggaggcc tcacactaat tggggggtgtg atgatgtgca tcgcctgccg gggcctggca   600
ccagaagaaa ccaactacaa agccgtttct tatcatgcct caggccacag tgttgcctac   660
aagcctggag gcttcaaggc cagcactggc tttgggtcca acaccaaaaa caagaagata   720
tacgatggag gtgcccgcac agaggacgag gtacaatctt atccttccaa gcacgactat   780
gtgtaa                                                              786
```